(12) United States Patent
Allen et al.

(10) Patent No.: US 12,319,922 B2
(45) Date of Patent: *Jun. 3, 2025

(54) METHODS AND COMPOSITIONS FOR SHORT STATURE PLANTS THROUGH MANIPULATION OF GIBBERELLIN METABOLISM TO INCREASE HARVESTABLE YIELD

(71) Applicant: MONSANTO TECHNOLOGY LLC, St. Louis, MO (US)

(72) Inventors: Edwards M. Allen, O'Fallon, MO (US); Jayanand Boddu, St. Louis, MO (US); Charles R. Dietrich, Chesterfield, MO (US); Alexander Goldshmidt, Davis, CA (US); Miya Howell, Ballwin, MO (US); Kevin R. Kosola, Wildwood, MO (US); Sivalinganna Manjunath, Chesterfield, MO (US); Anil Neelam, St. Louis, MO (US); Linda Rymarquis, High Ridge, MO (US); Thomas L. Slewinski, Chesterfield, MO (US); Tyamagondlu V. Venkatesh, St. Louis, MO (US); Huai Wang, St. Louis, MO (US)

(73) Assignee: MONSANTO TECHNOLOGY LLC, St. Louis, MO (US)

(*) Notice: Subject to any disclaimer, the term of this patent is extended or adjusted under 35 U.S.C. 154(b) by 428 days.

This patent is subject to a terminal disclaimer.

(21) Appl. No.: 17/713,344

(22) Filed: Apr. 5, 2022

(65) Prior Publication Data
US 2022/0364108 A1   Nov. 17, 2022

Related U.S. Application Data

(63) Continuation of application No. 16/847,244, filed on Apr. 13, 2020, now Pat. No. 11,319,550, which is a continuation of application No. 15/679,699, filed on Aug. 17, 2017, now Pat. No. 10,724,047.

(60) Provisional application No. 62/502,313, filed on May 5, 2017, provisional application No. 62/442,377, filed on Jan. 4, 2017, provisional application No. 62/376,298, filed on Aug. 17, 2016.

(51) Int. Cl.
C12N 15/82 (2006.01)

(52) U.S. Cl.
CPC ..... *C12N 15/8261* (2013.01); *C12N 15/8273* (2013.01); *C12N 15/8297* (2013.01)

(58) Field of Classification Search
None
See application file for complete search history.

(56) References Cited

U.S. PATENT DOCUMENTS

| | | |
|---|---|---|
| 5,159,135 A | 10/1992 | Umbeck |
| 5,188,958 A | 2/1993 | Moloney et al. |
| 5,322,938 A | 6/1994 | McPherson et al. |
| 5,352,605 A | 10/1994 | Fraley et al. |
| 5,463,174 A | 10/1995 | Moloney et al. |
| 5,510,474 A | 4/1996 | Quail et al. |
| 5,538,880 A | 7/1996 | Lundquist et al. |
| 5,550,318 A | 8/1996 | Adams et al. |
| 5,591,616 A | 1/1997 | Hiei et al. |
| 5,641,876 A | 6/1997 | McElroy et al. |
| 5,750,871 A | 5/1998 | Moloney et al. |
| 5,824,877 A | 10/1998 | Hinchee et al. |
| 5,850,019 A | 12/1998 | Maiti et al. |
| 5,939,539 A | 8/1999 | Lange et al. |
| 6,153,812 A | 11/2000 | Fry et al. |
| 6,160,208 A | 12/2000 | Lundquist et al. |
| 6,372,211 B1 | 4/2002 | Isaac et al. |
| 6,384,301 B1 | 5/2002 | Martinell et al. |
| 6,399,861 B1 | 6/2002 | Anderson et al. |
| 6,420,547 B1 | 7/2002 | Maiti et al. |
| 6,429,357 B1 | 8/2002 | McElroy et al. |
| 6,723,897 B2 | 4/2004 | Brown et al. |
| 7,049,490 B2 | 5/2006 | Tanaka et al. |
| 7,057,088 B2 | 6/2006 | Tanaka et al. |
| 7,138,567 B2 | 11/2006 | Okawa et al. |
| 7,154,028 B2 | 12/2006 | Tanaka et al. |
| 8,835,353 B2 | 9/2014 | Fugiel et al. |

(Continued)

FOREIGN PATENT DOCUMENTS

| | | |
|---|---|---|
| AU | 2016203359 A1 | 6/2016 |
| CN | 101440374 A | 5/2009 |

(Continued)

OTHER PUBLICATIONS

Song et al. (Gene 482.1-2 (2011): 34-42). (Year: 2011).*

(Continued)

*Primary Examiner* — Charles Logsdon
(74) *Attorney, Agent, or Firm* — Arnold & Porter Kaye Scholer LLP; David Lanzotti; David R. Marsh

(57) ABSTRACT

The present disclosure provides compositions and methods for altering gibberellin (GA) content in corn or other cereal plants. Methods and compositions are also provided for altering the expression of genes related to gibberellin biosynthesis through suppression, mutagenesis and/or editing of specific subtypes of GA20 or GA3 oxidase genes. Modified plant cells and plants having a suppression element or mutation reducing the expression or activity of a GA oxidase gene are further provided comprising reduced gibberellin levels and improved characteristics, such as reduced plant height and increased lodging resistance, but without offtypes.

83 Claims, 13 Drawing Sheets

Specification includes a Sequence Listing.

(56) References Cited

U.S. PATENT DOCUMENTS

| | | |
|---|---|---|
| 9,309,512 B2 | 4/2016 | Allen et al. |
| 2002/0053095 A1 | 5/2002 | Brown et al. |
| 2003/0233679 A1 | 12/2003 | Brown et al. |
| 2004/0034888 A1 | 2/2004 | Liu et al. |
| 2004/0053411 A1 | 3/2004 | Cullen et al. |
| 2004/0121321 A1 | 6/2004 | Brown et al. |
| 2004/0214272 A1 | 10/2004 | La Rosa et al. |
| 2004/0268441 A1 | 12/2004 | Vance et al. |
| 2005/0037988 A1 | 2/2005 | Zamore et al. |
| 2005/0064474 A1 | 3/2005 | Urnov et al. |
| 2005/0144669 A1 | 6/2005 | Reinhart et al. |
| 2005/0197253 A1 | 9/2005 | Stoller et al. |
| 2005/0251883 A1 | 11/2005 | Amasino et al. |
| 2006/0200878 A1 | 9/2006 | Lutfiyya et al. |
| 2006/0253933 A1 | 11/2006 | Brown et al. |
| 2007/0174931 A1 | 7/2007 | Brown et al. |
| 2007/0294789 A1 | 12/2007 | Ghiglione et al. |
| 2008/0034453 A1 | 2/2008 | Cheikh et al. |
| 2009/0031441 A1 | 1/2009 | Matsuoka et al. |
| 2009/0070898 A1 | 3/2009 | Allen et al. |
| 2009/0117617 A1 | 5/2009 | Holmes et al. |
| 2009/0313725 A1 | 12/2009 | Yu et al. |
| 2010/0095406 A1 | 4/2010 | Yu et al. |
| 2010/0107283 A1 | 4/2010 | Dasgupta et al. |
| 2011/0004958 A1 | 1/2011 | Aloni et al. |
| 2011/0035839 A1 | 2/2011 | Lutfiyya et al. |
| 2011/0145940 A1 | 6/2011 | Voytas et al. |
| 2011/0167517 A1 | 7/2011 | Danilevskaya et al. |
| 2011/0185456 A1 | 7/2011 | Cheikh et al. |
| 2011/0296555 A1 | 12/2011 | Ivashuta et al. |
| 2011/0301073 A1 | 12/2011 | Gregory et al. |
| 2012/0142062 A1 | 6/2012 | Doyon et al. |
| 2012/0174260 A1 | 7/2012 | Narva et al. |
| 2012/0216318 A1 | 8/2012 | La Rosa et al. |
| 2012/0297501 A1 | 11/2012 | Beghyn et al. |
| 2013/0117869 A1 | 5/2013 | Duchateau et al. |
| 2013/0260012 A1 | 10/2013 | Rommens et al. |
| 2013/0283461 A1 | 10/2013 | Abad et al. |
| 2013/0340111 A1* | 12/2013 | Burns ............... C12N 15/8218 426/627 |
| 2014/0165228 A1 | 6/2014 | Danilevskaya et al. |
| 2014/0344996 A1 | 11/2014 | Inze et al. |
| 2015/0052634 A1 | 2/2015 | Park et al. |
| 2015/0247154 A1 | 9/2015 | Ivashuta et al. |
| 2015/0307889 A1 | 10/2015 | Petolino et al. |
| 2015/0376641 A1 | 12/2015 | Etzioni et al. |
| 2016/0010109 A1 | 1/2016 | Albertsen et al. |
| 2016/0017349 A1 | 1/2016 | Ayele et al. |
| 2016/0046956 A1 | 2/2016 | Yu et al. |
| 2016/0050920 A1 | 2/2016 | Ott et al. |
| 2016/0076046 A1 | 3/2016 | Alexandrov et al. |

FOREIGN PATENT DOCUMENTS

| | | |
|---|---|---|
| CN | 102149821 A | 8/2011 |
| CN | 102174519 A | 9/2011 |
| EP | 1398382 B1 | 11/2005 |
| JP | 2001178468 A | 7/2001 |
| KR | 20150045611 A | 4/2015 |
| RU | 2013135491 A | 2/2015 |
| RU | 2013151447 A | 5/2015 |
| WO | WO 94/28141 A1 | 12/1994 |
| WO | WO 99/09174 A1 | 2/1999 |
| WO | WO 99/66029 A2 | 12/1999 |
| WO | WO 00/009722 A2 | 2/2000 |
| WO | WO 02/055725 A2 | 7/2002 |
| WO | WO 03/008540 A2 | 1/2003 |
| WO | WO 2006/032916 A2 | 3/2006 |
| WO | WO 2008/034648 A1 | 3/2008 |
| WO | WO 2010/002984 A1 | 1/2010 |
| WO | WO 2011/023537 A1 | 3/2011 |
| WO | WO 2013/037959 A1 | 3/2013 |
| WO | WO 2013/086499 A2 | 6/2013 |
| WO | WO 2014/055477 A2 | 4/2014 |
| WO | WO 2014/151749 A1 | 9/2014 |
| WO | WO 2015/168124 A1 | 11/2015 |

OTHER PUBLICATIONS

Appleford et al. "Decreased shoot stature and grain alpha-amylase activity following ectopic expression of a gibberellin 2-oxidase gene in transgenic wheat," *J Exp Bot.*, 58(12), pp. 3213-3226, (Oct. 2007) (electronic publication), available online, DOI: 10.1093/jXb/erm166.

Bensen et al., "Cloning and characterization of the maize An1 gene," *Plant Cell*, 7(1), pp. 75-84, (Jan. 1995) (electronic publication), available online, DOI: 10.1105/tpc.7.1.75.

Bhattacharyya-Pakrasi et al., "Specificity of a promoter from the rice tungro bacilliforrn virus for expression in phloem tissues," *Plant J.*, 4(1), pp. 71-79 (Jul. 1993) (electronic publication), available online, DOI: 10.1046/j.1365-313x.1993.04010071.x.

Bulley et al., "Modification of gibberellin biosynthesis in the grafted apple scion allows control of tree height independent of the rootstock," *Plant Biotechnol J.* 3(2):215-23 (Feb. 2002) (electronic publication), available online, DOI: 10.1111/j.1467-7652.2005.00119.x.

Carbonell et al, "Highly specific gene silencing in a monocot species by artificial microRNAs derived from chimeric miRNA precursors," *Plant J.* 82(6), pp. 1061-1075 (Jun. 2015) (electronic publication), available online, DOI: 10.1111/tpj.12835.

Cassani et al. "Characterization of the first dominant dwarf maize mutant carrying a single amino acid insertion in the VHYNP domain of the dwarf8 gene." *Molecular Breeding*, 24, pp. 375-385 (Jun. 2009) (electronic publication), available online, DOI: 10.1007/s11032-009-9298-3.

Chen et al, "Gibberellin and the plant growth retardant Paclobutrazol altered fruit shape and ripening in tomato," *Protoplasma*, 257(3), pp. 853-861 (May 2020) (electronic publication), available online, DOI: 10.1007/s00709-019-01471-2.

Chen et al., "Development of dwarfish and yield-effective GM maize through passivation of bioactive gibberellin," *Transgenic Res.*, 28(5-6), pp. 589-599, (Dec. 2019) (electronic publication), available online, DOI: 10.1007/s11248-019-00172-z.

Chinese Office Action and Search Report issued in Chinese Patent Application No. 201780063982.0, dated Jul. 28, 2022, with English translation (17 pages).

"Maize—global alliance for improving food security and the livelihoods of the resource-poor in the developing world: proposal submitted by CIMMYT and IITA to the CGIAR Consortium Board" *CIMMYT-IITA* pp. 1-184 (Jun. 2011) (electronic publication), available online: http://hdl.handle.net/10883/670.

Colbert et al., "High-Throughput Screening for Induced Point Mutations," *Plant Physiology*, 126(2), pp. 480-484, (Jun. 2001) (electronic publication), available online: https://doi.org/10.1104/pp. 126.2.480.

Dayan et al., "Leaf-induced gibberellin signaling is essential for internode elongation, cambial activity, and fiber differentiation in tobacco stems," *The Plant Cell* 24(1), pp. 66-79 (Jan. 2012) (electronic publication), available online, DOI: 10.1105/tpc.111.093096.

Dellaporta et al. "The Sex Determination Process in Maize," *Science*, 266(5190), pp. 1501-1505 (Dec. 1994) (electronic publication), available online, DOI: 10.1126/science.7985019.

Desgagné-Penix et al., "Expression of gibberellin 20-oxidase1 (AtGA20ox1) in *Arabidopsis* seedlings with altered auxin status is regulated at multiple levels," *J Exp Bot.*, 59(8), pp. 2057-2070 (May 2008) (electronic publication), available online, DOI: 10.1093/jxb/ern063.

FAO "The future of food and agriculture—Trends and challenges," *Food and Agriculture Organization of the United Nations (FAO)*, pp. 1-180 (2017) (electronic publication), available online: https://www.ncbi.nlm.nih.gov/pmc/articles/PMC9129074/.

(56) References Cited

OTHER PUBLICATIONS

Flint-Garcia et al., "Quantitative trait locus analysis of stalk strength in four maize populations." Crop Science 43(1), pp. 13-22 (Jan.-Feb. 2003) (electronic publication), available online: https://doi.org/10.2135/cropsci2003.1300a.

Fujioka et al., "The dominant non-gibberellin-responding dwarf mutant (D8) of maize accumulates native gibberellins," Proc Natl Acad Sci USA. 85(23), pp. 9031-9035 (Dec. 1988) (electronic publication), available online, DOI: 10.1073/pnas.85.23.9031.

Gastineau et al., "Model projected changes of extreme wind events in response to global warming." Geophysical Research Letters 36(L10810), 5 pages (May 2009) (electronic publication), available online: https://doi.org/10.1029/2009GL037500.

Han et al., "Generation of semi-dwaif rice (Oryza sativa L.) lines by CRISPR/Cas9-directed mutagenesis of OsGA20ox2 and proteomic analysis of unveiled changes caused by mutations," 3 Biotech., 9(387), 17 pages (Nov. 2019) (electronic publication), available online, DOI: 10.1007/s13205-019-1919-x.

Hay "Harvest index: a review of its use in plant breeding and crop physiology." Annals of applied biology, 126(1), pp. 137-216 (Feb. 1995) (electronic publication), available online: https://doi.org/10.1111/j.1744-7348.1995.tb05015.x.

Hedden, P. "Gibberellin biosynthesis, in higher plants." Chapter 2 in Annual Plant Reviews Book Series, vol. 49: The Gibberellins (Hedden, P. and Thomas, S.G. , eds), pp. 70-102 including cover page, Oxford, UK: Wiley, (pp: 37-72) (electronic publication) available online, DOI: 10.1002/9781119210436.ch2.

Heisel et al., "Characterization of unique small RNA populations from rice grain," PLoS One, 3(8):e2871, 10 pages (Aug. 2008). Available online, DOI: 10.1371/journal.pone.0002871.

Hoogendoorn et al., "Differences in leaf and stem anatomy related to plant height of tall and dwarf wheat (Triticum aestivum L.)." Journal of Plant Physiology 136(1), pp. 72-77 (Apr. 1990) (electronic publication), available online: https://www.sci-hub.se/10.1016/S0176-1617(11)81618-4.

Huang et al., "Activation of gibberellin 2-oxidase 6 decreases active gibberellin levels and creates a dominant semi-dwarf phenotype in rice (Oryza sativa L.)," J Genet Genomics. 37(1), pp. 23-36 (Jan. 2010) (electronic publication), available online, DOI: 10.1016/S1673-8527(09)60022-9.

Huang et al., "Overexpression of 20-oxidase confers a gibberellin-overproduction phenotype in Arabidopsis," Plant Physiol. 118(3), pp. 773-781 (Nov. 1998) (electronic publication), available online, DOI: 10.1104/pp. 118.3.773.

Itoh et al., "Modification of Rice Plant Height by Suppressing the Height-Controlling Gene D18, in Rice," Breed. Sci. 52, pp. 215-2018 (May 2002) (electronic publication), available online: https://doi.org/10.1270/jsbbs.52.215.

Jefferson et al., "GUS fusions: β-glucuronidase as a sensitive and versatile gene fusion marker in higher plants," EMBO J., 6(13), pp. 3901-3907 (Dec. 1987) (electronic publication), available online, DOI: 10.1002/j.1460-2075.1987.tb02730.x.

Kaufman et al., "Regulation of Growth and Cellular Differentiation in Developing Avena Internodes by Gibberellic Acid and Indole-3-acetic Acid," Am. J. Bot. 56(8), pp. 918-927 (Sep. 1969) (electronic publication), available online: https://doi.org/10.1002/j.1537-2197.1969.tb09742.x.

Keyes et al., "The Effects of dwarfing genes Rht1 and Rht2 on cellular dimensions and ate of leaf elongation in wheat," Ann. Bot. 64, pp. 683-690 (Jun. 1989) available online: https://doi.org/10.1093/oxfordjournals.aob.a087894.

Khan et al., "Impact of Nitrogen Regimes and Planting Densities on Stem Physiology, Lignin Biosynthesis and Grain Yield in Relation to Lodging Resistance in Winter Wheat (Triticum aestivum L.)," Cereal Res. Commun., 47(3), pp. 566-579 (Sep. 2019) (electronic publication), available online: http://real.mtak.hu/97099/1/0806.47.2019.21.

Khandagale et al. "Genome editing for targeted improvement of plants." Plant Biotechnol Rep 10, pp. 327-343 (Nov. 2016) (electronic publication), available online: https://doi.org/10.1007/s11816-016-0417-4.

Khush, "Green revolution: the way forward," Nat Rev Genet., 2(10), pp. 815-822 (Oct. 2001) (electronic publication), available online, DOI: 10.1038/35093585.

Knöller et al., "Brachytic2/ZmABCB1 functions in IAA export from intercalary meristems," Journal of Experimental Botany, 61(13), pp. 3689-3696, (Jun. 2010) (electronic publication), available online: DOI: 10.1093/jxb/erq180.

Koornneef et al., "Induction and analysis of gibberellin sensitive mutants in Arabidopsis thaliana (L.) Heynh," Theor Appl Genet. 58(6), pp. 257-263, (Nov. 1980) (electronic publication), available online, DOI: 10.1007/BF00265176.

Kurosawa, "Experimental Research on the Secretion of Gibberella fujikuoroi (Predictions)." Transactions of the Natural History Society of Formosa No. 87, pp. 213-227, (1926) (electronic publication), with English translation.

Last et al. "pEmu: an improved promoter for gene expression in cereal cells," Theoret. Appl. Genetics, 81, pp. 581-588 (May 1991) (electronic publication), available online: https://doi.org/10.1007/BF00226722.

Lin et al., "Validation of Potential Reference Genes for qPCR in Maize across Abiotic Stresses, Hormone Treatments, and Tissue Types," PLoS One, 9(5), e95445, pp. 1-11, (May 2014) (electronic publication), available online, DOI: 10.1371/journal.pone.0095445.

Liu et al., "Shortened Basal Internodes Encodes a Gibberellin 2-Oxidase and Contributes to Lodging Resistance in Rice," Molecular Plant, 11(2), pp. 288-299, (Feb. 2018) (electronic publication), available online: https://doi.org/10.1016/j.molp.2017.12.004.

Lo et al, "Ectopic expression of specific GA2 oxidase mutants promotes yield and stress tolerance in rice," Plant Biotechnol J. 15(7), pp. 850-864 (Jul. 2017) (electronic publication), available online at https://onlinelibrary.wiley.com/doi/pdf/10.1111/pbi.12681.

Lo et al., "A Novel Class of Gibberellin 2-OXidases Control Semidwarfism, Tillering, and Root Development in Rice," The Plant Cell 20(10), pp. 2603-2618 (Oct. 2008) (electronic publication), available online, DOI: 10.1105/tpc.108.060913.

Martin et al., "Correlated Responses of Yield and Other Agronomic Traits to Recurrent Selection for Stalk Quality in a Maize Synthetic." Crop Science 24(4), pp. 746-750, (Jul. 1984) (electronic publication), available online, DOI: 10.2135/cropsci1984.0011183X002400040028x.

Monna et al., "Positional cloning of rice semidwarfing gene, sd-1: rice "green revolution gene" encodes a mutant enzyme involved in gibberellin synthesis," DNA Res., 9(1), pp. 11-17 (Feb. 2002) (electronic publication), available online, DOI: 10.1093/dnares/9.1.11.

McCallum, et al., "Targeted screening for induced mutations." Nat Biotechnol 18, pp. 455-457 (Apr. 2000) (electronic publication), available online at https://doi.org/10.1038/74542.

Multani et al., "Loss of an MDR transporter in compact stalks of maize br2 and sorghum dw3 mutants," Science 302(5642), pp. 81-84 (Oct. 2003) (electronic publication), available online, DOI: 10.1126/science.1086072.

Nelissen et al., "A local Maximum in Gibberellin Levels Regulates Maize Leaf Growth by Spatial Control of Cell Division," Current Biology, 22(13), pp. 1183-1187 (Jul. 2012) (electronic publication), available online, DOI: 10.1016/j.cub.2012.04.065.

Novacek et al. "Twin Rows Minimally Impact Irrigated Maize Yield, Morphology, and Lodging," Agronomy Journal 105(1), pp. 268-276 (Jan. 2013) (electronic publication), available online: https://doi.org/10.2134/agronj2012.0301.

Novel et al., "Mutants of Escherichia coli K 12 affected for their growth on methyl--D-glucuronide: Location of embarrassed of structure of there—Dglucuronidase (uid HAS)," Mol Gen Genet. 120(4), pp. 319-335 (1973), With machine translation, available online, DOI: https://pubmed.ncbi.nlm.nih.gov/4568840/.

Ordonio et al., "Gibberellin deficiency pleiotropically induces culm bending in sorghum: an insight into sorghum semi-dwarf breeding,"

(56) References Cited

OTHER PUBLICATIONS

Scientific Reports 4(5287), pp. 1-10, (Jun. 2014) (electronic publication), available online, DOI: 10.1038/srep05287.
Otani et al., "Overexpression of the gibberellin 2-oxidase gene from Torenia fournieri induces dwarf phenotypes in the liliaceous monocotyledon *Tricyrtis* sp.," *J Plant Physiol.* 170(16), pp. 1416-1423, (Nov. 2013) (electronic publication), available online, DOI: 10.1016/j.jplph.2013.05.002.
Paciorek et al., "Targeted suppression of gibberellin biosynthetic genes ZmGA20ox3 and ZmGA20ox5 produces a short stature maize ideotype." *Plant Biotechnol J.*, 20(6), pp. 1140-1153, (Jun. 2022) (electronic publication), available online, DOI: 10.1111/pbi.13797.
Phillips et al., "Isolation and expression of three gibberellin 20-oxidase cDNA clones from *Arabidopsis*," *Plant Physiol.*, 108(3), pp. 1049-1057, (Jul. 1995) (electronic publication), available online, DOI: 10.1104/pp. 108.3.1049.
Phinney "Gibberellin A1 dwarfism and shoot elongation in higher plants," *Biol. Plant.* 27, 172-179, (Mar. 1985) (electronic publication), available online: https://link.springer.com/article/10.1007/BF02902157.
Portwood et al., "MaizeGDB 2018: the maize multi-genome genetics and genomics database," *Nucleic Acids Res.* 47(D1), pp. D1146-D1154, (Jan. 2019) (electronic publication), available online, DOI: 10.1093/nar/gky1046.
Ray et al, "Yield Trends Are Insufficient to Double Global Crop Production by 2050," *PLoS One*, 8(6):e66428, pp. 1-8 (Jun. 2013) (electronic publication), available online, DOI: 10.1371/journal.pone.0066428.
Rebers et al., "Regulation of gibberellin biosynthesis genes during flower and early fruit development of tomato," *Plant J.* 17(3), pp. 241-250 (Feb. 1999) (electronic publication), available online, DOI: 10.1046/j.1365-313x.1999.00366.x.
Rood "Application of Gibberellic Acid to Control Tillering in Early Maturing Maize," *Can. J. Plant Sci.* 65, pp. 901-911 (Oct. 1985) (electronic publication), downloaded Jul. 21, 2023, available online: https://doi.org/10.4141/cjps85-116.
Russell "Genetic Improvement of Maize Yields," *Agronomy*, 46, pp. 245-298 (Jan. 1991) (electronic publication), available online: https://doi.org/10.1016/S0065-2113(08)60582-9.
Schneider et al., "NIH Image to ImageJ: 25 years of image analysis," *Nat Methods*, 9(7), pp. 671-675 (Jul. 2012) (electronic publication), available online, DOI: 10.1038/nmeth.2089.
Schwab et al., "Highly specific gene silencing by artificial microRNAs in *Arabidopsis*," *The Plant Cell*, 18(5), pp. 1121-1133, (May 2006) (electronic publication), available online, DOI: 10.1105/tpc.105.039834.
Schwab et al., "Specific Effects of MicroRNAs on the Plant Transcriptome," *Developmental Cell*, 8(4), pp. 517-527 (Apr. 2005) (electronic publication), available online, DOI: 10.1016/j.devcel.2005.01.018.
Search Report issued in Chilean Patent Application No. 2019-00421, dated Jun. 4, 2020, with English translation (19 pages).
Search Report issued in Chilean Patent Application No. 2019-00421, dated Dec. 4, 2020, with English translation (28 pages).
Search Report issued in Chilean Patent Application No. 2019-00421, dated Oct. 23, 2023, with English translation (31 pages).
Search Report issued in Chilean Patent Application No. 2020-02239, dated Oct. 7, 2022, with machine translation (8 pages).
Search Report issued in Chilean Patent Application No. 2020-02239, dated Apr. 6, 2022, with machine translation (8 pages).
Search Report issued in Chilean Patent Application No. 2020-02240, dated Apr. 6, 2022, with machine translation (8 pages).
Search Report issued in Chilean Patent Application No. 2020-02240, dated Oct. 7, 2022, with machine translation (8 pages).
Search Report issued in Chilean Patent Application No. 2020-02241, dated Apr. 6, 2022, with machine translation (8 pages).
Search Report issued in Chilean Patent Application No. 2020-02241, dated Oct. 7, 2022, with machine translation (8 pages).
Search Report issued in Chilean Patent Application No. 2020-02242, dated Feb. 22, 202, with machine translation (8 pages).
Search Report issued in Chilean Patent Application No. 2020-02242, dated Oct. 7, 2022, with machine translation (8 pages).
Sekhon et al., "Genome-wide atlas of transcription during maize development," *The Plant Journal*, 66(4), pp. 553-563 (May 2011) (electronic publication), available online, DOI: 10.1111/j.1365-313X.2011.04527.x.
Shao et al., "Using CRISPR/Cas9 genome editing system to create MaGA20ox2 gene-modified semi-dwarf banana," *Plant Biotechnol J.* 18(1), pp. 17-19, (Jan. 2020) (electronic publication), available online, DOI: 10.1111/pbi.13216.
Sher et al., "Characterization of the Effect of Increased Plant Density on Canopy Morphology and Stalk Lodging Risk," Front Plant Sci., 9(1047), pp. 1-12, (Sep. 2018) (electronic publication), available online: DOI: 10.3389/fpls.2018.01047.
Shiferaw et al., "Crops that feed the world 6. Past successes and future challenges to the role played by maize in global food security," *Food Sec.* 3, pp. 307-327 (Aug. 2011) (electronic publication), available online: DOI: 10.1007/s12571-011-0140-5.
Sidorov et al., "Agrobacterium-Mediated Maize Transformation: Immature Embryos Versus Callus," *Methods Mol Biol.*, 526, pp. 47-58, (2009) (electronic publication), available online, DOI: 10.1007/978-1-59745-494-0_4.
Song et al., "Morphological Characteristics of Maize Canopy Development as Affected by Increased Plant Density," *PLoS One* 11(4):e0154084, pp. 1-10 (Apr. 2016) (electronic publication), available online, DOI: 10.1371/journal.pone.0154084.
Sponsel et al., "B2. Gibberellin Biosynthesis and Inactivation." In *Plant Hormones: Biosynthesis, Signal Transduction, action*!, (Davies, Peter J. , ed), pp. 63-94, (2010). Dordrecht Heidelberg London New York: Springer.
Sprangers et al., "Gibberellin Enhances the Anisotropy of Cell Expansion in the Growth Zone of the Maize Leaf," *Front Plant Sci.*, 11(1163), pp. 1-13 (Aug. 2020) (electronic publication), available online: DOI: 10.3389/fpls.2020.01163.
Stevenson et al., "Green Revolution research saved an estimated 18 to 27 million hectares from being brought into agricultural production," *Proc Natl Acad Sci USA*, 110(21), pp. 8363-8368 (May 2013), available online, DOI: 10.1073/pnas.1208065110.
Tiwari et al, "Artificial microRNA mediated gene silencing in plants: progress and perspectives," Plant Mol Biol. 86(1-2), pp. 1-18 (Sep. 2014) (electronic publication), available online, DOI: 10.1007/s11103-014-0224-7.
Vaucheret, "MicroRNA-Dependent Trans-Acting siRNA Production," *Science's STKE*, 2005(300), pp. pe43-pe43 (Sep. 2005) (electronic publication), available online DOI:10.1126/stke.3002005pe43.
Wang et al., "Effects of nitrogen application rate and plant density on lodging resistance in winter wheat," *Acta Agron. Sin.* 38(1), pp. 121-128 (2012) (with Machine translation) available online, DOI: 10.3724/SP.J.1006.2012.00121.
Wang et al., "The effect of mepiquat chloride on elongation of cotton (*Gossypium hirsutum* L.) internode is associated with low concentration of gibberellic acid," *Plant Sci.* 225, pp. 15-23, (Aug. 2014) (electronic publication), available online, DOI: 10.1016/j.plantsci.2014.05.005.
Wang et al., "Gibberellin in plant height control: old player, new story," *Plant Cell Rep.* 36(3), pp. 391-398 (Mar. 2017) (electronic publication), available online, DOI: 10.1007/s00299-017-2104-5.
Warthmann et al., "Highly specific gene silencing by artificial miRNAs in rice," *PLoS One.* 3(3):e1829 (Mar. 2008) (electronic publication), available online, DOI: 10.1371/journal.pone.0001829.
Waycott et al., "Phenotypic characterization of lettuce dwarf mutants and their response to applied gibberellins," *Plant Physiol.* 95(4), pp. 1162-1168 (Apr. 1990) (electronic publication), available online: DOI: 10.1104/pp. 95.4.1162.
Winkler et al., "Physiological genetics of the dominant gibberellin-nonresponsive maize dwarfs, Dwarf8 and Dwarf9." *Planta* 193, pp. 341-348 (Apr. 1994), available online, DOI: https://doi.org/10.1007/BF00201811.
Winkler et al., "The maize Dwarf3 gene encodes a cytochrome P450-mediated early step in Gibberellin biosynthesis," *The Plant*

(56) References Cited

OTHER PUBLICATIONS

*Cell.* 7(8), pp. 1307-1317 (Aug. 1995) (electronic publication), available online: DOI: 10.1105/tpc.7.8.1307.

Winter et al., "An "Electronic Fluorescent Pictograph" browser for exploring and analyzing large-scale biological data sets," *PLoS One* Issue 8 :e718, pp. 1-12 (Aug. 2007) (electronic publication), available online, DOI: 10.1371/journal.pone.0000718.

Xu et al., "Feedback Regulation of GA5 Expression and Metabolic Engineering of Gibberellin Levels in *Arabidopsis*," *Plant Cell.* 11(5), pp. 927-936 (May 1999) (electronic publication), available online, DOI: 10.1105/tpc.11.5.927.

Xue et al.,"How High Plant Density of Maize Affects Basal Internode Development and Strength Formation," *Crop Sci.* 56, pp. 3295-3306 (Nov.-Dec. 2016) published Oct. 6, 2016. Available online: https://doi.org/10.2135/cropsci2016.04.0243.

Yabuta, T. "On the crystal of gibberellin, a substance to promote plant growth," *J. Agric. Chem. Soc. Japan*, 14, pp. 1526 (1938), with English translation.

Yang et al. "Effects of nitrogen rate and transplanting density on physical and chemical characteristics and lodging resistance of culms in hybrid rice." *Acta Agronomica Sinica* 35.1, pp. 93-103, (Jan. 2009), with machine translation, available online: DOI:10.3724/SP.J.1006.2009.00093.

Yin et al., The regulatory regions of the rice tungro bacilliforrn virus promoter and interacting nuclear factors in rice (*Oryza sativa* L.). *The Plant J.* 7(6), pp. 969-980 (Jun. 1995). Available online: DOI: 10.1046/j.1365-313x.1995.07060969.x.

Zhao et al., "Temperature increase reduces global yields of major crops in four independent estimates," *Proc Natl Acad Sci USA.* 114(35), pp. 9326-9331 (Aug. 2017) (electronic publication), available online: DOI: 10.1073/pnas.1701762114.

Search Report issued in Brazilian Patent Application No. BR1120190031146, dated Mar. 21, 2023, with machine translation (10 pages).

Search Report issued in Columbian Patent Application No. NC2019/0002363, dated Oct. 31, 2023; with machine translation (4 pages).

Search Report issued in Columbian Patent Application No. NC2019/0002363, dated Mar. 8, 2024; with machine translation (4 pages).

Search Report dated Jul. 21, 2022, in Chinese Application 2017800639820 including English translation of related Office Action.

Allen et al., "Evolution of microRNA genes by inverted duplication of target gene sequences in *Arabidopsis thaliana*," *Nature Genetics*, 36:1282-1290 (2004).

Allen et al., "microRNA-directed phasing during trans-acting siRNA biogenesis in plants," *Cell*, 121(2):207-221 (2005).

Altschul et al., "Basic local alignment search tool," *Journal of Molecular Biology*, 215(3):403-410 (1990).

Altschul et al., "Gapped BLAST and PSI-BLAST: a new generation of protein database search program," *Nucleic Acids Research*, 25(17):3389-3402 (1997).

Ashikari et al., "Loss-of-function of a Rice Gibberellin Bio synthetic Gene, GA20 oxidase (GA20ox-2), Led to the Rice 'Green Revolution'," *Breeding Science*, 52:143-150 (2002).

Axtell et al., "A two-hit trigger for siRNA biogenesis in plants," *Cell*, 127:565-577 (2006).

Beurdeley et al., "Compact designer TALENs for efficient genome engineeling," *Nature Communications*, 4: 1762 (2013).

Cai et al., "Molecular Cloning, Characterization, and Expression Analysis of Genes Encoding Gibberellin 20-Oxidase in Dasypyrum Villosum Dwarf Mutant," *Plant Molecular Biology Reporter*, 30:1110-1116 (2012).

Carrera et al., "Changes in GA 20-oxidase gene expression strongly affect stem lenglh, tuber induction and tuber yield of potato plants," *The Plant Journal*, 22(3):247-256 (2000).

Cerrnak et al., "Efficient design and assembly of custom T ALEN and other TAL effector-based constructs for DNA targeting," *Nucleic Acids Research*, 39(12):e82 (2011).

Chen et al., "Identification and Functional Analysis of Flowering Related microRNAs in Common Wild Rice (*Oryza rufipogon* Griff.)," *PLoS ONE*, 8:e82844 (2013).

Chen et al., "New insight in the Gibberellin biosynthesis and signal transduction," *Plant Signaling & Behavior*, 10(5):e1000140-1-e1000140-3:(2015).

Chen et al., "The Maize DWARF 1 Encodes a Gibberellin 3-Oxidase and Is Dual Localized to the Nucleus and Cytosol," *Plant Physiology*, 166:2028-2039 (2014).

Chenna et al., "Multiple sequence alignment with the Clustal series of program," *Nucleic Acids Research*, 31(13):3497-3500 (2003).

Ciampitti et al., "A comprehensive study of plant density consequences on nitrogen uptake dynamics of maize plants from vegetative to reproductive stages," *Field Crops Research*, 121(1):2-18 (2011).

Coles et al., "Modification of gibberellin production and plant development in *Arabidopsis* by sense and antisense expression of gibberellin 20-oxidase genes," *The Plant Journal*, 17 (5):547-556 (1999).

Davis et al., "Gibberellin Biosynthesis in Maize. Metabolic Studies with GA1s, GA24, GA2s, GA1, and 2,3-Dehydro-GA91," *Plant Physiology*, 121(3):1037-1045 (1999).

Doyle et al., "Nucleic Acids TAL Effector-Nucleotide Targeter (TALE-NT) 2.0: tools for T AL effector design and target prediction," *Nucleic Acids Research*, 40(W1):17-122 (2012).

Du et al., "Cloning and characterization of an up-regulated GA 20-oxidase gene in hybIid maize," *Natural Science*, 19(2):161-166 (2009).

Eriksson et al., "$GA_4$ Is the Active Gibberellin in the Regulation of LEAFY Transcription and *Arabidopsis* Floral Initiation," *The Plant Cell*, 18(9):2172-2181 (2006).

Extended European Search Report dated Mar. 9, 2020, in European Patent Application No. 17842139.2.

Fagoaga et al., "Engineeiing of gibberellin levels in citrus by sense and antisense overexpression of a GA 20-oxidase gene modifies plant architecture," *Journal of Experimental Botany*, 58(6):1407-1420 (2007).

Fambnni et al., "The extreme dwarf phenotype of the GA-sensitive mutant of sunflower, dwarf2, is generated by a deletion in the ent-kaurenoic acid oxidase1 (HaKAO1) gene sequence," *Plant Molecular Biology*, 75:431-450 (2011).

Franco-Zorrilla et al., "Target mimicry provides a new mechanism for regulation of microRNA activity," *Nature Genetics*, 39: 1033-1037 (2007).

Gabsalilow et al., "Site- and strand-specific nicking of DNA by fusion proteins derived from MutH and I-SceI or TALE repeats," *Nucleic Acids Research*, 41(7):e83 (2013).

Gaj et al., "ZFN, TALEN and CRISPR/Cas-based methods for genome engineering," *Trends Biotechnology*, 31(7):397-405 (2013).

GenBank Accession No. AY105651., "*Zea mays* PCO130567 mRNA sequence," pp. 1-2 (2008).

GenBank Accession No. BT068785.2, "*Zea mays* full-length cDNA clone ZM_BFb0382B03 mRNA, complete eds.," pp. 1-2 (2012).

GenBank Accession No. EU963664, "*Zea mays* clone 265382 gibberellin 20 oxidase 2 mRNA, complete eds," pp. 1-2 (2008).

Griffiths-Jones et al., "Rfam: an RNA family database," *Nucleic Acids Research*, 31(1):439-441 (2003).

Gupta et al., "Gibberellic acid in plant, Still a mysteIy unresolved," *Plant Signaling & Behavior*, 8(9):e25504 (2013).

Han et al., "Gibberellin-associated cisgenes modify growth, stature and wood properties in Populus," *Plant Biotechnology Journal*, 9(2):162-178 (2011).

Hedden, "Gibberellin Biosynthesis: Enzymes, Genes and Their Regulation," *Annu. Rev. Plant Physiol. Plant Mol. Biol.*, 48:431-60 (1997).

Hedden, "The genes of the Green Revolution," *Trends in Genetics*, 19(1):5-9 (2003).

Helliwell et al., "Constructs and Methods for Hairpin RNA-Mediated Gene Silencing in Plants," *Methods in Enzymology*, 392:24-35 (2003).

Huang et al., "A Gibberellin-Mediated DELLA-NAC Signaling Cascade Regulates Cellulose Synthesis in Rice," *The Plant Cell*, 27(6):1681-1696 (2015).

(56) References Cited

OTHER PUBLICATIONS

International Search Report and Written Opinion mailed Dec. 28, 2017, in International Application No. PCT/US2017 /047405.
Jia et al., "GA-20 oxidase as a candidate for the semidwarf gene sdwl/denso in barley," Functional & Integrative Genomics, 9:255-262 (2009).
Jia et al., "Molecular characterization and functional analysis of barley semi-dwarf mutant Riso No. 9265," *BMC Genomics*, 16(927):1-11 (2015).
Jones-Rhoades et al., "Computational Identification of Plant MicroRNAs and Their Targets, Including a Stress-Induced miRNA," *Molecular Cell*, 14(6):787-799 (2004).
Kamthan et al., "Small RNAs in plants: recent development and application for crop improvement" *Frontiers in Plant Science*, 5:1-17 (2015).
Katoh et al., "Specific residues at every third position of siRNA shape its efficient RNAi activity," *Nucleic Acids Research*, 35(4):e27 (2007).
Khvorova et al., "Functional siRNAs and miRNAs Exhibit Strand Bias," *Cell*, 115(2):209-216 (2003).
Kim, "MicroRNA biogenesis: coordinated cropping and dicing," Nature Reviews Molecular Cell Biology, 6:376-385 (2005).
King et al., "Selective Deactivation of Gibberellins below the Shoot Apex is Critical to Flowering but Not to Stem Elongation of Lolium," *Molecular Plant*, 1(2):295-307 (2008).
Kobayashi et al., "Gibberellin Metabolism in Maize," *Plant Physiology*, 110(2):413-418 (1996).
Kusaba et al., "Isolation and expression analysis of gibberellin 20-oxidase homologue gene in apple," *Journal of Experimental Botany*, 52(335):375-376 (2001).
Lange et al., "Gibberellin Biosynthesis and the Regulation of Plant Development," *Plant Biology*, 8(3):281-290 (2006).
Larkin et al., "Clustal Wand Clustal X version 2.0," *Bioinformatics*, 23(21):2947-48 (2007).
Liu et al., "Analysis of Complementarity Requirements for Plant MicroRNA Targeting Using a Nicotiana benthamiana Quantitative Transient Assay," *The Plant Cell*, 26(2):741-753 (2014).
McElroy et al., "Construction of expression vectors based on the rice actin 1 (Actl) 5' region for use in monocot transformation," *Molecular and General Genetics MGG*, 231:150-160 (1991).
Mitchum et al., "Distinct and overlapping roles of two gibberellin 3-oxidases in *Arabidopsis* development," *The Plant Journal*, 45(5):804-818 (2006).
Molina et al., "Transformation of a Dwarf Arabi do psis Mutant Illustrates Gibberellin Hormone Physiology and the Function of a Green Revolution Gene," *Biochemistry and Molecular Biology Education*, 37(3): 170-177 (2009).
Mutasa-Göttgens et al., "Gibberellin as a factor in floral regulatory networks," *Journal of Experimental Botany*, 60(7):1979-1989 (2009).
Offtype—Definition of Offtype by Merriam-Webster, pp. 1, retrieved Jan. 5, 2021 <https://www.merriam-webster.com/dictionary/offtype>.
Oikawa et al., "A role of OsGA20ox1, encoding an isofonn of gibberellin 20-oxidase, for regulation of plant stature in rice," *Plant Molecular Biology*, 55:687-700 (2004).
Ookawa et al., "Precise estimation of genomic regions controlling lodging resistance using a set of reciprocal chromosome segment substitution lines in rice," *Scientific Reports*, 6(30572) pp. 12 (2016).
Parizotto et al., "In vivo investigation of the transcription, processing, endonucleolytic activity, and functional relevance of the spatial distribution of a plant miRNA," *Genes & Development*, 18:2237-2242 (2004).
Pater et al., "The promoter of the rice gene GOS2 is active in various different monocot tissues and binds rice nuclear factor ASF-1," *The Plant Journal*, 2(6):837-844 (1992).
Peiffer et al., "The Genetic Architecture of Maize Height," *Genetics*, 196(4):1337-1356 (2014).
Peng et al., "'Green revolution' genes encode mutant gibberellin response modulators," *Nature*, 400:256-261 (1999).
Petti et al., "Mapping of a Cellulose-Deficient Mutant Named dwarf1-1 in *Sorghum bicolor* to the Green Revolution Gene gibberellin20-oxidase Reveals a Positive Regulatory Association between Gibberellin and Cellulose Biosynthesis," *Plant Physiology*, 169(1):705-716 (2015).
Plackett et al., "Analysis of the Developmental Roles of the *Arabidopsis* Gibberellin 20-Oxidases Demonstrates That GA20ox1, -2 and -3 Are the Dominant Paralogs," *The Plant Cell*, 24(3):941-960 (2012).
Qiao et al., "Alteration of rice growth and development via antisense expression of OsGA20ox2 gene," *African Journal of Biotechnolog*, 12(5):3898-3904 (2013).
Qiao et al., "Modification of plant height Via RNAi suppression of OsGA20ox2 gene in rice," *Euphytica*, 158-35-45 (2007).
Qiao et al., "The Influence of RN Ai Targeting of OsGA20ox2 Gene on Plant Height in Rice," *Plant Molecular Biology Reporter*, 29:952-960 (2011).
Qin et al., "Gibberellin 20-Oxidase Gene OsGA20ox3 Regulates Plant Stature and Disease Development in Rice," *MPMI*, 26(2) :227-23 9 (2013).
Reynolds et al., "Rational siRNA design for RNA intetference," *Nature Biotechnology*, 22(3):326-330 (2004).
Rhoades et al., "Prediction of Plant MicroRNA Targets," *Cell*, 110(4):513-520 (2002).
Rieu et al., "The gibberellin biosynthetic genes AtGA20ox1 and AtGA20ox2 act, partially redundantly, to promote growth and development throughout the *Arabidopsis* life cycle," *The Plant Journal*, 53 :488-504 (2008).
Ross et al., "Gibberellin mutants," *Physiologia Plantarum*, 100(3):550-560 (1997).
Sarkar et al., "Relationship between gibberellins, height, and stress tolerance in barely (*Hordeum vulgare* L.) seedlings," *Plant Growth Regulation*, 42:125-135 (2004).
Sasaki et al., "A mutant gibberellin-synthesis gene in rice," *Nature*, 416:701-702 (2002).
Search Report dated Jun. 24, 2021, in Russian Patent Application 2019105536, and English translation of the same (pp. 1-4).
Sing, "The green revolution and the evolution of agricultural education and research in India," *Genome*, 42(4):557-561 (1999).
Song et al., "Association of the molecular regulation of ear leaf senescence/stress response and photosynthesis/metabolism with heterosis at the reproductive stage in maize," *Scientific Reports*, 6: 29843 (2016).
Song et al., "Flowering time regulation: photoperiod- and temperature-sensing in leaves," *Trends in Plant Science*, 18(10):575-583 (2013).
Song et al., "Genome-wide identification of gibberellins metabolic enzyme genes and expression profiling analysis during seed germination in maize," *Gene*, 482(1-2):34-42 (2011).
Spielmeyer et al., "Semidwarf (sd-1), "green revolution" rice, contains a defective gibberellin 20-oxidase gene," *PNAS*, 99(13):9043-9048 (2002).
Sun, "Gibberellin Metabolism, Perception and Signaling Pathways in *Arabidopsis*," *The Arabidopsis Book*, 2008(6): pp. 1-28 (2008).
Sunkar et al., "Novel and Stress-Regulated MicroRNAs and Other Small RNAs from *Arabidopsis*," *Plant Cell*, 16(8):2001-2019 (2004).
Supplementary Partial European Search Report dated Jan. 14, 2020, in European Patent Application No. 17842139.
Svitashev et al., "Targeted Mutagenesis, Precise Gene Editing, and Site-Specific Gene Insertion in Maize Using Cas9 and Guide RNA," *Plant Physiology*, 169(2):931-945 (2015).
Teng et al., "ZmGA3ox2, a candidate gene for a major QTL,qPH3.1, for plant height in maize," *The Plant Journal*, 73(3):405-416 (2013).
Thompson et al., "CLUSTAL W: Improving the sensitivity of progressive multiple sequence alignment through sequence weighting, position-specific gap penalties and weight matrix Choice," *Nucleic Acids Research*, 22(22):4673-4680 (1994).
Tollenaar et al., "Effect of Defoliation on Kernel Development in Maize," *Canadian Journal of Plant Science*, 58(1):207-212 (1978).
Tong et al., "Reply: Brassino steroid Promotes Cells Elongation by Regulating Both Synthesis and Signaling of Gibberellin: Critical Comments on Ross and Quittenden's Letter," *Plant Cell Advance Publication*, pp. 1-7 (2016).

(56) References Cited

OTHER PUBLICATIONS

Traore et al., "BT and Non-Bt Maize Growth and Development as Affected by Temperature and Drought Stress," *Agronomy Journal*, 92(5): 1027-1035 (2000).

Unterholzner et al., "Reply: Interaction Between Brassinosteroids and Gibberellins: Synthesis or Signaling? In *Arabidopsis* Both!," *Plant Cell Advance Publication*, pp. 1-8 (2016).

Urakami et al., "Immunomodulation of gibberellin biosynthesis using an anti-precursor gibberellin antibody confers gibberellin-deficient phenotypes," *Planta*, 228:863-873 (2008).

Voorend et al., "Overexpression of GA20-Oxidase1 impacts plant height, biomass allocation and sacchatification efficiency in maize," *Plant Biotechnology Journal*, 14(3):997-1007 (2016).

Voytas, "Plant Genome Engineering with Sequence-Specific Nucleases," *Annual Review of Plant Biology*, 64:327-35 (2013).

Wang et al., "Gibberellin Biosynthetic Deficiency Is Responsible for Maize Dominant Dwarf11 (D11) Mutant Phenotype: Physiological and Transcriptomic Evidence," *PLoS One*, 8(6):e66466:1-8 (2013).

Wang et al., "More than meets the eye? Factors that affect target selection by plant miRNAs and heterochromatic siRNAs," *Current Opinion Plant Biology*, 27:118-124 (2015).

Weng et al., "Genome-Wide Association Study Identifies Candidate Genes That Affect Plant Height in Chinese Elite Maize (*Zea mays* L.) Inbred Lines," *PLoS One*, 6(12):e29229 pp. 1-8 (2011).

Wu et al., "Target specificity of the CRISPR-Cas9 system," *Quantitative Biology*, 2(2):59-70 (2014).

Xiao et al., "Dissection of GA 20-oxidase members affecting tomato morphology by RNAi-mediated silencing," *Plant Growth Regulation*, 50:179-189 (2006).

Yamaguchi et al., "Gibberellin Acts Positively Then Negatively to Control Onset of Flower Formation in *Arabidopsis*," *Science*, 344(6184):638-641 (2014).

Yamaguchi, "Gibberellin Metabolism and its Regulation," *Annual Review of Plant Biology*, 59:225-251 (2008).

Yanik et al., "TALE-PvuII Fusion Proteins—Novel Tools for Gene Targeting," *PLoS One*, 8(12):e82539 pp. 1-13 (2013).

Yin et al., "In-Season Prediction of Corn Yield Using Plant Height under Major Production Systems," *Agronomy Journal*, 103(3):923-929 (2011).

Yoshikawa et al., "A pathway for the biogenesis of trans-acting siRNAs in *Arabidopsis*," *Genes & Development*, 19:2164-2175 (2005).

Zeng et al., "Both Natural and Designed Micro RN As Can Inhibit the Expression of Cognate mRNAs When Expressed in Human Cells," *Molecular Cell*, 9(6): 1327-1333 (2002).

Fujioka et al. "Qualitative and Quantitative Analyses of Gibberellins in Vegetative Shoots of Normal, dwarf-1, dwarf-2, dwarf-3, and dwarf-5 Seedlings of *Zea mays* L." *Plant Physiology* 88(4), pp. 1367-1372, (Dec. 1988).

Han et al., "Morphological Characterization and Transcriptome Analysis of New Dwarf and Narrow-Leaf (dnl2) Mutant in Maize," *International Journal of Molecular Sciences*, 23(2):795,pp. 1-21 (Jan. 2022).

Kantarek et al. "Identification of a novel, dominant dwarfing gene (Ddw4) and its effect on morphological traits of rye." *PLoS One* 13(6), e0199335, pp. 1-10, (Jun. 2018).

Plaza-Wüthrich et al., "Gibberellin Deficiency Confers Both Lodging and Drought Tolerance in Small Cereals," *Frontiers in Plant Science*, 7(643), pp. 1-14, (May 2016).

Wang et al., "Simultaneous editing of three homoeoalleles in hexaploid bread wheat confers heritable resistance to powdery mildew," *Nature biotechnology*, 32(9), pp. 947-951, (Sep. 2014).

Wu et al., "A gibberellin—deficient maize mutant exhibits altered plant height, stem strength and drought tolerance," *Plant Cell Rep*, 42, pp. 16867-1699 (Jul. 2023).

Xing et al., "A CRISPR/Cas9 toolkit for multiplex genome editing in plants," *BMC Plant Biology*, 14(327), pp. 1-12, (Dec. 2014).

Huang et al., "Divergence and adaptive evolution of the gibberellin oxidase genes in plants", *BMC Evolutionary Biology*, 15(207), pp. 1-15, (Sep. 2015).

\* cited by examiner

METHODS AND COMPOSITIONS FOR SHORT STATURE PLANTS THROUGH MANIPULATION OF GIBBERELLIN METABOLISM TO INCREASE HARVESTABLE YIELD

CROSS-REFERENCE TO RELATED APPLICATIONS

This application is a continuation of U.S. patent application Ser. No. 16/847,244, filed Apr. 13, 2020 (now U.S. Pat. No. 11,319,550), which is a continuation of U.S. patent application Ser. No. 15/679,699, filed Aug. 17, 2017 (now U.S. Pat. No. 10,724,047), which claims the benefit of U.S. Provisional Application No. 62/376,298, filed Aug. 17, 2016, U.S. Provisional Application No. 62/442,377, filed Jan. 4, 2017, and U.S. Provisional Application No. 62/502,313, filed May 5, 2017, all of which are incorporated by reference herein in their entireties.

INCORPORATION OF SEQUENCE LISTING

A sequence listing contained in the file named "P34494US08_SQ.txt" which is 293,557 bytes (measured in MS-Windows®) and was created on Apr. 4, 2022, is filed electronically herewith and incorporated by reference in its entirety.

BACKGROUND

Field

The present disclosure relates to compositions and methods for improving traits, such as lodging resistance and increased yield, in monocot or cereal plants including corn.

Related Art

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20$^{th}$ century, which was largely responsible for the Green Revolution. However, successful yield gains in other cereal crops, such as corn, have not been realized through manipulation of the GA pathway. Indeed, some mutations in the GA pathway genes have been associated with various off-types in corn that are incompatible with yield, which has led researchers away from finding semi-dwarf, high-yielding corn varieties via manipulation of the GA pathway.

There continues to be a need in the art for the development of monocot or cereal crop plants, such as corn, having increased yield and/or resistance to lodging.

SUMMARY

In a first aspect, the present disclosure provides a recombinant DNA construct comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a monocot or cereal plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30 or 33, and wherein the transcribable DNA sequence is operably linked to a plant-expressible promoter.

In a second aspect, the present disclosure provides a recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in a monocot or cereal plant or plant cell, the endogenous GA20 oxidase protein being at least 80%, at least 85%, at least 90%, at least 95%, at least 96%, at least 97%, at least 98%, at least 99%, at least 99.5%, or 100% identical to SEQ ID NO: 9, and wherein the transcribable DNA sequence is operably linked to a plant-expressible promoter.

In a third aspect, the present disclosure provides a recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in a monocot or cereal plant or plant cell, the endogenous GA20 oxidase protein being at least 80%, at least 85%, at least 90%, at least 95%, at least 96%, at least 97%, at least 98%, at least 99%, at least 99.5%, or 100% identical to SEQ ID NO: 15, and wherein the transcribable DNA sequence is operably linked to a plant-expressible promoter.

In a fourth aspect, the present disclosure provides a recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in a monocot or cereal plant or plant cell, the endogenous GA3 oxidase protein being at least 80%, at least 85%, at least 90%, at least 95%, at least 96%, at least 97%, at least 98%, at least 99%, at least 99.5%, or 100% identical to SEQ ID NO: 30 or 33, and wherein the transcribable DNA sequence is operably linked to a plant-expressible promoter.

In a fifth aspect, the present disclosure provides a recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in a monocot or cereal plant or plant cell, the endogenous GA20 oxidase protein being at least 80%, at least 85%, at least 90%, at least 95%, at least 96%, at least 97%, at least 98%, at least 99%, at least 99.5%, or 100% identical to SEQ ID NO: 12, and wherein the transcribable DNA sequence is operably linked to a plant-expressible promoter.

In a sixth aspect, the present disclosure provides a recombinant DNA construct comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous protein in a monocot or cereal plant or plant cell, the endogenous protein being at least 80%, at least 85%, at least 90%, at least 95%, at least 96%, at least 97%, at least 98%, at least 99%, at least 99.5%, or 100% identical to SEQ ID NO: 86, 90, 94, 97, 101, 104, 108, 112, 116, 118, 121, 125, 129, 133, or 136, and wherein the transcribable DNA sequence is operably linked to a plant-expressible promoter. In a further aspect, the present disclosure also provides a transformation vector comprising a recombinant DNA construct disclosed herein. In a further aspect, the present disclosure also provides a transgenic monocot or cereal plant, plant part or plant cell comprising a recombinant DNA construct disclosed here. In one aspect, a transgenic corn plant, plant part or plant cell is provided. In another aspect, a method is provided for producing a transgenic cereal plant, comprising: (a) transforming at least one cell of an explant with a recombinant DNA construct disclosed herein, and (b) regenerating or developing the transgenic cereal plant from the transformed explant. In another aspect, a cereal plant is transformed via *Agrobacterium* mediated transformation or particle bombardment.

In a seventh aspect, the present disclosure provides a method for lowering the level of at least one active GA molecule in the stem or stalk of a corn or cereal plant comprising: suppressing one or more GA3 oxidase or GA20 oxidase genes with a recombinant DNA construct in one or more tissues of the transgenic cereal or corn plant.

In an eighth aspect, the present disclosure provides a transgenic corn or cereal plant comprising a recombinant DNA construct, wherein the recombinant DNA construct comprises a transcribable DNA sequence encoding a non-coding RNA molecule that targets at least one endogenous GA20 or GA3 oxidase gene for suppression, the transcribable DNA sequence being operably linked to a plant-expressible promoter, and wherein the transgenic monocot or cereal plant has a shorter plant height relative to a wild-type control plant.

In a ninth aspect, the present disclosure provides a cereal plant comprising a mutation at or near an endogenous GA oxidase gene introduced by a mutagenesis technique, wherein the expression level of the endogenous GA oxidase gene is reduced or eliminated in the cereal plant, and wherein the cereal plant has a shorter plant height relative to a wild-type control plant.

In a tenth aspect, the present disclosure provides a corn or cereal plant comprising a genomic edit introduced via a targeted genome editing technique at or near the locus of an endogenous GA oxidase gene, wherein the expression level of the endogenous GA oxidase gene is reduced or eliminated relative to a control plant, and wherein the edited cereal plant has a shorter plant height relative to the control plant.

In an eleventh aspect, the present disclosure provides a composition comprising a guide RNA, wherein the guide RNA comprises a guide sequence that is at least 95%, at least 96%, at least 97%, at least 99%, or 100% identical or complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of an endogenous GA oxidase gene of a cereal plant. In one aspect, a composition further comprises an RNA-guided endonuclease.

In a twelfth aspect, the present disclosure provides a recombinant DNA construct comprising a transcribable DNA sequence encoding a non-coding guide RNA molecule, wherein the guide RNA molecule comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of an endogenous GA oxidase gene of a corn or cereal plant.

In a thirteenth aspect, the present disclosure provides a recombinant DNA donor template comprising at least one homology sequence, wherein the at least one homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of an endogenous GA oxidase gene of a corn or cereal plant.

In a fourteenth aspect, the present disclosure provides a recombinant DNA donor template comprising two homology arms including a first homology arm and a second homology arm, wherein the first homology arm comprises a sequence that is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a first flanking DNA sequence, wherein the second homology arm comprises a sequence that is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a second flanking DNA sequence, and wherein the first flanking DNA sequence and the second flanking DNA sequence are genomic sequences at or near the genomic locus of an endogenous GA oxidase gene of a corn or cereal plant. In one aspect, further provided is a DNA molecule or vector comprising a recombinant DNA donor template disclosed here. In another aspect, further provided is a bacterial or host cell comprising a recombinant DNA donor template disclosed here. In another aspect, further provided is corn or cereal plant, plant part or plant cell comprising the recombinant DNA construct disclosed here.

In a fifteenth aspect, the present disclosure provides an engineered site-specific nuclease that binds to a target site at or near the genomic locus of an endogenous GA oxidase gene of a corn or cereal plant and causes a double-strand break or nick at the target site.

In a sixteenth aspect, the present disclosure provides a recombinant DNA construct comprising a transgene encoding a site-specific nuclease, wherein the site-specific nuclease binds to a target site at or near the genomic locus of an endogenous GA oxidase gene of a monocot or cereal plant and causes a double-strand break or nick at the target site.

In a seventeenth aspect, the present disclosure provides a method for producing a transgenic corn or cereal plant, comprising: (a) transforming at least one cell of an explant with a recombinant DNA donor template disclosed here, and (b) regenerating or developing the transgenic corn or cereal plant from the transformed explant, wherein the transgenic corn or cereal plant comprises the insertion sequence of the recombinant DNA donor template.

In an eighteenth aspect, the present disclosure provides a method for producing a corn or cereal plant having a genomic edit at or near an endogenous GA oxidase gene, comprising: (a) introducing into at least one cell of an explant of the corn or cereal plant a site-specific nuclease or a recombinant DNA molecule comprising a transgene encoding the site-specific nuclease, wherein the site-specific nuclease binds to a target site at or near the genomic locus of the endogenous GA oxidase gene and causes a double-strand break or nick at the target site, and (b) regenerating or developing an edited corn or cereal plant from the at least one explant cell comprising the genomic edit at or near the endogenous GA oxidase gene of the edited monocot or cereal plant.

In a nineteenth aspect, the present disclosure provides a modified corn plant having a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and one or more of (i) an average stem or stalk diameter of greater than 18 mm, greater than 18.5 mm, greater than 19 mm, greater than 19.5 mm, greater than 20 mm, greater than 20.5 mm, greater than 21 mm, greater than 21.5 mm, or greater than 22 mm, (ii) improved lodging resistance relative to a wild type control plant, or (iii) improved drought tolerance relative to a wild type control plant.

In a twentieth aspect, the present disclosure provides a modified cereal plant having a reduced plant height relative to a wild type control plant, and (i) an increased stem or stalk diameter relative to a wild type control plant, (ii) improved lodging resistance relative to a wild type control plant, or (iii) improved drought tolerance relative to a wild type control plant.

DETAILED DESCRIPTION

Definitions

Figure 1:
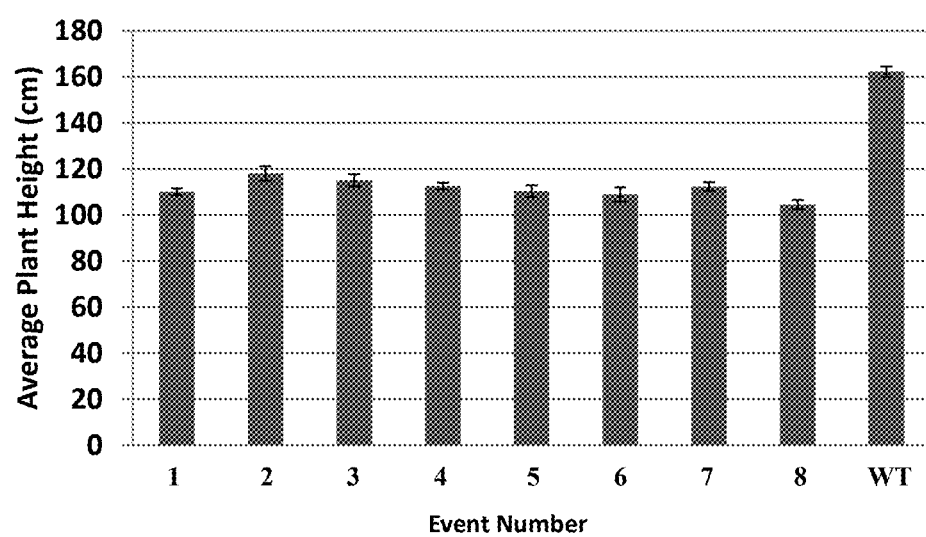
FIG. 1 shows reduced plant heights of corn inbred plants expressing a GA20 oxidase suppression construct across eight transformation events in comparison to inbred control plants.

To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

The term "cereal plant" as used herein refers a monocotyledonous (monocot) crop plant that is in the Poaceae or Gramineae family of grasses and is typically harvested for its seed, including, for example, wheat, corn, rice, millet, barley, sorghum, oat and rye.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" may also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

It is recognized that residue positions of proteins that are not identical often differ by conservative amino acid substitutions, where amino acid residues are substituted for other amino acid residues with similar size and chemical properties (e.g., charge, hydrophobicity, polarity, etc.), and therefore may not change the functional properties of the molecule. When sequences differ in conservative substitutions, the percent sequence similarity may be adjusted upwards to correct for the conservative nature of the non-identical substitution(s). Sequences that differ by such conservative substitutions are said to have "sequence similarity" or "similarity." Thus, "percent similarity" or "percent similar" as used herein in reference to two or more protein sequences is calculated by (i) comparing two optimally aligned protein sequences over a window of comparison, (ii) determining the number of positions at which the same or similar amino acid residue occurs in both sequences to yield the number of matched positions, (iii) dividing the number of matched positions by the total number of positions in the window of comparison (or the total length of the reference or query protein if a window of comparison is not specified), and then (iv) multiplying this quotient by 100% to yield the percent similarity. Conservative amino acid substitutions for proteins are known in the art.

For optimal alignment of sequences to calculate their percent identity or similarity, various pair-wise or multiple sequence alignment algorithms and programs are known in the art, such as ClustalW, or Basic Local Alignment Search Tool® (BLAST®), etc., that may be used to compare the sequence identity or similarity between two or more nucleotide or protein sequences. Although other alignment and comparison methods are known in the art, the alignment between two sequences (including the percent identity ranges described above) may be as determined by the ClustalW or BLAST® algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity may be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences may be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s).

The term "plant-expressible promoter" refers to a promoter that can initiate, assist, affect, cause, and/or promote the transcription and expression of its associated transcribable DNA sequence, coding sequence or gene in a plant cell or tissue.

The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature—e.g., the promoter or regulatory sequence has a different origin relative to the associated polynucleotide sequence and/or the promoter or regulatory sequence is not naturally occurring in a plant species to be transformed with the promoter or regulatory sequence.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., may comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., may also refer to a polynucleotide or protein molecule or sequence that has been genetically engineered and/or constructed outside of a cell. For example, a recombinant DNA molecule may comprise any engineered or man-made plasmid, vector, etc., and may include a linear or circular DNA molecule. Such plasmids, vectors, etc., may contain various maintenance elements including a prokaryotic origin of replication and selectable marker, as well as one or more transgenes or expression cassettes perhaps in addition to a plant selectable marker gene, etc.

As used herein, the term "isolated" refers to at least partially separating a molecule from other molecules typically associated with it in its natural state. In one embodiment, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

As used herein, an "encoding region" or "coding region" refers to a portion of a polynucleotide that encodes a functional unit or molecule (e.g., without being limiting, a mRNA, protein, or non-coding RNA sequence or molecule).

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more GA oxidase gene(s) relative to a wild-type or control plant, plant seed, plant part, plant cell, and/or plant genome, such as via (A) a transgenic event comprising a suppression construct or transcribable DNA sequence encoding a non-coding RNA that targets one or more GA3 and/or GA20 oxidase genes for suppression, or (B) a genome editing event or mutation affecting (e.g., reducing or eliminating) the expression level or activity of one or more endogenous GA3 and/or GA20 oxidase genes. Indeed, the term "modified" may further refer to a plant, plant seed, plant part, plant cell, and/or plant genome having one or more mutations affecting expression of one or more endogenous GA oxidase genes, such as one or more endogenous GA3 and/or GA20 oxidase genes, introduced through chemical mutagenesis, transposon insertion or excision, or any other known mutagenesis technique, or introduced through genome editing. For clarity, therefore, a modified plant, plant seed, plant part, plant cell, and/or plant genome includes a mutated, edited and/or transgenic plant, plant seed, plant part, plant cell, and/or plant genome having a modified expression level, expression pattern, and/or coding sequence of one or more GA oxidase gene(s) relative to a wild-type or control plant, plant seed, plant part, plant cell, and/or plant genome. Modified plants or seeds may contain various molecular changes that affect expression of GA oxidase gene(s), such as GA3 and/or GA20 oxidase gene(s), including genetic and/or epigenetic modifications. Modified plants, plant parts, seeds, etc., may have been subjected to mutagenesis, genome editing or site-directed integration (e.g., without being limiting, via methods using site-specific nucleases), genetic transformation (e.g., without being limiting, via methods of *Agrobacterium* transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more GA oxidase genes. A modified seed provided herein may give rise to a modified plant provided herein. A modified plant, plant seed, plant part, plant cell, or plant genome provided herein may comprise a recombinant DNA construct or vector or genome edit as provided herein. A "modified plant product" may be any product made from a modified plant, plant part, plant cell, or plant chromosome provided herein, or any portion or component thereof.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a transgenic and/or genome editing event(s) affecting one or more GA oxidase genes. For example, a control plant may be an inbred line that is the same as the inbred line used to make the modified plant, or a control plant may be the product of the same hybrid cross of inbred parental lines as the modified plant, except for the absence in the control plant of any transgenic or genome editing event(s) affecting one or more GA oxidase genes. For purposes of comparison to a modified plant, plant seed, plant part, plant cell and/or plant genome, a "wild-type plant" (or likewise a "wild-type" plant seed, plant part, plant cell and/or plant genome) refers to a non-transgenic and non-genome edited control plant, plant seed, plant part, plant cell and/or plant genome. As used herein, a "control" plant, plant seed, plant part, plant cell and/or plant genome may also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, a "target site" for genome editing refers to the location of a polynucleotide sequence within a plant genome that is bound and cleaved by a site-specific nuclease introducing a double stranded break (or single-stranded nick) into the nucleic acid backbone of the polynucleotide sequence and/or its complementary DNA strand. A target site may comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. A "target site" for a RNA-guided nuclease may comprise the sequence of either complementary strand of a double-stranded nucleic acid (DNA) molecule or chromosome at the target site. A site-specific nuclease may bind to a target site, such as via a non-coding guide RNA (e.g., without being limiting, a CRISPR RNA (crRNA) or a single-guide RNA (sgRNA) as described further below). A non-coding guide RNA provided herein may be complementary to a target site (e.g., complementary to either strand of a double-stranded nucleic acid molecule or chromosome at the target site). It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA may be tolerated. A "target site" also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some embodiments a target region may be subjected to a mutation, deletion, insertion or inversion. As used herein, "flanked" when used to describe a target region of a polynucleotide sequence or molecule, refers to two or more target sites of the polynucleotide sequence or molecule surrounding the target region, with one target site on each side of the target region. Apart from genome editing, the term "target site" may also be used in the context of gene suppression to refer to a portion of a mRNA molecule (e.g., a "recognition site") that is complementary to at least a portion of a non-coding RNA molecule (e.g., a miRNA, siRNA, etc.) encoded by a suppression construct.

As used herein, a "donor molecule", "donor template", or "donor template molecule" (collectively a "donor template"), which may be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" may be used for site-directed integration of a transgene or suppression construct, or as a template to introduce a mutation, such as an insertion, deletion, etc., into a target site within the genome of a plant. A targeted genome editing technique provided herein may comprise the use of one or more, two or more, three or more, four or more, or five or more donor molecules or templates. A "donor template" may be a single-stranded or double-stranded DNA or RNA molecule or plasmid. An "insertion sequence" of a donor template is a sequence designed for targeted insertion into the genome of a plant cell, which may be of any suitable length. For example, the insertion sequence of a donor template may be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length. A donor template may also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template.

An insertion sequence of a donor template may comprise one or more genes or sequences that each encode a transcribed non-coding RNA or mRNA sequence and/or a translated protein sequence. A transcribed sequence or gene of a donor template may encode a protein or a non-coding RNA molecule. An insertion sequence of a donor template may comprise a polynucleotide sequence that does not comprise a functional gene or an entire gene sequence (e.g., the donor template may simply comprise regulatory sequences, such as a promoter sequence, or only a portion of a gene or coding sequence), or may not contain any identifiable gene expression elements or any actively transcribed gene sequence. Further, the donor template may be linear or circular, and may be single-stranded or double-stranded. A donor template may be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively. An insertion sequence of a donor template provided herein may comprise a transcribable DNA sequence that may be transcribed into an RNA molecule, which may be non-coding and may or may not be operably linked to a promoter and/or other regulatory sequence.

According to some embodiments, a donor template may not comprise an insertion sequence, and instead comprise one or more homology sequences that include(s) one or more mutations, such as an insertion, deletion, substitution, etc., relative to the genomic sequence at a target site within the genome of a plant, such as at or near a GA3 oxidase or GA20 oxidase gene within the genome of a plant. Alternatively, a donor template may comprise an insertion sequence that does not comprise a coding or transcribable DNA sequence, wherein the insertion sequence is used to introduce one or more mutations into a target site within the genome of a plant, such as at or near a GA3 oxidase or GA20 oxidase gene within the genome of a plant.

A donor template provided herein may comprise at least one, at least two, at least three, at least four, at least five, at least six, at least seven, at least eight, at least nine, or at least ten genes or transcribable DNA sequences. Alternatively, a donor template may comprise no genes. Without being limiting, a gene or transcribable DNA sequence of a donor template may include, for example, an insecticidal resistance gene, an herbicide tolerance gene, a nitrogen use efficiency gene, a water use efficiency gene, a nutritional quality gene, a DNA binding gene, a selectable marker gene, an RNAi or suppression construct, a site-specific genome modification enzyme gene, a single guide RNA of a CRISPR/Cas9 system, a geminivirus-based expression cassette, or a plant viral expression vector system. According to other embodiments, an insertion sequence of a donor template may comprise a transcribable DNA sequence that encodes a non-coding RNA molecule, which may target a GA oxidase gene, such as a GA3 oxidase or GA20 oxidase gene, for suppression. A donor template may comprise a promoter, such as a tissue-specific or tissue-preferred promoter, a constitutive promoter, or an inducible promoter. A donor template may comprise a leader, enhancer, promoter, transcriptional start site, 5'-UTR, one or more exon(s), one or more intron(s), transcriptional termination site, region or sequence, 3'-UTR, and/or polyadenylation signal. The leader, enhancer, and/or promoter may be operably linked to a gene or transcribable DNA sequence encoding a non-coding RNA, a guide RNA, an mRNA and/or protein.

As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue(s) may comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters.

As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

As used herein, a "plant-expressible promoter" refers to a promoter that drives, causes or initiates expression of a transcribable DNA sequence or transgene operably linked to such promoter in one or more plant cells or tissues, such as one or more cells or tissues of a corn or cereal plant.

Description

Most grain producing grasses, such as wheat, rice and sorghum, produce both male and female structures within each floret of the panicle (i.e., they have a single reproductive structure). However, corn or maize is unique among the grain-producing grasses in that it forms separate male (tassel) and female (ear) inflorescences. Corn produces completely sexually dimorphic reproductive structures by selective abortion of male organs (anthers) in florets of the ear, and female organs (ovules) in the florets of the tassel within early stages of development. Precisely regulated gibberellin synthesis and signaling is critical to regulation of this selective abortion process, with the female reproductive ear being most sensitive to disruptions in the GA pathway. Indeed, the "anther ear" phenotype is the most common reproductive phenotype in GA corn mutants.

In contrast to corn, mutations in the gibberellin synthesis or signaling pathways that led to the "Green Revolution" in wheat, rice and sorghum had little impact on their reproductive structures because these crop species do not undergo the selective abortion process of the grain bearing panicle during development, and thus are not sensitive to disruptions in GA levels. The same mutations have not been utilized in corn because disruption of the GA synthesis and signaling pathway has repeatedly led to dramatic distortion and masculinization of the ear ("anther ear") and sterility (disrupted anther and microspore development) in the tassel, in addition to extreme dwarfing in some cases. See, e.g., Chen, Y. et al., "The Maize DWARF1 Encodes a Gibberellin 3-Oxidase and Is Dual Localized to the Nucleus and Cytosol," *Plant Physiology* 166: 2028-2039 (2014). These GA mutant phenotypes (off-types) in corn led to significant reductions in kernel production and a reduction in yield. Furthermore, production of anthers within the ear increases the likelihood of fungal or insect infections, which reduces the quality of the grain that is produced on those mutant ears. Forward breeding to develop semi-dwarf lines of corn has not been successful, and the reproductive off-types (as well as the extreme dwarfing) of GA mutants have been challenging to overcome. Thus, the same mutations in the GA pathway that led to the Green Revolution in other grasses have not yet been successful in corn.

Despite these prior difficulties in achieving higher grain yields in corn through manipulation of the GA pathway, the present inventors have discovered a way to manipulate GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants may also have one or more additional traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Without being bound by theory, it is proposed that incomplete suppression of GA20 or GA3 oxidase gene(s) and/or targeting of a subset of one or more GA oxidase gene(s) may be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, may be sufficient to produce a short-stature plant with increased lodging resistance, but without significant off-types in reproductive tissues. Expression of a GA20 or GA3 oxidase suppression element in a tissue-specific or tissue-preferred manner may be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) may be targeted for suppression using a vascular promoter, such as a rice tungro bacilliform virus (RTBV) promoter, that drives expression in vascular tissues of plants. As supported in the Examples below, the expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn or cereal plant that produce active GAs may reduce plant height and increase lodging resistance, and off-types may be avoided in those plants if active GA levels are not also significantly impacted or lowered in reproductive tissues, such as the developing female organ or ear of the plant. If active GA levels could be reduced in the stalk, stem, or internode(s) of corn or cereal plants without significantly affecting GA levels in reproductive tissues (e.g., the female or male reproductive organs or inflorescences), then corn or cereal plants having reduced plant height and increased lodging resistance could be created without off-types in the reproductive tissues of the plant.

Thus, recombinant DNA constructs and transgenic plants are provided herein comprising a GA20 or GA3 oxidase suppression element or sequence operably linked to a plant expressible promoter, which may be a tissue-specific or tissue-preferred promoter. Such a tissue-specific or tissue-preferred promoter may drive expression of its associated GA oxidase suppression element or sequence in one or more active GA-producing tissue(s) of the plant to suppress or reduce the level of active GAs produced in those tissue(s). Such a tissue-specific or tissue-preferred promoter may drive expression of its associated GA oxidase suppression construct or transgene during one or more vegetative stage(s) of development. Such a tissue-specific or tissue-preferred promoter may also have little or no expression in one or more cell(s) or tissue(s) of the developing female organ or ear of the plant to avoid the possibility of off-types in those reproductive tissues. According to some embodiments, the tissue-specific or tissue-preferred promoter is a vascular promoter, such as the RTBV promoter. The sequence of the RTBV promoter is provided herein as SEQ ID NO: 65, and a truncated version of the RTBV promoter is further provided herein as SEQ ID NO: 66.

Active or bioactive gibberellic acids (i.e., "active gibberellins" or "active GAs") are known in the art for a given plant species, as distinguished from inactive GAs. For example, active GAs in corn and higher plants include the following: GA1, GA3, GA4, and GA7. Thus, an "active GA-producing tissue" is a plant tissue that produces one or more active GAs.

In addition to suppressing GA20 oxidase genes in active GA-producing tissues of the plant with a vascular tissue promoter, it was surprisingly found that suppression of the same GA20 oxidase genes with various constitutive promoters could also cause the short, semi-dwarf stature phenotypes in corn, but without any visible off-types in the ear. Given that mutations in the GA pathway have previously been shown to cause off-types in reproductive tissues, it was surprising that constitutive suppression of GA20 oxidase did not cause similar reproductive phenotypes in the ear. Thus, it is further proposed that suppression of one or more GA20 oxidase genes could be carried out using a constitutive promoter to create a short stature, lodging-resistant corn or cereal plant without any significant or observable reproductive off-types in the plant. Other surprising observations were made when the same GA20 oxidase suppression construct was expressed in the stem, leaf or reproductive tissues. As described further below, targeted suppression of the same GA20 oxidase genes in the stem or ear tissues of corn plants did not cause the short stature, semi-dwarf phenotype. Moreover, directed expression of the GA20 oxidase suppression construct directly in reproductive tissues of the developing ear of corn plants with a female reproductive tissue (ear) promoter did not cause any significant or observable off-types in the ear. However, expression of the same GA20 oxidase suppression construct in leaf tissues was sufficient to cause a moderate short stature phenotype without significant or observable reproductive off-types in the plant.

Without being limited by theory, it is proposed that short stature, semi-dwarf phenotypes in corn and other cereal plants may result from a sufficient level of expression of a suppression construct targeting certain GA oxidase gene(s) in active GA-producing tissue(s) of the plant. At least for targeted suppression of certain GA20 oxidase genes in corn, restricting the pattern of expression to avoid reproductive ear tissues may not be necessary to avoid reproductive off-types in the developing ear. However, expression of the GA20 oxidase suppression construct at low levels, and/or in a limited number of plant tissues, may be insufficient to cause a significant short stature, semi-dwarf phenotype. Given that the observed semi-dwarf phenotype with targeted GA20 oxidase suppression is the result of shortening the stem internodes of the plant, it is surprising that suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), may be sufficient to produce semi-dwarf plants, even though the short stature trait is due to shortening of the stem internodes. Given that GAs can migrate through the vasculature of the plant, it is proposed that manipulating GA oxidase genes in plant tissue(s) where active GAs are produced may result in a short stature, semi-dwarf plant, even though this may be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues was found to cause a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. This semi-dwarf phenotype was also observed with expression of the same GA20 oxidase suppression construct using other vascular promoters.

According to embodiments of the present disclosure, modified cereal or corn plants are provided that have at least one beneficial agronomic trait and at least one female reproductive organ or ear that is substantially or completely free of off-types. The beneficial agronomic trait may include, for example, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. Off-types may include male (tassel or anther) sterility, reduced kernel or seed number, and/or the presence of one or more masculinized or male (or male-like) reproductive structures in the female organ or ear (e.g., anther ear) of the plant. A modified cereal or corn plant is provided herein that lacks significant off-types in the reproductive tissues of the plant. Such a modified cereal or corn plant may have a female reproductive organ or ear that appears normal relative to a control or wild-type plant. Indeed, modified cereal or corn plants are provided that comprise at least one reproductive organ or ear that does not have or exhibit, or is substantially or completely free of, off-types including male sterility, reduced kernel or seed number, and/or masculinized structure(s) in one or more female organs or ears. As used herein, a female organ or ear of a plant, such as corn, is "substantially free" of male reproductive structures if male reproductive structures are absent or nearly absent in the female organ or ear of the plant based on visual inspection of the female organ or ear at later reproductive stages. A female organ or ear of a plant, such as corn, is "completely free" of mature male reproductive structures if male reproductive structures are absent or not observed or observable in the female organ or ear of the plant, such as a corn plant, by visual inspection of the female organ or ear at later reproductive stages. A female organ or ear of a plant, such as corn, without significant off-types and substantially free of male reproductive structures in the ear may have a number of kernels or seeds per female organ or ear of the plant that is at least 90%, at least 95%, at least 96%, at least 97%, at least 98%, at least 99%, at least 99.5%, at least 99.6%, at least 99.7%, at least 99.8%, or at least 99.9% of the number of kernels or seeds per female organ or ear of a wild-type or control plant. Likewise, a female organ or ear of a plant, such as corn, without significant off-types and substantially free of male reproductive structures in the ear may have an average kernel or seed weight per female organ or ear of the plant that is at least 90%, at least 95%, at least 96%, at least 97%, at least 98%, at least 99%, at least 99.5%, at least 99.6%, at least 99.7%, at least 99.8%, or at least 99.9% of the average kernel or seed weight per female organ or ear of a wild-type or control plant. A female organ or ear of a plant, such as corn, that is completely free of mature male reproductive structures may have a number of kernels or seeds per female organ or ear of the plant that is about the same as a wild-type or control plant. In other words, the reproductive development of the female organ or ear of the plant may be normal or substantially normal. However, the number of seeds or kernels per female organ or ear may depend on other factors that affect resource utilization and development of the plant. Indeed, the number of kernels or seeds per female organ or ear of the plant, and/or the kernel or seed weight per female organ or ear of the plant, may be about the same or greater than a wild-type or control plant.

The plant hormone gibberellin plays an important role in a number of plant developmental processes including germination, cell elongation, flowering, embryogenesis and seed development. Certain biosynthetic enzymes (e.g., GA20 oxidase and GA3 oxidase) and catabolic enzymes (e.g., GA2 oxidase) in the GA pathway are critical to affecting active GA levels in plant tissues. Thus, in addition to suppression of certain GA20 oxidase genes, it is further proposed that suppression of a GA3 oxidase gene in a constitutive or tissue-specific or tissue-preferred manner may also produce corn plants having a short stature phenotype and increased lodging resistance, with possible increased yield, but without off-types in the ear. Thus, according to some embodiments, constructs and transgenes are provided comprising a GA3 oxidase suppression element or sequence operably linked to a constitutive or tissue-specific or tissue-preferred promoter, such as a vascular or leaf promoter. According to some embodiments, the tissue-specific or tissue-preferred promoter is a vascular promoter, such as the RTBV promoter. However, other types of tissue-specific or tissue preferred promoters may potentially be used for GA3 oxidase suppression in active GA-producing tissues of a corn or cereal plant to produce a semi-dwarf phenotype without significant off-types.

Any method known in the art for suppression of a target gene may be used to suppress GA oxidase gene(s) according to embodiments of the present invention including expression of antisense RNAs, double stranded RNAs (dsRNAs) or inverted repeat RNA sequences, or via co-suppression or RNA interference (RNAi) through expression of small interfering RNAs (siRNAs), short hairpin RNAs (shRNAs), trans-acting siRNAs (ta-siRNAs), or micro RNAs (miR-NAs). Furthermore, sense and/or antisense RNA molecules may be used that target the coding and/or non-coding genomic sequences or regions within or near a GA oxidase gene to cause silencing of the gene. Accordingly, any of these methods may be used for the targeted suppression of an endogenous GA20 oxidase(s) or GA3 oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

The term "suppression" as used herein, refers to a lowering, reduction or elimination of the expression level of a mRNA and/or protein encoded by a target gene in a plant, plant cell or plant tissue at one or more stage(s) of plant development, as compared to the expression level of such target mRNA and/or protein in a wild-type or control plant, cell or tissue at the same stage(s) of plant development. According to some embodiments, a modified or transgenic plant is provided having a GA20 oxidase gene expression level that is reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. According to some embodiments, a modified or transgenic plant is provided having a GA3 oxidase gene expression level that is reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. According to some embodiments, a modified or transgenic plant is provided having a GA20 oxidase gene expression level that is reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant. According to some embodiments, a modified or transgenic plant is provided having a GA3 oxidase gene expression level that is reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant. According to these embodiments, the at least one tissue of a modified or transgenic plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In some embodiments, suppression of an endogenous GA20 oxidase gene or a GA3 oxidase gene is tissue-specific (e.g., only in leaf and/or vascular tissue). Suppression of a GA20 oxidase gene may be constitutive and/or vascular or leaf tissue specific or preferred. In other embodiments, suppression of a GA20 oxidase gene or a GA3 oxidase gene is constitutive and not tissue-specific. According to some embodiments, expression of an endogenous GA20 oxidase gene and/or a GA3 oxidase gene is reduced in one or more tissue types (e.g., in leaf and/or vascular tissue(s)) of a modified or transgenic plant as compared to the same tissue(s) of a control plant.

According to embodiments of the present disclosure, a recombinant DNA molecule, construct or vector is provided comprising a suppression element targeting GA20 oxidase or GA3 oxidase gene(s) that is operably linked to a plant-expressible constitutive or tissue-specific or tissue-preferred promoter. The suppression element may comprise a transcribable DNA sequence of at least 19 nucleotides in length, such as from about 19 nucleotides in length to about 27 nucleotides in length, or 19, 20, 21, 22, 23, 24, 25, 26, or 27 nucleotides in length, wherein the transcribable DNA sequence corresponds to at least a portion of the target GA oxidase gene to be suppressed, and/or to a DNA sequence complementary thereto. The suppression element may be 19-30, 19-50, 19-100, 19-200, 19-300, 19-500, 19-1000, 19-1500, 19-2000, 19-3000, 19-4000, or 19-5000 nucleotides in length. The suppression element may be at least 19, at least 20, at least 21, at least 22, or at least 23 nucleotides or more in length (e.g., at least 25, at least 30, at least 50, at least 100, at least 200, at least 300, at least 500, at least 1000, at least 1500, at least 2000, at least 3000, at least 4000, or at least 5000 nucleotides in length). Depending on the length and sequence of a suppression element, one or more sequence mismatches or non-complementary bases, such as 1, 2, 3, 4, 5, 6, 7, 8 or more mismatches, may be tolerated without a loss of suppression if the non-coding RNA molecule encoded by the suppression element is still able to sufficiently hybridize and bind to the target mRNA molecule of the GA20 oxidase or GA3 oxidase gene(s). Indeed, even shorter RNAi suppression elements ranging from about 19 nucleotides to about 27 nucleotides in length may have one or more mismatches or non-complementary bases, yet still be effective at suppressing a target GA oxidase gene. Accordingly, a sense or anti-sense suppression element sequence may be at least 80%, at least 85%, at least 90%, at least 95%, at least 96%, at least 97%, at least 98%, at least 99%, at least 99.5% or 100% identical to a corresponding sequence of at least a segment or portion of the targeted GA oxidase gene, or its complementary sequence, respectively.

A suppression element or transcribable DNA sequence of the present invention for targeted suppression of GA oxidase gene(s) may include one or more of the following: (a) a DNA sequence that includes at least one anti-sense DNA sequence that is anti-sense or complementary to at least one segment or portion of the targeted GA oxidase gene; (b) a DNA sequence that includes multiple copies of at least one anti-sense DNA sequence that is anti-sense or complementary to at least one segment or portion of the targeted GA oxidase gene; (c) a DNA sequence that includes at least one sense DNA sequence that comprises at least one segment or portion of the targeted GA oxidase gene; (d) a DNA sequence that includes multiple copies of at least one sense DNA sequence that each comprise at least one segment or portion of the targeted GA oxidase gene; (e) a DNA sequence that includes an inverted repeat of a segment or portion of a targeted GA oxidase gene and/or transcribes into RNA for suppressing the targeted GA oxidase gene by forming double-stranded RNA, wherein the transcribed RNA includes at least one anti-sense DNA sequence that is anti-sense or complementary to at least one segment or portion of the targeted GA oxidase gene and at least one sense DNA sequence that comprises at least one segment or portion of the targeted GA oxidase gene; (f) a DNA sequence that is transcribed into RNA for suppressing the targeted GA oxidase gene by forming a single double-stranded RNA and includes multiple serial anti-sense DNA sequences that are each anti-sense or complementary to at least one segment or portion of the targeted GA oxidase gene and multiple serial sense DNA sequences that each comprise at least one segment or portion of the targeted GA oxidase gene; (g) a DNA sequence that is transcribed into RNA for suppressing the targeted GA oxidase gene by forming multiple double strands of RNA and includes multiple anti-sense DNA sequences that are each anti-sense or complementary to at least one segment or portion of the targeted GA oxidase gene and multiple sense DNA sequences that each comprise at least one segment or portion of the targeted GA oxidase gene, wherein the multiple anti-sense DNA segments and multiple sense DNA segments are arranged in a series of inverted repeats; (h) a DNA sequence that includes nucleotides derived from a miRNA, preferably a plant miRNA; (i) a DNA sequence that includes a miRNA precursor that encodes an artificial miRNA complementary to at least one segment or portion of the targeted GA oxidase gene; (j) a DNA sequence that includes nucleotides of a siRNA; (k) a DNA sequence that is transcribed into an RNA aptamer capable of binding to a ligand; and (l) a DNA sequence that is transcribed into an RNA aptamer capable of binding to a ligand and DNA that transcribes into a regulatory RNA capable of regulating expression of the targeted GA oxidase gene, wherein the regulation of the targeted GA oxidase gene is dependent on the conformation of the regulatory RNA, and the conformation of the regulatory RNA is allosterically affected by the binding state of the RNA aptamer by the ligand. Any of these gene suppression elements, whether transcribed into a single stranded or double-stranded RNA, may be designed to suppress more than one GA oxidase target gene, depending on the number and sequence of the suppression element(s).

Multiple sense and/or anti-sense suppression elements for more than one GA oxidase target may be arranged serially in tandem or arranged in tandem segments or repeats, such as tandem inverted repeats, which may also be interrupted by one or more spacer sequence(s), and the sequence of each suppression element may target one or more GA oxidase gene(s). Furthermore, the sense or anti-sense sequence of the suppression element may not be perfectly matched or complementary to the targeted GA oxidase gene sequence, depending on the sequence and length of the suppression element. Even shorter RNAi suppression elements from about 19 nucleotides to about 27 nucleotides in length may have one or more mismatches or non-complementary bases, yet still be effective at suppressing the target GA oxidase gene. Accordingly, a sense or anti-sense suppression element sequence may be at least 80%, at least 85%, at least 90%, at least 95%, at least 96%, at least 97%, at least 98%, at least 99%, at least 99.5% or 100% identical to a corresponding sequence of at least a segment or portion of the targeted GA oxidase gene, or its complementary sequence, respectively.

For anti-sense suppression, the transcribable DNA sequence or suppression element comprises a sequence that is anti-sense or complementary to at least a portion or segment of the targeted GA oxidase gene. The suppression element may comprise multiple anti-sense sequences that are complementary to one or more portions or segments of the targeted GA oxidase gene(s), or multiple copies of an anti-sense sequence that is complementary to a targeted GA oxidase gene. The anti-sense suppression element sequence may be at least 80%, at least 85%, at least 90%, at least 95%, at least 96%, at least 97%, at least 98%, at least 99%, at least 99.5% or 100% identical to a DNA sequence that is complementary to at least a segment or portion of the targeted GA oxidase gene. In other words, the anti-sense suppression element sequence may be at least 80%, at least 85%, at least 90%, at least 95%, at least 96%, at least 97%, at least 98%, at least 99%, at least 99.5% or 100% complementary to the targeted GA oxidase gene.

For suppression of GA oxidase gene(s) using an inverted repeat or a transcribed dsRNA, a transcribable DNA sequence or suppression element may comprise a sense sequence that comprises a segment or portion of a targeted GA oxidase gene and an anti-sense sequence that is complementary to a segment or portion of the targeted GA oxidase gene, wherein the sense and anti-sense DNA sequences are arranged in tandem. The sense and/or anti-sense sequences, respectively, may each be less than 100% identical or complementary to a segment or portion of the targeted GA oxidase gene as described above. The sense and anti-sense sequences may be separated by a spacer sequence, such that the RNA molecule transcribed from the suppression element forms a stem, loop or stem-loop structure between the sense and anti-sense sequences. The suppression element may instead comprise multiple sense and anti-sense sequences that are arranged in tandem, which may also be separated by one or more spacer sequences. Such suppression elements comprising multiple sense and anti-sense sequences may be arranged as a series of sense sequences followed by a series of anti-sense sequences, or as a series of tandemly arranged sense and anti-sense sequences. Alternatively, one or more sense DNA sequences may be expressed separately from the one or more anti-sense sequences (i.e., one or more sense DNA sequences may be expressed from a first transcribable DNA sequence, and one or more anti-sense DNA sequences may be expressed from a second transcribable DNA sequence, wherein the first and second transcribable DNA sequences are expressed as separate transcripts).

For suppression of GA oxidase gene(s) using a microRNA (miRNA), the transcribable DNA sequence or suppression element may comprise a DNA sequence derived from a miRNA sequence native to a virus or eukaryote, such as an animal or plant, or modified or derived from such a native miRNA sequence. Such native or native-derived miRNA sequences may form a fold back structure and serve as a scaffold for the precursor miRNA (pre-miRNA), and may correspond to the stem region of a native miRNA precursor sequence, such as from a native (or native-derived) primary-miRNA (pri-miRNA) or pre-miRNA sequence. However, in addition to these native or native-derived miRNA scaffold or preprocessed sequences, engineered or synthetic miRNAs of the present embodiments further comprise a sequence corresponding to a segment or portion of the targeted GA oxidase gene(s). Thus, in addition to the pre-processed or scaffold miRNA sequences, the suppression element may further comprise a sense and/or anti-sense sequence that corresponds to a segment or portion of a targeted GA oxidase gene, and/or a sequence that is complementary thereto, although one or more sequence mismatches may be tolerated.

Engineered miRNAs are useful for targeted gene suppression with increased specificity. See, e.g., Parizotto et al., *Genes Dev.* 18:2237-2242 (2004), and U.S. Patent Application Publication Nos. 2004/0053411, 2004/0268441, 2005/0144669, and 2005/0037988, the contents and disclosures of which are incorporated herein by reference. miRNAs are non-protein coding RNAs. When a miRNA precursor molecule is cleaved, a mature miRNA is formed that is typically from about 19 to about 25 nucleotides in length (commonly from about 20 to about 24 nucleotides in length in plants), such as 19, 20, 21, 22, 23, 24, or 25 nucleotides in length, and has a sequence corresponding to the gene targeted for suppression and/or its complement. The mature miRNA hybridizes to target mRNA transcripts and guides the binding of a complex of proteins to the target transcripts, which may function to inhibit translation and/or result in degradation of the transcript, thus negatively regulating or suppressing expression of the targeted gene. miRNA precursors are also useful in plants for directing in-phase production of siRNAs, trans-acting siRNAs (ta-siRNAs), in a process that requires a RNA-dependent RNA polymerase to cause suppression of a target gene. See, e.g., Allen et al., *Cell* 121:207-221 (2005), Vaucheret *Science STKE,* 2005:pe43

(2005), and Yoshikawa et al. *Genes Dev.*, 19:2164-2175 (2005), the contents and disclosures of which are incorporated herein by reference.

Plant miRNAs regulate their target genes by recognizing and binding to a complementary or near-perfectly complementary sequence (miRNA recognition site) in the target mRNA transcript, followed by cleavage of the transcript by RNase III enzymes, such as ARGONAUTE1. In plants, certain mismatches between a given miRNA recognition site and the corresponding mature miRNA are typically not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) Nature Genetics, 39:1033-1037; and Axtell et al. (2006) Cell, 127:565-577.

Many microRNA genes (MIR genes) have been identified and made publicly available in a database ("miRBase", available on line at microrna.sanger.ac.uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). For a review of miRNA biogenesis, see Kim (2005) Nature Rev. Mol. Cell. Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (foldback structures containing a stem-loop arrangement that is processed to the mature miRNA) as well as the usual 5' "cap" and polyadenylated tail of an mRNA. See, for example, FIG. 1 in Kim (2005) Nature Rev. Mol. Cell. Biol., 6:376-385.

Transgenic expression of miRNAs (whether a naturally occurring sequence or an artificial sequence) can be employed to regulate expression of the miRNA's target gene or genes. Recognition sites of miRNAs have been validated in all regions of a mRNA, including the 5' untranslated region, coding region, intron region, and 3' untranslated region, indicating that the position of the miRNA target or recognition site relative to the coding sequence may not necessarily affect suppression (see, e.g., Jones-Rhoades and Bartel (2004). Mol. Cell, 14:787-799, Rhoades et al. (2002) Cell, 110:513-520, Allen et al. (2004) Nat. Genet., 36:1282-1290, Sunkar and Zhu (2004) Plant Cell, 16:2001-2019). miRNAs are important regulatory elements in eukaryotes, and transgenic suppression with miRNAs is a useful tool for manipulating biological pathways and responses. A description of native miRNAs, their precursors, recognition sites, and promoters is provided in U.S. Patent Application Publication No. 2006/0200878, the contents and disclosures of which are incorporated herein by reference.

Designing an artificial miRNA sequence can be achieved by substituting nucleotides in the stem region of a miRNA precursor with a sequence that is complementary to the intended target, as demonstrated, for example, by Zeng et al. (2002) Mol. Cell, 9:1327-1333. According to many embodiments, the target may be a sequence of a GA20 oxidase gene or a GA3 oxidase gene. One non-limiting example of a general method for determining nucleotide changes in a native miRNA sequence to produce an engineered miRNA precursor for a target of interest includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402); cDNA and/or genomic DNA sequences may be used to identify target transcript orthologues and any potential matches to unrelated genes, thereby avoiding unintentional silencing or suppression of non-target sequences; (b) Analyzing the target gene for undesirable sequences (e.g., matches to sequences from non-target species), and score each potential target sequence for GC content, Reynolds score (see Reynolds et al. (2004) Nature Biotechnol., 22:326-330), and functional asymmetry characterized by a negative difference in free energy ("ΔΔG") (see Khvorova et al. (2003) Cell, 115:209-216). Preferably, target sequences (e.g., 19-mers) may be selected that have all or most of the following characteristics: (1) a Reynolds score >4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. In one aspect, a non-coding RNA molecule used herein to suppress a target gene (e.g., a GA20 or GA3 oxidase gene) is designed to have a target sequence exhibiting one or more, two or more, three or more, four or more, or five or more of the foregoing characteristics. Positions at every third nucleotide of a suppression element may be important in influencing RNAi efficacy; for example, an algorithm, "siExplorer" is publicly available at rna.chem.t.u-tokyo.ac.jp/siexplorer.htm (see Katoh and Suzuki (2007) Nucleic Acids Res., 10.1093/nar/gkl1120); (c) Determining a reverse complement of the selected target sequence (e.g., 19-mer) to use in making a modified mature miRNA. Relative to a 19-mer sequence, an additional nucleotide at position 20 may be matched to the selected target or recognition sequence, and the nucleotide at position 21 may be chosen to either be unpaired to prevent spreading of silencing on the target transcript or paired to the target sequence to promote spreading of silencing on the target transcript; and (d) Transforming the artificial miRNA into a plant.

According to embodiments of the present disclosure, a recombinant DNA molecule, construct or vector is provided comprising a transcribable DNA sequence or suppression element encoding a miRNA or precursor miRNA molecule for targeted suppression of a GA oxidase gene(s). Such a transcribable DNA sequence and suppression element may comprise a sequence of at least 19 nucleotides in length that corresponds to one or more GA oxidase gene(s) and/or a sequence complementary to one or more GA oxidase gene(s), although one or more sequence mismatches or non-base-paired nucleotides may be tolerated.

GA oxidase gene(s) may also be suppressed using one or more small interfering RNAs (siRNAs). The siRNA pathway involves the non-phased cleavage of a longer double-stranded RNA intermediate ("RNA duplex") into small interfering RNAs (siRNAs). The size or length of siRNAs ranges from about 19 to about 25 nucleotides or base pairs, but common classes of siRNAs include those containing 21 or 24 base pairs. Thus, a transcribable DNA sequence or suppression element may encode a RNA molecule that is at least about 19 to about 25 nucleotides (or more) in length, such as at least 19, 20, 21, 22, 23, 24, or 25 nucleotides in length. For siRNA suppression, a recombinant DNA molecule, construct or vector is thus provided comprising a transcribable DNA sequence and suppression element encoding a siRNA molecule for targeted suppression of a GA oxidase gene(s). Such a transcribable DNA sequence and suppression element may be at least 19 nucleotides in length and have a sequence corresponding to one or more GA oxidase gene(s), and/or a sequence complementary to one or more GA oxidase gene(s).

GA oxidase gene(s) may also be suppressed using one or more trans-acting small interfering RNAs (ta-siRNAs). In the to-siRNA pathway, miRNAs serve to guide in-phase processing of siRNA primary transcripts in a process that requires an RNA-dependent RNA polymerase for production of a double-stranded RNA precursor. ta-siRNAs are defined by lack of secondary structure, a miRNA target site that initiates production of double-stranded RNA, requirements of DCL4 and an RNA-dependent RNA polymerase (RDR6), and production of multiple perfectly phased ~21-nt small RNAs with perfectly matched duplexes with 2-nucleotide 3' overhangs (see Allen et al. (2005) Cell, 121:207-221). The size or length of ta-siRNAs ranges from about 20 to about 22 nucleotides or base pairs, but are mostly commonly 21 base pairs. Thus, a transcribable DNA sequence or suppression element of the present invention may encode a RNA molecule that is at least about 20 to about 22 nucleotides in length, such as 20, 21, or 22 nucleotides in length. For ta-siRNA suppression, a recombinant DNA molecule, construct or vector is thus provided comprising a transcribable DNA sequence or suppression element encoding a ta-siRNA molecule for targeted suppression of a GA oxidase gene(s). Such a transcribable DNA sequence and suppression element may be at least 20 nucleotides in length and have a sequence corresponding to one or more GA oxidase gene(s) and/or a sequence complementary to one or more GA oxidase gene(s). For methods of constructing suitable ta-siRNA scaffolds, see, e.g., U.S. Pat. No. 9,309,512, which is incorporated herein by reference in its entirety.

According to embodiments of the present invention, a recombinant DNA molecule, vector or construct is provided comprising a transcribable DNA sequence encoding a non-coding RNA molecule that binds or hybridizes to a target mRNA in a plant cell, wherein the target mRNA molecule encodes a GA20 or GA3 oxidase gene, and wherein the transcribable DNA sequence is operably linked to a constitutive or tissue-specific or tissue-preferred promoter. In addition to targeting a mature mRNA sequence, a non-coding RNA molecule may instead target an intronic sequence of a GA oxidase gene or mRNA transcript, or a GA oxidase mRNA sequence overlapping coding and non-coding sequences. According to other embodiments, a recombinant DNA molecule, vector or construct is provided comprising a transcribable DNA sequence encoding a non-coding RNA (precursor) molecule that is cleaved or processed into a mature non-coding RNA molecule that binds or hybridizes to a target mRNA in a plant cell, wherein the target mRNA molecule encodes a GA20 or GA3 oxidase protein, and wherein the transcribable DNA sequence is operably linked to a constitutive or tissue-specific or tissue-preferred promoter. For purposes of the present disclosure, a "non-coding RNA molecule" is a RNA molecule that does not encode a protein. Non-limiting examples of a non-coding RNA molecule include a microRNA (miRNA), a miRNA precursor, a small interfering RNA (siRNA), a siRNA precursor, a small RNA (18-26 nt in length) and precursors encoding the same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA).

According to embodiments of the present disclosure, suitable tissue-specific or tissue preferred promoters for expression of a GA20 oxidase or GA3 oxidase suppression element may include those promoters that drive or cause expression of its associated suppression element or sequence at least in the vascular and/or leaf tissue(s) of a corn or cereal plant, or possibly other tissues in the case of GA3 oxidase. Expression of the GA oxidase suppression element or construct with a tissue-specific or tissue-preferred promoter may also occur in other tissues of the cereal or corn plant outside of the vascular and leaf tissues, but active GA levels in the developing reproductive tissues of the plant (particularly in the female reproductive organ or ear) are preferably not significantly reduced or impacted (relative to wild type or control plants), such that development of the female organ or ear may proceed normally in the transgenic plant without off-types in the ear and a loss in yield potential.

Any vascular promoters known in the art may potentially be used as the tissue-specific or tissue-preferred promoter. Examples of vascular promoters include the RTBV promoter (see, e.g., SEQ ID NO: 65), a known sucrose synthase gene promoter, such as a corn sucrose synthase-1 (Sus1 or Sh1) promoter (see, e.g., SEQ ID NO: 67), a corn Sh1 gene paralog promoter, a barley sucrose synthase promoter (Ss1) promoter, a rice sucrose synthase-1 (RSs1) promoter (see, e.g., SEQ ID NO: 68), or a rice sucrose synthase-2 (RSs2) promoter (see, e.g., SEQ ID NO: 69), a known sucrose transporter gene promoter, such as a rice sucrose transporter promoter (SUT1) (see, e.g., SEQ ID NO: 70), or various known viral promoters, such as a *Commelina* yellow mottle virus (CoYMV) promoter, a wheat dwarf geminivirus (WDV) large intergenic region (LIR) promoter, a maize streak geminivirus (MSV) coat protein (CP) promoter, or a rice yellow stripe 1 (YS1)-like or OsYSL2 promoter (SEQ ID NO: 71), and any functional sequence portion or truncation of any of the foregoing promoters with a similar pattern of expression, such as a truncated RTBV promoter (see, e.g., SEQ ID NO: 66).

Any leaf promoters known in the art may potentially be used as the tissue-specific or tissue-preferred promoter. Examples of leaf promoters include a corn pyruvate phosphate dikinase or PPDK promoter (see, e.g., SEQ ID NO: 72), a corn fructose 1,6 bisphosphate aldolase or FDA promoter (see, e.g., SEQ ID NO: 73), and a rice Nadh-Gogat promoter (see, e.g., SEQ ID NO: 74), and any functional sequence portion or truncation of any of the foregoing promoters with a similar pattern of expression. Other examples of leaf promoters from monocot plant genes include a ribulose biphosphate carboxylase (RuBisCO) or RuBisCO small subunit (RBCS) promoter, a chlorophyll a/b binding protein gene promoter, a phosphoenolpyruvate carboxylase (PEPC) promoter, and a Myb gene promoter, and any functional sequence portion or truncation of any of these promoters with a similar pattern of expression.

Any other vascular and/or leaf promoters known in the art may also be used, including promoter sequences from related genes (e.g., sucrose synthase, sucrose transporter, and viral gene promoter sequences) from the same or different plant species or virus that have a similar pattern of expression. Further provided are promoter sequences with a high degree of homology to any of the foregoing. For example, a vascular promoter may comprise a DNA sequence that is at least at least 70%, at least 80%, at least 85%, at least 90%, at least 95%, at least 96%, at least 97%, at least 98%, at least 99%, at least 99.5% or 100% identical to one or more of SEQ ID NOs: 65, 66, 67, 68, 69, 70, and 71, any functional sequence portion or truncation thereof, and/or any sequence complementary to any of the foregoing sequences; a leaf promoter may comprise, for example, a DNA sequence that is at least at least 70%, at least 80%, at least 85%, at least 90%, at least 95%, at least 96%, at least 97%, at least 98%, at least 99%, at least 99.5% or 100% identical to one or more of SEQ ID NOs: 72, 73, and 74, any functional sequence portion or truncation thereof, and/or any sequence complementary to any of the foregoing sequences; and a constitutive promoter may comprise a DNA sequence that is at least at least 70%, at least 80%, at least 85%, at least 90%, at least 95%, at least 96%, at least 97%, at least 98%, at least 99%, at least 99.5% or 100% identical to one or more of SEQ ID NOs: 75, 76, 77, 78, 79, 80, 81, 82, and 83, any functional sequence portion or truncation thereof, and/or any sequence complementary to any of the foregoing sequences. Examples of vascular and/or leaf promoters may further include other known, engineered and/or later-identified promoter sequences shown to have a pattern of expression in vascular and/or leaf tissue(s) of a cereal or corn plant. Furthermore, any known or later-identified constitutive promoter may also be used for expression of a GA20 oxidase or GA3 oxidase suppression element. Common examples of constitutive promoters are provided below.

As understood in the art, the term "promoter" may generally refer to a DNA sequence that contains an RNA polymerase binding site, transcription start site, and/or TATA box and assists or promotes the transcription and expression of an associated transcribable polynucleotide sequence and/or gene (or transgene). A promoter may be synthetic or artificial and/or engineered, varied or derived from a known or naturally occurring promoter sequence. A promoter may be a chimeric promoter comprising a combination of two or more heterologous sequences. A promoter of the present invention may thus include variants of promoter sequences that are similar in composition, but not identical to, other promoter sequence(s) known or provided herein. A promoter may be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or nearly all tissues of the plant are referred to as "constitutive" promoters. However, the expression level with a "constitutive promoter" is not necessarily uniform across different tissue types and cells. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential or predominant expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A tissue-specific or tissue-preferred promoter may also be defined in terms of the specific or preferred tissue(s) in which it drives expression of its associated transcribable DNA sequence or suppression element. For example, a promoter that causes specific expression in vascular tissues may be referred to as a "vascular-specific promoter", whereas a promoter that causes preferential or predominant expression in vascular tissues may be referred to as a "vascular-preferred promoter". Likewise, a promoter that causes specific expression in leaf tissues may be referred to as a "leaf-specific promoter", whereas a promoter that causes preferential or predominant expression in leaf tissues may be referred to as a "leaf-preferred promoter". An "inducible" promoter is a promoter that initiates transcription in response to an environmental stimulus such as cold, drought or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed, as defined above.

Several of the GA oxidases in cereal plants consist of a family of related GA oxidase genes. For example, corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1, and the DNA and protein sequences by SEQ ID NOs for each of these GA3 oxidase genes are provided in Table 2.

TABLE 1

DNA and protein sequences by sequence identifier for GA20 oxidase genes in corn.

| GA20 oxidase Gene | cDNA | Coding Sequence (CDS) | Protein |
|---|---|---|---|
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
|---|---|---|---|
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |

The genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

The genomic DNA sequence of GA3 oxidase_1 is provided in SEQ ID NO: 36, and the genomic DNA sequence of GA3 oxidase_2 is provided in SEQ ID NO: 37. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon; nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. For the GA3 oxidase_2 gene, nucleotides 1-38 of SEQ ID NO: 37 correspond to the 5-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR.

In addition to phenotypic observations with targeting the GA20 oxidase_3 and/or GA20 oxidase_5 gene(s), or the GA3 oxidase_1 and/or GA3 oxidase_2 gene(s), for suppression, a semi-dwarf phenotype is also observed with suppression of the GA20 oxidase_4 gene. The genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

According to embodiments of the present disclosure, a recombinant DNA molecule, vector or construct is provided comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least a segment or portion of a mRNA molecule (i) expressed from an endogenous GA oxidase gene and/or (ii) encoding an endogenous GA oxidase protein in the plant, wherein the transcribable DNA sequence is operably linked to a plant-expressible promoter, and wherein the plant is a cereal or corn plant.

According to some embodiments, a non-coding RNA molecule targets GA20 oxidase gene(s), such as GA20 oxidase_3 and/or GA20 oxidase_5 gene(s), for suppression and comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 7, 8, 13 and 14. According to some embodiments, a non-coding RNA molecule is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to one or both of SEQ ID NOs: 9 and 15. According to further embodiments, a non-coding RNA molecule may comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% similar to one or both of SEQ ID NOs: 9 and 15. In addition to targeting a mature mRNA sequence (including either or both of the untranslated or exonic sequences), a non-coding RNA molecule may further target the intronic sequences of a GA20 oxidase gene or transcript.

According to some embodiments, a non-coding RNA molecule targets GA3 oxidase gene(s) for suppression and comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31 and 32. According to other embodiments, a non-coding RNA molecule is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to one or both of SEQ ID NOs: 30 and 33. According to further embodiments, a non-coding RNA molecule may comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% similar to one or both of SEQ ID NOs: 30 and 33. In addition to targeting a mature mRNA sequence (including either or both of the untranslated or exonic sequences), a non-coding RNA molecule may further target the intronic sequences of a GA3 oxidase gene or transcript.

According to some embodiments, a non-coding RNA molecule targets GA20 oxidase_4 gene for suppression and comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or both of SEQ ID NOs: 10 and 11. According to other embodiments, a non-coding RNA molecule is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to one or both of SEQ ID NO: 12. According to further embodiments, a non-coding RNA molecule may comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% similar to SEQ ID NOs: 12. In addition to targeting a mature mRNA sequence (including either or both of the untranslated or exonic sequences), a non-coding RNA molecule may further target the intronic sequences of a GA20 oxidase gene or transcript.

According to many embodiments, the non-coding RNA molecule encoded by the transcribable DNA sequence of the recombinant DNA molecule, vector or construct may be a precursor miRNA or siRNA that is processed or cleaved in a plant cell to form a mature miRNA or siRNA that targets a GA20 oxidase or GA3 oxidase gene.

According to embodiments of the present invention, GA levels may be reduced in the stalk or stem of a cereal or corn plant by targeting only a limited subset of genes within a GA oxidase family for suppression. Without being bound by theory, it is proposed that targeting of a limited number of genes within a GA oxidase family for suppression may produce the short stature phenotype and resistance to lodging in transgenic plants, but without off-types in the reproductive or ear tissues of the plant due to differential expression among GA oxidase genes, sufficient compensation for the suppressed GA oxidase gene(s) by other GA oxidase gene(s) in those reproductive tissues, and/or incomplete suppression of the targeted GA oxidase gene(s). Thus, not only may off-types be avoided by limiting expression or suppression of GA oxidase gene(s) with a tissue-specific or tissue preferred promoter, it is proposed that a limited subset of GA oxidase genes (e.g., a limited number of GA20 oxidase genes) may be targeted for suppression, such that the other GA oxidase genes within the same gene family (e.g., other GA20 oxidase genes) may compensate for loss of expression of the suppressed GA oxidase gene(s) in those tissues. Incomplete suppression of the targeted GA oxidase gene(s) may also allow for a sufficient level of expression of the targeted GA oxidase gene(s) in one or more tissues to avoid off-types or undesirable traits in the plant that would negatively affect crop yield, such as reproductive off-types or excessive shortening of plant height. Unlike complete loss-of-function mutations in a gene, suppression may allow for partial activity of the targeted gene to persist. Since the different GA20 oxidase genes have different patterns of expression in plants, targeting of a limited subset of GA20 oxidase genes for suppression may allow for modification of certain traits while avoiding off-types previously associated with GA mutants in cereal plants. In other words, the growth, developmental and reproductive traits or off-types previously associated with GA mutants in corn and other cereal crops may be decoupled by targeting only a limited number or subset (i.e., one or more, but not all) of the GA20 or GA3 oxidase genes and/or by incomplete suppression of a targeted GA oxidase gene. By transgenically targeting a subset of one or more endogenous GA3 or GA20 oxidase genes for suppression within a plant, a more pervasive pattern of expression (e.g., with a constitutive promoter) may be used to produce semi-dwarf plants without significant reproductive off-types and/or other undesirable traits in the plant, even with expression of the transgenic construct in reproductive tissue(s). Indeed, suppression elements and constructs are provided herein that selectively target the GA20 oxidase_3 and/or GA20 oxidase_5 genes (identified in Table 1 above) for suppression, which may be operably linked to a vascular, leaf and/or constitutive promoter.

With a suppression construct that only targets a limited subset of GA20 oxidase genes, such as the GA20 oxidase_3, GA20 oxidase_4, and/or GA20 oxidase_5 gene(s), or which targets the GA3 oxidase_1 and/or GA3 oxidase_2 gene(s), restricting the pattern of expression of the suppression element may be less crucial for obtaining normal reproductive development of the cereal or corn plant and avoidance of off-types in the female organ or ear due to compensation, etc., from the other GA20 and/or GA3 oxidase genes. Therefore, expression of a suppression construct and element, selectively or preferentially targeting, for instance, the GA20 oxidase_3 and/or GA20 oxidase_5 gene(s), the GA20 oxidase_4 gene, and/or the GA3 oxidase_1 and/or GA3 oxidase_2 gene(s) in corn, or similar genes and homologs in other cereal plants, may be driven by a variety of different plant-expressible promoter types including constitutive and tissue-specific or tissue-preferred promoters, such as a vascular or leaf promoter, which may include, for example, the RTBV promoter introduced above (e.g., a promoter comprising the RTBV (SEQ ID NO: 65) or truncated RTBV (SEQ ID NO: 66) sequence), and any other promoters that drive expression in tissues encompassing much or all of the vascular and/or leaf tissue(s) of a plant. Any known or later-identified constitutive promoter with a sufficiently high level of expression may also be used for expression of a suppression construct targeting a subset of GA20 and/or GA3 oxidase genes in corn, particularly the GA20 oxidase_3 and/or GA20 oxidase_5 gene(s), the GA20 oxidase_4 gene, and/or the GA3 oxidase_1 and/or GA3 oxidase_2 gene(s), or similar genes and homologs in other cereal plants.

Examples of constitutive promoters that may be used in monocot plants, such as cereal or corn plants, include, for example, various actin gene promoters, such as a rice Actin 1 promoter (see, e.g., U.S. Pat. No. 5,641,876; see also SEQ ID NO: 75 or SEQ ID NO: 76) and a rice Actin 2 promoter (see, e.g., U.S. Pat. No. 6,429,357; see also, e.g., SEQ ID NO: 77 or SEQ ID NO: 78), a CaMV 35S or 19S promoter (see, e.g., U.S. Pat. No. 5,352,605; see also, e.g., SEQ ID NO: 79 for CaMV 35S), a maize ubiquitin promoter (see, e.g., U.S. Pat. No. 5,510,474), a *Coix lacryma-jobi* polyubiquitin promoter (see, e.g., SEQ ID NO: 80), a rice or maize Gos2 promoter (see, e.g., Pater et al., The Plant Journal, 2(6): 837-44 1992; see also, e.g., SEQ ID NO: 81 for the rice Gos2 promoter), a FMV 35S promoter (see, e.g., U.S. Pat. No. 6,372,211), a dual enhanced CMV promoter (see, e.g., U.S. Pat. No. 5,322,938), a MMV promoter (see, e.g., U.S. Pat. No. 6,420,547; see also, e.g., SEQ ID NO: 82), a PCLSV promoter (see, e.g., U.S. Pat. No. 5,850,019; see also, e.g., SEQ ID NO: 83), an Emu promoter (see, e.g., Last et al., Theor. Appl. Genet. 81:581 (1991); and Mcelroy et al., Mol. Gen. Genet. 231:150 (1991)), a tubulin promoter from maize, rice or other species, a nopaline synthase (nos) promoter, an octopine synthase (ocs) promoter, a mannopine synthase (mas) promoter, or a plant alcohol dehydrogenase (e.g., maize Adh1) promoter, any other promoters including viral promoters known or later-identified in the art to provide constitutive expression in a cereal or corn plant, any other constitutive promoters known in the art that may be used in monocot or cereal plants, and any functional sequence portion or truncation of any of the foregoing promoters.

A sufficient level of expression of a transcribable DNA sequence encoding a non-coding RNA molecule targeting a GA oxidase gene for suppression may be necessary to produce a short stature, semi-dwarf phenotype that resists lodging, since lower levels of expression may be insufficient to lower active GA levels in the plant to a sufficient extent to cause a significant phenotype. Thus, tissue-specific and tissue-preferred promoters that drive, etc., a moderate or strong level of expression of their associated transcribable DNA sequence in active GA-producing tissue(s) of a plant may be preferred. Furthermore, such tissue-specific and tissue-preferred should drive, etc., expression of their associated transcribable DNA sequence during one or more vegetative stage(s) of plant development when the plant is growing and/or elongating including one or more of the following vegetative stage(s): $V_E$, V1, V2, V3, V4, V5, V6, V7, V8, V9, V10, V11, V12, V13, V14, Vn, $V_T$, such as expression at least during V3-V12, V4-V12, V5-V12, V6-V12, V7-V12, V8-V12, V3-V14, V5-V14, V6-V14, V7-V14, V8-V14, V9-V14, V10-V14, etc., or during any other range of vegetative stages when growth and/or elongation of the plant is occurring.

According to many embodiments, the plant-expressible promoter may preferably drive expression constitutively or in at least a portion of the vascular and/or leaf tissues of the plant. Different promoters driving expression of a suppression element targeting the endogenous GA20 oxidase_3 and/or GA20 oxidase_5 gene(s), the GA20 oxidase_4 gene, the GA3 oxidase_1 and/or GA3 oxidase_2 gene(s) in corn, or similar genes and homologs in other cereal plants, may be effective at reducing plant height and increasing lodging resistance to varying degrees depending on their particular pattern and strength of expression in the plant. However, some tissue-specific and tissue-preferred promoters driving expression of a GA20 or GA3 oxidase suppression element in a plant may not produce a significant short stature or anti-lodging phenotypes due to the spatial-temporal pattern of expression of the promoter during plant development, and/or the amount or strength of expression of the promoter being too low or weak. Furthermore, some suppression constructs may only reduce and not eliminate expression of the targeted GA20 or GA3 oxidase gene(s) when expressed in a plant, and thus depending on the pattern and strength of expression with a given promoter, the pattern and level of expression of the GA20 or GA3 oxidase suppression construct with such a promoter may not be sufficient to produce an observable plant height and lodging resistance phenotype in plants.

According to present embodiments, a recombinant DNA molecule, vector or construct for suppression of one or more endogenous GA20 or GA3 oxidase gene(s) in a plant is provided comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least a segment or portion of a mRNA molecule expressed from an endogenous GA oxidase gene and encoding an endogenous GA oxidase protein in the plant, wherein the transcribable DNA sequence is operably linked to a plant-expressible promoter, and wherein the plant is a cereal or corn plant. As stated above, in addition to targeting a mature mRNA sequence, a non-coding RNA molecule may further target the intronic sequence(s) of a GA oxidase gene or transcript. According to many embodiments, a non-coding RNA molecule may target a GA20 oxidase_3 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 or SEQ ID NO: 8. According to some embodiments, a non-coding RNA molecule targeting a GA20 oxidase_3 gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 7 or SEQ ID NO: 8. According to some embodiments, a non-coding RNA molecule may target a GA20 oxidase gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 9. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein that is at least 80%, at least 85%, at least 90%, at least 95%, at least 96%, at least 97%, at least 98%, at least 99%, at least 99.5%, or 100% similar to SEQ ID NO: 9.

As mentioned above, a non-coding RNA molecule may target an intron sequence of a GA oxidase gene instead of, or in addition to, an exonic, 5' UTR or 3' UTR of the GA oxidase gene. Thus, a non-coding RNA molecule targeting the GA20 oxidase_3 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 34, and/or of nucleotides 3666-3775 or 4098-5314 of SEQ ID NO: 34. It is important to note that the sequences provided herein for the GA20 oxidase_3 gene may vary across the diversity of corn plants, lines and germplasms due to polymorphisms and/or the presence of different alleles of the gene. Furthermore, a GA20 oxidase_3 gene may be expressed as alternatively spliced isoforms that may give rise to different mRNA, cDNA and coding sequences that can affect the design of a suppression construct and non-coding RNA molecule. Thus, a non-coding RNA molecule targeting a GA20 oxidase_3 gene for suppression may be more broadly defined as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 34.

According to embodiments of the present disclosure, a recombinant DNA molecule, vector or construct for suppression of an endogenous GA20 oxidase_5 gene in a plant is provided comprising a transcribable DNA sequence encoding a non-coding RNA molecule, wherein the non-coding RNA molecule targeting the GA20 oxidase_5 gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or SEQ ID NO: 14. According to some embodiments, a non-coding RNA molecule targeting the GA20 oxidase_5 gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 13 or SEQ ID NO: 14. According to some embodiments, a non-coding RNA molecule may target a GA20 oxidase gene for suppression comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 15. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein that is at least 80%, at least 85%, at least 90%, at least 95%, at least 96%, at least 97%, at least 98%, at least 99%, at least 99.5%, or 100% similar to SEQ ID NO: 15.

As mentioned above, a non-coding RNA molecule may target an intron sequence of a GA oxidase gene instead of, or in addition to, an exonic or untranslated region of the mature mRNA of the GA oxidase gene. Thus, a non-coding RNA molecule targeting the GA20 oxidase_5 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 35, and/or of nucleotides 3792-3906 or 4476-5197 of SEQ ID NO: 35. The sequences provided herein for GA20 oxidase_5 may vary across the diversity of corn plants, lines and germplasms due to polymorphisms and/or the presence of different alleles of the gene. Furthermore, a GA20 oxidase_5 gene may be expressed as alternatively spliced isoforms that may give rise to different mRNA, cDNA and coding sequences that can affect the design of a suppression construct and non-coding RNA molecule. Thus, a non-coding RNA molecule targeting a GA20 oxidase_3 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 35.

According to further embodiments, a recombinant DNA molecule, vector or construct for joint suppression of endogenous GA20 oxidase_3 and GA20 oxidase_5 genes in a plant is provided comprising a transcribable DNA sequence encoding a non-coding RNA molecule, wherein the non-coding RNA molecule targeting the GA20 oxidase_3 and GA20 oxidase_5 genes for suppression comprises a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 and/or SEQ ID NO: 8, and (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 and/or SEQ ID NO: 14. According to some of these embodiments, the non-coding RNA molecule jointly targeting the GA20 oxidase_3 and GA20 oxidase_5 genes for suppression may be complementary to at least 19 consecutive nucleotides, but no more than 27 consecutive nucleotides, such as complementary to 19, 20, 21, 22, 23, 24, 25, 26, or 27 consecutive nucleotides, of (i) SEQ ID NO: 7 (and/or SEQ ID NO: 8) and (ii) SEQ ID NO: 13 (and/or SEQ ID NO: 14). According to many embodiments, the non-coding RNA molecule jointly targeting the GA20 oxidase_3 and GA20 oxidase_5 genes for suppression comprises a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 9, and (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 15. As mentioned above, the non-coding RNA molecule may target an intron sequence of a GA oxidase gene. Thus, the non-coding RNA molecule may target an intron sequence(s) of one or both of the GA20 oxidase_3 and/or GA20 oxidase_5 gene(s) as identified above.

According to particular embodiments, the non-coding RNA molecule encoded by a transcribable DNA sequence comprises (i) a sequence that is at least 95%, at least 96%, at least 97%, at least 98%, at least 99%, at least 99.5%, or 100% complementary to SEQ ID NO: 39, 41, 43 or 45, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 40, 42, 44 or 46. According to some embodiments, the non-coding RNA molecule encoded by a transcribable DNA sequence may comprise a sequence with one or more mismatches, such as 1, 2, 3, 4, 5 or more complementary mismatches, relative to the sequence of a target or recognition site of a targeted GA20 oxidase gene mRNA, such as a sequence that is nearly complementary to SEQ ID NO: 40 but with one or more complementary mismatches relative to SEQ ID NO: 40. According to a particular embodiment, the non-coding RNA molecule encoded by the transcribable DNA sequence comprises a sequence that is 100% identical to SEQ ID NO: 40, which is 100% complementary to a target sequence within the cDNA and coding sequences of the GA20 oxidase_3 (i.e., SEQ ID NOs: 7 and 8, respectively), and/or to a corresponding sequence of a mRNA encoded by an endogenous GA20 oxidase_3 gene. However, the sequence of a non-coding RNA molecule encoded by a transcribable DNA sequence that is 100% identical to SEQ ID NO: 40, 42, 44 or 46 may not be perfectly complementary to a target sequence within the cDNA and coding sequences of the GA20 oxidase_5 gene (i.e., SEQ ID NOs: 13 and 14, respectively), and/or to a corresponding sequence of a mRNA encoded by an endogenous GA20 oxidase_5 gene. For example, the closest complementary match between the non-coding RNA molecule or miRNA sequence in SEQ ID NO: 40 and the cDNA and coding sequences of the GA20 oxidase_5 gene may include one mismatch at the first position of SEQ ID NO: 39 (i.e., the "C" at the first position of SEQ ID NO: 39 is replaced with a "G"; i.e., GTCCATCATGCGGTGCAACTA). However, the non-coding RNA molecule or miRNA sequence in SEQ ID NO: 40 may still bind and hybridize to the mRNA encoded by the endogenous GA20 oxidase_5 gene despite this slight mismatch.

According to embodiments of the present disclosure, a recombinant DNA molecule, vector or construct for suppression of one or more endogenous GA3 oxidase gene(s) in a plant is provided comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least a segment or portion of a mRNA molecule expressed from an endogenous GA3 oxidase gene and encoding an endogenous GA3 oxidase protein in the plant, wherein the transcribable DNA sequence is operably linked to a plant-expressible promoter, and wherein the plant is a cereal or corn plant. In addition to targeting a mature mRNA sequence, a non-coding RNA molecule may further target the intronic sequences of a GA3 oxidase gene or transcript.

According to some embodiments, a non-coding RNA molecule may target a GA3 oxidase_1 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 28 or SEQ ID NO: 29. According to some embodiments, a non-coding RNA molecule targeting a GA3 oxidase gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 28 or SEQ ID NO: 29. According to some embodiments, a non-coding RNA molecule targeting a GA3 oxidase gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 30. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein that is at least 80%, at least 85%, at least 90%, at least 95%, at least 96%, at least 97%, at least 98%, at least 99%, at least 99.5%, or 100% similar to SEQ ID NO: 30.

As mentioned above, a non-coding RNA molecule may target an intron sequence of a GA3 oxidase gene instead of, or in addition to, an exonic, 5' UTR or 3' UTR of the GA oxidase gene. Thus, a non-coding RNA molecule targeting the GA3 oxidase_1 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 36, and/or of nucleotides 515-879 or 1039-1158 of SEQ ID NO: 36. The sequences provided herein for GA3 oxidase_1 may vary across the diversity of corn plants, lines and germplasms due to polymorphisms and/or the presence of different alleles of the gene. Furthermore, a GA3 oxidase_1 gene may be expressed as alternatively spliced isoforms that may give rise to different mRNA, cDNA and coding sequences that can affect the design of a suppression construct and non-coding RNA molecule. Thus, a non-coding RNA molecule targeting a GA3 oxidase_1 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 36.

According to some embodiments, a non-coding RNA molecule may target a GA3 oxidase_2 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 31 or SEQ ID NO: 32. According to some embodiments, a non-coding RNA molecule targeting the GA3 oxidase gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 31 or SEQ ID NO: 32. According to some embodiments, a non-coding RNA molecule targeting the GA3 oxidase gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 33. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein that is at least 80%, at least 85%, at least 90%, at least 95%, at least 96%, at least 97%, at least 98%, at least 99%, at least 99.5%, or 100% similar to SEQ ID NO: 33.

As mentioned above, a non-coding RNA molecule may target an intron sequence of a GA3 oxidase gene instead of, or in addition to, an exonic, 5' UTR or 3' UTR of the GA3 oxidase gene. Thus, a non-coding RNA molecule targeting the GA3 oxidase_2 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 37, and/or of nucleotides 533-692 or 852-982 of SEQ ID NO: 37. The sequences provided herein for GA3 oxidase_2 may vary across the diversity of corn plants, lines and germplasms due to polymorphisms and/or the presence of different alleles of the gene. Furthermore, a GA3 oxidase_2 gene may be expressed as alternatively spliced isoforms that may give rise to different mRNA, cDNA and coding sequences that can affect the design of a suppression construct and non-coding RNA molecule. Thus, a non-coding RNA molecule targeting a GA3 oxidase_2 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 37.

According to particular embodiments, a non-coding RNA molecule encoded by a transcribable DNA sequence for targeting a GA3 oxidase gene comprises (i) a sequence that is at least 95%, at least 96%, at least 97%, at least 98%, at least 99%, at least 99.5%, or 100% complementary to SEQ ID NO: 57 or 59, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 58 or 60. According to some embodiments, the non-coding RNA molecule encoded by a transcribable DNA sequence may comprise a sequence with one or more mismatches, such as 1, 2, 3, 4, 5 or more complementary mismatches, relative to the sequence of a target or recognition site of a targeted GA3 oxidase gene mRNA, such as a sequence that is nearly complementary to SEQ ID NO: 57 or 59 but with one or more complementary mismatches relative to SEQ ID NO: 57 or 59. According to a particular embodiment, the non-coding RNA molecule encoded by the transcribable DNA sequence comprises a sequence that is 100% identical to SEQ ID NO: 58 or 60, which is 100% complementary to a target sequence within the cDNA and coding sequences of a GA3 oxidase_1 or GA3 oxidase_2 gene in corn (i.e., SEQ ID NOs: 28, 29, 31 and/or 32), and/or to a corresponding sequence of a mRNA encoded by an endogenous GA3 oxidase_1 or GA3 oxidase_2 gene.

According to some embodiments, a non-coding RNA molecule may target a GA20 oxidase_4 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 10 or SEQ ID NO: 11. According to some embodiments, a non-coding RNA molecule targeting a GA20 oxidase_4 gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 10 or SEQ ID NO: 11. According to some embodiments, a non-coding RNA molecule targeting the GA20 oxidase gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 12. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein that is at least 80%, at least 85%, at least 90%, at least 95%, at least 96%, at least 97%, at least 98%, at least 99%, at least 99.5%, or 100% similar to SEQ ID NO: 12.

As mentioned above, a non-coding RNA molecule may target an intron sequence of a GA20 oxidase gene instead of, or in addition to, an exonic, 5' UTR or 3' UTR of the GA20 oxidase gene. Thus, a non-coding RNA molecule targeting a GA20 oxidase_4 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 38, and/or of nucleotides 1996-2083 or 2412-2516 of SEQ ID NO: 38. The sequences provided herein for GA20 oxidase_4 may vary across the diversity of corn plants, lines and germplasms due to polymorphisms and/or the presence of different alleles of the gene. Furthermore, a GA20 oxidase_4 gene may be expressed as alternatively spliced isoforms that may give rise to different mRNA, cDNA and coding sequences that can affect the design of a suppression construct and non-coding RNA molecule. Thus, a non-coding RNA molecule targeting a GA20 oxidase_4 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 38.

According to particular embodiments, a non-coding RNA molecule encoded by a transcribable DNA sequence for targeting a GA20 oxidase_4 gene comprises (i) a sequence that is at least 95%, at least 96%, at least 97%, at least 98%, at least 99%, at least 99.5%, or 100% complementary to SEQ ID NO: 61, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 62. According to some embodiments, the non-coding RNA molecule encoded by a transcribable DNA sequence may comprise a sequence with one or more mismatches, such as 1, 2, 3, 4, 5 or more complementary mismatches, relative to the sequence of a target or recognition site of a targeted GA20 oxidase gene mRNA, such as a sequence that is nearly complementary to SEQ ID NO: 61 but with one or more complementary mismatches relative to SEQ ID NO: 61. According to a particular embodiment, the non-coding RNA molecule encoded by the transcribable DNA sequence comprises a sequence that is 100% identical to SEQ ID NO: 62, which is 100% complementary to a target sequence within the cDNA and coding sequences of a GA20 oxidase_4 gene in corn (i.e., SEQ ID NO: 10 or 11), and/or to a corresponding sequence of a mRNA encoded by an endogenous GA20 oxidase_4 gene.

According to embodiments of the present disclosure, a recombinant DNA construct is provided comprising a transcribable DNA sequence encoding a non-coding RNA molecule targeting an endogenous GA20 oxidase_3 and/or the GA20 oxidase_5 gene(s) for suppression, wherein the transcribable DNA sequence is operably linked to a constitutive, tissue-specific or tissue-preferred promoter, and wherein the transcribable DNA sequence causes the expression level of an endogenous GA20 oxidase_3 and/or the GA20 oxidase_5 gene(s) to become reduced or lowered in one or more tissue(s) of a plant transformed with the transcribable DNA sequence. Such a non-coding RNA molecule encoded by the transcribable DNA sequence may comprise a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 9, and/or (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 15.

According to embodiments of the present disclosure, a recombinant DNA construct is provided comprising a transcribable DNA sequence encoding a non-coding RNA molecule targeting an endogenous GA3 oxidase_1 and/or the GA3 oxidase_2 gene(s) for suppression, wherein the transcribable DNA sequence is operably linked to a constitutive, tissue-specific or tissue-preferred promoter, and wherein the transcribable DNA sequence causes the expression level of an endogenous GA3 oxidase_1 and/or the GA3 oxidase_2 gene(s) to become reduced or lowered in one or more tissue(s) of a plant transformed with the transcribable DNA sequence. Such a non-coding RNA molecule encoded by the transcribable DNA sequence may comprise a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 30, and/or (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 33.

According to embodiments of the present disclosure, a recombinant DNA construct is provided comprising a transcribable DNA sequence encoding a non-coding RNA molecule targeting an endogenous GA20 oxidase_4 gene for suppression, wherein the transcribable DNA sequence is operably linked to a constitutive, tissue-specific or tissue-preferred promoter, and wherein the transcribable DNA sequence causes the expression level of an endogenous GA20 oxidase_4 gene to become reduced or lowered in one or more tissue(s) of a plant transformed with the transcribable DNA sequence. Such a non-coding RNA molecule encoded by the transcribable DNA sequence may comprise a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 12.

According to many embodiments, a modified or transgenic plant is provided that is transformed with a recombinant DNA construct comprising a transcribable DNA sequence encoding a non-coding RNA molecule targeting an endogenous GA20 oxidase_3 and/or GA20 oxidase_5 gene(s) for suppression, and/or has an endogenous GA20 oxidase_3 and/or GA20 oxidase_5 gene(s) edited through targeted genome editing techniques, as provided herein, wherein the transcribable DNA sequence is operably linked to a constitutive promoter or a tissue-specific or tissue-preferred promoter, such as a vascular promoter or a leaf promoter, and wherein the expression level of the endogenous GA20 oxidase_3 and/or GA20 oxidase_5 gene(s) is eliminated, reduced or lowered in one or more plant tissue(s), such as one or more vascular and/or leaf tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant. According to many embodiments, a modified or transgenic plant is provided that is transformed with a recombinant DNA construct comprising a transcribable DNA sequence encoding a non-coding RNA molecule targeting an endogenous GA20 oxidase_3 and/or GA20 oxidase_5 gene(s) for suppression, and/or has an endogenous GA20 oxidase_3 and/or GA20 oxidase_5 gene(s) edited through targeted genome editing techniques to reduce or eliminate its level of expression and/or activity, wherein the transcribable DNA sequence is operably linked to a constitutive promoter or a tissue-specific or tissue-preferred promoter, such as a vascular promoter or a leaf promoter, and wherein the level of one or more active GAs, such as GA1, GA3, GA4, and/or GA7, is reduced or lowered in one or more plant tissue(s), such as one or more stem, internode, vascular and/or leaf tissue(s) or one or more stem and/or internode tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant.

According to many embodiments, a modified or transgenic plant is provided that is transformed with a recombinant DNA construct comprising a transcribable DNA sequence encoding a non-coding RNA molecule targeting an endogenous GA3 oxidase_1 and/or GA3 oxidase_2 gene(s) for suppression, and/or has an endogenous GA3 oxidase_1 or GA3 oxidase_2 gene edited through targeted genome editing techniques, as provided herein, wherein the transcribable DNA sequence is operably linked to a constitutive promoter or a tissue-specific or tissue-preferred promoter, such as a vascular promoter or a leaf promoter, and wherein the expression level of the endogenous GA3 oxidase_1 and/or GA3 oxidase_2 gene(s) is eliminated, reduced or lowered in one or more plant tissue(s), such as one or more vascular and/or leaf tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant. According to many embodiments, a modified or transgenic plant is provided that is transformed with a recombinant DNA construct comprising a transcribable DNA sequence encoding a non-coding RNA molecule targeting an endogenous GA3 oxidase_1 and/or GA3 oxidase_2 gene(s) for suppression, and/or has an endogenous GA3 oxidase_1 and/or GA3 oxidase_2 gene edited through targeted genome editing techniques to reduce or eliminate its level of expression and/or activity, wherein the transcribable DNA sequence is operably linked to a constitutive promoter or a tissue-specific or tissue-preferred promoter, such as a vascular promoter or a leaf promoter, and wherein the level of one or more active GAs, such as GA1, GA3, GA4, and/or GA7, is reduced or lowered in one or more plant tissue(s), such as one or more stem, internode, vascular and/or leaf tissue(s) or one or more stem and/or internode tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant.

According to many embodiments, a modified or transgenic plant is provided that is transformed with a recombinant DNA construct comprising a transcribable DNA sequence encoding a non-coding RNA molecule targeting an endogenous GA20 oxidase_4 gene for suppression, and/or has an endogenous GA20 oxidase_4 gene edited through targeted genome editing techniques, as provided herein, wherein the transcribable DNA sequence is operably linked to a constitutive promoter or a tissue-specific or tissue-preferred promoter, such as a vascular promoter or a leaf promoter, and wherein the expression level of the endogenous GA20 oxidase_4 gene(s) is eliminated, reduced or lowered in one or more plant tissue(s), such as one or more vascular and/or leaf tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant. According to many embodiments, a modified or transgenic plant is provided that is transformed with a recombinant DNA construct comprising a transcribable DNA sequence encoding a non-coding RNA molecule targeting an endogenous GA20 oxidase_4 gene(s) for suppression, and/or has an endogenous GA20 oxidase_4 gene edited through targeted genome editing techniques to reduce or eliminate its level of expression and/or activity, wherein the transcribable DNA sequence is operably linked to a constitutive promoter or a tissue-specific or tissue-preferred promoter, such as a vascular promoter or a leaf promoter, and wherein the level of one or more active GAs, such as GA1, GA3, GA4, and/or GA7, is reduced or lowered in one or more plant tissue(s), such as one or more stem, internode, vascular and/or leaf tissue(s) or one or more stem and/or internode tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant.

According to many embodiments, a modified or transgenic plant is provided that is transformed with a recombinant DNA construct comprising a transcribable DNA sequence encoding a non-coding RNA molecule targeting an endogenous GA20 oxidase_3, GA20 oxidase_4, and/or GA20 oxidase_5 gene(s) for suppression, is transformed with a recombinant DNA construct comprising a transcribable DNA sequence encoding a non-coding RNA molecule targeting an endogenous GA3 oxidase_1 and/or the GA3 oxidase_2 gene(s) for suppression, and/or has an endogenous GA20 oxidase_3, GA20 oxidase_4, or the GA20 oxidase_5 gene edited through targeted genome editing techniques, to reduce or eliminate its level of expression and/or activity, as provided herein, wherein the transcribable DNA sequence is operably linked to a constitutive promoter or a tissue-specific or tissue-preferred promoter, such as a vascular promoter or a leaf promoter, and wherein the modified or transgenic plant has one or more of the following traits: a semi-dwarf or reduced plant height or stature, decreased stem internode length, increased lodging resistance, and/or increased stem or stalk diameter. Such a modified or transgenic plant may not have any significant reproductive off-types. A modified or transgenic plant may have one or more of the following additional traits: reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and anthocyanin area in leaves under normal and/or nitrogen or water limiting stress conditions, increased ear weight, increased kernel number, increased kernel weight, increased yield, and/or increased harvest index. According to many of these embodiments, the level of expression and/or activity of an endogenous GA20 oxidase_3, GA20 oxidase_4, and/or GA20 oxidase_5 gene(s), or an endogenous GA3 oxidase_1 and/or GA3 oxidase_2 gene(s), may be eliminated, reduced or lowered in one or more plant tissue(s), such as one or more vascular and/or leaf tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant, and/or the level of one or more active GAs, such as GA1, GA3, GA4, and/or GA7, is reduced or lowered in one or more plant tissue(s), such as one or more stem, internode, vascular and/or leaf tissue(s), or one or more stem and/or internode tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant.

According to many of the embodiments described in the above paragraphs, the non-coding RNA molecule encoded by the transcribable DNA sequence of the recombinant DNA molecule, vector or construct may be a precursor miRNA or siRNA that may be subsequently processed or cleaved in a plant cell to form a mature miRNA or siRNA.

A recombinant DNA molecule, construct or vector of the present disclosure may comprise a transcribable DNA sequence encoding a non-coding RNA molecule that targets an endogenous GA oxidase gene for suppression, wherein the transcribable DNA sequence is operatively linked to a plant-expressible promoter, such as a constitutive or vascular and/or leaf promoter. For purposes of the present disclosure, a non-coding RNA molecule encoded by a transcribable DNA sequence that targets an endogenous GA oxidase gene for suppression may include a mature non-coding RNA molecule that targets an endogenous GA oxidase gene for suppression, and/or a precursor RNA molecule that may become processed in a plant cell into a mature non-coding RNA molecule, such as a miRNA or siRNA, that targets an endogenous GA oxidase gene for suppression. In addition to its associated promoter, a transcribable DNA sequence encoding a non-coding RNA molecule for suppression of an endogenous GA oxidase gene may also be operatively linked to one or more additional regulatory element(s), such as an enhancer(s), leader, transcription start site (TSS), linker, 5' and 3' untranslated region(s) (UTRs), intron(s), polyadenylation signal, termination region or sequence, etc., that are suitable, necessary or preferred for strengthening, regulating or allowing expression of the transcribable DNA sequence in a plant cell. Such additional regulatory element(s) may be optional and/or used to enhance or optimize expression of the transgene or transcribable DNA sequence. As provided herein, an "enhancer" may be distinguished from a "promoter" in that an enhancer typically lacks a transcription start site, TATA box, or equivalent sequence and is thus insufficient alone to drive transcription. As used herein, a "leader" may be defined generally as the DNA sequence of the 5'-UTR of a gene (or transgene) between the transcription start site (TSS) and 5' end of the transcribable DNA sequence or protein coding sequence start site of the transgene.

According to further embodiments, methods are provided for transforming a plant cell, tissue or explant with a recombinant DNA molecule or construct comprising a transcribable DNA sequence or transgene operably linked to a plant-expressible promoter to produce a transgenic plant. The transcribable DNA sequence may encode a non-coding RNA molecule that targets a GA oxidase gene(s) for suppression, or a RNA precursor that is processed into a mature RNA molecule, such as a miRNA or siRNA, that targets one or more GA oxidase gene(s) for suppression. Numerous methods for transforming chromosomes or plastids in a plant cell with a recombinant DNA molecule or construct are known in the art, which may be used according to method embodiments of the present invention to produce a transgenic plant cell and plant. Any suitable method or technique for transformation of a plant cell known in the art may be used according to present methods. Effective methods for transformation of plants include bacterially mediated transformation, such as *Agrobacterium*-mediated or *Rhizobium*-mediated transformation, and microprojectile or particle bombardment-mediated transformation. A variety of methods are known in the art for transforming explants with a transformation vector via bacterially mediated transformation or microprojectile or particle bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art.

Methods of transforming plant cells and explants are well known by persons of ordinary skill in the art. Methods for transforming plant cells by microprojectile bombardment with particles coated with recombinant DNA are provided, for example, in U.S. Pat. Nos. 5,550,318; 5,538,880 6,160, 208; 6,399,861; and 6,153,812, and *Agrobacterium*-mediated transformation is described, for example, in U.S. Pat. Nos. 5,159,135; 5,824,877; 5,591,616; 6,384,301; 5,750, 871; 5,463,174; and 5,188,958, all of which are incorporated herein by reference. Additional methods for transforming plants can be found in, for example, Compendium of Transgenic Crop Plants (2009) Blackwell Publishing. Any suitable method of plant transformation known or later developed in the art can be used to transform a plant cell or explant with any of the nucleic acid molecules, constructs or vectors provided herein.

Transgenic plants produced by transformation methods may be chimeric or non-chimeric for the transformation event depending on the methods and explants used. Methods are further provided for expressing a non-coding RNA molecule that targets an endogenous GA oxidase gene for suppression in one or more plant cells or tissues under the control of a plant-expressible promoter, such as a constitutive, tissue-specific, tissue-preferred, vascular and/or leaf promoter as provided herein. Such methods may be used to create transgenic cereal or corn plants having a shorter, semi-dwarf stature, reduced internode length, increased stalk/stem diameter, and/or improved lodging resistance. Such transgenic cereal or corn plants may further have other traits that may be beneficial for yield, such as reduced green snap, deeper roots, increased leaf area, earlier canopy closure, improved drought tolerance, increased nitrogen use efficiency, increased water use efficiency, higher stomatal conductance, lower ear height, increased foliar water content, reduced anthocyanin content and/or area in leaves under normal or nitrogen or water limiting stress conditions, increased ear weight, increased seed or kernel number, increased seed or kernel weight, increased yield, and/or increased harvest index, relative to a wild type or control plant. As used herein, "harvest index" refers to the mass of the harvested grain divided by the total mass of the above-ground biomass of the plant over a harvested area.

Transgenic plants expressing a GA oxidase transgene or non-coding RNA molecule that targets an endogenous GA oxidase gene for suppression may have an earlier canopy closure (e.g., approximately one day earlier, or 12-48 hours, 12-36 hours, 18-36 hours, or about 24 hours earlier canopy closure) than a wild type or control plant. Although transgenic plants expressing a GA oxidase transgene or non-coding RNA molecule that targets an endogenous GA oxidase gene for suppression may have a lower ear height than a wild type or control plant, the height of the ear may generally be at least 18 inches above the ground. Transgenic plants expressing a non-coding RNA molecule that targets an endogenous GA oxidase gene for suppression may have greater biomass and/or leaf area during one or more late vegetative stages (e.g., V8-V12) than a wild type or control plant. Transgenic plants expressing a GA oxidase transgene or non-coding RNA molecule that targets an endogenous GA oxidase gene for suppression may have deeper roots during later vegetative stages when grown in the field, than a wild type or control plant, which may be due to an increased root front velocity. These transgenic plants may reach a depth 90 cm below ground sooner (e.g., 10-25 days sooner, 15-25 days sooner, or about 20 days sooner) than a wild type or control plant, which may occur by the vegetative to reproductive transition of the plant (e.g., by V16/R1 at about 50 days after planting as opposed at about 70 days after planting for control plants).

Recipient cell(s) or explant or cellular targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, a callus cell, a chloroplast, a stomatal cell, a trichome cell, a root hair cell, a storage root cell, or a vascular tissue cell, a seed, embryo, meristem, cotyledon, hypocotyl, endosperm, root, shoot, stem, node, callus, cell suspension, protoplast, flower, leaf, pollen, anther, ovary, ovule, pericarp, bud, and/or vascular tissue, or any transformable portion of any of the foregoing. For plant transformation, any target cell(s), tissue(s), explant(s), etc., that may be used to receive a recombinant DNA transformation vector or molecule of the present disclosure may be collectively be referred to as an "explant" for transformation. Preferably, a transformable or transformed explant cell or tissue may be further developed or regenerated into a plant. Any cell or explant from which a fertile plant can be grown or regenerated is contemplated as a useful recipient cell or explant for practice of this disclosure (i.e., as a target explant for transformation). Callus can be initiated or created from various tissue sources, including, but not limited to, embryos or parts of embryos, non-embryonic seed tissues, seedling apical meristems, microspores, and the like. Any cells that are capable of proliferating as callus may serve as recipient cells for transformation. Transformation methods and materials for making transgenic plants (e.g., various media and recipient target cells or explants and methods of transformation and subsequent regeneration of into transgenic plants) are known in the art.

Transformation of a target plant material or explant may be practiced in tissue culture on nutrient media, for example a mixture of nutrients that allow cells to grow in vitro or cell culture. Transformed explants, cells or tissues may be subjected to additional culturing steps, such as callus induction, selection, regeneration, etc., as known in the art. Transformation may also be carried out without creation or use of a callus tissue. Transformed cells, tissues or explants containing a recombinant DNA sequence insertion or event may be grown, developed or regenerated into transgenic plants in culture, plugs, or soil according to methods known in the art. Transgenic plants may be further crossed to themselves or other plants to produce transgenic seeds and progeny. A transgenic plant may also be prepared by crossing a first plant comprising the recombinant DNA sequence or transformation event with a second plant lacking the insertion. For example, a recombinant DNA construct or sequence may be introduced into a first plant line that is amenable to transformation, which may then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line, but for the introduction of the recombinant DNA construct or sequence.

A transgenic or edited plant, plant part, cell, or explant provided herein may be of an elite variety or an elite line. An elite variety or an elite line refers to a variety that has resulted from breeding and selection for superior agronomic performance. A transgenic or edited plant, cell, or explant provided herein may be a hybrid plant, cell, or explant. As used herein, a "hybrid" is created by crossing two plants from different varieties, lines, inbreds, or species, such that the progeny comprises genetic material from each parent. Skilled artisans recognize that higher order hybrids can be generated as well. For example, a first hybrid can be made by crossing Variety A with Variety B to create a A×B hybrid, and a second hybrid can be made by crossing Variety C with Variety D to create an C×D hybrid. The first and second hybrids can be further crossed to create the higher order hybrid (A×B)×(C×D) comprising genetic information from all four parent varieties.

According to embodiments of the present disclosure, a modified plant is provided comprising a GA oxidase suppression element that targets two or more GA oxidase genes for suppression, or a combination of two or more GA oxidase suppression element(s) and/or gene edit(s). A recombinant DNA construct or vector may comprise a single cassette or suppression element comprising a transcribable DNA sequence designed or chosen to encode a non-coding RNA molecule that is complementary to mRNA recognition or target sequences of two or more GA oxidase genes including at least a first GA oxidase gene and a second GA oxidase gene—i.e., the mRNAs of the targeted GA oxidase genes share an identical or nearly identical (or similar) sequence such that a single suppression element and encoded non-coding RNA molecule can target each of the targeted GA oxidase genes for suppression. For example, an expression cassette and suppression construct is provided herein comprising a transcribable DNA sequence that encodes a single non-coding RNA molecule that targets both the GA20 oxidase_3 and GA20 oxidase_5 genes for suppression.

According to other embodiments, a recombinant DNA construct or vector may comprise two or more suppression elements or sequences that may be stacked together in a construct or vector either in tandem in a single expression cassette or separately in two or more expression cassettes. A recombinant DNA construct or vector may comprise a single expression cassette or suppression element comprising a transcribable DNA sequence that encodes a non-coding RNA molecule comprising two or more targeting sequences arranged in tandem, including at least a first targeting sequence and a second targeting sequence, wherein the first targeting sequence is complementary to a mRNA recognition or target site of a first GA oxidase gene, and the second targeting sequence is complementary to a mRNA recognition or target site of a second GA oxidase gene, and wherein the transcribable DNA sequence is operably linked to a plant-expressible promoter. The plant-expressible promoter may be a constitutive promoter, or a tissue-specific or tissue-preferred promoter, as provided herein. The non-coding RNA molecule may be expressed as a pre-miRNA that becomes processed into two or more mature miRNAs including at least a first mature miRNA and a second miRNA, wherein the first miRNA comprises a targeting sequence that is complementary to the mRNA recognition or target site of the first GA oxidase gene, and the second miRNA comprises a targeting sequence that is complementary to the mRNA recognition or target site of the second GA oxidase gene.

According to other embodiments, a recombinant DNA construct or vector may comprise two or more expression cassettes including a first expression cassette and a second expression cassette, wherein the first expression cassette comprises a first transcribable DNA sequence operably linked to a first plant-expressible promoter, and the second expression cassette comprises a second transcribable DNA sequence operably linked to a second plant-expressible promoter, wherein the first transcribable DNA sequence encodes a first non-coding RNA molecule comprising a targeting sequence that is complementary to a mRNA recognition or target site of a first GA oxidase gene, and the second transcribable DNA sequence encodes a second non-coding RNA molecule comprising a targeting sequence that is complementary to a mRNA recognition or target site of a second GA oxidase gene. The first and second plant-expressible promoters may each be a constitutive promoter, or a tissue-specific or tissue-preferred promoter, as provided herein, and the first and second plant-expressible promoters may be the same or different promoters.

According to other embodiments, two or more suppression elements or constructs targeting GA oxidase gene(s) and/or GA oxidase gene edit(s) may be combined in a modified plant by crossing two or more plants together in one or more generations to produce a modified plant having a desired combination of suppression element(s) and/or gene edit(s). According to these embodiments, a first modified plant comprising a suppression element or construct targeting a GA oxidase gene(s) (or a GA oxidase gene edit) may be crossed to a second modified plant comprising a suppression element or construct targeting a GA oxidase gene(s) (or a GA oxidase gene edit), such that a modified progeny plant may be made comprising a first suppression element or construct and a second suppression element or construct, a suppression element or construct and a GA oxidase gene edit, or a first GA oxidase gene edit and a second GA oxidase gene edit. Alternatively, a modified plant comprising two or more suppression elements or constructs targeting GA oxidase gene(s) and/or GA oxidase gene edit(s) may be made by (i) co-transforming a first suppression element or construct and a second suppression element or construct (each targeting a GA oxidase gene for suppression), (ii) transforming a modified plant with a second suppression element or construct, wherein the modified plant already comprises a first suppression element or construct, (iii) transforming a modified plant with a suppression element or construct, wherein the modified plant already comprises an edited GA oxidase gene, (iv) transforming a modified plant with a construct(s) for making one or more edits in GA oxidase gene(s), wherein the modified plant already comprises a suppression element or construct, or (v) transforming with construct(s) for making two or more edits in GA oxidase gene(s).

According to embodiments of the present disclosure, modified plants are provided comprising two or more constructs targeting GA oxidase gene(s) for suppression including a first recombinant DNA construct and a second recombinant DNA construct, wherein the first recombinant DNA construct comprises a first transcribable DNA sequence encoding a first non-coding RNA molecule that is complementary to a mRNA recognition or target sequence of a first GA oxidase gene, and the second recombinant DNA construct comprises a second transcribable DNA sequence encoding a second non-coding RNA molecule that is complementary to a mRNA recognition or target sequence of a second GA oxidase gene. The first and second recombinant DNA constructs may be stacked in a single vector and transformed into a plant as a single event, or present in separate vectors or constructs that may be transformed as separate events. According to these embodiments, the first GA oxidase gene may be a GA20 oxidase_3, GA20 oxidase_5, GA20 oxidase_4, GA3 oxidase_1, or GA3 oxidase_2 gene, the first non-coding RNA molecule is complementary to a recognition or target sequence of an mRNA expressed from such GA oxidase gene, and the second GA oxidase gene may be a GA20 oxidase_3, GA20 oxidase_5, GA20 oxidase_4, GA3 oxidase_1, or GA3 oxidase_2 gene. According to some embodiments, the first and second GA oxidase genes may be the same or different GA oxidase gene(s). Alternatively, the second GA oxidase gene may be another GA oxidase gene, such as a GA20 oxidase_1, GA20 oxidase_2, GA20 oxidase_6, GA20 oxidase_7, GA20 oxidase_8, or GA20 oxidase_9 gene, and the second non-coding RNA molecule is complementary to a recognition or target sequence of an mRNA expressed from such GA oxidase gene.

According to embodiments of the present disclosure, modified plants are provided comprising a recombinant DNA construct targeting GA oxidase genes for suppression comprising a transcribable DNA sequence encoding a non-coding RNA molecule that comprises two or more targeting sequences arranged in tandem including at least a first targeting sequence that is complementary to a mRNA recognition or target sequence of a first GA oxidase gene and a second targeting sequence that is complementary to a mRNA recognition or target sequence of a second GA oxidase gene. The non-coding RNA molecule may be expressed as a pre-miRNA that becomes processed into two or more mature miRNAs including at least a first mature miRNA and a second miRNA, wherein the first miRNA comprises the first targeting sequence that is complementary to the mRNA recognition or target site of the first GA oxidase gene, and the second miRNA comprises the second targeting sequence that is complementary to the mRNA recognition or target site of the second GA oxidase gene. According to these embodiments, the first GA oxidase gene may be a GA20 oxidase_3, GA20 oxidase_5, GA20 oxidase_4, GA3 oxidase_1, or GA3 oxidase_2 gene, the first non-coding RNA molecule is complementary to a recognition or target sequence of an mRNA expressed from such GA oxidase gene, and the second GA oxidase gene may be a GA20 oxidase_3, GA20 oxidase_5, GA20 oxidase_4, GA3 oxidase_1, or GA3 oxidase_2 gene. According to some embodiments, the first and second GA oxidase genes may be the same or different GA oxidase gene(s). Alternatively, the second GA oxidase gene may be another GA oxidase gene, such as a GA20 oxidase_1, GA20 oxidase_2, GA20 oxidase_6, GA20 oxidase_7, GA20 oxidase_8, or GA20 oxidase_9 gene, and the second non-coding RNA molecule is complementary to a recognition or target sequence of an mRNA expressed from such GA oxidase gene.

In the above stacking scenarios, and regardless of whether the targeting sequences are stacked in tandem in a single transcribable DNA sequence (or expression cassette) or in separate transcribable DNA sequences (or expression cassettes), the second GA oxidase gene may be a GA oxidase gene other than a GA20 oxidase_3, GA20 oxidase_5, GA20 oxidase_4, GA3 oxidase_1, or GA3 oxidase_2 gene, such as a GA20 oxidase_1, GA20 oxidase_2, GA20 oxidase_6, GA20 oxidase_7, GA20 oxidase_8, or GA20 oxidase_9 gene. According to these embodiments, the second targeting sequence of a non-coding RNA molecule may be at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of any one or more of SEQ ID NOs: 1, 2, 4, 5, 16, 17, 19, 20, 22, 23, 25, and/or 26. According to some embodiments, the second targeting sequence of a non-coding RNA molecule may be complementary to at least 19 consecutive nucleotides, but no more than 27 consecutive nucleotides, such as complementary to 19, 20, 21, 22, 23, 24, 25, 26, or 27 consecutive nucleotides, of any one or more of SEQ ID NOs: 1, 2, 4, 5, 16, 17, 19, 20, 22, 23, 25, and/or 26. According to some embodiments, the second targeting sequence of a non-coding RNA molecule may be at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in the plant that is at least 80%, at least 85%, at least 90%, at least 95%, at least 96%, at least 97%, at least 98%, at least 99%, at least 99.5%, or 100% identical to any one or more of SEQ ID NOs: 3, 6, 18, 21, 24, and/or 27. According to further embodiments, the second targeting sequence of a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein that is at least 80%, at least 85%, at least 90%, at least 95%, at least 96%, at least 97%, at least 98%, at least 99%, at least 99.5%, or 100% similar to any one or more of SEQ ID NO: 3, 6, 18, 21, 24, and/or 27.

A recombinant DNA molecule or construct of the present disclosure may comprise or be included within a DNA transformation vector for use in transformation of a target plant cell, tissue or explant. Such a transformation vector may generally comprise sequences or elements necessary or beneficial for effective transformation in addition to at least one transgene, expression cassette and/or transcribable DNA sequence encoding a GA oxidase gene or a non-coding RNA molecule targeting an endogenous GA oxidase gene for suppression. For *Agrobacterium*-mediated, *Rhizobia*-mediated or other bacteria-mediated transformation, the transformation vector may comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. Thus, a transcribable DNA sequence, transgene or expression cassette encoding a non-coding RNA molecule targeting an endogenous GA oxidase gene for suppression may be located between the left and right borders of the T-DNA, perhaps along with an additional transgene(s) or expression cassette(s), such as a plant selectable marker transgene and/or other gene(s) of agronomic interest that may confer a trait or phenotype of agronomic interest to a plant. According to alternative embodiments, the transcribable DNA sequence, transgene or expression cassette encoding a non-coding RNA molecule targeting an endogenous GA oxidase gene for suppression and the plant selectable marker transgene (or other gene of agronomic interest) may be present in separate T-DNA segments on the same or different recombinant DNA molecule(s), such as for co-transformation. A transformation vector or construct may further comprise prokaryotic maintenance elements, which may be located in the vector outside of the T-DNA region(s).

A plant selectable marker transgene in a transformation vector or construct of the present disclosure may be used to assist in the selection of transformed cells or tissue due to the presence of a selection agent, such as an antibiotic or herbicide, wherein the plant selectable marker transgene provides tolerance or resistance to the selection agent. Thus, the selection agent may bias or favor the survival, development, growth, proliferation, etc., of transformed cells expressing the plant selectable marker gene, such as to increase the proportion of transformed cells or tissues in the R0 plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes may also be used, which provide an ability to visually screen for transformants, such as luciferase or green fluorescent protein (GFP), or a gene expressing a beta glucuronidase or uidA gene (GUS) for which various chromogenic substrates are known. In some embodiments, a vector or polynucleotide provided herein comprises at least one selectable marker gene selected from the group consisting of nptII, aph IV, aadA, aac3, aacC4, bar, pat, DMO, EPSPS, aroA, GFP, and GUS. Plant transformation may also be carried out in the absence of selection during one or more steps or stages of culturing, developing or regenerating transformed explants, tissues, plants and/or plant parts.

According to present embodiments, methods for transforming a plant cell, tissue or explant with a recombinant DNA molecule or construct may further include site-directed or targeted integration. According to these methods, a portion of a recombinant DNA donor template molecule (i.e., an insertion sequence) may be inserted or integrated at a desired site or locus within the plant genome. The insertion sequence of the donor template may comprise a transgene or construct, such as a transgene or transcribable DNA sequence encoding a non-coding RNA molecule that targets an endogenous GA oxidase gene for suppression. The donor template may also have one or two homology arms flanking the insertion sequence to promote the targeted insertion event through homologous recombination and/or homology-directed repair. Each homology arm may be at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence within the genome of a monocot or cereal plant. Thus, a recombinant DNA molecule of the present disclosure may comprise a donor template for site-directed or targeted integration of a transgene or construct, such as a transgene or transcribable DNA sequence encoding a non-coding RNA molecule that targets an endogenous GA oxidase gene for suppression, into the genome of a plant.

Any site or locus within the genome of a plant may potentially be chosen for site-directed integration of a transgene, construct or transcribable DNA sequence provided herein. For site-directed integration, a double-strand break (DSB) or nick may first be made at a selected genomic locus with a site-specific nuclease, such as, for example, a zinc-finger nuclease, an engineered or native meganuclease, a TALE-endonuclease, or an RNA-guided endonuclease (e.g., Cas9 or Cpf1). Any method known in the art for site-directed integration may be used. In the presence of a donor template molecule with an insertion sequence, the DSB or nick may then be repaired by homologous recombination between homology arm(s) of the donor template and the plant genome, or by non-homologous end joining (NHEJ), resulting in site-directed integration of the insertion sequence into the plant genome to create the targeted insertion event at the site of the DSB or nick. Thus, site-specific insertion or integration of a transgene, construct or sequence may be achieved.

The introduction of a DSB or nick may also be used to introduce targeted mutations in the genome of a plant. According to this approach, mutations, such as deletions, insertions, inversions and/or substitutions may be introduced at a target site via imperfect repair of the DSB or nick to produce a knock-out or knock-down of a GA oxidase gene. Such mutations may be generated by imperfect repair of the targeted locus even without the use of a donor template molecule. A "knock-out" of a GA oxidase gene may be achieved by inducing a DSB or nick at or near the endogenous locus of the GA oxidase gene that results in non-expression of the GA oxidase protein or expression of a non-functional protein, whereas a "knock-down" of a GA oxidase gene may be achieved in a similar manner by inducing a DSB or nick at or near the endogenous locus of the GA oxidase gene that is repaired imperfectly at a site that does not affect the coding sequence of the GA oxidase gene in a manner that would eliminate the function of the encoded GA oxidase protein. For example, the site of the DSB or nick within the endogenous locus may be in the upstream or 5' region of the GA oxidase gene (e.g., a promoter and/or enhancer sequence) to affect or reduce its level of expression. Similarly, such targeted knock-out or knock-down mutations of a GA oxidase gene may be generated with a donor template molecule to direct a particular or desired mutation at or near the target site via repair of the DSB or nick. The donor template molecule may comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a GA oxidase gene may be achieved by deleting or inverting at least a portion of the gene or by introducing a frame shift or premature stop codon into the coding sequence of the gene. A deletion of a portion of a GA oxidase gene may also be introduced by generating DSBs or nicks at two target sites and causing a deletion of the intervening target region flanked by the target sites.

A site-specific nuclease provided herein may be selected from the group consisting of a zinc-finger nuclease (ZFN), a meganuclease, an RNA-guided endonuclease, a TALE-endonuclease (TALEN), a recombinase, a transposase, or any combination thereof. See, e.g., Khandagale, K. et al., "Genome editing for targeted improvement in plants," *Plant Biotechnol Rep* 10: 327-343 (2016); and Gaj, T. et al., "ZFN, TALEN and CRISPR/Cas-based methods for genome engineering," *Trends Biotechnol.* 31(7): 397-405 (2013), the contents and disclosures of which are incorporated herein by reference. A recombinase may be a serine recombinase attached to a DNA recognition motif, a tyrosine recombinase attached to a DNA recognition motif or other recombinase enzyme known in the art. A recombinase or transposase may be a DNA transposase or recombinase attached to a DNA binding domain. A tyrosine recombinase attached to a DNA recognition motif may be selected from the group consisting of a Cre recombinase, a Flp recombinase, and a Tnp1 recombinase. According to some embodiments, a Cre recombinase or a Gin recombinase provided herein is tethered to a zinc-finger DNA binding domain. In another embodiment, a serine recombinase attached to a DNA recognition motif provided herein is selected from the group consisting of a PhiC31 integrase, an R4 integrase, and a TP-901 integrase. In another embodiment, a DNA transposase attached to a DNA binding domain provided herein is selected from the group consisting of a TALE-piggyBac and TALE-Mutator.

According to embodiments of the present disclosure, an RNA-guided endonuclease may be selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, and homologs or modified versions thereof, Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo) and homologs or modified versions thereof. According to some embodiments, an RNA-guided endonuclease may be a Cas9 or Cpf1 enzyme.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1. In another aspect, a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, an RNA-guided nuclease provided herein is selected from the group consisting of a Cas9 or a Cpf1. In another aspect, an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

For RNA-guided endonucleases, a guide RNA (gRNA) molecule is further provided to direct the endonuclease to a target site in the genome of the plant via base-pairing or hybridization to cause a DSB or nick at or near the target site. The gRNA may be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. As understood in the art, a "guide RNA" may comprise, for example, a CRISPR RNA (crRNA), a single-chain guide RNA (sgRNA), or any other RNA molecule that may guide or direct an endonuclease to a specific target site in the genome. A "single-chain guide RNA" (or "sgRNA") is a RNA molecule comprising a crRNA covalently linked a tracrRNA by a linker sequence, which may be expressed as a single RNA transcript or molecule. The guide RNA comprises a guide or targeting sequence that is identical or complementary to a target site within the plant genome, such as at or near a GA oxidase gene. A protospacer-adjacent motif (PAM) may be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. See, e.g., Wu, X. et al., "Target specificity of the CRISPR-Cas9 system," Quant Biol. 2(2): 59-70 (2014), the content and disclosure of which is incorporated herein by reference. The genomic PAM sequence on the sense (+) strand adjacent to the target site (relative to the targeting sequence of the guide RNA) may comprise 5'-NGG-3'. However, the corresponding sequence of the guide RNA (i.e., immediately downstream (3') to the targeting sequence of the guide RNA) may generally not be complementary to the genomic PAM sequence. The guide RNA may typically be a non-coding RNA molecule that does not encode a protein. The guide sequence of the guide RNA may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

For genome editing at or near the GA20 oxidase_3 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 34 or a sequence complementary thereto (e.g., 12, 13, 14, 15, 16, 17, 18, 19, 20, 21, 22, 23, 24, 25 or more consecutive nucleotides of SEQ ID NO: 34 or a sequence complementary thereto). For genome editing at or near the GA20 oxidase_5 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 35 or a sequence complementary thereto (e.g., 10, 11, 12, 13, 14, 15, 16, 17, 18, 19, 20, 21, 22, 23, 24, 25 or more consecutive nucleotides of SEQ ID NO: 35 or a sequence complementary thereto). As used herein, the term "consecutive" in reference to a polynucleotide or protein sequence means without deletions or gaps in the sequence.

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA20 oxidase_3 or GA20 oxidase_5 gene to mutate one or more promoter and/or regulatory sequences of the gene and affect or reduce its level of expression. For knockdown (and possibly knockout) of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3096 of SEQ ID NO: 34, the nucleotide sequence range 3666-3775 of SEQ ID NO: 34, the nucleotide sequence range 4098-5314 of SEQ ID NO: 34, the nucleotide sequence range 5585-5800 of SEQ ID NO: 34, or the nucleotide sequence range 5801-8800 of SEQ ID NO: 34, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3096, 3666-3775, 4098-5314, 5585-5800, 5801-8800, or 5585-8800 of SEQ ID NO: 34, or a sequence complementary thereto).

For knockdown (and possibly knockout) of the GA20 oxidase_5 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3000 of SEQ ID NO: 35, the nucleotide sequence range 1-3000 of SEQ ID NO: 35, the nucleotide sequence range 3792-3906 of SEQ ID NO: 35, the nucleotide sequence range 4476-5197 of SEQ ID NO: 35, or the nucleotide sequence range 5860-8859 of SEQ ID NO: 35, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3000, 3792-3906, 4476-5197, or 5860-8859 of SEQ ID NO: 35, or a sequence complementary thereto).

For knockout (and possibly knockdown) mutations through genome editing, an RNA-guided endonuclease may be targeted to a coding and/or intron sequence of a GA20 oxidase_3 or GA20 oxidase_5 gene to potentially eliminate expression and/or activity of a functional GA oxidase protein from the gene. However, a knockout of a GA oxidase gene expression may also be achieved in some cases by targeting the upstream and/or 5'UTR sequence(s) of the gene, or other sequences at or near the genomic locus of the gene. Thus, a knockout of a GA oxidase gene expression may be achieved by targeting a genomic sequence at or near the site or locus of a targeted GA20 oxidase_3 or GA20 oxidase_5 gene, an upstream or downstream sequence, such as a promoter and/or enhancer sequence, or an intron, 5'UTR, and/or 3'UTR sequence, of a GA20 oxidase_3 or GA20 oxidase_5 gene, as described above for knockdown of a GA20 oxidase_3 or GA20 oxidase_5 gene.

For knockout (and possibly knockdown) of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3097-5584 of SEQ ID NO: 34, the nucleotide sequence range 3097-3665 of SEQ ID NO: 34, the nucleotide sequence range 3776-4097 of SEQ ID NO: 34, or the nucleotide sequence range 5315-5584 of SEQ ID NO: 34, or a sequence complementary thereto (e.g., 10, 11, 12, 13, 14, 15, 16, 17, 18, 19, 20, 21, 22, 23, 24, 25 or more consecutive nucleotides within the nucleotide sequence range 3097-5584, 3097-3665, 3097-3775, 3665-4097, 3776-4097, 3776-5314, 4098-5584, or 5315-5584 of SEQ ID NO: 34, or a sequence complementary thereto).

For knockout (and possibly knockdown) of the GA20 oxidase_5 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3001-5473 of SEQ ID NO: 35, the nucleotide sequence range 3001-3791 of SEQ ID NO: 35, the nucleotide sequence range 3907-4475 of SEQ ID NO: 35, or the nucleotide sequence range 5198-5473 of SEQ ID NO: 35, or a sequence complementary thereto (e.g., 10, 11, 12, 13, 14, 15, 16, 17, 18, 19, 20, 21, 22, 23, 24, 25 or more consecutive nucleotides within the nucleotide sequence range 3001-5473, 3001-3791, 3001-3906, 3792-4475, 3907-4475, 3907-5197, 4476-5473, or 5198-5473 of SEQ ID NO: 35, or a sequence complementary thereto).

According to some embodiments, a guide RNA for targeting an endogenous GA20 oxidase_3 and/or GA20 oxidase_5 gene is provided comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 138-167.

For genome editing at or near the GA20 oxidase_4 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 38 or a sequence complementary thereto (e.g., 12, 13, 14, 15, 16, 17, 18, 19, 20, 21, 22, 23, 24, 25 or more consecutive nucleotides of SEQ ID NO: 38 or a sequence complementary thereto).

For knockout (and possibly knockdown) mutations through genome editing, an RNA-guided endonuclease may be targeted to a coding and/or intron sequence of a GA20 oxidase_4 gene to potentially eliminate expression and/or activity of a functional GA20 oxidase_4 protein from the gene. For the GA20 oxidase_4 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1544-2852 of SEQ ID NO: 38, the nucleotide sequence range 1544-1995 of SEQ ID NO: 38, the nucleotide sequence range 2084-2411 of SEQ ID NO: 38, or the nucleotide sequence range 2517-2852 of SEQ ID NO: 38, or a sequence complementary thereto (e.g., 10, 11, 12, 13, 14, 15, 16, 17, 18, 19, 20, 21, 22, 23, 24, 25 or more consecutive nucleotides within the nucleotide sequence range 1544-2852, 1544-1995, 1544-2083, 1996-2411, 2084-2411, 2084-2516, 2412-2852, or 2517-2852 of SEQ ID NO: 38, or a sequence complementary thereto).

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA20 oxidase_4 gene to mutate one or more promoter and/or regulatory sequences of the gene and affect or reduce its level of expression. For knockdown of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-1416 of SEQ ID NO: 38, the nucleotide sequence range 1417-1543 of SEQ ID NO: 38, the nucleotide sequence range 1996-2083 of SEQ ID NO: 38, the nucleotide sequence range 2412-2516 of SEQ ID NO: 38, the nucleotide sequence range 2853-3066 of SEQ ID NO: 38, or the nucleotide sequence range 3067-4465 of SEQ ID NO: 38, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-1416, 1417-1543, 1-1543, 1996-2083, 2412-2516, 2853-3066, 3067-4465 or 2853-4465 of SEQ ID NO: 38, or a sequence complementary thereto).

In addition to the guide sequence, a guide RNA may further comprise one or more other structural or scaffold sequence(s), which may bind or interact with an RNA-guided endonuclease. Such scaffold or structural sequences may further interact with other RNA molecules (e.g., tracrRNA). Methods and techniques for designing targeting constructs and guide RNAs for genome editing and site-directed integration at a target site within the genome of a plant using an RNA-guided endonuclease are known in the art.

According to some embodiments, recombinant DNA constructs and vectors are provided comprising a polynucleotide sequence encoding a site-specific nuclease, such as a zinc-finger nuclease (ZFN), a meganuclease, an RNA-guided endonuclease, a TALE-endonuclease (TALEN), a recombinase, or a transposase, wherein the coding sequence is operably linked to a plant expressible promoter. For RNA-guided endonucleases, recombinant DNA constructs and vectors are further provided comprising a polynucleotide sequence encoding a guide RNA, wherein the guide RNA comprises a guide sequence of sufficient length having a percent identity or complementarity to a target site within the genome of a plant, such as at or near a targeted GA oxidase gene. According to some embodiments, a polynucleotide sequence of a recombinant DNA construct and vector that encodes a site-specific nuclease or a guide RNA may be operably linked to a plant expressible promoter, such as an inducible promoter, a constitutive promoter, a tissue-specific promoter, etc.

According to some embodiments, a recombinant DNA construct or vector may comprise a first polynucleotide sequence encoding a site-specific nuclease and a second polynucleotide sequence encoding a guide RNA that may be introduced into a plant cell together via plant transformation techniques. Alternatively, two recombinant DNA constructs or vectors may be provided including a first recombinant DNA construct or vector and a second DNA construct or vector that may be introduced into a plant cell together or sequentially via plant transformation techniques, wherein the first recombinant DNA construct or vector comprises a polynucleotide sequence encoding a site-specific nuclease and the second recombinant DNA construct or vector comprises a polynucleotide sequence encoding a guide RNA. According to some embodiments, a recombinant DNA construct or vector comprising a polynucleotide sequence encoding a site-specific nuclease may be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA may be introduced via plant transformation techniques into a plant cell that already comprises (or is transformed with) a recombinant DNA construct or vector comprising a polynucleotide sequence encoding a site-specific nuclease. According to yet further embodiments, a first plant comprising (or transformed with) a recombinant DNA construct or vector comprising a polynucleotide sequence encoding a site-specific nuclease may be crossed with a second plant comprising (or transformed with) a recombinant DNA construct or vector comprising a polynucleotide sequence encoding a guide RNA. Such recombinant DNA constructs or vectors may be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif. The protein structure of the site-specific nuclease (or the fused/attached/tethered DNA binding domain) may target the site-specific nuclease to the target site. According to many of these embodiments, non-RNA-guided site-specific nucleases, such as recombinases, zinc finger nucleases (ZFNs), meganucleases, and TALENs, may be designed, engineered and constructed according to known methods to target and bind to a target site at or near the genomic locus of an endogenous GA oxidase gene of a corn or cereal plant, such as the GA20 oxidase_3 gene or the GA20 oxidase_5 gene in corn, to create a DSB or nick at such genomic locus to knockout or knockdown expression of the GA oxidase gene via repair of the DSB or nick. For example, an engineered site-specific nuclease, such as a recombinase, zinc finger nuclease (ZFN), meganuclease, or TALEN, may be designed to target and bind to (i) a target site within the genome of a plant corresponding to a sequence within SEQ ID NO: 34, or its complementary sequence, to create a DSB or nick at the genomic locus for the GA20 oxidase_3 gene, (ii) a target site within the genome of a plant corresponding to a sequence within SEQ ID NO: 35, or its complementary sequence, to create a DSB or nick at the genomic locus for the GA20 oxidase_5 gene, or (iii) a target site within the genome of a plant corresponding to a sequence within SEQ ID NO: 38, or its complementary sequence, to create a DSB or nick at the genomic locus for the GA20 oxidase_4 gene, which may then lead to the creation of a mutation or insertion of a sequence at the site of the DSB or nick, through cellular repair mechanisms, which may be guided by a donor molecule or template.

In an aspect, a targeted genome editing technique described herein may comprise the use of a recombinase. In some embodiments, a tyrosine recombinase attached, etc., to a DNA recognition domain or motif may be selected from the group consisting of a Cre recombinase, a Flp recombinase, and a Tnp1 recombinase. In an aspect, a Cre recombinase or a Gin recombinase provided herein may be tethered to a zinc-finger DNA binding domain. The Flp-FRT site-directed recombination system may come from the 2μ plasmid from the baker's yeast Saccharomyces cerevisiae. In this system, Flp recombinase (flippase) may recombine sequences between flippase recognition target (FRT) sites. FRT sites comprise 34 nucleotides. Flp may bind to the "arms" of the FRT sites (one arm is in reverse orientation) and cleaves the FRT site at either end of an intervening nucleic acid sequence. After cleavage, Flp may recombine nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase may recombine a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions −1, +2, +3, and +6 relative to the start of the zinc finger α-helix, which contribute to site-specific binding to the target site, can be changed and customized to fit specific target sequences. The other amino acids may form a consensus backbone to generate ZFNs with different sequence specificities. Methods and rules for designing ZFNs for targeting and binding to specific target sequences are known in the art. See, e.g., US Patent App. Nos. 2005/0064474, 2009/0117617, and 2012/0142062, the contents and disclosures of which are incorporated herein by reference. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or Agrobacterium-mediated transformation). The ZFNs may be introduced as ZFN proteins, as polynucleotides encoding ZFN proteins, and/or as combinations of proteins and protein-encoding polynucleotides.

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or Agrobacterium-mediated transformation).

TALENs are artificial restriction enzymes generated by fusing the transcription activator-like effector (TALE) DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also refers to one or both members of a pair of TALENs that work together to cleave DNA at the same site.

Transcription activator-like effectors (TALEs) can be engineered to bind practically any DNA sequence, such as at or near the genomic locus of a GA oxidase gene in a plant. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39:e82; and tale-nt.cac.cornell.edu/about. In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation). See, e.g., US Patent App. Nos. 2011/0145940, 2011/0301073, and 2013/0117869, the contents and disclosures of which are incorporated herein by reference.

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase. As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant. An "edit" or "genomic edit" in the singular refers to one such targeted mutation, deletion, inversion, substitution or insertion, whereas "edits" or "genomic edits" refers to two or more targeted mutation(s), deletion(s), inversion(s), substitution(s) and/or insertion(s), with each "edit" being introduced via a targeted genome editing technique.

Given that suppression of GA20 oxidase_3, GA20 oxidase_4, and/or GA20 oxidase_5 genes in corn produces plants having a shorter plant height and internode length in addition to other beneficial traits, it is proposed that expression of one or more of these genes may be reduced or eliminated through genome editing one or more of these gene(s) to provide similar beneficial traits to corn plants. Given further that constitutive expression of suppression constructs targeting these GA20 oxidase genes produces corn plants having the beneficial short height traits without off-types in the ear, and that expression directly in reproductive ear tissues also does not give rise to reproductive off-types, it is proposed that one or more of these gene loci may be edited to knock-down or knock-out their expression to produce similar effects in corn plants. Targeted gene editing approaches could be used to modify the sequence of the promoter and/or regulatory region(s) of one or more of the GA20 oxidase_3, GA20 oxidase_4, and/or GA20 oxidase_5 genes to knock-down or knock-out expression of these gene(s), such as through targeted deletions, insertions, mutations, or other sequence changes. Indeed, the promoter and/or regulatory region(s) or sequence(s), or the 5'-UTR, 3'UTR, and/or intron sequence(s), of one or more of the GA20 oxidase_3, GA20 oxidase_4, and/or GA20 oxidase_5 genes may be largely deleted or mutated. Alternatively, all or a portion of the coding (exon), 5-UTR, 3'UTR, and/or intron sequence(s) of one or more of the GA20 oxidase_3, GA20 oxidase_4, and/or GA20 oxidase_5 genes may be edited, deleted, mutated, or otherwise modified to knock-down or knock-out expression or activity of these gene(s). Such targeted modifications to the GA20 oxidase_3, GA20 oxidase_4, and/or GA20 oxidase_5 gene loci may be achieved using any suitable genome editing technology known in the art, such as via repair of a double strand break (DSB) or nick introduced by a site-specific nuclease, such as, for example, a zinc-finger nuclease, an engineered or native meganuclease, a TALE-endonuclease, or an RNA-guided endonuclease (e.g., Cas9 or Cpf1). Such repair of the DSB or nick may introduce spontaneous or stochastic deletions, additions, mutations, etc., at the targeted site where the DSB or nick was introduced, or repair of the site may involve the use of a donor template molecule to direct or cause a preferred or specific deletion, addition, mutation, etc., at the targeted site.

As provided herein, a plant transformed with a recombinant DNA molecule or transformation vector comprising a transgene encoding a transcribable DNA sequence encoding a non-coding RNA molecule that targets an endogenous GA oxidase gene for suppression may include a variety of monocot or cereal plants, such as maize/corn and other monocot or cereal plants that have separate male and female flowers (similarly to corn) and may thus be susceptible to off-types in female reproductive organs, structures or tissues with mutations to the GA pathway.

The present compositions and methods may be further applicable to other cereal plants that would benefit from a reduced plant height and/or increased resistance to lodging. Such plants may be transformed with recombinant DNA molecules or constructs to suppress one or more endogenous GA20 and/or GA3 oxidase genes in the plant according to the methods and approaches provided herein to produce a cereal plant that may be shorter and/or resistant to lodging. Indeed, a cereal plant ectopically expressing a transcribable DNA sequence encoding a non-coding RNA molecule that targets an endogenous GA oxidase gene for suppression may have a variety of beneficial traits, such as shorter stature or plant height, shorter internode length, increased stalk/stem diameter, improved lodging resistance, in addition to other improved yield-related and/or drought tolerant traits as provided herein, relative to a wild-type or control plant not having the transgene or transcribable DNA sequence. As described further below, cereal crop plants that have already been modified to have increased yield and resist lodging through mutations in the GA pathway, such as wheat, rice, millet, barley and sorghum, may instead be transformed with a recombinant DNA molecule or construct as provided herein. Unlike many of the GA pathway mutations in these crops which may be recessive, transgenic constructs expressing a suppression element targeting an endogenous biosynthetic GA oxidase gene in those crops may be dominant even when hemizygous or present in the plant as a single copy. Thus, plants that may be transformed with a recombinant DNA molecule or construct expressing a suppression construct may potentially include a variety of monocot or cereal crops. Having a dominant transgenic locus that causes a semi-dwarf, lodging resistant phenotype may be advantageous and preferred over a recessive mutant allele for the same phenotype due to benefits in breeding and trait integration.

According to embodiments of the present disclosure, it is further proposed that GA oxidase genes in other cereal plants having the greatest sequence identity/similarity to the GA20 oxidase_3, GA20 oxidase_4, GA20 oxidase_5, GA3 oxidase_1, and/or GA3 oxidase_2 genes in corn that are shown herein to produce a short stature, semi-dwarf phenotype and other beneficial traits when suppressed with a recombinant DNA suppression construct, may also be targets for suppression to produce transgenic cereal plants having similar semi-dwarf and/or lodging resistance phenotypes. Table 3 provides a list of GA oxidase genes from other cereal plants (sorghum—*Sorghum bicolor*; rice—*Oryza sativa*; foxtail millet—*Setaria Italica*; wheat—*Triticum aestivum*; and barley—*Hordeum vulgare*) having a high degree of sequence identity with one of the GA oxidase genes in corn that when suppressed produces a short stature, semi-dwarf phenotype.

TABLE 3

Homologs of corn GA oxidase genes from other cereal crop plants.

| Gene Name | Cereal Species | Corn Homolog | cDNA (SEQ ID NO) | CDS (SEQ ID NO) | Protein (SEQ ID NO) | Genomic (SEQ ID NO) |
|---|---|---|---|---|---|---|
| GA20 oxidase 2 | *Sorghum bicolor* | GA20 Ox_3/ GA20 Ox_5 | 84 | 85 | 86 | 87 |
| GA20 oxidase 2-like | *Setaria italica* | GA20 Ox_3/ GA20 Ox_5 | 88 | 89 | 90 | 91 |
| GA20 oxidase 2 | *Oryza sativa* | GA20 Ox_3/ GA20 Ox_5 | 92 | 93 | 94 | 95 |
| GA20 oxidase-D2 | *Triticum aestivum* | GA20 Ox_3/ GA20 Ox_5 | — | 96 | 97 | 98 |
| Fe2OG dioxygenase | *Hordeum vulgare* | GA20 Ox_3/ GA20 Ox_5 | 99 | 100 | 101 | — |
| Probable 2-ODD | *Sorghum bicolor* | GA20 Ox_4 | 102 | 103 | 104 | 105 |
| flavonol synthase/flavanone 3-hydroxylase-like | *Setaria italica* | GA20 Ox_4 | 106 | 107 | 108 | 109 |
| naringenin, 2-oxoglutamte 3-dioxygenase | *Oryza sativa* | GA20 Ox_4 | 110 | 111 | 112 | 113 |
| Fe2OG dioxygenase | *Triticum aestivum* | GA20 Ox_4 | 114 | 115 | 116 | 117 |

TABLE 3-continued

Homologs of corn GA oxidase genes from other cereal crop plants.

| Gene Name | Cereal Species | Corn Homolog | cDNA (SEQ ID NO) | CDS (SEQ ID NO) | Protein (SEQ ID NO) | Genomic (SEQ ID NO) |
|---|---|---|---|---|---|---|
| Fe2OG dioxygenase | *Hordeum vulgare* | GA20 Ox_4 | — | — | 118 | — |
| GA3-beta-dioxygenase 2-2 | *Sorghum bicolor* | GA3 Ox_1/ GA3 Ox_2 | 119 | 120 | 121 | 122 |
| GA3-beta-dioxygenase 2-2-like | *Setaria italica* | GA3 Ox-1/ GA3 Ox_2 | 123 | 124 | 125 | 126 |
| GA3-beta-dioxygenase 2-3 | *Oryza sativa* | GA3 Ox_1/ GA3 Ox_2 | 127 | 128 | 129 | 130 |
| GA3-beta-hydroxylase | *Hordeum vulgare* | GA3 Ox_1/ GA3 Ox_2 | 131 | 132 | 133 | — |
| GA3ox-D2 protein | *Triticum aestivum* | GA3 Ox_1/ GA3 Ox_2 | 134 | 135 | 136 | 137 |

According to another aspect of the present disclosure, a recombinant DNA molecule, vector or construct is provided for suppression of an endogenous GA oxidase (or GA oxidase-like) gene in a cereal plant, the recombinant DNA molecule, vector or construct comprising a transcribable DNA sequence encoding a non-coding RNA molecule, wherein the non-coding RNA molecule comprises a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of any one or more of SEQ ID NO: 84, 85, 87, 88, 89, 91, 92, 93, 95, 96, 98, 99, 100, 102, 103, 105, 106, 107, 109, 110, 111, 113, 114, 115, 119, 120, 122, 123, 124, 126, 127, 128, 130, 131, 132, 134, 135, and/or 137, and/or (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding a protein in the cereal plant that is at least 80%, at least 85%, at least 90%, at least 95%, at least 96%, at least 97%, at least 98%, at least 99%, at least 99.5%, or 100% identical to any one or more of SEQ ID NO: 86, 90, 94, 97, 101, 104, 108, 112, 116, 118, 121, 125, 129, 133, and/or 136. Likewise, a non-coding RNA molecule may target an endogenous GA oxidase (or GA oxidase-like) gene in a cereal plant having a percent identity to the GA oxidase gene(s) shown to affect plant height in corn. Thus, a non-coding RNA molecule is further provided comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous protein in a cereal plant that is at least 80%, at least 85%, at least 90%, at least 95%, at least 96%, at least 97%, at least 98%, at least 99%, at least 99.5%, or 100% identical to any one or more of SEQ ID NO: 9, 12, 15, 30, and/or 33. As mentioned above, the non-coding RNA molecule may target an exon, intron and/or UTR sequence of a GA oxidase (or GA oxidase-like) gene.

Further provided are methods for introducing or transforming into a cereal plant, plant part, or plant cell any of the foregoing constructs, vectors, or constructs, according to any of the methods described herein, which may be constructed in any suitable manner described herein including different stacking or joint targeting arrangements, as well as modified cereal plants, plant parts, plant tissues, and plant cells made thereby and/or comprising any such recombinant DNA molecule, vector or construct. Since a non-coding RNA molecule expressed from the above constructs would be designed to target an endogenous GA oxidase gene, the cereal plant transformed with such recombinant DNA molecules, vectors or constructs should preferably correspond to the species of origin for the target sequence, or closely related species, strains, germplasms, lines, etc. For example, a suppression construct complementary to SEQ ID NO: 84 should be used to transform a sorghum plant, such as a *Sorghum bicolor* plant, or perhaps related sorghum species, strains, etc., that would be expected to have a closely related or similar GA oxidase (or GA oxidase-like) gene sequence.

The genomic sequences for each of the above identified genes from cereal plants are further provided in Table 3, which may be used to target those genes for genome editing according to any known technique. Any site-specific nuclease and method may be used as described herein to generate a DSB or nick at or near the genomic locus for the gene, which may be repaired imperfectly or via template-mediated recombination to create mutations, etc., at, near or within the gene. Suitable nucleases may be selected from the group consisting of a zinc-finger nuclease (ZFN), a meganuclease, an RNA-guided endonuclease, a TALE-endonuclease (TALEN), a recombinase, a transposase, or any combination thereof. For an RNA-guided endonuclease, a recombinant DNA construct or vector is provided comprising a guide RNA may be used to direct the nuclease to the target site. Accordingly, a guide RNA for editing a GA oxidase (or GA-oxidase-like) gene in a cereal crop may comprise a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of any one or more of SEQ ID NO: 84, 85, 87, 88, 89, 91, 92, 93, 95, 96, 98, 99, 100, 102, 103, 105, 106, 107, 109, 110, 111, 113, 114, 115, 119, 120, 122, 123, 124, 126, 127, 128, 130, 131, 132, 134, 135, and/or 137. For site-specific nucleases that are not RNA-guided, such as a zinc-finger nuclease (ZFN), a meganuclease, a TALE-endonuclease (TALEN), a recombinase, and/or a transposase, the genomic target specificity for editing is determined by its protein structure, particularly its DNA binding domain. Such site-specific nucleases may be chosen, designed or engineered to bind and cut a desired target site at or near any of the above GA oxidase (or GA oxidase-like) genes within the genome of a cereal plant. Similar to transformation with a suppression construct, a cereal plant transformed with a particular guide RNA, or a recombinant DNA molecule, vector or construct encoding a guide RNA, should preferably be the species in which the targeted genomic sequence exists, or a closely related species, strain, germplasm, line, etc., such that the guide RNA is able to recognize and bind to the desired target cut site.

Further provided are methods for introducing or transforming into a cereal plant, plant part, or plant cell any guide RNA described above, or any construct, vector, or construct encoding such a guide RNA, perhaps in addition to an RNA-guided nuclease, according to any of the methods described herein, as well as modified cereal plants, plant parts, plant tissues, and plant cells made thereby and/or comprising any such recombinant DNA molecule, vector or construct and/or an edited GA oxidase (or GA oxidase-like) gene. Modified cereal plants having an edited GA oxidase (or GA oxidase-like) gene, and/or a suppression element targeting a GA oxidase (or GA oxidase-like) gene, may have one or more beneficial traits provided herein, such as a shorter plant height, shorter internode length, increased stalk/stem diameter, improved lodging resistance, and/or drought tolerance, relative to a wild-type or control plant not having any such edit or suppression element. In addition to genome editing, mutations in a GA oxidase (or GA oxidase-like) gene may be introduced through other mutagenesis techniques as described herein According to another aspect of the present disclosure, a transgenic plant(s), plant cell(s), seed(s), and plant part(s) are provided comprising a transformation event or insertion into the genome of at least one plant cell thereof, wherein the transformation event or insertion comprises a recombinant DNA sequence, construct or expression cassette comprising a transcribable DNA sequence encoding a non-coding RNA molecule that targets an endogenous GA oxidase gene for suppression, wherein the transcribable DNA sequence is operably linked to a plant-expressible promoter, such as a constitutive, vascular and/or leaf promoter. Such a transgenic plant may be produced by any suitable transformation method as provided above, to produce a transgenic $R_0$ plant, which may then be selfed or crossed to other plants to generate $R_1$ seed and subsequent progeny generations and seed through additional crosses, etc. Embodiments of the present disclosure further include a plant cell, tissue, explant, plant part, etc., comprising one or more transgenic cells having a transformation event or genomic insertion of a recombinant DNA or polynucleotide sequence comprising a transcribable DNA sequence encoding a non-coding RNA molecule that targets an endogenous GA oxidase gene for suppression.

Transgenic plants, plant cells, seeds, and plant parts of the present disclosure may be homozygous or hemizygous for a transgenic event or insertion of a transcribable DNA sequence for suppression of a GA oxidase gene into the genome of at least one plant cell thereof, or a targeted genome editing event, and plants, plant cells, seeds, and plant parts of the present embodiments may contain any number of copies of such transgenic event(s), insertion(s) and/or edit(s). The dosage or amount of expression of a transgene or transcribable DNA sequence may be altered by its zygosity and/or number of copies, which may affect the degree or extent of phenotypic changes in the transgenic plant, etc. As introduced above, transgenic plants provided herein may include a variety of monocot or cereal plants, and even crop plants, such as wheat, rice and sorghum, already having increased yield and/or lodging resistance due to prior breeding efforts and mutations of the GA pathway in these plants. Advantages of using a transgene or transcribable DNA sequence to express a suppression element targeting a biosynthetic GA oxidase gene include not only the ability to limit expression in a tissue-specific or tissue-preferred manner, but also the potential dominance (e.g., dominant negative effects) of a single or hemizygous copy of the transcribable DNA sequence to cause the beneficial short-stature, semi-dwarf traits or phenotypes in crop plants. Thus, recombinant DNA molecules or constructs of the present disclosure may be used to create beneficial traits in a variety of monocot or cereal plants without off-types using only a single copy of the transgenic event, insertion or construct. Unlike previously described mutations or alleles in the GA pathway that are recessive and require plants to be homozygous for the mutant allele, plants transformed with the GA-modifying transgenes and suppression constructs of the present disclosure may improve traits, yield and crop breeding efforts by facilitating the production of hybrid cereal plants since they only require a single or hemizygous copy of the transgene or suppression construct.

According to some embodiments, a transgenic or modified cereal or corn plant comprising a GA oxidase transgene or transcribable DNA sequence for suppression of an endogenous GA oxidase gene, or a genome edited GA oxidase gene, may be further characterized as having one or more beneficial traits, such as a shorter stature or semi-dwarf plant height, reduced internode length, increased stalk/stem diameter, improved lodging resistance, reduced green snap, deeper roots, increased leaf area, earlier canopy closure, increased foliar water content and/or higher stomatal conductance under water limiting conditions, reduced anthocyanin content and/or area in leaves under normal or nitrogen or water limiting stress conditions, improved yield-related traits including a larger female reproductive organ or ear, an increase in ear weight, harvest index, yield, seed or kernel number, and/or seed or kernel weight, relative to a wild type or control plant. Such a transgenic cereal or corn plant may further have increased stress tolerance, such as increased drought tolerance, nitrogen utilization, and/or tolerance to high density planting.

For purposes of the present disclosure, a "plant" includes an explant, plant part, seedling, plantlet or whole plant at any stage of regeneration or development. As used herein, a "transgenic plant" refers to a plant whose genome has been altered by the integration or insertion of a recombinant DNA molecule, construct or sequence. A transgenic plant includes an $R_0$ plant developed or regenerated from an originally transformed plant cell(s) as well as progeny transgenic plants in later generations or crosses from the $R_0$ transgenic plant. As used herein, a "plant part" may refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure may be viable, nonviable, regenerable, and/or non-regenerable. A "propagule" may include any plant part that can grow into an entire plant.

According to present embodiments, a plant cell transformed with a construct or molecule comprising a transcribable DNA sequence for suppression of an endogenous GA oxidase gene, or with a construct used for genome editing, may include any plant cell that is competent for transformation as understood in the art based on the method of transformation, such as a meristem cell, an embryonic cell, a callus cell, etc. As used herein, a "transgenic plant cell" simply refers to any plant cell that is transformed with a stably-integrated recombinant DNA molecule, construct or sequence. A transgenic plant cell may include an originally-transformed plant cell, a transgenic plant cell of a regenerated or developed $R_0$ plant, a transgenic plant cell cultured from another transgenic plant cell, or a transgenic plant cell from any progeny plant or offspring of the transformed $R_0$ plant, including cell(s) of a plant seed or embryo, or a cultured plant cell, callus cell, etc.

Embodiments of the present disclosure further include methods for making or producing transgenic or modified plants, such as by transformation, genome editing, crossing, etc., wherein the method comprises introducing a recombinant DNA molecule, construct or sequence comprising a GA oxidase transgene or a transcribable DNA sequence for suppression of an endogenous GA oxidase gene into a plant cell, or editing the genomic locus of an endogenous GA oxidase gene, and then regenerating or developing the transgenic or modified plant from the transformed or edited plant cell, which may be performed under selection pressure favoring a transgenic event. Such methods may comprise transforming a plant cell with a recombinant DNA molecule, construct or sequence comprising the transcribable DNA sequence for suppression of an endogenous GA oxidase gene, and selecting for a plant having one or more altered phenotypes or traits, such as one or more of the following traits at one or more stages of development: shorter or semi-dwarf stature or plant height, shorter internode length in one or more internode(s), increased stalk/stem diameter, improved lodging resistance, reduced green snap, deeper roots, increased leaf area, earlier canopy closure, increased foliar water content and/or higher stomatal conductance under water limiting conditions, reduced anthocyanin content and/or area in leaves under normal or nitrogen or water limiting stress conditions, improved yield-related traits including a larger female reproductive organ or ear, an increase in ear weight, harvest index, yield, seed or kernel number, and/or seed or kernel weight, increased stress tolerance, such as increased drought tolerance, increased nitrogen utilization, and/or increased tolerance to high density planting, as compared to a wild type or control plant.

According to another aspect of the present disclosure, methods are provided for planting a modified or transgenic plant(s) provided herein at a normal/standard or high density in field. According to some embodiments, the yield of a crop plant per acre (or per land area) may be increased by planting a modified or transgenic plant(s) of the present disclosure at a higher density in the field. As described herein, modified or transgenic plants expressing a transcribable DNA sequence that encodes a non-coding RNA molecule targeting an endogenous GA oxidase gene for suppression, or having a genome-edited GA oxidase gene, may have reduced plant height, shorter internode(s), increased stalk/stem diameter, and/or increased lodging resistance. It is proposed that modified or transgenic plants may tolerate high density planting conditions since an increase in stem diameter may resist lodging and the shorter plant height may allow for increased light penetrance to the lower leaves under high density planting conditions. Thus, modified or transgenic plants provided herein may be planted at a higher density to increase the yield per acre (or land area) in the field. For row crops, higher density may be achieved by planting a greater number of seeds/plants per row length and/or by decreasing the spacing between rows.

According to some embodiments, a modified or transgenic crop plant may be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified or transgenic crop plant may be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre. As an example, corn plants may be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

According to embodiments of the present disclosure, a modified corn plant(s) is/are provided that comprise (i) a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or (ii) an average stem or stalk diameter of at least 18 mm, at least 18.5 mm, at least 19 mm, at least 19.5 mm, at least 20 mm, at least 20.5 mm, at least 21 mm, at least 21.5 mm, or at least 22 mm. Stated a different way, a modified corn plant(s) is/are provided that comprise a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or an average stem or stalk diameter that is greater than 18 mm, greater than 18.5 mm, greater than 19 mm, greater than 19.5 mm, greater than 20 mm, greater than 20.5 mm, greater than 21 mm, greater than 21.5 mm, or greater than 22 mm. Any such plant height trait or range that is expressed in millimeters (mm) may be converted into a different unit of measurement based on known conversions (e.g., one inch is equal to 2.54 cm or 25.4 millimeters, and millimeters (mm), centimeters (cm) and meters (m) only differ by one or more powers of ten). Thus, any measurement provided herein is further described in terms of any other comparable units of measurement according to known and established conversions. However, the exact plant height and/or stem diameter of a modified corn plant may depend on the environment and genetic background. Thus, the change in plant height and/or stem diameter of a modified corn plant may instead be described in terms of a minimum difference or percent change relative to a control plant. A modified corn plant may further comprise at least one ear that is substantially free of male reproductive tissues or structures or other off-types.

According to embodiments of the present disclosure, modified corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant may be substantially free of off-types, such as male reproductive tissues or structures in one or more ears of the modified corn plant.

According to embodiments of the present disclosure, modified corn plants are provided that have (i) a plant height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a wild-type or control plant, and/or (ii) a stem or stalk diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of the wild-type or control plant. According to embodiments of the present disclosure, a modified corn plant may have a reduced plant height that is no more than 20%, 25%, 30%, 35%, 40%, 45%, 50%, 55%, or 60% shorter than the height of a wild-type or control plant, and/or a stem or stalk diameter that is less than (or not more than) 10%, 15%, 20%, 25%, 30%, 35%, 40%, 45%, 50%, 55%, 60%, 65%, 70%, 75%, 80%, 85%, 90%, 95%, or 100% greater than the stem or stalk diameter of a wild-type or control plant. For example, a modified plant may have (i) a plant height that is at least 10%, at least 15%, or at least 20% less or shorter (i.e., greater than or equal to 10%, 15%, or 20% shorter), but not greater or more than 50% shorter, than a wild type or control plant, and/or (ii) a stem or stalk diameter that is that is at least 5%, at least 10%, or at least 15% greater, but not more than 30%, 35%, or 40% greater, than a wild type or control plant. For clarity, the phrases "at least 20% shorter" and "greater than or equal to 20% shorter" would exclude, for example, 10% shorter. Likewise for clarity, the phrases "not greater than 50% shorter", "no more than 50% shorter" and "not more than 50% shorter" would exclude 60% shorter; the phrase "at least 5% greater" would exclude 2% greater; and the phrases "not more than 30% greater" and "no more than 30% greater" would exclude 40% greater.

According to embodiments of the present disclosure, modified corn plants are provided that comprise a height between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the height of a wild-type or control plant, and/or a stem or stalk diameter that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, between 50% and 75%, between 8% and 20%, or between 8% and 15% greater than the stem or stalk diameter of the wild-type or control plant.

According to embodiments of the present disclosure, modified corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a wild-type or control plant. The "minus-2 internode" of a corn plant refers to the second internode below the ear of the plant, and the "minus-4 internode" of a corn plant refers to the fourth internode below the ear of the plant According to many embodiments, modified corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a wild-type or control plant.

According to embodiments of the present disclosure, modified corn plants are provided that comprise an ear weight (individually or on average) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the ear weight of a wild-type or control plant. A modified corn plant provided herein may comprise an ear weight that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% greater than the ear weight of a wild-type or control plant.

According to embodiments of the present disclosure, modified corn or cereal plants are provided that have a harvest index of at least 0.57, at least 0.58, at least 0.59, at least 0.60, at least 0.61, at least 0.62, at least 0.63, at least 0.64, or at least 0.65 (or greater). A modified corn plant may comprise a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. A modified corn plant may have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant may have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a wild-type or control plant.

According to embodiments of the present disclosure, modified corn or cereal plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant may have an increase in harvestable yield between 1 and 10, between 1 and 8, between 2 and 8, between 2 and 6, between 2 and 5, between 2.5 and 4.5, or between 3 and 4 bushels per acre. A modified corn plant may have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant may have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a wild-type or control plant.

According to embodiments of the present disclosure, a modified cereal or corn plant is provided that has a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a wild-type or control plant. A modified cereal or corn plant may have a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a wild-type or control plant. Further provided are populations of cereal or corn plants having increased lodging resistance and a reduced lodging frequency. Populations of modified cereal or corn plants are provided having a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a population of wild-type or control plants. A population of modified corn plants may comprise a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a population of wild-type or control plants, which may be expressed as an average over a specified number of plants or crop area of equal density.

According to embodiments of the present disclosure, modified corn plants are provided having a significantly reduced or decreased plant height (e.g., 2000 mm or less) and a significantly increased stem diameter (e.g., 18 mm or more), relative to a wild-type or control plant. According to these embodiments, the decrease or reduction in plant height and increase in stem diameter may be within any of the height, diameter or percentage ranges recited herein. Such modified corn plants having a reduced plant height and increased stem diameter relative to a wild-type or control plant may be transformed with a transcribable DNA sequence encoding a non-coding RNA molecule that targets at least one GA20 oxidase gene and/or at least one GA3 oxidase gene for suppression. Modified corn plants having a significantly reduced plant height and/or a significantly increased stem diameter relative to a wild-type or control plant may further have at least one ear that is substantially free of male reproductive tissues or structures and/or other off-types. Modified corn plants having a significantly reduced plant height and/or an increased stem diameter relative to a wild-type or control plant may have reduced activity of one or more GA20 oxidase and/or GA3 oxidase gene(s) in one or more tissue(s) of the plant, such as one or more vascular and/or leaf tissue(s) of the plant, relative to the same tissue(s) of the wild-type or control plant. According to many embodiments, modified corn plants may comprise at least one polynucleotide or transcribable DNA sequence encoding a non-coding RNA molecule operably linked to a promoter, which may be a constitutive, tissue-specific or tissue-preferred promoter, wherein the non-coding RNA molecule targets at least one GA20 oxidase and/or GA3 oxidase gene(s) for suppression as provided herein. The non-coding RNA molecule may be a miRNA, siRNA, or miRNA or siRNA precursor molecule. According to some embodiments, modified corn plants having a significantly reduced plant height and/or an increased stem diameter relative to a wild-type or control plant may further have an increased harvest index and/or increased lodging resistance relative to the wild-type or control plant.

Modified corn or cereal plants having a significantly reduced plant height and/or a significantly increased stem diameter relative to a wild-type or control plant may comprise a mutation (e.g., an insertion, deletion, substitution, etc.) in a GA oxidase gene introduced through a gene editing technology or other mutagenesis technique, wherein expression of the GA oxidase gene is reduced or eliminated in one or more tissues of the modified plant. Such modified corn plants having a reduced plant height and/or an increased stem diameter relative to a wild-type or control plant may further have an increased harvest index and/or increased lodging resistance relative to the wild-type or control plant. Such modified corn plants may be substantially free of off-types, such as male reproductive tissues or structures and/or other off-types in at least one ear of the modified plants. Plant mutagenesis techniques (excluding genome editing) may include chemical mutagenesis (i.e., treatment with a chemical mutagen, such as an azide, hydroxylamine, nitrous acid, acridine, nucleotide base analog, or alkylating agent—e.g., EMS (ethylmethane sulfonate), MNU (N-methyl-N-nitrosourea), etc.), physical mutagenesis (e.g., gamma rays, X-rays, UV, ion beam, other forms of radiation, etc.), and insertional mutagenesis (e.g., transposon or T-DNA insertion). Plants or various plant parts, plant tissues or plant cells may be subjected to mutagenesis. Treated plants may be reproduced to collect seeds or produce a progeny plant, and treated plant parts, plant tissues or plant cells may be developed or regenerated into plants or other plant tissues. Mutations generated with chemical or physical mutagenesis techniques may include a frameshift, missense or nonsense mutation leading to loss of function or expression of a targeted gene, such as a GA3 or GA20 oxidase gene.

One method for mutagenesis of a gene is called "TILL-ING" (for targeting induced local lesions in genomes), in which mutations are created in a plant cell or tissue, preferably in the seed, reproductive tissue or germline of a plant, for example, using a mutagen, such as an EMS treatment. The resulting plants are grown and self-fertilized, and the progeny are used to prepare DNA samples. PCR amplification and sequencing of a nucleic acid sequence of a GA oxidase gene may be used to identify whether a mutated plant has a mutation in the GA oxidase gene. Plants having mutations in the GA oxidase gene may then be tested for an altered trait, such as reduced plant height. Alternatively, mutagenized plants may be tested for an altered trait, such as reduced plant height, and then PCR amplification and sequencing of a nucleic acid sequence of a GA oxidase gene may be used to determine whether a plant having the altered trait also has a mutation in the GA oxidase gene. See, e.g., Colbert et al., 2001, *Plant Physiol* 126:480-484; and McCallum et al., 2000, Nature Biotechnology 18:455-457. TILLING can be used to identify mutations that alter the expression a gene or the activity of proteins encoded by a gene, which may be used to introduce and select for a targeted mutation in a GA oxidase gene of a corn or cereal plant.

Corn or cereal plants that have been subjected to a mutagenesis or genome editing treatment may be screened and selected based on an observable phenotype (e.g., any phenotype described herein, such as shorter plant height, increased stem/stalk diameter, etc.), or using a selection agent with a selectable marker (e.g., herbicide, etc.), a screenable marker, or a molecular technique (e.g., lower GA levels, lower GA oxidase transcript or protein levels, presence of transgene or transcribable sequence, etc.). Such screening and/or selecting techniques may be used to identify and select plants having a mutation in a GA oxidase gene that leads to a desirable plant phenotype.

According to embodiments of the present disclosure, a population of modified corn or cereal plants are provided, wherein the population of modified corn or cereal plants have an average plant height that is significantly less, and/or an average stem or stalk diameter that is significantly more, than a population of wild-type or control plants. The population of modified corn or cereal plants may share ancestry with a single modified corn or cereal plant and/or have a single transgenic GA oxidase suppression construct insertion, event or edit in common. Modified corn plants within a population of modified corn plants may generally comprise at least one ear that is substantially free of male reproductive tissues or structures and/or other off-types. A population of modified corn or cereal plants may have increased lodging resistance on average or per number of plants or field area than a population of wild-type or control plants. The population of modified corn or cereal plants may have a lodging frequency that is at least 5%, at least 10%, at least 20%, at least 30%, at least 40%, at least 50%, at least 60%, at least 70% at least 80%, at least 90%, or 100% less (or lower) than a population of control corn or cereal plants. A population of modified corn plants may have a harvest index of at least 0.57 or greater.

According to embodiments of the present invention, modified corn or cereal plants are provided having a reduced gibberellin content (in active form) in at least the stem and internode tissue(s), such as the stem, internode, leaf and/or vascular tissue(s), as compared to the same tissue(s) of wild-type or control plants. According to many embodiments, modified corn or cereal plants are provided having a significantly reduced plant height and/or a significantly increased stem diameter relative to wild-type or control plants, wherein the modified corn or cereal plants further have significantly reduced or decreased level(s) of active gibberellins or active GAs (e.g., one or more of GA1, GA3, GA4, and/or GA7) in one or more stem, internode, leaf and/or vascular tissue(s), relative to the same tissue(s) of the wild-type or control plants. For example, the level of one or more active GAs in the stem, internode, leaf and/or vascular tissue(s) of a modified corn or cereal plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn plant.

According to some embodiments, a modified corn or cereal plant may comprise an active gibberellin (GA) level(s) (e.g., one or more of GA1, GA3, GA4, and/or GA7) in one or more stem, internode, leaf and/or vascular tissue(s) that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or (or lower) than in the same tissue(s) of a wild-type or control corn plant. A modified corn or cereal plant having a reduced active gibberellin (GA) level(s) in one or more stem, internode, leaf and/or vascular tissue(s) may further be substantially free of off-types, such as male reproductive tissues or structures and/or other off-types in at least one ear of a modified corn plant.

According to embodiments of the present disclosure, modified corn or cereal plants are provided having a significantly reduced or eliminated expression level of one or more GA3 oxidase and/or GA20 oxidase gene transcript(s) and/or protein(s) in one or more tissue(s), such as one or more stem, internode, leaf and/or vascular tissue(s), of the modified plants, as compared to the same tissue(s) of wild-type or control plants. According to many embodiments, a modified corn or cereal plant is provided comprising a significantly reduced plant height and/or a significantly increased stem diameter relative to wild-type or control plants, wherein the modified corn or cereal plant has a significantly reduced or eliminated expression level of one or more GA20 oxidase and/or GA3 oxidase gene transcript(s) and/or protein(s) in one or more tissues, such as one or more stem, internode, leaf and/or vascular tissue(s), of the modified plant, as compared to the same tissue(s) of a wild-type or control corn plant. For example, a modified corn or cereal plant has a significantly reduced or eliminated expression level of a GA20 oxidase_3 and/or GA20 oxidase_5 gene transcript(s) and/or protein(s), and/or a significantly reduced or eliminated expression level of a GA3 oxidase_1 and/or GA3 oxidase_2 gene transcript(s) and/or protein(s), in one or more stem, internode, leaf and/or vascular tissue(s) of the modified plant, as compared to the same tissue(s) of a wild-type or control plant. For example, the level of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn or cereal plant.

According to some embodiments, a modified corn or cereal plant may comprise level(s) of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or lower than in the same tissue(s) of a wild-type or control corn or cereal plant. A modified corn or cereal plant having a reduced or eliminated expression level of at least one GA20 oxidase and/or GA3 oxidase gene(s) in one or more tissue(s), may also be substantially free of off-types, such as male reproductive tissues or structures and/or other off-types in at least one ear of the modified corn plant.

According to some embodiments, methods are provided comprising reducing or eliminating the expression of at least one GA20 oxidase gene and/or at least one GA3 oxidase gene in a crop plant, such as in one or more stem, internode, vascular and/or leaf tissue of the crop plant, wherein the expression of the at least one GA20 oxidase gene and/or at least one GA3 oxidase gene(s) is/are not significantly altered or changed in at least one reproductive tissue of the plant, and/or wherein the level(s) of one or more active GAs is/are not significantly altered or changed in at least one reproductive tissue of the plant, as compared to a wild-type or control plant. According to many embodiments, the expression level(s) of at least one GA20 oxidase or GA3 oxidase gene is reduced or eliminated in at least one tissue of a modified plant with a recombinant DNA construct comprising a transcribable DNA sequence encoding a suppression element for the GA20 oxidase or GA3 oxidase gene, such as at least one mature miRNA or miRNA precursor that is processed into a mature miRNA, wherein the miRNA is able to reduce or suppress the expression level of the at least one GA20 oxidase or GA3 oxidase gene, and wherein the transcribable DNA sequence is operably linked to a constitutive, tissue-specific or tissue-preferred promoter.

Methods and techniques are provided for screening for, and/or identifying, cells or plants, etc., for the presence of targeted edits or transgenes, and selecting cells or plants comprising targeted edits or transgenes, which may be based on one or more phenotypes or traits, or on the presence or absence of a molecular marker or polynucleotide or protein sequence in the cells or plants. Nucleic acids can be isolated and detected using techniques known in the art. For example, nucleic acids can be isolated and detected using, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis. Any method known in the art may be used to screen for, and/or identify, cells, plants, etc., having a transgene or genome edit in its genome, which may be based on any suitable form of visual observation, selection, molecular technique, etc.

In some embodiments, methods are provided for detecting recombinant nucleic acids and/or polypeptides in plant cells. For example, nucleic acids may be detected using hybridization probes or through production of amplicons using PCR with primers as known in the art. Hybridization between nucleic acids is discussed in Sambrook et al. (1989, Molecular Cloning: A Laboratory Manual, 2nd Ed., Cold Spring Harbor Laboratory Press, Cold Spring Harbor, NY). Polypeptides can be detected using antibodies. Techniques for detecting polypeptides using antibodies include enzyme linked immunosorbent assays (ELISAs), Western blots, immunoprecipitations, immunofluorescence, and the like. An antibody provided herein may be a polyclonal antibody or a monoclonal antibody. An antibody having specific binding affinity for a polypeptide provided herein can be generated using methods known in the art. An antibody or hybridization probe may be attached to a solid support, such as a tube, plate or well, using methods known in the art.

Detection (e.g., of an amplification product, of a hybridization complex, of a polypeptide) can be accomplished using detectable labels that may be attached or associated with a hybridization probe or antibody. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified, edited or transgenic plants or plant cells can be through any methodologies known to those skilled in the art of molecular biology. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina®, PacBio®, Ion Torrent™, etc.) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known in the art.

EMBODIMENTS

The following paragraphs list a subset of exemplary embodiments.

Embodiment 1. A recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in a cereal plant or plant cell, the endogenous GA20 oxidase protein being at least 80%, at least 85%, at least 90%, at least 95%, at least 96%, at least 97%, at least 98%, at least 99%, at least 99.5%, or 100% identical to SEQ ID NO: 9, and wherein the transcribable DNA sequence is operably linked to a plant-expressible promoter.

Embodiment 2. The recombinant DNA construct of Embodiment 1, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 or SEQ ID NO: 8.

Embodiment 3. The recombinant DNA construct of Embodiment 1, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in a monocot or cereal plant or plant cell, the endogenous GA20 oxidase protein being at least 80%, at least 85%, at least 90%, at least 95%, at least 96%, at least 97%, at least 98%, at least 99%, at least 99.5%, or 100% identical to SEQ ID NO: 15.

Embodiment 4. The recombinant DNA construct of Embodiment 3, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or SEQ ID NO: 14.

Embodiment 5. The recombinant DNA construct of Embodiment 1, wherein the plant-expressible promoter is a vascular promoter.

Embodiment 6. The recombinant DNA construct of Embodiment 5, wherein the vascular promoter comprises one of the following: a sucrose synthase promoter, a sucrose transporter promoter, a Sh1 promoter, Commelina yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, or a rice yellow stripe 2 (OsYSL2) promoter.

Embodiment 7. The recombinant DNA construct of Embodiment 5, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70, or SEQ ID NO: 71, or a functional portion thereof.

Embodiment 8. The recombinant DNA construct of Embodiment 1, wherein the plant-expressible promoter is a RTBV promoter.

Embodiment 9. The recombinant DNA construct of Embodiment 8, wherein the plant-expressible promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

Embodiment 10. The recombinant DNA construct of Embodiment 1, wherein the plant-expressible promoter is a leaf promoter.

Embodiment 11. The recombinant DNA construct of Embodiment 10, wherein the leaf promoter comprises one of the following: a RuBisCO promoter, a PPDK promoter, a FDA promoter, a Nadh-Gogat promoter, a chlorophyll a/b binding protein gene promoter, a phosphoenolpyruvate carboxylase (PEPC) promoter, or a Myb gene promoter.

Embodiment 12. The recombinant DNA construct of Embodiment 10, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

Embodiment 13. The recombinant DNA construct of Embodiment 1, wherein the plant-expressible promoter is a constitutive promoter.

Embodiment 14. The recombinant DNA construct of Embodiment 13, wherein the constitutive promoter is selected from the group consisting of: an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, or a maize alcohol dehydrogenase, or a functional portion thereof.

Embodiment 15. The recombinant DNA construct of Embodiment 13, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

Embodiment 16. The recombinant DNA construct of Embodiment 1, wherein the non-coding RNA molecule encoded by the transcribable DNA sequence is a precursor miRNA or siRNA that is processed or cleaved in a plant cell to form a mature miRNA or siRNA.

Embodiment 17. A transformation vector comprising the recombinant DNA construct of Embodiment 1.

Embodiment 18. A transgenic cereal plant, plant part or plant cell comprising the recombinant DNA construct of Embodiment 1.

Embodiment 19. The transgenic cereal plant of Embodiment 18, wherein the transgenic plant has one or more of the following traits relative to a control plant: shorter plant height, increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content, and area in leaves under normal or nitrogen-limiting or water-limiting stress conditions, increased ear weight, increased harvest index, increased yield, increased seed number, increased seed weight, and/or increased prolificacy.

Embodiment 20. The transgenic cereal plant of Embodiment 18, wherein the transgenic plant has a shorter plant height and/or improved lodging resistance.

Embodiment 21. The transgenic cereal plant of Embodiment 18, wherein the height of the transgenic plant is at least 10%, at least 20%, at least 25%, at least 30%, at least 35%, or at least 40% shorter than a wild-type control plant.

Embodiment 22. The transgenic cereal plant of Embodiment 18, wherein the stalk or stem diameter of the transgenic plant at one or more stem internodes is at least 5%, at least 10%, at least 15%, at least 20%, at least 25%, at least 30%, at least 35%, or at least 40% greater than the stalk or stem diameter at the same one or more internodes of a wild-type control plant.

Embodiment 23. The transgenic cereal plant of any one of Embodiments 18, wherein the transgenic cereal plant is a corn plant, and wherein the stalk or stem diameter of the transgenic corn plant at one or more of the first, second, third, and/or fourth internode below the ear is at least 5%, at least 10%, at least 15%, at least 20%, at least 25%, at least 30%, at least 35%, or at least 40% greater than the same internode of a wild-type control plant.

Embodiment 24. The transgenic cereal plant of Embodiment 18, wherein the level of one or more active GAs in at least one internode tissue of the stem or stalk of the transgenic plant is lower than the same internode tissue of a wild-type control plant.

Embodiment 25. The transgenic cereal plant of Embodiment 18, wherein the level of one or more active GAs in at least one internode tissue of the stem or stalk of the transgenic plant is at least 5%, at least 10%, at least 15%, at least 20%, at least 25%, at least 30%, at least 35%, or at least 40% lower than the same internode tissue of a wild-type control plant.

Embodiment 26. A transgenic corn plant, plant part or plant cell comprising the recombinant DNA construct of Embodiment 1.

Embodiment 27. A method for producing a transgenic cereal plant, comprising: (a) transforming at least one cell of an explant with the recombinant DNA construct of Embodiment 1, and (b) regenerating or developing the transgenic cereal plant from the transformed explant.

Embodiment 28. The method of Embodiment 25, wherein the cereal plant is transformed via *Agrobacterium* mediated transformation or particle bombardment.

Embodiment 29. A recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in a monocot or cereal plant or plant cell, the endogenous GA20 oxidase protein being at least 80%, at least 85%, at least 90%, at least 95%, at least 96%, at least 97%, at least 98%, at least 99%, at least 99.5%, or 100% identical to SEQ ID NO: 15, and wherein the transcribable DNA sequence is operably linked to a plant-expressible promoter.

Embodiment 30. The recombinant DNA construct of Embodiment 29, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or SEQ ID NO: 14.

Embodiment 31. The recombinant DNA construct of Embodiment 29, wherein the plant-expressible promoter is a vascular promoter.

Embodiment 32. The recombinant DNA construct of Embodiment 31, wherein the vascular promoter comprises one of the following: a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, or a rice yellow stripe 2 (OsYSL2) promoter.

Embodiment 33. The recombinant DNA construct of Embodiment 31, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70, or SEQ ID NO: 71, or a functional portion thereof.

Embodiment 34. The recombinant DNA construct of Embodiment 29, wherein the plant-expressible promoter is a RTBV promoter.

Embodiment 35. The recombinant DNA construct of Embodiment 34, wherein the plant-expressible promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

Embodiment 36. The recombinant DNA construct of Embodiment 29, wherein the plant-expressible promoter is a leaf promoter.

Embodiment 37. The recombinant DNA construct of Embodiment 36, wherein the leaf promoter comprises one of the following: a RuBisCO promoter, a PPDK promoter, a FDA promoter, a Nadh-Gogat promoter, a chlorophyll a/b binding protein gene promoter, a phosphoenolpyruvate carboxylase (PEPC) promoter, or a Myb gene promoter.

Embodiment 38. The recombinant DNA construct of Embodiment 36, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

Embodiment 39. The recombinant DNA construct of Embodiment 29, wherein the plant-expressible promoter is a constitutive promoter.

Embodiment 40. The recombinant DNA construct of Embodiment 39, wherein the constitutive promoter is selected from the group consisting of: an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, or a maize alcohol dehydrogenase, or a functional portion thereof.

Embodiment 41. The recombinant DNA construct of Embodiment 39, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

Embodiment 42. The recombinant DNA construct of Embodiment 29, wherein the non-coding RNA molecule encoded by the transcribable DNA sequence is a precursor miRNA or siRNA that is processed or cleaved in a plant cell to form a mature miRNA or siRNA.

Embodiment 43. A transformation vector comprising the recombinant DNA construct of Embodiment 29.

Embodiment 44. A transgenic cereal plant, plant part or plant cell comprising the recombinant DNA construct of Embodiment 29.

Embodiment 45. The transgenic cereal plant of Embodiment 44, wherein the transgenic plant has one or more of the following traits relative to a control plant: shorter plant height, increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, and/or increased prolificacy.

Embodiment 46. The transgenic cereal plant of Embodiment 44, wherein the transgenic plant has a shorter plant height and/or improved lodging resistance.

Embodiment 47. The transgenic cereal plant of Embodiment 44, wherein the height of the transgenic plant is at least 10%, at least 20%, at least 25%, at least 30%, at least 35%, or at least 40% shorter than a wild-type control plant.

Embodiment 48. The transgenic cereal plant of Embodiment 44, wherein the stalk or stem diameter of the transgenic plant at one or more stem internodes is at least 5%, at least 10%, at least 15%, at least 20%, at least 25%, at least 30%, at least 35%, or at least 40% greater than the stalk or stem diameter at the same one or more internodes of a wild-type control plant.

Embodiment 49. The transgenic cereal plant of any one of Embodiments 44, wherein the transgenic cereal plant is a corn plant, and wherein the stalk or stem diameter of the transgenic corn plant at one or more of the first, second, third, and/or fourth internode below the ear is at least 5%, at least 10%, at least 15%, at least 20%, at least 25%, at least 30%, at least 35%, or at least 40% greater than the same internode of a wild-type control plant.

Embodiment 50. The transgenic cereal plant of Embodiment 44, wherein the level of one or more active GAs in at least one internode tissue of the stem or stalk of the transgenic plant is lower than the same internode tissue of a wild-type control plant.

Embodiment 51. The transgenic cereal plant of Embodiment 44, wherein the level of one or more active GAs in at least one internode tissue of the stem or stalk of the transgenic plant is at least 5%, at least 10%, at least 15%, at least 20%, at least 25%, at least 30%, at least 35%, or at least 40% lower than the same internode tissue of a wild-type control plant.

Embodiment 52. A transgenic corn plant, plant part or plant cell comprising the recombinant DNA construct of Embodiment 29.

Embodiment 53. A method for producing a transgenic cereal plant, comprising: (a) transforming at least one cell of an explant with the recombinant DNA construct of Embodiment 29, and (b) regenerating or developing the transgenic cereal plant from the transformed explant.

Embodiment 54. The method of Embodiment 29, wherein the cereal plant is transformed via *Agrobacterium* mediated transformation or particle bombardment.

Embodiment 55. A recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in a monocot or cereal plant or plant cell, the endogenous GA3 oxidase protein being at least 80%, at least 85%, at least 90%, at least 95%, at least 96%, at least 97%, at least 98%, at least 99%, at least 99.5%, or 100% identical to SEQ ID NO: 30 or 33, and wherein the transcribable DNA sequence is operably linked to a plant-expressible promoter.

Embodiment 56. The recombinant DNA construct of Embodiment 55, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 28, 29, 31 or 32.

Embodiment 57. The recombinant DNA construct of Embodiment 55, wherein the plant-expressible promoter is a vascular promoter.

Embodiment 58. The recombinant DNA construct of Embodiment 57, wherein the vascular promoter comprises one of the following: a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, or a rice yellow stripe 2 (OsYSL2) promoter.

Embodiment 59. The recombinant DNA construct of Embodiment 57, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70, or SEQ ID NO: 71, or a functional portion thereof.

Embodiment 60. The recombinant DNA construct of Embodiment 55, wherein the plant-expressible promoter is a RTBV promoter.

Embodiment 61. The recombinant DNA construct of Embodiment 60, wherein the plant-expressible promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

Embodiment 62. The recombinant DNA construct of Embodiment 55, wherein the plant-expressible promoter is a leaf promoter.

Embodiment 63. The recombinant DNA construct of Embodiment 62, wherein the leaf promoter comprises one of the following: a RuBisCO promoter, a PPDK promoter, a FDA promoter, a Nadh-Gogat promoter, a chlorophyll a/b binding protein gene promoter, a phosphoenolpyruvate carboxylase (PEPC) promoter, or a Myb gene promoter.

Embodiment 64. The recombinant DNA construct of Embodiment 62, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

Embodiment 65. The recombinant DNA construct of Embodiment 55, wherein the plant-expressible promoter is a constitutive promoter.

Embodiment 66. The recombinant DNA construct of Embodiment 65, wherein the constitutive promoter is selected from the group consisting of: an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, or a maize alcohol dehydrogenase, or a functional portion thereof.

Embodiment 67. The recombinant DNA construct of Embodiment 65, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

Embodiment 68. The recombinant DNA construct of Embodiment 55, wherein the non-coding RNA molecule encoded by the transcribable DNA sequence is a precursor miRNA or siRNA that is processed or cleaved in a plant cell to form a mature miRNA or siRNA.

Embodiment 69. A transformation vector comprising the recombinant DNA construct of Embodiment 55.

Embodiment 70. A transgenic cereal plant, plant part or plant cell comprising the recombinant DNA construct of Embodiment 55.

Embodiment 71. The transgenic cereal plant of Embodiment 70, wherein the transgenic plant has one or more of the following traits relative to a control plant: shorter plant height, increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, and/or increased prolificacy.

Embodiment 72. The transgenic cereal plant of Embodiment 70, wherein the transgenic plant has a shorter plant height and/or improved lodging resistance.

Embodiment 73. The transgenic cereal plant of Embodiment 70, wherein the height of the transgenic plant is at least 10%, at least 20%, at least 25%, at least 30%, at least 35%, or at least 40% shorter than a wild-type control plant.

Embodiment 74. The transgenic cereal plant of Embodiment 70, wherein the stalk or stem diameter of the transgenic plant at one or more stem internodes is at least 5%, at least 10%, at least 15%, at least 20%, at least 25%, at least 30%, at least 35%, or at least 40% greater than the stalk or stem diameter at the same one or more internodes of a wild-type control plant.

Embodiment 75. The transgenic cereal plant of any one of Embodiments 70, wherein the transgenic cereal plant is a corn plant, and wherein the stalk or stem diameter of the transgenic corn plant at one or more of the first, second, third, and/or fourth internode below the ear is at least 5%, at least 10%, at least 15%, at least 20%, at least 25%, at least 30%, at least 35%, or at least 40% greater than the same internode of a wild-type control plant.

Embodiment 76. The transgenic cereal plant of Embodiment 70, wherein the level of one or more active GAs in at least one internode tissue of the stem or stalk of the transgenic plant is lower than the same internode tissue of a wild-type control plant.

Embodiment 77. The transgenic cereal plant of Embodiment 70, wherein the level of one or more active GAs in at least one internode tissue of the stem or stalk of the transgenic plant is at least 5%, at least 10%, at least 15%, at least 20%, at least 25%, at least 30%, at least 35%, or at least 40% lower than the same internode tissue of a wild-type control plant.

Embodiment 78. A transgenic corn plant, plant part or plant cell comprising the recombinant DNA construct of Embodiment 55.

Embodiment 79. A method for producing a transgenic cereal plant, comprising: (a) transforming at least one cell of an explant with the recombinant DNA construct of Embodiment 55, and (b) regenerating or developing the transgenic cereal plant from the transformed explant.

Embodiment 80. The method of Embodiment 79, wherein the cereal plant is transformed via *Agrobacterium* mediated transformation or particle bombardment.

Embodiment 81. A recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in a monocot or cereal plant or plant cell, the endogenous GA20 oxidase protein being at least 80%, at least 85%, at least 90%, at least 95%, at least 96%, at least 97%, at least 98%, at least 99%, at least 99.5%, or 100% identical to SEQ ID NO: 12, and wherein the transcribable DNA sequence is operably linked to a plant-expressible promoter.

Embodiment 82. The recombinant DNA construct of Embodiment 81, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 10 or 11.

Embodiment 83. The recombinant DNA construct of Embodiment 81, wherein the plant-expressible promoter is a vascular promoter.

Embodiment 84. The recombinant DNA construct of Embodiment 83, wherein the vascular promoter comprises one of the following: a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, or a rice yellow stripe 2 (OsYSL2) promoter.

Embodiment 85. The recombinant DNA construct of Embodiment 83, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70, or SEQ ID NO: 71, or a functional portion thereof.

Embodiment 86. The recombinant DNA construct of Embodiment 81, wherein the plant-expressible promoter is a RTBV promoter.

Embodiment 87. The recombinant DNA construct of Embodiment 86, wherein the plant-expressible promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

Embodiment 88. The recombinant DNA construct of Embodiment 81, wherein the plant-expressible promoter is a leaf promoter.

Embodiment 89. The recombinant DNA construct of Embodiment 88, wherein the leaf promoter comprises one of the following: a RuBisCO promoter, a PPDK promoter, a FDA promoter, a Nadh-Gogat promoter, a chlorophyll a/b binding protein gene promoter, a phosphoenolpyruvate carboxylase (PEPC) promoter, or a Myb gene promoter.

Embodiment 90. The recombinant DNA construct of Embodiment 88, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

Embodiment 91. The recombinant DNA construct of Embodiment 81, wherein the plant-expressible promoter is a constitutive promoter.

Embodiment 92. The recombinant DNA construct of Embodiment 91, wherein the constitutive promoter is selected from the group consisting of: an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, or a maize alcohol dehydrogenase, or a functional portion thereof.

Embodiment 93. The recombinant DNA construct of Embodiment 91, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

Embodiment 94. The recombinant DNA construct of Embodiment 81, wherein the non-coding RNA molecule encoded by the transcribable DNA sequence is a precursor miRNA or siRNA that is processed or cleaved in a plant cell to form a mature miRNA or siRNA.

Embodiment 95. A transformation vector comprising the recombinant DNA construct of Embodiment 81.

Embodiment 96. A transgenic cereal plant, plant part or plant cell comprising the recombinant DNA construct of Embodiment 81.

Embodiment 97. The transgenic cereal plant of Embodiment 96, wherein the transgenic plant has one or more of the following traits relative to a control plant: shorter plant height, increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, and/or increased prolificacy.

Embodiment 98. The transgenic cereal plant of Embodiment 96, wherein the transgenic plant has a shorter plant height and/or improved lodging resistance.

Embodiment 99. The transgenic cereal plant of Embodiment 96, wherein the height of the transgenic plant is at least 10%, at least 20%, at least 25%, at least 30%, at least 35%, or at least 40% shorter than a wild-type control plant.

Embodiment 100. The transgenic cereal plant of Embodiment 96, wherein the stalk or stem diameter of the transgenic plant at one or more stem internodes is at least 5%, at least 10%, at least 15%, at least 20%, at least 25%, at least 30%, at least 35%, or at least 40% greater than the stalk or stem diameter at the same one or more internodes of a wild-type control plant.

Embodiment 101. The transgenic cereal plant of any one of Embodiments 96, wherein the transgenic cereal plant is a corn plant, and wherein the stalk or stem diameter of the transgenic corn plant at one or more of the first, second, third, and/or fourth internode below the ear is at least 5%, at least 10%, at least 15%, at least 20%, at least 25%, at least 30%, at least 35%, or at least 40% greater than the same internode of a wild-type control plant.

Embodiment 102. The transgenic cereal plant of Embodiment 96, wherein the level of one or more active GAs in at least one internode tissue of the stem or stalk of the transgenic plant is lower than the same internode tissue of a wild-type control plant.

Embodiment 103. The transgenic cereal plant of Embodiment 96, wherein the level of one or more active GAs in at least one internode tissue of the stem or stalk of the transgenic plant is at least 5%, at least 10%, at least 15%, at least 20%, at least 25%, at least 30%, at least 35%, or at least 40% lower than the same internode tissue of a wild-type control plant.

Embodiment 104. A transgenic corn plant, plant part or plant cell comprising the recombinant DNA construct of Embodiment 81.

Embodiment 105. A method for producing a transgenic cereal plant, comprising: (a) transforming at least one cell of an explant with the recombinant DNA construct of Embodiment 81, and (b) regenerating or developing the transgenic cereal plant from the transformed explant.

Embodiment 106. The method of Embodiment 105, wherein the cereal plant is transformed via *Agrobacterium* mediated transformation or particle bombardment.

Embodiment 107. The recombinant DNA construct of Embodiment 1, 29, 55 or 81, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a monocot or cereal plant or plant cell, the endogenous GA oxidase protein being at least 80%, at least 85%, at least 90%, at least 95%, at least 96%, at least 97%, at least 98%, at least 99%, at least 99.5%, or 100% identical to one or more of SEQ ID NOs: 3, 6, 9, 12, 15, 18, 21, 24, 27, 30 and 33.

Embodiment 108. The recombinant DNA construct of Embodiment 107, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 1, 2, 4, 5, 7, 8, 10, 11, 13, 14, 16, 17, 19, 20, 22, 23, 25, 26, 28, 29, 31, and 32.

Embodiment 109. A recombinant DNA construct comprising a transcribable DNA sequence encoding a non-coding RNA molecule, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous protein in a monocot or cereal plant or plant cell, the endogenous protein being at least 80%, at least 85%, at least 90%, at least 95%, at least 96%, at least 97%, at least 98%, at least 99%, at least 99.5%, or 100% identical to SEQ ID NO: 86, 90, 94, 97, 101, 104, 108, 112, 116, 118, 121, 125, 129, 133, or 136, and wherein the transcribable DNA sequence is operably linked to a plant-expressible promoter.

Embodiment 110. The recombinant DNA construct of Embodiment 109, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 84, 85, 87, 88, 89, 91, 92, 93, 95, 96, 98, 99, 100, 102, 103, 105, 106, 107, 109, 110, 111, 113, 114, 115, 119, 120, 122, 123, 124, 126, 127, 128, 130, 131, 132, 134, 135, or 137.

Embodiment 111. The recombinant DNA construct of Embodiment 109, wherein the plant-expressible promoter is a vascular promoter.

Embodiment 112. The recombinant DNA construct of Embodiment 109, wherein the plant-expressible promoter is a RTBV promoter.

Embodiment 113. The recombinant DNA construct of Embodiment 109, wherein the plant-expressible promoter is a leaf promoter.

Embodiment 114. The recombinant DNA construct of Embodiment 109, wherein the plant-expressible promoter is a constitutive promoter.

Embodiment 115. A transformation vector comprising the recombinant DNA construct of Embodiment 81.

Embodiment 116. A transgenic cereal plant, plant part or plant cell comprising the recombinant DNA construct of Embodiment 109.

Embodiment 117. The transgenic cereal plant of Embodiment 116, wherein the transgenic plant has a shorter plant height and/or improved lodging resistance.

Embodiment 118. The transgenic cereal plant of Embodiment 116, wherein the level of one or more active GAs in at least one internode tissue of the stem or stalk of the transgenic plant is lower than the same internode tissue of a wild-type control plant.

Embodiment 119. A method for producing a transgenic cereal plant, comprising: (a) transforming at least one cell of an explant with the recombinant DNA construct of Embodiment 116, and (b) regenerating or developing the transgenic cereal plant from the transformed explant.

Embodiment 120. The method of Embodiment 119, wherein the cereal plant is transformed via *Agrobacterium* mediated transformation or particle bombardment.

Embodiment 121. A method for lowering the level of at least one active GA molecule in the stem or stalk of a corn or cereal plant comprising: suppressing one or more GA3 oxidase or GA20 oxidase genes with a recombinant DNA construct in one or more tissues of the transgenic cereal or corn plant.

Embodiment 122. The method of Embodiment 121, wherein the recombinant DNA construct encodes a non-coding RNA molecule that targets one or more GA3 or GA20 oxidase genes for suppression, wherein the transcribable DNA sequence is operably linked to a plant-expressible promoter.

Embodiment 123. The method of Embodiment 122, wherein the plant-expressible promoter is a vascular promoter.

Embodiment 124. The method of Embodiment 122, wherein the plant-expressible promoter is a RTBV promoter.

Embodiment 125. The method of Embodiment 122, wherein the plant-expressible promoter is a constitutive promoter.

Embodiment 126. The method of Embodiment 122, wherein the plant-expressible promoter is a leaf promoter.

Embodiment 127. The method of Embodiment 121, wherein the transgenic corn or cereal plant is a corn plant.

Embodiment 128. A transgenic corn or cereal plant comprising a recombinant DNA construct, wherein the recombinant DNA construct comprises a transcribable DNA sequence encoding a non-coding RNA molecule that targets at least one endogenous GA20 or GA3 oxidase gene for suppression, the transcribable DNA sequence being operably linked to a plant-expressible promoter, and wherein the transgenic monocot or cereal plant has a shorter plant height relative to a wild-type control plant.

Embodiment 129. The transgenic corn or cereal plant of Embodiment 128, wherein the transgenic plant has one or more of the following additional traits relative to the control plant: increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen or water limiting stress conditions, increased ear weight, increased harvest index, increased yield, increased seed number, increased seed weight, and increased prolificacy.

Embodiment 130. The transgenic corn or cereal plant of Embodiment 128, wherein the height of the transgenic plant is at least 10%, at least 20%, at least 25%, at least 30%, at least 35%, or at least 40% shorter than the control plant.

Embodiment 131. The transgenic corn or cereal plant of Embodiment 128, wherein the stalk or stem diameter of the transgenic plant at one or more stem internodes is at least 5%, at least 10%, at least 15%, at least 20%, at least 25%, at least 30%, at least 35%, or at least 40% greater than the control plant.

Embodiment 132. The transgenic corn or cereal plant of any one of Embodiments 128, wherein the level of one or more active GAs in at least one internode tissue of the stem or stalk of the transgenic plant is lower than the same internode tissue of the control plant.

Embodiment 133. The transgenic corn or cereal plant of any one of Embodiments 128, wherein the level of one or more active GAs in at least one internode tissue of the stem or stalk of the transgenic plant is at least 5%, at least 10%, at least 15%, at least 20%, at least 25%, at least 30%, at least 35%, or at least 40% lower than the same internode tissue of the control plant.

Embodiment 134. The transgenic corn or cereal plant of any one of Embodiments 128, wherein the transgenic plant does not have any significant off-types in at least one female organ or ear.

Embodiment 135. The transgenic corn or cereal plant of any one of Embodiments 128, wherein the transgenic cereal plant is a corn plant, and wherein the non-coding RNA molecule targets the endogenous GA20 oxidase_3 and/or GA20 oxidase_5 gene(s) for suppression.

Embodiment 136. The transgenic corn or cereal plant of Embodiment 128, wherein the plant-expressible promoter is a vascular promoter.

Embodiment 137. The transgenic corn or cereal plant of Embodiment 128, wherein the plant-expressible promoter is a RTBV promoter.

Embodiment 138. The transgenic corn or cereal plant of Embodiment 128, wherein the plant-expressible promoter is a constitutive promoter.

Embodiment 139. The transgenic corn or cereal plant of Embodiment 128, wherein the plant-expressible promoter is a leaf promoter.

Embodiment 140. The transgenic corn or cereal plant of Embodiment 128, wherein the transgenic plant has one or more of the following additional traits relative to the control plant: increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen or water limiting stress conditions, increased ear weight, increased harvest index, increased yield, increased seed number, increased seed weight, and increased prolificacy.

Embodiment 141. A cereal plant comprising a mutation at or near an endogenous GA oxidase gene introduced by a mutagenesis technique, wherein the expression level of the endogenous GA oxidase gene is reduced or eliminated in the cereal plant, and wherein the cereal plant has a shorter plant height relative to a wild-type control plant.

Embodiment 142. The cereal plant of Embodiment 141, wherein the cereal plant comprising the mutation has one or more of the following additional traits relative to the control plant: increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen or water limiting stress conditions, increased ear weight, increased harvest index, increased yield, increased seed number, increased seed weight, and increased prolificacy.

Embodiment 143. The cereal plant of Embodiment 141, wherein the height of the cereal plant is at least 10%, at least 20%, at least 25%, at least 30%, at least 35%, or at least 40% shorter than the control plant.

Embodiment 144. The cereal plant of Embodiment 141, wherein the stalk or stem diameter of the cereal plant at one or more stem internodes is at least 5%, at least 10%, at least 15%, at least 20%, at least 25%, at least 30%, at least 35%, or at least 40% greater than the control plant.

Embodiment 145. The cereal plant of Embodiment 141, wherein the level of one or more active GAs in at least one internode tissue of the stem or stalk of the cereal plant is lower than the same internode tissue of the control plant.

Embodiment 146. The cereal plant of Embodiment 141, wherein the level of one or more active GAs in at least one internode tissue of the stem or stalk of the cereal plant is at least 5%, at least 10%, at least 15%, at least 20%, at least 25%, at least 30%, at least 35%, or at least 40% lower than the same internode tissue of the control plant.

Embodiment 147. The cereal plant of Embodiment 141, wherein the cereal plant does not have any significant off-types in at least one female organ or ear.

Embodiment 148. The cereal plant of Embodiment 141, wherein the cereal plant is a corn plant.

Embodiment 149. A corn or cereal plant comprising a genomic edit introduced via a targeted genome editing technique at or near the locus of an endogenous GA oxidase gene, wherein the expression level of the endogenous GA oxidase gene is reduced or eliminated relative to a control plant, and wherein the edited cereal plant has a shorter plant height relative to the control plant.

Embodiment 150. The edited corn or cereal plant of Embodiment 149, wherein the edited plant has one or more of the following additional traits relative to the control plant: increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen or water limiting stress conditions, increased ear weight, increased harvest index, increased yield, increased seed number, increased seed weight, and increased prolificacy.

Embodiment 151. The edited corn or cereal plant of Embodiment 149, wherein the height of the edited plant is at least 10%, at least 20%, at least 25%, at least 30%, at least 35%, or at least 40% shorter than the control plant.

Embodiment 152. The edited corn or cereal plant of Embodiment 149, wherein the stalk or stem diameter of the edited plant at one or more stem internodes is at least 5%, at least 10%, at least 15%, at least 20%, at least 25%, at least 30%, at least 35%, or at least 40% greater than the control plant.

Embodiment 153. The edited corn or cereal plant of Embodiment 149, wherein the level of one or more active GAs in at least one internode tissue of the stem or stalk of the edited plant is lower than the same internode tissue of the control plant.

Embodiment 154. The edited corn or cereal plant of Embodiment 149, wherein the level of one or more active GAs in at least one internode tissue of the stem or stalk of the edited plant is at least 5%, at least 10%, at least 15%, at least 20%, at least 25%, at least 30%, at least 35%, or at least 40% lower than the same internode tissue of the control plant.

Embodiment 155. The edited corn or cereal plant of Embodiment 149, wherein the edited plant does not have any significant off-types in at least one female organ or ear.

Embodiment 156. The edited corn or cereal plant of Embodiment 149, wherein the genomic edit is introduced using a meganuclease, a zinc-finger nuclease (ZFN), a RNA-guided endonuclease, a TALE-endonuclease (TALEN), a recombinase, or a transposase.

Embodiment 157. The edited corn or cereal plant of Embodiment 149, wherein the genomic edit comprises a substitution, deletion, insertion, or inversion of one or more nucleotides relative to the sequence of the endogenous GA oxidase gene in the control plant.

Embodiment 158. A composition comprising a guide RNA, wherein the guide RNA comprises a guide sequence that is at least 95%, at least 96%, at least 97%, at least 99%, or 100% identical or complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of an endogenous GA oxidase gene of a cereal plant.

Embodiment 159. The composition of Embodiment 158, wherein the guide RNA molecule comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35 or 38, or a sequence complementary thereto.

Embodiment 160. The composition of Embodiment 158, wherein the guide RNA molecule comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 87, 91, 95, 98, 105, 109, 113, 117, 122, 126, 130 or 137, or a sequence complementary thereto.

Embodiment 161. The composition of Embodiment 158, further comprising an RNA-guided endonuclease.

Embodiment 162. The composition of Embodiment 161, wherein the RNA-guided endonuclease in the presence of the guide RNA molecule causes a double strand break or nick at or near the target DNA sequence in the genome of the cereal plant.

Embodiment 163. The composition of Embodiment 161, wherein the RNA-guided endonuclease is selected from the group consisting of Cas1, Cas1B, Cas2, Cas3, Cas4, Cas5, Cash, Cas7, Cas8, Cas9, Cas10, Csy1, Csy2, Csy3, Cse1, Cse2, Csc1, Csc2, Csa5, Csn1, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx12, Csx15, Csf1, Csf2, Csf3, Csf4, Cpf1, CasX, CasY, Argonaute, and any homologs or modified versions thereof having RNA-guided endonuclease activity.

Embodiment 164. The composition of Embodiment 158, further comprising a recombinant DNA donor template comprising at least one homology sequence or homology arm, wherein the at least one homology sequence or homology arm is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of the endogenous GA oxidase gene of a corn or cereal plant.

Embodiment 165. A recombinant DNA construct comprising a transcribable DNA sequence encoding a non-coding guide RNA molecule, wherein the guide RNA molecule comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of an endogenous GA oxidase gene of a corn or cereal plant.

Embodiment 166. The recombinant DNA construct of Embodiment 165, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35 or 38, or a sequence complementary thereto.

Embodiment 167. The recombinant DNA construct of Embodiment 165, wherein the guide RNA molecule comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 87, 91, 95, 98, 105, 109, 113, 117, 122, 126, 130 or 137, or a sequence complementary thereto.

Embodiment 168. The recombinant DNA construct of Embodiment 165, wherein the transcribable DNA sequence is operably linked to a plant-expressible promoter.

Embodiment 169. The recombinant DNA construct of Embodiment 165, wherein the guide RNA molecule is a CRISPR RNA (crRNA) or a single-chain guide RNA (sgRNA).

Embodiment 170. The recombinant DNA construct of Embodiment 165, wherein the guide RNA comprises a sequence complementary to a protospacer adjacent motif (PAM) sequence present in the genome of the cereal plant immediately adjacent to the target DNA sequence at or near the genomic locus of the endogenous GA oxidase gene.

Embodiment 171. The recombinant DNA construct of any one of Embodiment 165, wherein the PAM sequence comprises a canonical 5'-NGG-3' sequence.

Embodiment 172. The recombinant DNA construct of Embodiment 165, wherein the endogenous GA oxidase gene encodes a protein that is at least 80%, at least 85%, at least 90%, at least 95%, at least 96%, at least 97%, at least 98%, at least 99%, at least 99.5%, or 100% identical to SEQ ID NO: 9, 12 or 15.

Embodiment 173. A DNA molecule comprising the recombinant DNA construct of Embodiment 165.

Embodiment 174. A transformation vector comprising the recombinant DNA construct of Embodiment 165.

Embodiment 175. A bacterial cell comprising the recombinant DNA construct of Embodiment 165.

Embodiment 176. A corn or cereal plant, plant part or plant cell comprising the recombinant DNA construct of Embodiment 165.

Embodiment 177. A composition comprising the recombinant DNA construct of Embodiment 165.

Embodiment 178. The composition of Embodiment 177, further comprising a RNA-guided endonuclease.

Embodiment 179. The composition of Embodiment 177, wherein the RNA-guided endonuclease is selected from the group consisting of Cas1, Cas1B, Cas2, Cas3, Cas4, Cas5, Cash, Cas7, Cas8, Cas9, Cas10, Csy1, Csy2, Csy3, Cse1, Cse2, Csc1, Csc2, Csa5, Csn1, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, Argonaute, and homologs or modified versions thereof having RNA-guided endonuclease activity.

Embodiment 180. The composition of Embodiment 177, further comprising a second recombinant DNA construct comprising a second transcribable DNA sequence encoding the RNA-guided endonuclease.

Embodiment 181. The composition of Embodiment 177, comprising a DNA molecule or vector comprising the recombinant DNA construct and the second recombinant DNA construct.

Embodiment 182. The composition of Embodiment 177, comprising a first DNA molecule or vector and a second DNA molecule or vector, wherein the first DNA molecule or vector comprises the recombinant DNA construct encoding the guide RNA molecule, and the second DNA molecule or vector comprises the second recombinant DNA construct encoding the RNA-guided endonuclease.

Embodiment 183. The composition of Embodiment 177, further comprising a recombinant DNA donor template comprising at least one homology sequence or homology arm, wherein the at least one homology sequence or homology arm is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of an endogenous GA oxidase gene of a corn or cereal plant.

Embodiment 184. A recombinant DNA donor template comprising at least one homology sequence, wherein the at least one homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of an endogenous GA oxidase gene of a corn or cereal plant.

Embodiment 185. The recombinant DNA donor template of Embodiment 184, wherein the at least one homology sequence comprises at least one mutation relative to the complementary strand of the target DNA sequence at or near the genomic locus of the endogenous GA oxidase gene.

Embodiment 186. The recombinant DNA donor template of Embodiment 185, wherein the at least one mutation comprises a substitution, deletion, insertion, or inversion of one or more nucleotides relative to the complementary strand of the target DNA sequence.

Embodiment 187. The recombinant DNA donor template of Embodiment 184, wherein the at least one homology sequence is at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35 or 38, or a sequence complementary thereto.

Embodiment 188. The recombinant DNA donor template of Embodiment 184, wherein the at least one homology sequence is at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 87, 91, 95, 98, 105, 109, 113, 117, 122, 126, 130 or 137, or a sequence complementary thereto.

Embodiment 189. A recombinant DNA donor template comprising two homology arms including a first homology arm and a second homology arm, wherein the first homology arm comprises a sequence that is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a first flanking DNA sequence, wherein the second homology arm comprises a sequence that is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a second flanking DNA sequence, and wherein the first flanking DNA sequence and the second flanking DNA sequence are genomic sequences at or near the genomic locus of an endogenous GA oxidase gene of a corn or cereal plant.

Embodiment 190. The recombinant DNA donor template of Embodiment 189, further comprising an insertion sequence located between the first homology arm and the second homology arm.

Embodiment 191. The recombinant DNA donor template of Embodiment 189, wherein the insertion sequence comprises at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, at least 500, at least 750, at least 1000, at least 2500, or at least 5000 nucleotides.

Embodiment 192. The recombinant DNA donor template of Embodiment 189, wherein each homology arm is at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35 or 38, or a sequence complementary thereto.

Embodiment 193. The recombinant DNA donor template of Embodiment 189, wherein each homology arm is at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 87, 91, 95, 98, 105, 109, 113, 117, 122, 126, 130 or 137, or a sequence complementary thereto.

Embodiment 194. The recombinant DNA donor template of Embodiment 189, wherein one or more nucleotides present in the genome of the monocot or cereal plant between the first flanking DNA sequence and the second flanking DNA sequence are absent in the recombinant DNA donor template molecule between the first homology arm and the second homology arm.

Embodiment 195. The recombinant DNA donor template of Embodiment 194, wherein at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, at least 500, at least 750, at least 1000, at least 2500, or at least 5000 nucleotides present in the genome of the monocot or cereal plant between the first and second flanking DNA sequences are absent in the recombinant DNA donor template molecule between the first and second homology arms.

Embodiment 196. A DNA molecule or vector comprising the recombinant DNA donor template of Embodiment 189.

Embodiment 197. A bacterial or host cell comprising the recombinant DNA donor template of Embodiment 189.

Embodiment 198. A corn or cereal plant, plant part or plant cell comprising the recombinant DNA construct of Embodiment 189.

Embodiment 199. An engineered site-specific nuclease that binds to a target site at or near the genomic locus of an endogenous GA oxidase gene of a corn or cereal plant and causes a double-strand break or nick at the target site.

Embodiment 200. The engineered site-specific nuclease of Embodiment 199, wherein the site-specific nuclease is a meganuclease or homing endonuclease.

Embodiment 201. The engineered site-specific nuclease of Embodiment 200, wherein the engineered meganuclease or homing endonuclease comprises a scaffold or base enzyme selected from the group consisting of I-CreI, I-CeuI, I-MsoI, I-SceI, I-AniI, and I-DmoI.

Embodiment 202. The engineered site-specific nuclease of Embodiment 199, wherein the site-specific nuclease is a zinc finger nuclease (ZFN) comprising a DNA binding domain and a cleavage domain.

Embodiment 203. The engineered zinc finger nuclease of Embodiment 202, wherein the cleavage domain is a FokI nuclease domain.

Embodiment 204. The engineered site-specific nuclease of Embodiment 199, wherein the site-specific nuclease is a transcription activator-like effector nuclease (TALEN) comprising a DNA binding domain and a cleavage domain.

Embodiment 205. The engineered TALEN of Embodiment 204, wherein the cleavage domain is selected from the group consisting of a PvuII nuclease domain, a MutH nuclease domain, a TelI nuclease domain, a FokI nuclease domain, an AlwI nuclease domain, a MlyI nuclease domain, a SbfI nuclease domain, a SdaI nuclease domain, a StsI nuclease domain, a CleDORF nuclease domain, a Clo051 nuclease domain, and a Pept071 nuclease domain.

Embodiment 206. The engineered site-specific nuclease of Embodiment 199, wherein the target site bound by the site-specific nuclease is at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35 or 38, or a sequence complementary thereto.

Embodiment 207. The engineered site-specific nuclease of Embodiment 199, wherein the target site bound by the site-specific nuclease is at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 87, 91, 95, 98, 105, 109, 113, 117, 122, 126, 130 or 137, or a sequence complementary thereto.

Embodiment 208. A recombinant DNA construct comprising a transgene encoding a site-specific nuclease, wherein the site-specific nuclease binds to a target site at or near the genomic locus of an endogenous GA oxidase gene of a monocot or cereal plant and causes a double-strand break or nick at the target site.

Embodiment 209. The recombinant DNA construct of Embodiment 208, wherein the transgene is operably linked to a plant-expressible promoter.

Embodiment 210. The recombinant DNA construct of Embodiment 208, wherein the site-specific nuclease is a meganuclease or homing endonuclease, a zinc finger nuclease, or a transcription activator-like effector nuclease (TALEN).

Embodiment 211. A DNA molecule or vector comprising the recombinant DNA construct of Embodiment 208.

Embodiment 212. A bacterial or host cell comprising the recombinant DNA construct of Embodiment 208.

Embodiment 213. A corn or cereal plant, plant part or plant cell comprising the recombinant DNA construct of Embodiment 208.

Embodiment 214. A recombinant DNA donor template comprising at least one homology arm and an insertion sequence, wherein the at least one homology arm is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a genomic DNA sequence of a corn or cereal plant, and wherein the insertion sequence comprises a recombinant DNA construct comprising a transcribable DNA sequence encoding a non-coding RNA molecule, wherein the non-coding RNA molecule targets for suppression one or more endogenous GA20 or GA3 oxidase genes in a monocot or cereal plant or plant cell, and wherein the transcribable DNA sequence is operably linked to a plant-expressible promoter.

Embodiment 215. The recombinant DNA donor template of Embodiment 214, wherein the at least one homology arm comprises two homology arms including a first homology arm and a second homology arm, wherein the first homology arm comprises a sequence that is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a first flanking DNA sequence, and the second homology arm comprises a sequence that is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a second flanking DNA sequence, wherein the first flanking DNA sequence and the second flanking DNA sequence are genomic sequences at or near the same genomic locus of a monocot or cereal plant, and wherein the insertion sequence is located between the first homology arm and the second homology arm and comprises a recombinant DNA construct comprising a transcribable DNA sequence encoding a non-coding RNA molecule.

Embodiment 216. The recombinant DNA donor template of Embodiment 215, wherein the transcribable DNA sequence is operably linked to a plant-expressible promoter.

Embodiment 217. The recombinant DNA donor template of Embodiment 215, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding a GA oxidase protein that is at least 80%, at least 85%, at least 90%, at least 95%, at least 96%, at least 97%, at least 98%, at least 99%, at least 99.5%, or 100% identical to SEQ ID NO: 9, 12, 15, 30 or 33.

Embodiment 218. The recombinant DNA donor template of Embodiment 215, wherein the non-coding RNA molecule comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding a GA oxidase protein that is at least 80%, at least 85%, at least 90%, at least 95%, at least 96%, at least 97%, at least 98%, at least 99%, at least 99.5%, or 100% identical to SEQ ID NO: 86, 90, 94, 97, 101, 104, 108, 112, 116, 118, 121, 125, 129, 133, or 136.

Embodiment 219. A composition comprising the recombinant DNA donor template of Embodiment 214.

Embodiment 220. A bacterial or host cell comprising the recombinant DNA donor template of Embodiment 214.

Embodiment 221. A transgenic corn or cereal plant, plant part or plant cell comprising the insertion sequence of the recombinant DNA donor template of Embodiment 214.

Embodiment 222. The transgenic corn or cereal plant of Embodiment 214, wherein the transgenic plant has one or more of the following traits relative to a control plant: shorter plant height, increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen or water limiting stress conditions, increased ear weight, increased harvest index, increased yield, increased seed number, increased seed weight, and/or increased prolificacy.

Embodiment 223. The transgenic corn or cereal plant of Embodiment 222, wherein the transgenic plant has a shorter plant height and/or improved lodging resistance.

Embodiment 224. The transgenic corn or cereal plant of Embodiments 222, wherein the height of the transgenic plant is at least 10%, at least 20%, at least 25%, at least 30%, at least 35%, or at least 40% shorter than a control plant.

Embodiment 225. The transgenic corn or cereal plant of Embodiments 222, wherein the level of one or more active GAs in at least one internode tissue of the stem or stalk of the transgenic plant is lower than the same internode tissue of a control plant.

Embodiment 226. A method for producing a transgenic corn or cereal plant, comprising: (a) transforming at least one cell of an explant with the recombinant DNA donor template of Embodiment 215, and (b) regenerating or developing the transgenic corn or cereal plant from the transformed explant, wherein the transgenic corn or cereal plant comprises the insertion sequence of the recombinant DNA donor template.

Embodiment 227. The method of Embodiment 226, wherein the monocot or cereal plant is transformed via *Agrobacterium* mediated transformation or particle bombardment.

Embodiment 228. A method for producing a corn or cereal plant having a genomic edit at or near an endogenous GA oxidase gene, comprising: (a) introducing into at least one cell of an explant of the corn or cereal plant a site-specific nuclease or a recombinant DNA molecule comprising a transgene encoding the site-specific nuclease, wherein the site-specific nuclease binds to a target site at or near the genomic locus of the endogenous GA oxidase gene and causes a double-strand break or nick at the target site, and (b) regenerating or developing an edited corn or cereal plant from the at least one explant cell comprising the genomic edit at or near the endogenous GA oxidase gene of the edited corn or cereal plant.

Embodiment 229. The method of Embodiment 228, wherein the introducing step (a) further comprises introducing a DNA donor template comprising at least one homology sequence or homology arm, wherein the at least one homology sequence or homology arm is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of the endogenous GA oxidase gene of the corn or cereal plant.

Embodiment 230. The method of Embodiment 228, further comprising: (c) selecting the edited corn or cereal plant.

Embodiment 231. The method of Embodiment 230, wherein the selecting step (c) comprises determining if the endogenous GA oxidase gene locus was edited using a molecular assay.

Embodiment 232. The method of Embodiment 230, wherein the selecting step (c) comprises determining if the endogenous GA oxidase gene was edited by observing a plant phenotype.

Embodiment 233. The method of Embodiment 231, wherein the plant phenotype is a decrease in plant height relative to a control plant.

Embodiment 234. The method of Embodiment 228, wherein the introducing step (a) creates at least one mutation at or near the genomic locus of the endogenous GA oxidase gene, and wherein the mutation comprises a substitution, deletion, insertion, or inversion of one or more nucleotides relative to the genomic DNA sequence of a control plant.

Embodiment 235. A modified corn plant having a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and either (i) an average stem or stalk diameter of greater than 18 mm, greater than 18.5 mm, greater than 19 mm, greater than 19.5 mm, greater than 20 mm, greater than 20.5 mm, greater than 21 mm, greater than 21.5 mm, or greater than 22 mm, (ii) improved lodging resistance relative to a wild type control plant, or (iii) improved drought tolerance relative to a wild type control plant.

Embodiment 236. The modified corn plant of Embodiment 235, wherein the corn plant has one or more of the following traits relative to a wild type control plant: increased stalk/stem diameter, improved lodging resistance, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen or water limiting stress conditions, increased ear weight, increased harvest index, increased yield, increased seed number, increased seed weight, and/or increased prolificacy.

Embodiment 237. The modified corn plant of Embodiment 235, wherein the level of one or more active GAs in at least one internode tissue of the stem or stalk of the corn plant is lower than the same internode tissue of a wild type control plant.

Embodiment 238. A modified cereal plant having a reduced plant height relative to a wild type control plant, and (i) an increased stem or stalk diameter relative to a wild type control plant, (ii) improved lodging resistance relative to a wild type control plant, or (iii) improved drought tolerance relative to a wild type control plant.

Embodiment 239. The modified cereal plant of Embodiment 238, wherein the level of one or more active GAs in the stem or stalk of the cereal plant is lower than in a wild type control plant.

EXAMPLES

Example 1. Reduced Plant Height in Inbred Corn Lines Across Transformation Events for the GA20 Oxidase Suppression Element An inbred corn plant line was transformed via *Agrobacterium* mediated transformation with a transformation vector having an expression construct comprising a transcribable DNA sequence with a sequence (SEQ ID NO: 39) encoding a targeting sequence (SEQ ID NO: 40) of a miRNA under the control of a rice tungro bacilliform virus (RTBV) promoter (SEQ ID NO: 65) that is known to cause expression in vascular tissues of plants. The miRNA encoded by the construct comprises a RNA sequence that targets the GA20 oxidase_3 and GA20 oxidase_5 genes in corn plants for suppression. Several transformation events were generated with this construct, and these transformants were tested in the greenhouse to determine if they had reduced plant height relative to non-transgenic wild type control plants. As can be seen in FIG. 1, a significant reduction in plant height was consistently observed in transgenic plants expressing the suppression construct across several transformation events (see Events 1-8) relative to wild type (WT) control plants. Plant height for each of the transformation events was calculated as an average among approximately 10 plants for each event and compared to the average height for control plants. Standard errors were calculated for each event and the control plants, which are represented as error bars in FIG. 1. Furthermore, ear development in each of these transformants appeared normal.

As can be seen from the results of this experiment, average plant height in plants expressing the miRNA targeting the GA20 oxidase_3 and GA20 oxidase_5 genes for suppression had consistently reduced plant heights of up to 35% relative to control plants across multiple events. This data supports the conclusion that the effects seen with this suppression construct are not due to insertion of the construct at any one locus within the plant genome.

This data further indicates that expression of this GA20 oxidase suppression construct using the RTBV vascular promoter is effective at causing these plant height phenotypes. In addition, early data in R0 corn plants constitutively expressing the same GA20 oxidase suppression construct under the control of different constitutive promoters also produce short stature plants (see Example 15 below). Thus, expression of the targeted GA20 oxidase suppression construct may be effective at reducing plant height and providing the other beneficial anti-lodging and yield-related traits described herein given that different expression patterns including vascular and constitutive expression provide similar plant height phenotypes without apparent off-types in the ear.

Figure 2A:
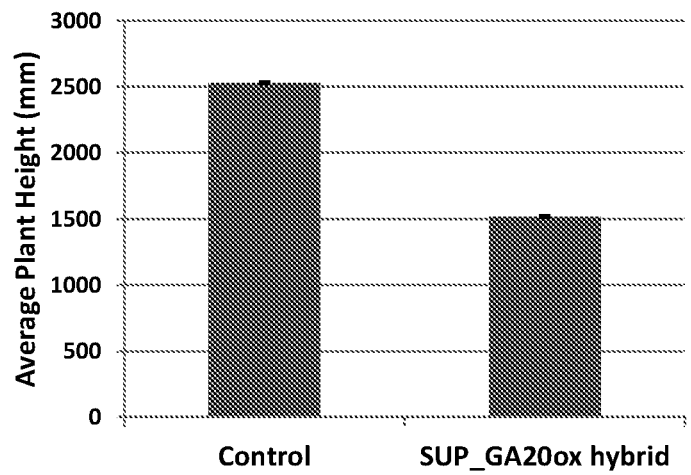
FIG. 2A shows a reduced plant height on average of hybrid corn plants expressing a GA20 oxidase suppression construct in comparison to hybrid control plants.
Figure 2B:
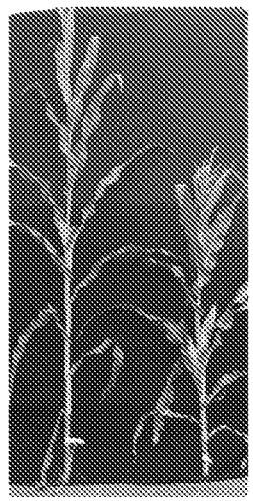
FIG. 2B shows an image of a wild type hybrid control plant (left) next to a hybrid corn plant expressing a GA20 oxidase suppression construct (right) having a reduced plant height.

Example 2. Reduced Plant Height in Hybrid Corn Plants Expressing the GA20 Oxidase Suppression Element Hybrid corn plants carrying the GA20 oxidase suppression construct described in Example 1 also showed reduced plant height relative to wild type control plants when grown under field conditions. Average plant height of transgenic hybrid corn plants expressing the GA20 oxidase suppression element in 10 microplots was calculated and compared to average plant height of (non-transgenic) wild type control hybrid corn plants in 32 microplots. Each microplot for the transgenic and non-transgenic control included approximately 6 plants, although the actual number of plants per plot may vary depending on the number of plants that germinate and develop into plants having ears. As can be seen in FIG. 2A, a significant reduction in average plant height was observed in transgenic hybrid plants expressing the suppression construct (SUP-GA20ox hybrid), relative to wild type hybrid corn plants (Control). Standard errors were calculated for the transgenic hybrid and control plants, which are represented as error bars in FIG. 2A. An image of a hybrid control plant (left) next to a transgenic hybrid plant expressing the GA20 oxidase suppression element (right) is further shown in FIG. 2B.

In this experiment, average plant height of field grown hybrid corn plants expressing the miRNA targeting the GA20 oxidase_3 and GA20 oxidase_5 genes was reduced by about 40% relative to wild type hybrid control plants. This data shows that the plant height phenotype is present in hybrid corn plants in addition to inbred lines. However, overall biomass in this experiment appeared neutral in the semi-dwarf corn plants compared to controls.

Figure 3A:
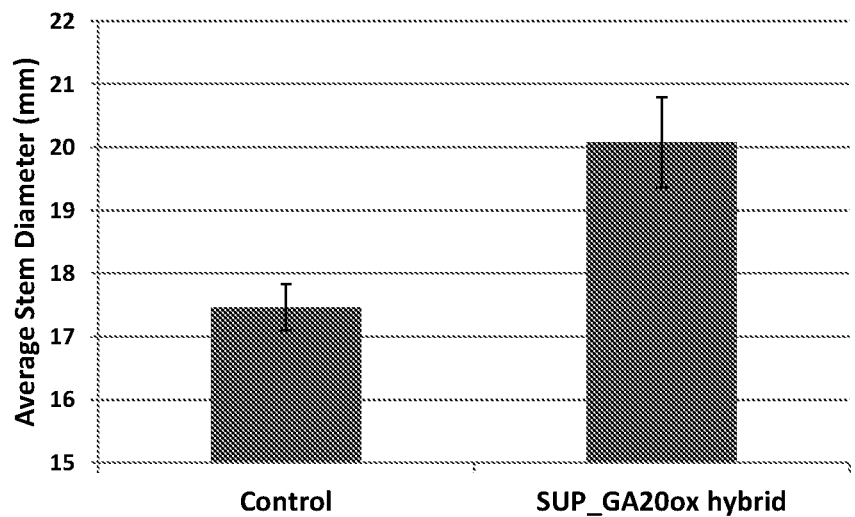
FIG. 3A shows an increased stem diameter on average of hybrid corn plants expressing a GA20 oxidase suppression construct in comparison to hybrid control plants.
Figure 3B:
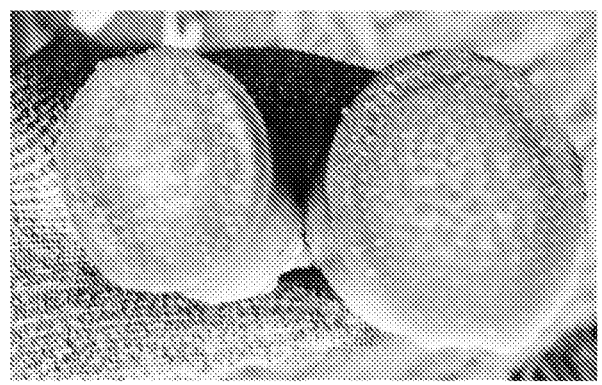
FIG. 3B shows an image of a cross-section of the stalk of a wild type hybrid control plant (left) next to a cross-section of the stalk of a hybrid corn plant expressing a GA20 oxidase suppression construct (right) having an increased stem diameter.

Example 3. Increased Stem Diameter in Hybrid Corn Plants Expressing the GA20 Oxidase Suppression Element Hybrid corn plants carrying the GA20 oxidase suppression construct described in Example 1 also showed increased stem diameter relative to wild type control plants when grown under field conditions. Stem diameter was measured on the second internode below the primary ear. Average stem diameter of transgenic hybrid corn plants expressing the GA20 oxidase suppression element in 8 microplots was calculated and compared to the average stem diameter of (non-transgenic) wild type control hybrid corn plants in 8 microplots. Each microplot included approximately 6 plants. As can be seen in FIG. 3A, a significant increase in average stem diameter was observed in transgenic hybrid plants expressing the suppression construct (SUP-GA20ox hybrid), relative to wild type hybrid corn plants (Control). Standard errors were calculated for the transgenic hybrid and control plants, which are represented as error bars in FIG. 3A. An image of the cross-section of a stalk from a hybrid control plant (Control; left) is shown next to the cross-section of a stalk from a transgenic hybrid plant expressing the GA20 oxidase suppression element (SUP_GA20ox; right) is further shown in FIG. 3B.

In this experiment, average stem diameter of field grown hybrid corn plants expressing the miRNA targeting the GA20 oxidase_3 and GA20 oxidase_5 genes was increased about 13% relative to wild type hybrid control plants. This data shows that hybrid corn plants expressing the GA20 oxidase miRNA may have thicker stalks in addition to the reduced plant height phenotype.

Figure 4:
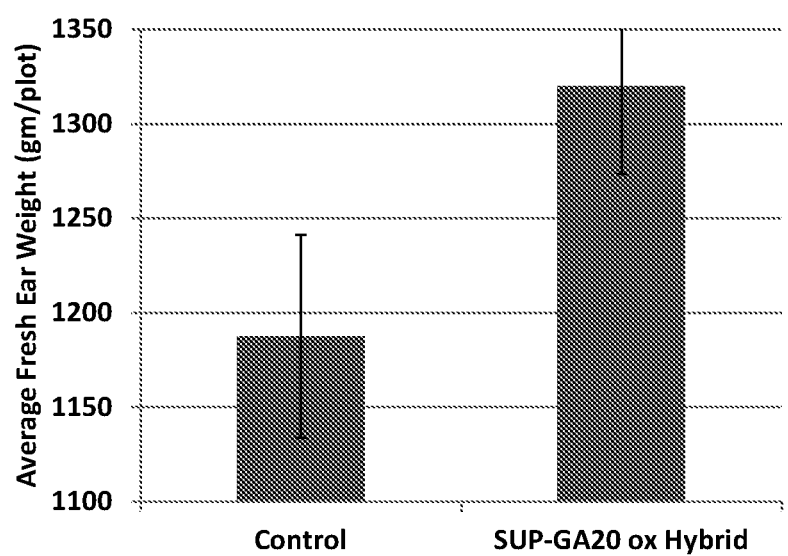
FIG. 4 shows an increased fresh ear weight on average of hybrid corn plants expressing a GA20 oxidase suppression construct in comparison to hybrid control plants.
Figure 5:
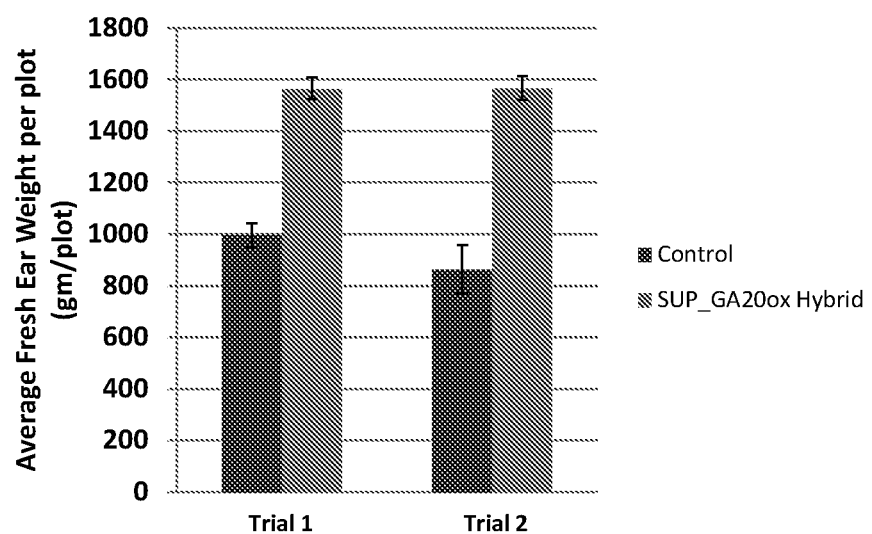
FIG. 5 shows the increased fresh ear weight on average of hybrid corn plants expressing a GA20 oxidase suppression construct in two field trials in comparison to wild type hybrid control plants in response to a wind event that caused greater lodging in the hybrid control plants.

Example 4. Hybrid Corn Plants Expressing the GA20 Oxidase Suppression Element had an Increase in Fresh Ear Weight Hybrid corn plants carrying the GA20 oxidase suppression construct described in Example 1 also showed an increase in fresh ear weight relative to wild type control plants when grown under field conditions. Average fresh ear weight per plot of transgenic hybrid corn plants expressing the GA20 oxidase suppression element in 24 microplots was calculated and compared to the average fresh ear weight of (non-transgenic) hybrid corn control plants in 8 microplots. Again, each microplot included about 6 plants. As can be seen in FIG. 4, an increase in average fresh ear weight per plot was observed in transgenic hybrid plants expressing the suppression construct (SUP-GA20ox hybrid), relative to wild type hybrid corn plants (Control), and ear and kernel development appeared normal. Standard deviations for this experiment were calculated for the transgenic hybrid and control plants, which are represented as error bars in FIG. 4. As shown in FIG. 5, similar results were obtained at another field testing site that also experienced wind damage.

In this experiment, average fresh ear weight of field grown hybrid corn plants expressing the miRNA targeting the GA20 oxidase_3 and GA20 oxidase_5 genes was increased relative to wild type hybrid control plants, indicating that these transgenic plants may further have improved yield-related traits. However, these results are based on observational data without a large-scale statistical comparison to controls, and yield performance should be tested under broad acre conditions.

Example 5. Hybrid Corn Plants Expressing the GA20 Oxidase Suppression Element Displayed Increased Resistance to Lodging At a field testing location, wind damage to pre-flowering hybrid corn plants demonstrated an increased lodging resistance with plants expressing the GA20 oxidase suppression construct described in Example 1, relative to wild type hybrid control plants. While the wild type (non-transgenic) hybrid control plants were visually lodged in response to this high wind event, transgenic hybrid corn plants expressing the GA20 oxidase suppression element in a neighboring field location resisted lodging damage. To evaluate the effects of lodging resistance by hybrid corn plants expressing the GA20 oxidase suppression construct, average fresh ear weights per plot of transgenic GA20 oxidase-suppressing hybrid corn plants across two field trial locations experiencing the lodging damage, were compared to average fresh ear weights of wild type hybrid control plants. Data collected from these two trials indicated that the hybrid control plants had average fresh ear weights that were reduced by about 57% and 81%, respectively in the two trials, relative to hybrid plants expressing the GA20 oxidase suppression construct.

The visual observation that transgenic GA20 oxidase-suppressing hybrid corn plants had increased lodging resistance than non-transgenic control plants, along with the increase in average fresh ear weight in these trials with the transgenic GA20 oxidase-suppressing plants, indicate that increased lodging resistance may translate into an increase in average fresh ear weight. Thus, increased lodging resistance in GA20 oxidase-suppressing plants may further increase the yield potential/stability of these transgenic corn plants by resisting the effects of lodging during severe weather events.

Figure 6:
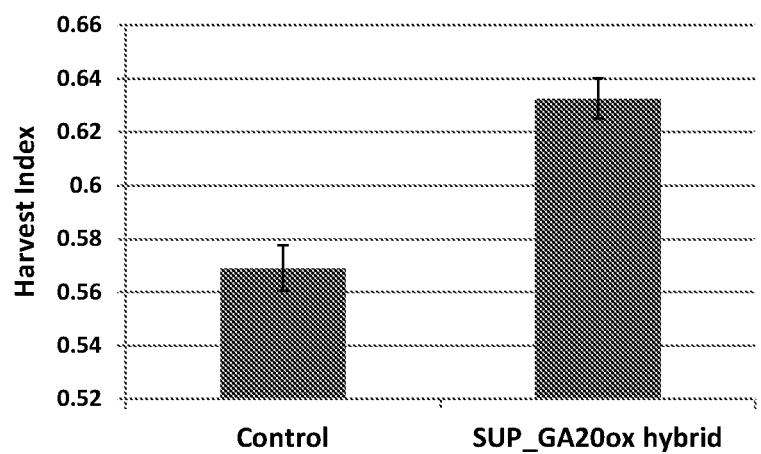
FIG. 6 shows an increased harvest index of hybrid corn plants expressing a GA20 oxidase suppression construct in comparison to hybrid control plants.

Example 6. Hybrid Corn Plants Expressing the GA20 Oxidase Suppression Element had an Increase in Harvest Index Hybrid corn plants carrying the GA20 oxidase suppression construct described in Example 1 further showed an increase in harvest index relative to wild type control plants when grown under field conditions. The harvest index of transgenic hybrid corn plants expressing the GA20 oxidase suppression element was determined from plants grown in 8 microplots and compared to non-transgenic hybrid corn control plants. Each microplot included approximately 6 plants. As can be seen in FIG. 6, a significant increase in harvest index was observed in the transgenic hybrid plants expressing the suppression construct (SUP-GA20ox hybrid), relative to wild type hybrid corn plants (Control). Standard errors were calculated for the transgenic hybrid and control plants, which are represented as error bars in FIG. 6.

In this experiment, the harvest index of field grown hybrid corn plants expressing the miRNA targeting the GA20 oxidase_3 and GA20 oxidase_5 genes was increased about 11% relative to wild type hybrid control plants. This increase in harvest index was further associated with a reduction in stover weight as compared to wild type control plants, but no difference in total dry biomass weight was observed in the transgenic plants.

Figure 7:
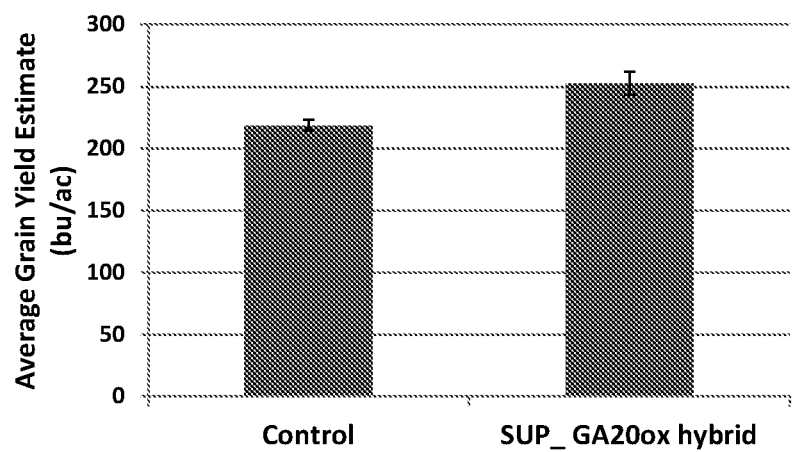
FIG. 7 shows an increase in the average grain yield estimate of hybrid corn plants expressing a GA20 oxidase suppression construct in comparison to hybrid control plants.

Example 7. Hybrid Corn Plants Expressing the GA20 Oxidase Suppression Element had an Increase in Average Grain Yield Estimate The average grain yield estimate for hybrid corn plants expressing the GA20 oxidase suppression element (identified in Example 1) was calculated from 16 microplots in the field (with approximately 6 plants per plot). The calculated average grain yield estimate for these transgenic hybrid corn plants suppressing GA20 oxidase was increased by about 15% over corn hybrid control plants (FIG. 7). Grain yield estimate is a metric that provides a general estimation of expected yield based on the ear trait metrics. Grain yield estimate is derived from hand harvested ears on small plots, and units are kg/ha (instead of bu/ac). Grain yield estimate (kg/ha) is calculated by the formula (Kernel number per unit area (kernels/m$^2$)×Single Kernel Weight (mg)×15.5%/100).

Figure 8:
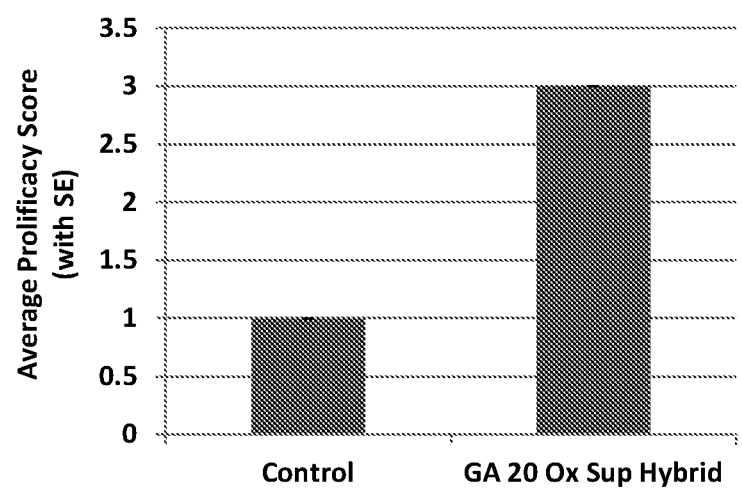
FIG. 8 shows an increased prolificacy score on average of hybrid corn plants expressing a GA20 oxidase suppression construct in comparison to hybrid control plants.

Example 8. Hybrid Corn Plants Expressing the GA20 Oxidase Suppression Element had an Increase in Average Prolificacy Score Hybrid corn plants expressing the GA20 oxidase suppression element (identified in Example 1) was also shown in a microplot experiment to have increased prolificacy and secondary ears as compared to non-transgenic hybrid control plants. The prolificacy score was determined from 10 microplots of the transgenic hybrid corn plants in the field (with approximately 6 plants per plot). As shown in FIG. 8, the average prolificacy score of transgenic hybrid corn plants suppressing the GA 20 oxidase was 3, whereas the average prolificacy score of control plants was 1. To determine the prolificacy score, plants were assayed for the development of secondary ears at the R1 stage of development. Plants were rated on the following scale: 1=Little or no secondary ear formation; 2=Silks are prominent on the secondary ear; 3=Developed secondary ear emerged from the ear leaf sheath; and 4=Good secondary ear development similar to the primary ear. End-of-season harvest further indicated at least some secondary ears were productive with normally developed kernels.

Example 9. Broad-Acre Yield and Trait Trials in the Field with Hybrid Corn Plants Transformed with the GA20 Oxidase Suppression Construct The GA20 oxidase suppression construct described in Example 1 was transformed into a female commercial corn inbred line, and a number of transformation events were created. The transformed plants were grown and self-crossed to bulk up sufficient seeds, and then crossed to various male commercial corn inbred lines to produce hybrid corn plants. Each distinct male inbred line used to produce the male-female hybrid is called a tester. The hybrid corn plants with different testers were then grown on broad acres in the field according to standard agronomic practice (SAP). The planting density for SAP was 34,000 plants per acres with 30" row spacing.

For yield trials, four different transformation events expressing the GA20 oxidase suppression construct were crossed to 2 different commercial tester lines. The hybrid corn plants were then tested in 16 geographic locations across 6 US Midwest states. Yield of transgenic hybrid corn plants across these locations was calculated and compared to the yield of non-transgenic hybrid corn control plants. Table 4 provides the yield difference in bushels/acre between the transgenic hybrid corn plants for each event as compared to a non-transgenic control. A negative number indicates a yield decrease. Yield differences with a statistical p-value of less than 0.2 are indicated in Table 4 with bold and italic font. This notation is also used to indicate statistical significance for the remaining tables in these Examples, unless otherwise noted. As shown in Table 4 under the SAP heading, a significant increase in yield was observed in transgenic hybrid corn plants expressing the suppression construct (transgenic plants) under SAP conditions, relative to wild type hybrid corn plants (Control). The significant increase in yield was observed across 4 transgenic events, and 2 tester lines.

A comparable broad-acre yield trial was conducted under high density (HD) planting conditions with 42,000 plants per acre and 30" row spacing, and compared to standard agronomic practice (SAP) density. The differences in yield under HD conditions are provided in Table 4 under the HD heading. Mixed results were obtained under these high density conditions with yield varying across events and testers. However, an increase in yield was observed for two events with one of the two testers, and the possibility remains for higher yield across a greater number of germplasms under different high density conditions.

TABLE 4

Broad-acre yield difference between transgenic plants and control, under SAP and HD

| | SAP | | | HD | | |
|---|---|---|---|---|---|---|
| | Tester-1 | Tester-2 | Across Testers | Tester-1 | Tester-2 | Across Testers |
| Across Events | 3.7 | 3.9 | 4 | 3.5 | *-10.7* | -3.9 |
| Event-1 | *7.5* | 2.7 | *5.1* | 7.5 | -4.3 | 1.3 |
| Event-2 | 3.2 | *7.0* | *5.6* | -5.1 | *-14.9* | *-10.3* |
| Event-3 | 2.3 | 1.8 | 2 | *7.6* | *-9* | -0.7 |
| Event-4 | 1.7 | 4.6 | 3.4 | 3.1 | *-14.2* | *-6.1* |

Trait trials were also conducted in the field to measure a number of developmental and reproductive traits. These trials were conducted under normal density (SAP) as described above and ultra high density (UHD) planting conditions of 54,000 plants per acre with 20" row spacing. The trials were conducted in hybrid corn plants with 7 transformation events and 3 testers, and the data for each tester was pooled over the 7 events.

Table 5 summarizes the trait trial results in hybrid corn plants. The measurement is either a percent difference, or a difference of days or number of leaves, between the transgenic plants and the control. Where appropriate, the development stage, such as R3, etc., at which the measurement was taken, is indicated in parenthesis under the column "Trait Name". Pollen shedding is measured in terms of the number of days from germination to 50% of plants shedding pollen. Silking emergence is measured in terms of the number of days from germination to 50% of plants silking. Pollen-silk interval is a measure of the number of days from 50% of plants shedding pollen to silking. Stalk strength is a measure of the amount of force at which the stalk segment breaks laterally, using a stalk breaker instrument. Leaf area index (LAI) is a dimensionless quantity that characterizes the extent of the plant canopy, defined as the one-sided green leaf area per unit ground surface area within a broadleaf canopy space.

TABLE 5

Trait differences between transgenic and control plants under SAP and UHD.

| | | 30" SAP | | | 20" UHD | | |
|---|---|---|---|---|---|---|---|
| Measurement | Trait Name | Tester-1 | Tester-2 | Tester-3 | Tester-1 | Tester-2 | Tester-3 |
| % Delta | Plant height (R3) | *-46* | *-47.7* | *45.2* | *-38.3* | *-42.3* | *-41.6* |
| | Plant height below 6 ft | *YES* | *YES* | *YES* | *YES* | *YES* | *YES* |
| | Ear height (R3) | *-35.3* | *-39.8* | *-38.8* | *-48.3* | *-51.4* | *-48.4* |
| | Ear height above 18 inches | *YES* | *YES* | *YES* | *YES* | *YES* | *YES* |
| % Delta | Internode length (ear minus 2) (R3) | *-34.2* | *-34.7* | *-34* | *-44.9* | *-36.4* | *-42.3* |
| | Internode length (ear minus 4) (R3) | *-54.2* | *-49.4* | *-54.9* | *-60.1* | *-55.7* | *-59.4* |
| | Stalk Diameter (2 nodes below ear) (R3) | 4.4 | 5.8 | 4.5 | *37.7* | *43.1* | *35.5* |
| | Stalk Diameter (4 nodes below ear) (R3) | 3.9 | -1.6 | 1 | *16.3* | *15.6* | *16.5* |
| | Stalk strength 2nd node below ear (R5) | 10.2 | 0.1 | 0.7 | *50.1* | *115* | N/A |
| | Stalk strength 4th node below ear (R5) | -13.6 | *-22.3* | -11.5 | *13.3* | *78.4* | N/A |
| Days | Pollen-silk interval | *-0.88* | *-1* | *-0.5* | *0* | *-0.33* | *-0.07* |
| | Pollen shedding | *1.5* | 0.75 | *0.13* | *-0.21* | *0.31* | *-0.91* |
| | Silking emergence | *0.63* | 0.25 | *-0.38* | *-0.26* | *-0.06* | *-1.03* |
| Number | Green leaf # (R4) | *-1.4* | *-1.4* | *-1.7* | *-1.7* | *-1.4* | *-1.4* |
| | Green leaf # (R5) | *-1.8* | *-1.7* | *-1.6* | *-2.1* | *-1* | *-1.7* |
| | Green leaf # (7 days | -0.5 | *-0.4* | -0.3 | *-1.1* | -0.3 | *-0.6* |

TABLE 5-continued

Trait differences between transgenic and control plants under SAP and UHD.

| Measurement | Trait Name | 30" SAP | | | 20" UHD | | |
|---|---|---|---|---|---|---|---|
| | | Tester-1 | Tester-2 | Tester-3 | Tester-1 | Tester-2 | Tester-3 |
| | after R5) | | | | | | |
| | Green leaf # (14 days after R5) | *-0.2* | −0.4 | −0.2 | *-0.7* | −0.3 | *-0.3* |
| % Delta | Leaf area index (V6) | *30.8* | *33.9* | *51.5* | *-33.2* | *-14.8* | 16.6 |
| | Leaf area index (V8) | *20.1* | −1.4 | 15.4 | *37.5* | *29.7* | *32.5* |
| | Leaf area index (V10) | 10.7 | 2 | 8.5 | *25.9* | *27.9* | 7.7 |
| | Leaf area index (V12) | 2.3 | −5.4 | 3.6 | *20.2* | *19* | *15.7* |

As shown in Table 5, a significant decrease in plant height, ear height, and internode length was observed in transgenic plants relative to the control. The transgenic plants consistently exhibited plant heights below 6 feet, and ear heights above 18 inches, allowing harvesting by combine without modification to the machinery. In this experiment, increased stalk diameter was observed particularly under higher density planting conditions.

Table 6 summarizes the ear trait trial results for hybrid corn. The trials were conducted in hybrid corn plants with 7 transformation events and 3 testers, and the data for each tester was pooled over the 7 events. The measurements are the percent delta difference between the transgenic plants and the control. Where appropriate, the development stage, such as R3, etc., at which the measurement was taken, is indicated in parenthesis under the column "Trait Name". Ear area is a measure of the plot average size of an ear in terms of area from a 2-dimensional view taken by imaging the ear, including kernels and void. Ear diameter is a measures the plot average of the ear diameter measured as the maximal "wide" axis of the ear over its widest section. Ear length is a measure of the plot average of the length of ear measured from the tip of the ear in a straight line to the base of the ear node. Ear tip void pct is a measure of the plot average of the area percentage of void at the top 30% area of the ear, from a 2-dimensional view taken by imaging the ear, including kernels and void. Ear void measures the plot average of the area percentage of void on an ear, from a 2-dimensional view, is measured by imaging the ear, including kernels and void. Grain yield estimate is defined in Example 7. Kernels per unit area is measured as the plot average of the number of kernels per unit area of the field. Ears were collected from a set row length, typically one meter, and shelled and combined to count the kernels, and the count was then converted to the total kernels per unit area of the field. Single kernel weight measures the plot average of weight per kernel. It is calculated as the ratio of (sample kernel weight adjusted to 15.5% moisture)/(sample kernel number). Kernels per ear is a measure of the plot average of the number of kernels per ear. It is calculated as (total kernel weight/(Single Kernel Weight*total ear count), where total kernel weight and total ear count are measured from ear samples over an area between 0.19 to 10 square meters.

TABLE 6

Ear trait differences between transgenic and control plants, under SAP and UHD.

| Trait Name | 30" SAP | | | 20" UHD | | |
|---|---|---|---|---|---|---|
| | Tester-1 | Tester-2 | Tester-3 | Tester-1 | Tester-2 | Tester-3 |
| Ear area (R6) (cm$^2$) | *5.5* | *11.6* | *4.8* | *14.9* | *16.9* | 8.8 |
| Ear diameter (R6) (mm) | 2.2 | −0.7 | *-2.5* | −1.7 | 1.3 | −1.8 |
| Ear length (R6) (cm) | *7.3* | *12.5* | *7.4* | *15.4* | *14.3* | *11.1* |
| Ear tip void_pct (R6) (%) | −9.1 | −1.1 | 7.7 | −5.8 | 24 | 11.1 |
| Ear void (R6) (%) | −3.3 | 1.9 | 9.5 | −6.7 | 10 | 16.4 |
| Grain yield estimate (R6) (kg/hectare) | 2.8 | −4.6 | −5.0 | 0.2 | 19.2 | 0.9 |
| Kernels per unit area (R6) (kernels/m$^2$) | −0.7 | −9.8 | −6.7 | *11.6* | *34.4* | 9 |
| Kernels per ear (R6) (count) | −3.2 | 0.5 | −3.5 | *19.1* | *35.2* | 6.5 |
| Single kernel weight (R6) (mg) | 1.8 | 5.1 | 1.1 | *-10.5* | *-12.3* | −7.5 |

As shown in Table 6, there was a significant increase in ear area and ear length observed in these experiments for the transgenic plants as compared to the control. There was also a noticeable decrease in the ear diameter. In this experiment, the grain yield estimate was mostly neutral between transgenic plants and the control.

Additional data was collected in the field at standard density across 8 events crossed to one tester showing a reduction in plant height, ear height, and internode length, and an increase in stem diameter and harvest index, as compared to a control (data not shown). Plant heights were measured from the ground to the uppermost ligulated leaf at R3 stage. Ear heights were measured from the ground to the ear node at R3 stage. Stalk diameters were measured at the middle of the stalk internode 2 nodes below the ear, unless otherwise indicated. These data demonstrated high penetrance of plant height and stalk traits across events, although an increase in prolificacy (or the number of secondary ears) was not significant or pronounced in these studies.

Figure 9:
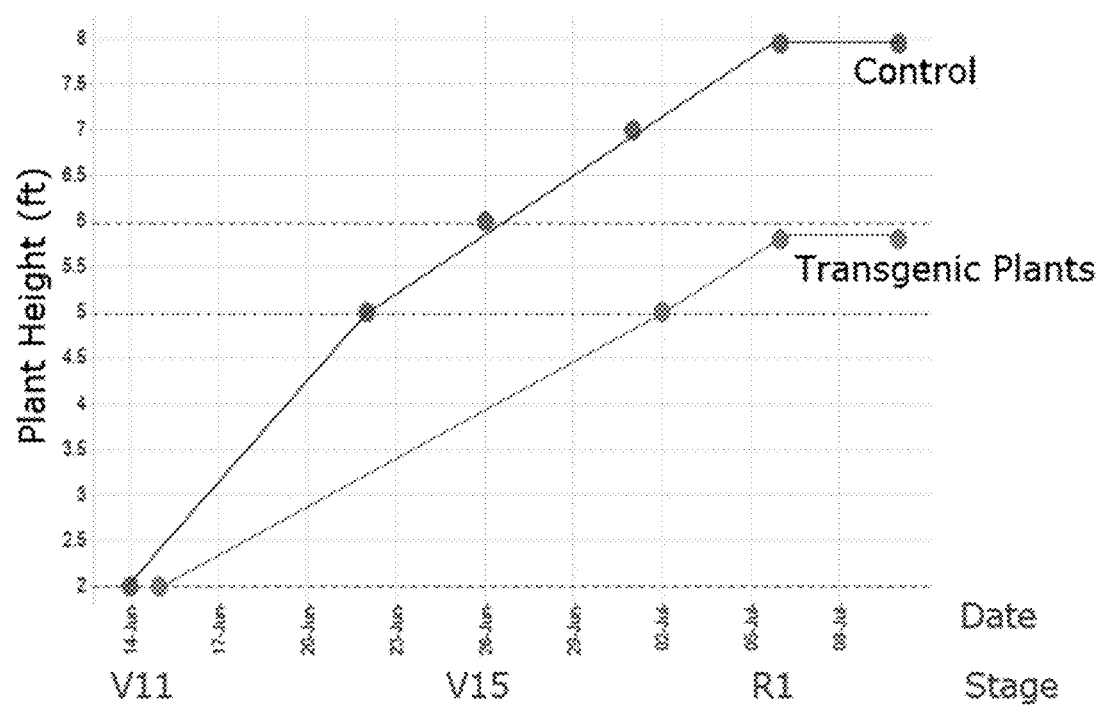
FIG. 9 shows the change in plant height over time during developmental stages V11 to beyond R1 between transgenic corn plants and control.

In a separate experiment, plant height growth was measured from V11 to R1 stage and beyond. FIG. 9 shows the differences in plant height between transgenic plants and the control over this time frame. Drawn on the figure are dotted lines for 5-foot and 6-foot heights for reference.

Example 10. Transgenic Plants Exhibited Enhanced Traits Under Nitrogen and Water Stress Conditions in Controlled Environment Conditions This example illustrates the enhanced water and nitrogen stress response of transgenic corn plants having the GA20 oxidase suppression construct described in Example 1 versus the control, in an automated greenhouse (AGH) or the field as indicated. The apparatus and the methods for automated phenotypic assaying of plants in AGH are disclosed, for example, in U.S. Patent Publication No. 2011/0135161, which is incorporated herein by reference in its entirety.

In the AGH setting, corn plants were tested under five different conditions including non-stress, mild and moderate nitrogen deficit, and mild and moderate water deficit stress conditions. The corn plants were grown under the stress-specific conditions shown in Table 7.

TABLE 7

Description of the five AGH growth conditions.

| Condition | Volumetric Water Content (VWC) | Nitrogen Concentration |
|---|---|---|
| No stress | 50% | 8 mM |
| Water Stress: mild | 40% | 8 mM |
| Water Stress: moderate | 35% | 8 mM |
| Nitrogen Stress: mild | 50% | 6 mM |
| Nitrogen Stress: moderate | 50% | 4 mM |

Water deficit is defined as a specific Volumetric Water Content (VWC) that is lower than the VWC of a non-stressed plant. For example, a non-stressed plant might be maintained at 50% VWC, and the VWC for a water-deficit assay might be defined between 35% to 40% VWC. Data were collected using visible light and hyperspectral imaging as well as direct measurement of pot weight and amount of water and nutrient applied to individual plants on a daily basis. Nitrogen deficit is defined (in part) as a specific mM concentration of nitrogen that is lower than the nitrogen concentration of a non-stressed plant. For example, a non-stressed plant might be maintained at 8 mM nitrogen, while the nitrogen concentration applied in a nitrogen-deficit assay might be maintained at a concentration between 4 to 6 mM.

Up to ten parameters were measured for each screen. The visible light color imaging based measurements are: plant height, biomass, and canopy area. Plant Height (PlntH) refers to the distance from the top of the pot to the highest point of the plant derived from a side image (mm). Biomass (Bmass) is defined as the estimated shoot fresh weight (g) of the plant obtained from images acquired from multiple angles of view. Canopy Area (Cnop) is defined as leaf area as seen in a top-down image ($mm^2$). Anthocyanin score and area, chlorophyll score and concentration, and water content score were measured with hyperspectral imaging. Anthocyanin Score (AntS) is an estimate of anthocyanin in the leaf canopy obtained from a top-down hyperspectral image. Anthocyanin Area (AntA) is an estimate of anthocyanin in the stem obtained from a side-view hyperspectral image. Chlorophyll Score (ClrpS) and Chlorophyll Concentration (ClrpC) are both measurements of chlorophyll in the leaf canopy obtained from a top-down hyperspectral image, where Chlorophyll Score measures in relative units, and Chlorophyll Concentration is measured in parts per million (ppm) units. Foliar Water Content (FlrWtrCt) is a measurement of water in the leaf canopy obtained from a top-down hyperspectral image. Water Use Efficiency (WUE) is derived from the grams of plant biomass per liter of water added. Water Applied (WtrAp) is a direct measurement of water added to a pot (pot with no hole) during the course of an experiment. These physiological trials were set up so that tested transgenic plants were compared to the control. Transgenic plants of two transformation events were measured in comparison with the control. All data are in percent delta difference of the transgenic plant with respect to the control. Data point with statistical p-value <0.1 were shown in bold italic font. Other data points have p-value>0.1.

Table 8 summarizes the AGH trait trial results as measured at 21 days from planting in the vegetative stage, whereas Table 9 summarizes the AGH trait trial results as measured at 55 days from planting in the reproductive stage, in transgenic plants having one of two events of the GA20 oxidase suppression construct described in Example 1 relative to control plants.

TABLE 8

Transgenic versus control plants in the greenhouse under normal and stress conditions, 21 days from planting.

| | Event-1 | | | | | Event 2 | | | | |
|---|---|---|---|---|---|---|---|---|---|---|
| | No stress | Nitrogen stress | | Water stress | | No stress | Nitrogen stress | | Water stress | |
| Trait Name | | Mild | Moderate | Mild | Moderate | | Mild | Moderate | Mild | Moderate |
| Plant Height | *-17.6* | *-20.1* | *-19* | *-21.2* | *-20.8* | *-16.1* | *-19.9* | *-21.6* | *-22.4* | *-21.3* |
| Biomass | -0.06 | *-8.9* | *5.61* | *-7.48* | *8.47* | -0.32 | *-8.11* | -1.77 | *-6.45* | -1.48 |
| Canopy area | 0.79 | *-7.6* | *11.4* | 1.45 | *16.9* | 0.36 | *-4.84* | *5.62* | 4.38 | 2.75 |
| Foliar water content | *18.6* | *23* | *16.3* | *55* | 10.1 | *8.9* | *30.9* | *15.5* | *55.9* | *21.4* |
| Anthocyanin area | *-38.9* | *-28.9* | *-35.4* | *-41* | *-55.5* | *-42.3* | *-39.7* | *-35.4* | *-46* | *-26* |
| Anthocyanin score | -10.21 | -14.5 | -2.9 | *129.5* | 2.4 | *78.1* | 4.5 | 3.3 | *119.6* | -2.5 |
| Chlorophyll concentration | 1.2 | 0.68 | 0.04 | *-5.84* | 3.27 | *-8.56* | -2.03 | -3.46 | -4.14 | 2.05 |

| | Transgenic versus control plants in the greenhouse under normal and stress conditions, 55 days from planting. | | | | | | | | |
|---|---|---|---|---|---|---|---|---|---|
| | Event-1 | | | | | Event-2 | | | |
| | No stress | Nitrogen stress | | Water stress | | No stress | Nitrogen stress | | Water stress | |
| Trait Name | | Mild | Moderate | Mild | Moderate | | Mild | Moderate | Mild | Moderate |
| Plant height | -31.9 | N/A | N/A | -40.7 | -25.4 | -33.3 | N/A | N/A | -41.3 | -29.6 |
| Biomass | -26.1 | N/A | N/A | -25.2 | -5.5 | -26.1 | N/A | N/A | -26.8 | -13.7 |
| Ear weight | 60.7 | 28.7 | 36 | 10.7 | 203.3 | 75.7 | 40.4 | 33.5 | 23.2 | 109.9 |
| Stover weight | -12.9 | -12.1 | -15.8 | -13.7 | 0 | -12.1 | -11.9 | -22.9 | -11.4 | -6.8 |
| Harvest index | -74.6 | -42.5 | -60.4 | 25.9 | 192 | 90.7 | 54.1 | 65 | 35.3 | 120.5 |
| Water applied | -8 | N/A | N/A | -16.8 | 3.4 | -11.3 | N/A | N/A | -16.3 | -2.3 |
| WUE | -19.2 | N/A | N/A | -10.1 | -8.5 | -16.5 | N/A | N/A | -12.5 | -11.3 |

As shown in Table 8, in comparison with the control, transgenic plants exhibited some enhanced traits related to stress resistance and maintained other positive traits under stress conditions. The plant height decreased significantly across all treatments and was not affected by stress condition. Biomass and canopy area were neutral in no-stress condition but increased in more severe stress conditions. The foliar water content increased significantly in no-stress and stress conditions, indicating that the transgenic plants retained more water in leaf tissues. The anthocyanin area decreased significantly in no-stress and stress conditions, indicating there was no nitrogen deficiency in the transgenic plants.

As shown in Table 9, in comparison with the control, transgenic plants exhibited significant decrease in the trait areas of Water Applied, WUE, biomass and stover weight, indicating that the transgenic plants had improved water use efficiency, with plants of lower biomass requiring less water. Harvest index increased significantly under non-stress and stress conditions.

Figure 10:
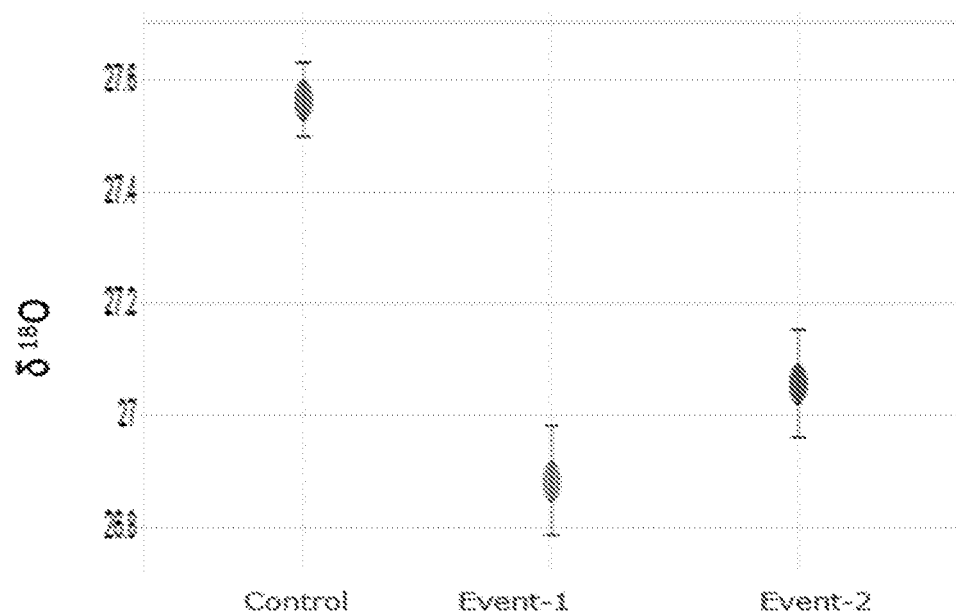
FIG. 10 shows a graph comparing measurements of stable oxygen isotope ratios ($\delta^{18}O$) as an indication of stomatal conductance and water levels in leaf tissue at R5 stage between transgenic corn plants and control.

Example 11. Transgenic Plants Exhibited Increased Drought Tolerance, Stomatal Conductance, and Root Front Velocity at Reproductive Stages at Both Standard and High Density in the Field Direct observations were made of decreased leaf rolling in transgenic corn plants having the GA20 oxidase suppression construct from Example 1 under drought conditions in the field compared to control plants. Corn leaf rolling occurs when leaf water potential drops below a threshold of approximately −1.1 MPa. Stomatal conductance also decreases under water stress. Stable oxygen isotope ratios ($\delta^{18}O$) were used as an index of the stomatal conductance, which is inversely proportional to stomatal conductance. A significant decrease of $\delta^{18}O$, and thus a significant increase in the stomatal conductance, in transgenic plants over the control was observed from ear leaf samples collected at R5 stage (see FIG. 10). Data was taken from transgenic plants across two transformation events and averaged across 10 testers with 2 reps per tester. Increased $\delta^{18}O$ in the leaf of control plants indicates that stomatal conductance was lower for the control. In conjunction with the reduced leaf rolling observed in the field, the significant increase of stomatal conductance in leaves of transgenic plants from yield trials at 15 out of 16 field locations indicates improved leaf water status during late vegetative growth for the transgenic plants.

Figure 11:
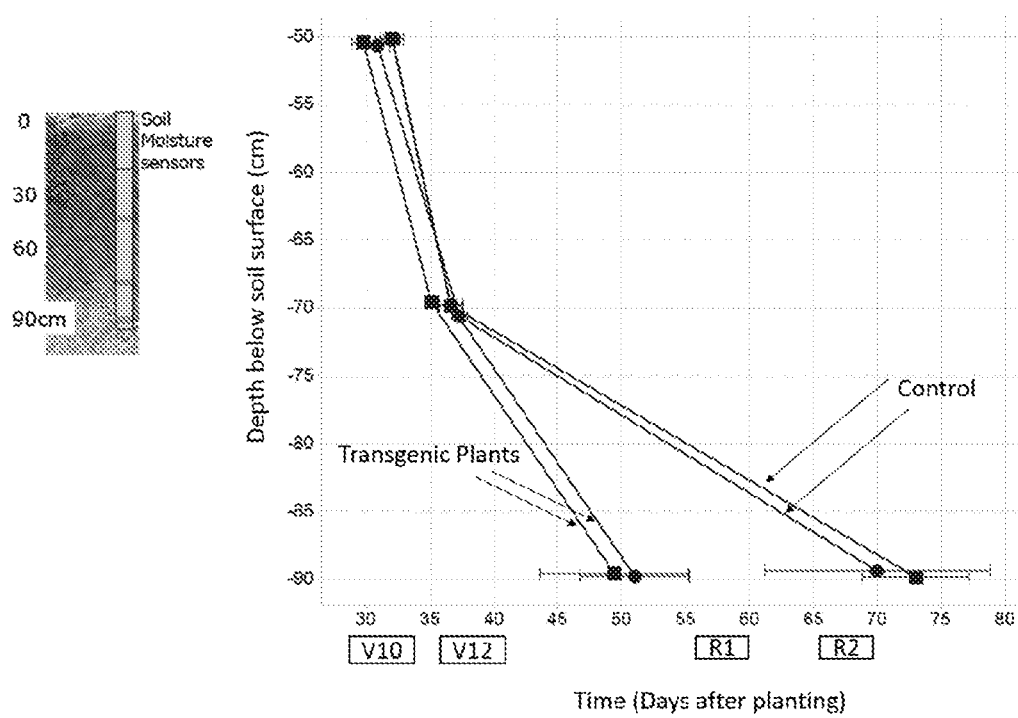
FIG. 11 shows a graph comparing root front velocity during developmental stages V10 to beyond R2 between transgenic and control plants at both SAP and HD conditions using sensors at different soil depths that detect changes in water levels indicating the presence of roots at that depth.

Effective water uptake by the roots is an important factor in plant growth. To measure the developmental progress of rooting depth, Sentek® SOLO soil moisture capacitance probes were installed at V4 stage within the row between plants at one field location. Soil moisture was measured on an hourly basis with capacitance sensors at depths of 10, 20, 30, 50, 70, 90, 120, and 150 cm from the ground level. The depth of the rooting front was inferred by the presence of diurnal patterns in soil moisture depletion recorded by the sensors. Root activity was already present at 10, 20, and 30 cm depth at the time of installation at V4 stage. We detected the first occurrence of soil moisture depletion at 50, 70, and 90 cm depths. The soil at 120 and 150 cam depth was saturated throughout the growing season. While root growth may have reached these depths, we were not able to detect root activity at these depths for this experiment due to the inability to detect soil moisture depletion in a saturated zone. FIG. 11 shows the time (days after planting) for the frontal root of the plant to reach various depths on the Y axis. Lines with circles are for plants at 30-inch row spacing and 34,000 plants per acre planting density, and lines with squares are for plants at 20-inch row spacing, and 55,000 plants per acre planting density. Growth stages are shown on the X axis.

As shown in FIG. 11, root growth was similar in this experiment between transgenic and control plants up to V12, with roots reaching 50 and 70 cm depth at about 30 and 36 days after planting, respectively. However, the transgenic plant roots reached 90 cm depth at or before R1 (i.e., at about day 50 after planting), or about 20 days earlier than control plant roots. The transgenic plants exhibited increased rooting front velocity after V11/V12 stage, which may lead to increased drought avoidance during the critical period of plant development around flowering. This increase in rooting front velocity may allow the transgenic plants to take advantage of deeper reserves of soil water during the critical period around R1 stage, possibly allowing drought effects on flowering and pollination to be avoided, reduced or minimized. Improved pollination under drought conditions may likely improve kernel set and yield potential.

To complement the above field experiment with moisture sensors, root front velocity for transgenic corn plants having the GA20 oxidase suppression construct from Example 1 (n=10) was measured in a root box experiment and compared to wild-type control plants (n=9). Plexiglass root boxes (5 feet tall and six-by-eight inches in cross section; ½ inch wall thickness) were filled with a mix of #10 field soil/vermiculite/perlite (1:1:1 ratio) and used for root visualization for each plant. Maximum rooting depth in each box was measured at regular intervals after planting (approximately every two days). In this experiment, median root front depth of transgenic plants was consistently greater or deeper than WT control plants starting at about 21 days after planting (i.e., at about V4 stage) and continuing until at least 34 days after planting when measurements were stopped (data not shown). This observation in controlled environment root boxes is consistent with the increased root depth observed with moisture sensors in the field and shows that deeper roots may occur at earlier developmental stages, although differences in root depth were not detected in the field experiment until after V11/V12 stage.

Although the root traits measured in the controlled environment experiments described in Example 14 below generally did not show a significant difference in root depth (or only a minimal difference), the vermiculite experiment in Example 14 was performed at V3 stage before the difference in root depth was observed in the root box experiment in this Example 11 (i.e., starting around V4 stage), and although the aeroponic apparatus experiment in Example 14 was performed at V5 stage, the aeroponic system does not have any plant-soil interaction (unlike the vermiculite experiments) that might affect normal (or more natural) root growth and development.

Figure 12A:
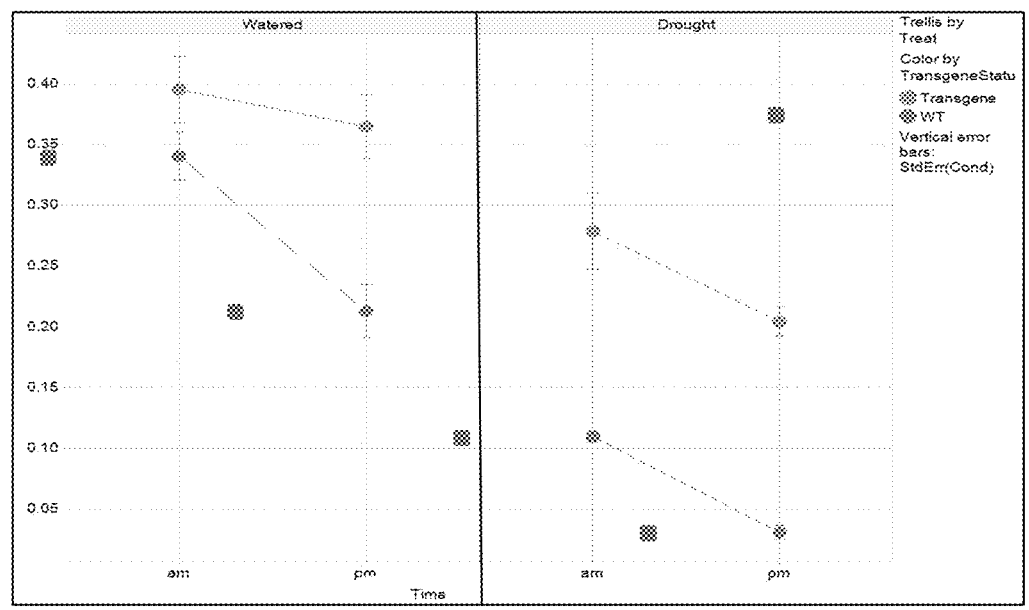
FIG. 12A shows differences in stomatal conductance during the morning and afternoon between transgenic corn plants and control under normal and drought conditions in the greenhouse.
Figure 12B:
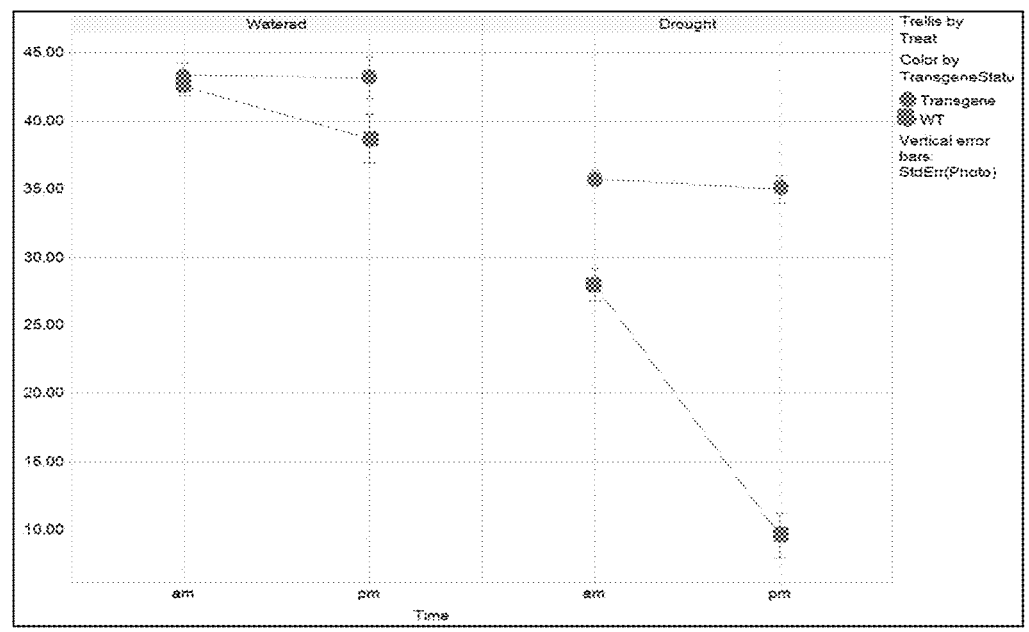
FIG. 12B shows differences in photosynthesis during the morning and afternoon between transgenic corn plants and control under normal and drought conditions in the greenhouse.

Example 12. Transgenic Plants have Higher Stomatal Conductance in Normal and Drought Conditions and Maintain Higher Photosynthesis Capacity Under Drought Stress Stomatal conductance and photosynthesis levels in leaves under normal and drought conditions was also measured in the greenhouse. For this experiment, transgenic plants with the GA20 oxidase suppression construct from Example 1 and wild-type control plants were subjected to a well watered (1500 ml water per day) or limited water/chronic drought (1000 ml water per day) treatment. Twenty (20) reps of the wild-type control plants and ten (10) reps per event (two events total) for the GA20 oxidase suppression construct were subjected to the well watered treatment, and one-hundred and forty (140) reps of the wild-type control plants and seventy (70) reps per event (two events total) for the GA20 oxidase suppression construct were subjected to the limited water/chronic drought treatment. Border plants of appropriate height (hybrids for WT plants and inbreds for transgenic plants) were placed around the perimeter of the experimental plants in the greenhouse to normalize the effects of shading. Diurnal stomatal conductance and photosynthesis measurements were taken in the morning and afternoon with a LI-COR® device at V12 stage per manufacturer's instructions. As shown in FIG. 12A, stomatal conductance was found to be consistently higher for the transgenic plants under both well-watered and drought conditions at both daily time points. Transgenic plants were also observed to have less leaf rolling under the drought condition. As further shown in FIG. 12B, a higher photosynthesis rate was also observed in response to drought conditions that did not significantly respond to increased sunlight in the afternoon, unlike control plants that showed a drop in the rate of photosynthesis in the afternoon particularly under drought conditions.

These results (in combination with the separate field observations above) demonstrate that the transgenic plants with the GA20 oxidase suppression construct not only had higher gas exchange and photosynthesis in the leaf, but maintained a higher gas exchange and photosynthesis in the leaf in response to water limiting/chronic drought conditions. It was further observed that transgenic plants had a lower leaf temperature than control plants (data not shown). Thus, it is predicted that transgenic plants expressing a GA20 oxidase suppression construct may have greater drought tolerance and an ability to maintain photosynthesis under water limiting conditions as compared to controls. Without being bound by theory, it is further proposed that the deeper roots observed for transgenic plants with the GA20 oxidase suppression construct (particularly during late vegetative and early reproductive stages) may contribute to the drought tolerance of these transgenic plant.

Example 13. Transgenic Plants Exhibited Reproductive Traits Comparable to Those of the Control in Greenhouse Conditions Transgenic corn plants having the GA20 oxidase suppression construct described in Example 1 and control plants were grown in pots in the greenhouse to reproductive R1 stage, and reproductive traits were measured in V8 and R1 stages. Data were taken for transgenic plants of two transformation events (Table 10). The data are provided either in terms of a difference in the number of days, or as a percent difference, for the transgenic plants as compared to a wild-type control, and significant changes are in bold. Trait names are defined in Examples 9 and 10 above. Specific observations of the traits and trait classes of flowering, immature ear, mature ear and tassel are summarized in the table. Overall, reproductive development in transgenic plants was nearly equivalent to control plants with only a few slight or minor changes.

TABLE 10

Greenhouse reproductive traits of transgenic plants vs control.

| Class | Trait | Event-1 | Event-2 | Observations |
|---|---|---|---|---|
| Development (R1) | Plant Height | -17.60% | -14% | Shorter plant |
| | Leaf Tip Number | 2% | 1.10% | Slight increase in leaf numbers (0.3) |
| Flowering (R1) | Days to 50% Silking and 50% Pollen Shed | -0.4 day | -0.5 day | Slightly delayed pollen shedding time with normal silking time; lower ASI |
| | Days to 50% Pollen Shedding | 1.10% | 1.10% | |
| | Days to 50% Visible Silk | 0.40% | -0.10% | |
| Immature Ear (V8) | Immature Ear Diameter at base | -28.50% | -22.60% | Slower initiation of ear development |
| | Immature Ear Internode Length | -6.10% | -4.20% | |
| | Immature Ear Length | -42% | -31% | |
| | Immature Kernels/Row Longitudinally | -38.70% | -29.70% | |
| Mature Ear (R1) | Kernels/Row Longitudinally | -1% | -0.40% | Properly developed mature ear |
| | Kernel Row Number | 2.20% | 0% | |
| | Total floret number | 1.10% | -0.50% | |
| | Shank internode number | -3.60% | 0.10% | |
| Tassel (R1) | Number of Tassel Branches | -5.40% | -3.80% | Properly developed tassel but with shorter |
| | Primary Lateral Tassel Branch | -10.40% | -9.10% | |

TABLE 10-continued

Greenhouse reproductive traits of transgenic plants vs control.

| Class | Trait | Event-1 | Event-2 | Observations |
|---|---|---|---|---|
| | Number Secondary Lateral Tassel Branch Number | −17.60% | −13.70% | first internode |
| | Rachilla Floret Density | −8.50% | −0.40% | |
| | First Tassel Internode Length | *−34.10%* | *−32.70%* | |

Example 14. Root Traits of Transgenic and Control Plants in Greenhouse Conditions Transgenic plants having the GA20 oxidase suppression construct described in Example 1 and control plants were grown in the greenhouse in vermiculite medium to V3 stage or in an aeroponic apparatus to V5 stage. Plants were extracted and roots washed for direct or optical imaging measurements of the root traits. Transgenic plants of 4 transformation events were tested in comparison to a control. Measurement results are summarized in Table 11 and 12 for plants from vermiculite medium growth, or in the aeroponic growth apparatus, respectively. Root Branch Point Number measures the number of root branch tip points of a plant through imaging of the plant root. The root system image was skeletonized for the root length measurement. Up to 40 images were taken at various angles around the root vertical axis and the measurement was averaged over the images. Root Total Length measures the cumulative length of roots of a plant, as if the roots were all lined up in a row, through imaging of the root system of the plant. The root system image was skeletonized for the root length measurement. Up to 40 images were taken at various angles around the root vertical axis and measurement was averaged over the images. Data in Tables 11 and 12 are the percent delta difference of the transgenic plants in comparison to the control with significant changes presented in bold.

TABLE 11

Greenhouse root traits of transgenic plants vs control at V3, in vermiculite medium

| | Event-1 | Event-2 | Event-3 | Event-4 |
|---|---|---|---|---|
| Average Root Diameter | *−12.2* | *−9.3* | *−13.8* | −5.9 |
| Root Branch Point Number | *12.6* | 5.8 | *11.7* | −0.4 |
| Root Dry Weight | 1 | −5.6 | −7.1 | −5 |
| Root Surface Area | 2.2 | −6.2 | −6 | 0 |
| Root Total Length | *10* | −1.9 | 3 | 1.4 |
| Plant Height | *−15.7* | *−14.4* | *−12.3* | *−17.3* |
| Shoot Dry Weight | −3.6 | −2 | −4.5 | −7.7 |
| Shoot to Root Ratio | −1.5 | 3.4 | 1.8 | −3.4 |

TABLE 12

Greenhouse root traits of transgenic plants vs control at V5, in aeroponic apparatus.

| | Event-1 | Event-2 | Event-3 | Event-4 |
|---|---|---|---|---|
| Root Branch Point Number | −6.18 | 5.01 | 5.63 | 6.38 |
| Root Total Length | −1.47 | 5.43 | 2.46 | 6.92 |
| Average Root Width | −1.12 | −5.05 | −5.23 | −3.56 |

TABLE 12-continued

Greenhouse root traits of transgenic plants vs control at V5, in aeroponic apparatus.

| | Event-1 | Event-2 | Event-3 | Event-4 |
|---|---|---|---|---|
| Root Volume | −1.1 | −4.21 | −8.47 | −1.09 |
| Root Dry Weight | 5.21 | −7.51 | −2.61 | 4.52 |
| Root Surface Area | −1.51 | 0.93 | −2.71 | 3.06 |
| Plant Height | *−13.84* | *−16.29* | *−14.02* | *−12.83* |
| Shoot Dry Weight | *−9.04* | *−16.58* | *−11.58* | *−7.06* |
| Total Dry Weight | −4.41 | *−14.19* | −8.54 | −3.24 |
| Shoot/Root Ratio | *−17.16* | *−13.13* | *−10.17* | *−13.52* |

As shown in Tables 11 and 12, the transgenic plants exhibited significant decrease in plant heights at V3 and V5 stages, but only minor variations in the overall root architecture were observed in these experiments between transgenic and control plants.

Example 15. Phenotypic Observations of Transgenic Plants with Alternate Promoters In Examples 1 through 14, transgenic plants contained a GA20 oxidase suppression element operably linked to an RTBV promoter. Corn plants were also transformed with the same suppression element operably linked to various other promoters, to test how different patterns of expression of the GA20 oxidase suppression element might affect plant height and other phenotypes.

Transgenic plants (R0 plants) regenerated from explants transformed with constructs operably linked to various promoters were observed at R5 growth stage in the greenhouse, and the ears were observed after being peeled back for dry down. The various promoters tested are identified in Table 13. Observations were made for plants of multiple transformation events for each construct containing a different promoter in comparison to control plants of the same breeding line without the GA20 oxidase suppression construct. The results of these observations are summarized in Table 13 across transformation events for each construct.

TABLE 13

Summary of R0 observations of transgenic plants with a miRNA suppression construct for GA20 oxidase under the control of different promoters.

| Promoter Name | Expression pattern | R0 plants observations |
|---|---|---|
| RTBV promoter | vascular enhanced | short; no off type |
| CAMV e35S promoter | constitutive | some short (variable); no off type |
| Coix lacryma-jobi polyubiquitin promoter | constitutive | some short (variable); no off type |
| rice actin promoter | constitutive | some short (variable); no off type |
| rice Gos2 promoter | constitutive | some short (variable); no off type |
| Enhancer + RTBV promoter | constitutive | short; no off type |
| C1 | constitutive | Short |
| corn PPDK promoter | leaf enhanced, high | mid-short; no off type |
| corn FDA promoter | leaf enhanced, medium | some short (variable); no off type |
| rice Nadh-Gogat promoter | leaf enhanced, low | mid-short; no off type |
| rice Cyp2 promoter | vascular enhanced | some short (variable); no off type |
| V1 | vascular enhanced | short; no off type |
| V2 | vascular enhanced | normal height; no off type |

TABLE 13-continued

Summary of R0 observations of transgenic plants with a miRNA suppression construct for GA20 oxidase under the control of different promoters.

| Promoter Name | Expression pattern | R0 plants observations |
| --- | --- | --- |
| V3 | vascular enhanced | normal height; no off-type |
| MMV.FLT promoter | stem enhanced, high | normal height; no off-type |
| S1 | stem enhanced, medium | normal height; no off-type |
| S2 | stem enhanced, medium | normal height; no off-type |
| S3 | stem enhanced, medium | normal height; no off-type |
| SETit.lfr promoter | root enhanced, high vascular enhanced | mid-short; no off-type |
| Rice Rcc3 promoter | root enhanced, low | normal height; no off-type |
| Rice Expb promoter | ear enhanced, high | normal height; no off-type |
| Maize H2a promoter | ear enhanced, low | normal height; no off-type |

As shown in Table 13, in comparison with controls, R0 transgenic plants with the GA20 oxidase suppression construct did not exhibit any significant off-types by observation for all of the promoters tested. Even expression directly in reproductive ear tissues did not cause any observable off-types. Plant heights were clearly decreased not only for the RTBV promoter construct (in the previous Examples), but also for transgenic plants having the same GA20 oxidase suppression construct operably linked to various constitutive promoters, leaf promoters at different expression levels, some vascular promoters, and a root promoter with a high expression level. An engineered promoter with constitutive expression (C1) linked to the GA20 oxidase suppression construct was tested and also found to cause a short stature phenotype. Similarly, at least one engineered promoter with vascular expression (V1) linked to the GA20 oxidase suppression construct was found to cause a short stature phenotype, in addition to the vascular rice Cyp2 promoter, although plants with two other engineered vascular promoters (V2, V3), and three engineered stem promoters (S1, S2, S3), did not have a reduced plant height. However, changing the transcriptional terminator sequence for the GA20 oxidase suppression construct under the control of the RTBV promoter did not alter the short stature phenotype (not shown in Table 11). As used herein, the term "mid-short" refers to a moderate reduction in plant height (relative to the reduction in plant height observed with the RTBV promoter), and an observation of "some short" means that there was some variation in the amount of reduction in plant height.

These results show that expression of the GA20 oxidase suppression element with constitutive promoters consistently produced a short stature phenotype, although there was some variability in the plant height phenotypes observed with these constitutive promoters. Likewise, a combination of the RTBV promoter with an enhancer element to convert the pattern of expression from vascular to constitutive still produced a short stature phenotype (indicating the sufficiency of the RTBV promoter). A few of the vascular promoters including the RTBV promoter produced a short stature phenotype, but a couple other engineered vascular promoters did not produce the short stature phenotype, which may be attributed to a lower expression level with these promoters. None of the stem promoters produced a short stature phenotype, indicating that expression of the GA20 suppression construct in the stem was not sufficient to produce this phenotype. Surprisingly, expression of the GA20 suppression construct in the leaf consistently produced short stature phenotypes with different levels of expression, although the results were somewhat variable. This data indicates that the production of active GAs in leaf tissue contributes to plant growth and ultimately plant height, even though such vertical growth occurs in the stem or stalk of the plant. Expression of the GA20 oxidase suppression construct with various root promoters generally did not produce a short stature phenotype, although one root promoter did produce a moderate phenotype, which may be due to additional expression in above-ground plant tissues.

R0 plants were then self-crossed and the resulting seeds were grown in the nursery to generate homozygous inbred progeny plants (R1 plants). Observations of R1 progeny transgenic plants with some of the promoter constructs (at least 4 transformation events per construct;) were made at the R1 developmental stage, in comparison to control plants of the same breeding line without the GA20 oxidase suppression construct. Like the R0 plants, R1 progeny plants expressing the GA20 oxidase suppression construct with each of the RTBV, CAMV e35S, and *Coix lacryma-jobi* polyubiquitin promoters were also found to have a short stature, semi-dwarf phenotype without any significant off-types observed.

Example 16. Phenotypic Observations of Transgenic Corn Plants with Constructs Targeting Different GA Oxidase Genes The Examples above demonstrate that a miRNA-expressing construct targeting the GA20 oxidase_3 and GA20 oxidase_5 genes for suppression, and operably linked to a plant-expressible vascular, constitutive and/or leaf promoter, may be used to generate a short stature, semi-dwarf corn plant. To test how targeting different GA20 or GA3 oxidase genes, or different portions of the GA20 oxidase_3 and/or GA20 oxidase_5 genes, for suppression might affect plant height, several constructs were generated and transformed into corn plants. Constructs were also made with the same targeting sequence as in the above Examples, but with a different miRNA backbone sequence (two from corn miRNAs, one from a soybean miRNA, and one from a cotton miRNA—the construct in the above Examples used a rice miRNA backbone sequence). Table 14 provides a list of these additional suppression constructs, along with observations of transgenic R0 plants comprising these constructs in the greenhouse (in comparison to wild-type control plants). Constructs targeting (i) GA20 oxidase_1/GA20 oxidase_2, (ii) GA20 oxidase_3/GA20 oxidase_9, (iii) GA20 oxidase_7/GA20 oxidase_8, and (iv) GA20 oxidase_3/GA20 oxidase_5 (with different miRNA backbones), each encoded a miRNA with a single targeting sequence complementary to both gene targets, whereas the stacks of (i) the individual GA20 oxidase_3 and GA20 oxidase_5 targeting sequences, (ii) the individual GA20 oxidase_4 and GA20 oxidase_6 targeting sequences, and (iii) the individual GA20 oxidase_4 and GA20 oxidase_7/8 targeting sequences, were each expressed as a single pre-miRNA with the two targeting sequences arranged in tandem that become cleaved and separated into two mature miRNAs. Table 14 provides the miRNA targeting sequence and the cDNA sequence complementary to the miRNA targeting sequence. For the GA20 oxidase_1/GA20 oxidase_2 construct, the asterisk (*) indicates that the alignment length between the targeting sequence of the miRNA and the mRNA target or recognition site was shorter (17 vs. 20 nucleotides) for GA20 oxidase_1 than for GA20 oxidase_2. Similarly for the GA20 oxidase_3/GA20 oxidase_9 construct, the asterisk (*) indicates that the alignment length between the targeting sequence of the miRNA and the mRNA target or recognition site was shorter (17 vs. 20 nucleotides) for GA20 oxidase_9 than for GA20 oxidase_3. For each of the constructs listed in Table 14, no significant off-types were observed, apart from the observations provided in the table.

TABLE 14

Summary of R0 observations of transgenic plants with miRNA suppression constructs targeting different GA oxidase genes.

| Targeted Gene(s) (Construct/ Promoter) | mRNA Targeted Area | cDNA Target Sequence (SEQ ID NO) | miRNA Targeting Sequence (SEQ ID NO) | Observations |
|---|---|---|---|---|
| GA20 oxidase_1 and GA20 oxidase_2 (RTBV promoter) | 1: exon* 2: exon | 47 | 48 | All events tall (WT) |
| GA20 oxidase_3 and GA20 oxidase_9 (RTBV promoter) | 3: exon 9: exon* | 49 | 50 | All events tall (WT) |
| GA20 oxidase_7 and GA20 oxidase_8 (RTBV promoter) | exon | 51 | 52 | All events - tall (WT) |
| GA20 oxidase_3 (Individual; RTBV and 35 S promoter) | UTR | 53 | 54 | Events slightly shorter (~6 inches vs. WT) |
| GA20 oxidase_5 (Individual; RTBV and 35 S promoter) | UTR | 55 | 56 | All events - tall (WT) |
| GA20 oxidase_3 and GA20 oxidase_5 (Individuals; Tandem stack) | 3: UTR 5: UTR | 53 55 | 54 56 | All events - shorter |
| GA20 oxidase_3 and GA20 oxidase_5 (Different miRNA backbones) (RTBV promoter) | 3/5: exons | 39 | 40 | All events/constructs - shorter |
| GA3 oxidase_1 (RTBV promoter) | UTR | 57 | 58 | All events - tall (WT) (only 3 events observed) |
| GA3 oxidase_1 (CAMV e35S promoter) | UTR | 57 | 58 | Some events - shorter |
| GA3 oxidase_2 (RTBV promoter) | exon | 59 | 60 | All events - shorter (darker green leaves) |
| GA3 oxidase_2 (CAMV e35S promoter) | exon | 59 | 60 | Some events - shorter |
| GA20 oxidase_4 and GA20 oxidase_6 (Individuals; Tandem stack) | 4: exon 6: exon | 61 63 | 62 64 | Some events - moderately shorter (~20%) |
| GA20 oxidase_4 and GA20 oxidase_7/8 (Individuals; Tandem stack) | 4: exon 7/8: exon | 61 51 | 62 52 | Some events - moderately shorter (~20%) |

The observations summarized in Table 14 demonstrate that targeting of several other GA20 oxidase genes did not produce a short stature, semi-dwarf phenotype. None of the constructs targeting (i) the related GA20 oxidase_1 and GA20 oxidase_2 genes, (ii) the related GA20 oxidase_3 and GA20 oxidase_9 genes, (iii) the related GA20 oxidase_7 and GA20 oxidase_8 genes, or (iv) the GA20 oxidase_9 gene alone produced an observable short stature, semi-dwarf phenotype in R0 plants. In contrast, those constructs encoding a single miRNA jointly targeting the GA20 oxidase_3 and GA20 oxidase_5 genes in transgenic R0 and R1 plants did produce a short stature, semi-dwarf phenotype, even if a different transcriptional termination sequence or different miRNA backbones are used (total of 5 miRNA backbone sequences tested). In addition, targeting different sequences of the GA20 oxidase_3 and GA20 oxidase_5 genes still produced semi-dwarf plants. Interestingly, suppression constructs that were designed to target either of the GA20 oxidase_3 and GA20 oxidase_5 genes individually did not produce a short stature, semi-dwarf phenotype, unlike constructs jointly targeting the GA20 oxidase_3 and GA20 oxidase_5 genes, although the construct individually targeting the GA20 oxidase_3 gene did produce a slight reduction in plant height. However, transgenic plants having a tandem vector stack of the suppression constructs individually targeting the GA20 oxidase_3 and GA20 oxidase_5 genes did produce a short stature, semi-dwarf phenotype similar to constructs encoding a single miRNA jointly targeting the GA20 oxidase_3 and GA20 oxidase_5 genes. These data demonstrate that a short stature, semi-dwarf phenotype is observed with constructs targeting both of the GA20 oxidase_3 and GA20 oxidase_5 genes, but the full semi-dwarf phenotype is not observed with targeting of the GA20 oxidase_3 and GA20 oxidase_5 genes individually for suppression (only a slight reduction in height with targeting GA20 oxidase_3, and no plant height phenotype observed with targeting GA20 oxidase_5). Moreover, no plant height phenotype was observed with targeting the GA20 oxidase_1, GA20 oxidase_2, GA20 oxidase_6, GA20 oxidase_7, GA20 oxidase_8, and/or GA20 oxidase_9 gene(s) as described.

Apart from the GA20 oxidase_3 and GA20 oxidase_5 genes, a moderate reduction in plant height was observed in R0 transgenic plants with a suppression construct comprising two targeting sequences in tandem complementary to jointly target (i) the GA20 oxidase_4 and GA20 oxidase_6 genes, or (ii) the GA20 oxidase_4, GA20 oxidase_7 and GA20 oxidase_8 genes—one of the two targeting sequences targets both the GA20 oxidase_7 and GA20 oxidase_8 genes. Given that a separate construct that targets the GA20 oxidase_7 and GA20 oxidase_8 genes did not produce a plant height phenotype, and the suppression construct targeting the GA20 oxidase_4 and GA20 oxidase_6 genes produced a plant height phenotype that was similar to the suppression construct targeting the GA20 oxidase_4, GA20 oxidase_7 and GA20 oxidase_8 genes, it is believed that targeting of the GA20 oxidase_4 gene is largely (if not fully) responsible for the plant height phenotype observed in these transgenic plants. Furthermore, transgenic corn plants with constructs targeting the GA3 oxidase_1 or GA3 oxidase_2 genes also displayed a reduction in plant height, although there was some variability in this phenotype depending on the constitutive promoter. Thus, in addition the GA20 oxidase_3 and GA20 oxidase_5 genes, the GA20 oxidase_4, GA3 oxidase_1, and GA3 oxidase_2 genes may also be targeted for suppression to produce short stature, semi-dwarf plants.

Example 17. Phenotypic Observations of Corn Plants Having an Edited GA20 Oxidase_3 or GA20 Oxidase_5 Gene In addition to the above suppression constructs, several genome-edited mutations were created in the endogenous GA20 oxidase_3 and GA20 oxidase_5 genes in corn plants to test for the phenotypic effect of knocking out each of these genes. A series of ten single-chain guide RNA (sgRNAs) encoding targeting constructs were created for each of the GA20 oxidase_3 and GA20 oxidase_5 genes that target different positions along the genomic sequence for each gene. An additional series of ten sgRNAs were created that each target both of the GA20 oxidase_3 and GA20 oxidase_5 genes, at similar or different positions along the genomic sequence for each gene. Targeted genome edits were made by delivering the sgRNA along with expression of a Cas9 protein to corn explants to cause a DSB or nick to occur at or near the genomic target site for the gRNA, which may then be imperfectly repaired to introduce a mutation at or near the target site. The presence of a mutation was subsequently confirmed by RFLP analysis and/or sequencing of plants. Table 15 below provides a list of the guide RNA (gRNA) constructs that were tested, which may be used for genome editing of one or both of the GA20 oxidase_3 and GA20 oxidase_5 gene(s) with a RNA-guided endonuclease. These guide RNA constructs are generally designed to target the coding sequences of the GA20 oxidase_3 and GA20 oxidase_5 genes, but some of the joint targeting constructs may instead target a UTR sequence of one of the two genes. These gRNAs may be used with a suitable endonuclease to produce a double stranded break (DSB) or nick in the genome at or near the genomic target site of the respective gRNA, which may be imperfectly repaired to produce a mutation (e.g., an insertion, deletion, substitution, etc.). Transgenic plants that were homozygous for an edited GA20 oxidase_3 gene or homozygous for an edited GA20 oxidase_5 gene were generated from a few of the constructs (see bold text). Events were also generated from constructs targeting both genes for editing. For the constructs jointly targeting the GA20 oxidase_3 and GA20 oxidase_5 genes, the coding sequence (CDS) coordinates are provided in reference to one of the two genes as indicated in parenthesis. Table 15 further shows which constructs produced gene editing events, whether those events were homozygous or heterozygous in the R0 plants, and the ±numbers in parenthesis indicate the likely sequence change with the mutation (e.g., +1 means an insertion of 1 nucleotide, etc., and larger or more complicated Indels are labeled "del." or insert."). For stacked targeting of GA20 oxidase_3 and GA20 oxidase_5, the identity of the mutated gene is also provided in parenthesis. Consistent with the results for the suppression constructs, transgenic plants homozygous for an edited GA20 oxidase_3 or GA20 oxidase_5 gene did not have a short stature, semi-dwarf phenotype and had a normal plant height relative to control plants (See constructs GA20 oxidase_3-D and GA20 oxidase_3-G, and constructs GA20 oxidase_5-B and GA20 oxidase_5-G in Table 15), indicating that knockout of only one of these genes is not sufficient to produce the semi-dwarf phenotype.

TABLE 15

Guide RNAs (gRNAs) targeting GA20 oxidase_3 and GA oxidase_5 genes for editing.

| gRNA Gene Target | gRNA Targeting Sequence (SEQ ID NO) | Gene CDS coordinates | Events Generated |
|---|---|---|---|
| GA20 oxidase_3-A | 138 | 552-572 | — |
| GA20 oxidase_3-B | 139 | 879-899 | — |
| GA20 oxidase_3-C | 140 | 147-167 | — |
| GA20 oxidase_3-D | 141 | 526-546 | 1. homozygous (−1) 2. heterozygous (−1) 3. bi-allelic (−2, +1) |
| GA20 oxidase_3-E | 142 | 446-466 | — |
| GA20 oxidase_3-F | 143 | 2227-2247 | — |
| GA20 oxidase_3-G | 144 | 548-568 | 1. homozygous (+1) 2. heterozygous (−1) 3. bi-allelic (+1, −1) |

TABLE 15-continued

Guide RNAs (gRNAs) targeting GA20 oxidase_3
and GA oxidase_5 genes for editing.

| gRNA Gene Target | gRNA Targeting Sequence (SEQ ID NO) | Gene CDS coordinates | Events Generated |
|---|---|---|---|
| GA20 oxidase_3-H | 145 | 547-567 | — |
| GA20 oxidase_3-I | 146 | 43-63 | — |
| GA20 oxidase_3-J | 147 | 548-567 | — |
| GA20 oxidase_5-A | 148 | 356-376 (+) | 1. heterozygous (−1) |
| GA20 oxidase_5-B | 149 | 99-119 | 1. homozygous (−1) |
| | | | 2. heterozygous (+1) |
| | | | 3. heterozygous (+1, −7) |
| | | | 4. heterozygous (−3, −1) |
| GA20 oxidase_5-C | 150 | 369-389 | — |
| GA20 oxidase_5-D | 151 | 48-68 | — |
| GA20 oxidase_5-E | 152 | 356-376 (−) | — |
| GA20 oxidase 5-F | 153 | 748-768 | 1. heterozygous (−1, +1) |
| GA20 oxidase 5-G | 154 | 770-790 | 1. homozygous (−1) |
| | | | 2. homozygous (−1) |
| GA20 oxidase_5-H | 155 | 10-30 | — |
| GA20 oxidase_5-I | 156 | 262-282 | — |
| GA20 oxidase_5-J | 157 | 768-788 | — |
| GA20 oxidase_3/5-A | 158 | 290 . . . 310 (GA20 Ox_3) | — |
| GA20 oxidase_3/5-B | 159 | 289 . . . 309 (GA20 Ox_3) | — |
| GA20 oxidase_3/5-C | 160 | 270 . . . 290 (GA20 Ox_5) | — |
| GA20 oxidase_3/5-D | 161 | 49 . . . 69 (GA20 Ox_3) | — |
| GA20 oxidase_3/5-E | 162 | 265 . . . 285 (GA20 Ox 5) | 1. heterozygous (O × 5, +1) |
| GA20 oxidase 3/5-F | 163 | 419 . . . 439 (GA20 Ox_3) | 1. hetero (O × 3, (+1, −1) hetero (O × 5, +1, del.) 2. hetero (O × 3, +1, del.) hetero (O × 5, +1, insert.) |
| GA20 oxidase_3/5-G | 164 | 110 . . . 130 (GA20 Ox_3) | — |
| GA20 oxidase_3/5-H | 165 | 634 . . . 654 (GA20 Ox_5) | — |
| GA20 oxidase_3/5-I | 166 | 98 . . . 118 (GA20 Ox_5) | — |
| GA20 oxidase_3/5-J | 167 | 517 . . . 537 (GA20 Ox_5) | — |

Example 18. Suppression Construct Targeting GA20 Oxidase_3 and GA20 Oxidase_5 Genes Reduces GA20 Oxidase Transcript and Active GA Levels in the Plant To determine how GA20 oxidase transcript levels were affected in transgenic plants with the suppression construct targeting the GA20 oxidase_3 and GA20 oxidase_5 genes, whole tissues from various parts of transgenic plants grown in the greenhouse were taken at different vegetative stages (V3, V8, and V14), and mRNA transcript levels for each of the GA20 oxidase genes were analyzed using a TaqMan® assay. For these experiments, total RNA was extracted using a Direct-Zol RNA extraction kit from Zymo Research™ and treated with Turbo™ DNase to reduce genomic DNA contamination. RNA was then reverse transcribed to generate double-stranded cDNA. Reverse transcription quantitative PCR was performed with gene specific primers and FAM labeled TaqMan® probes on the Bio-Rad® CFX96 Real Time System. Quality control metrics were calculated using tissue specific standards to determine qPCR efficiency and total RNA that had not undergone reverse transcription to account for residual genomic DNA contamination. The difference between cycle threshold values for genes of interest versus normalizer genes determined the relative quantity of each gene transcript in each tissue. This relative quantity was calculated using either one (18S) or the geometric mean of two (18S and ELF1A) normalizer genes.

In this experiment, the level of the GA20 oxidase_3 transcript was reduced in most of the vegetative tissues at these stages, including leaf and stem tissue at V3, internode tissue at V8, and leaf and internode tissue at V14, although the level of GA20 oxidase_3 transcript in V3 root and V8 leaf appeared unchanged (data not shown). Furthermore, the level of GA20 oxidase_5 transcript for this experiment was generally unchanged in the vegetative tissues tested (data not shown), although the level of expression of the GA20 oxidase_5 transcript was relatively low in these tissues. Neither GA20 oxidase_3 nor GA20 oxidase_5 were significantly reduced in root tissue samples of transgenic plants. Each of the other GA20 oxidase genes (i.e., the 1, 2, 4 and 6-9 subtypes) were generally unchanged or increased in some tissues of the transgenic plants.

A similar experiment was conducted with reproductive tissues from transgenic plants expressing the same suppression construct. Whole tissues from various parts of transgenic plants grown in the greenhouse were taken at different reproductive stages (R1 and R3), and mRNA transcript levels for each of the GA20 oxidase genes were analyzed using a TaqMan® assay. In this experiment, the levels of GA20 oxidase_3 and GA20 oxidase_5 transcripts were mostly unchanged in R1 leaf, ear, tassel and internode and R3 leaf and internode, relative to controls (data not shown). Results for the other GA20 oxidase genes were mostly mixed or neutral (data not shown).

These data show that the level of GA20 oxidase_3 transcripts in transgenic corn plants during vegetative stages was generally reduced in this experiment, but appears mostly unchanged relative to control plant tissues during later reproductive stages. Although a clear reduction in the level of GA20 oxidase_5 gene transcripts was not generally observed in these transgenic plant tissues, the expression level of this gene was relatively low. Thus, changes in its expression level may have been difficult to detect with this method. In addition, the suppression construct appears to be specific to the targeted GA20 oxidase genes since no consistent reduction in expression level was observed in this experiment for any of the other GA20 oxidase genes.

Figure 13A:
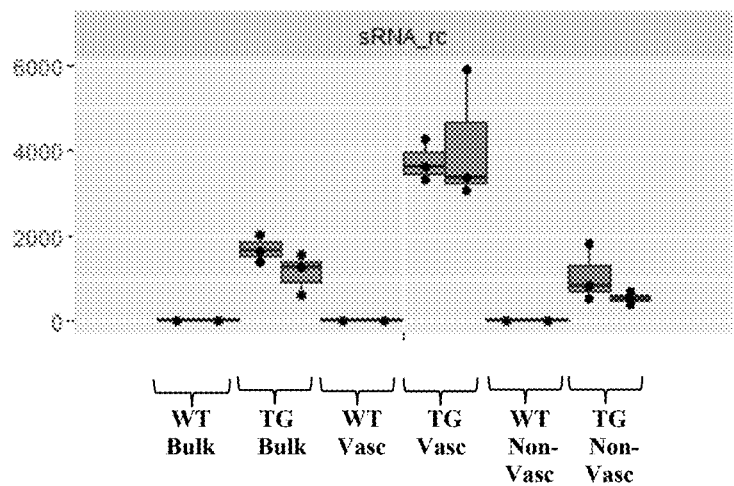
FIG. 13A shows differences in miRNA expression levels in bulk stem tissue, or separated vascular and non-vascular stem tissues, of transgenic corn plants versus control.

In a separate experiment, GA20 oxidase expression levels were determined in stem tissues of transgenic plants expressing the suppression construct from the prior Examples (targeting the GA20 oxidase_3 and GA20 oxidase_5 genes for suppression under the control of the RTBV promoter), in comparison to a wild-type control. Tissue samples were taken from V3-V6 stems/stalks and parts of those stems were further dissected to separate vascular and non-vascular tissues to determine differential expression levels among these tissues. Transcript expression levels were determined using a RNA sequencing (RNA-Seq) approach for quantitative comparison between transgenic and wild-type plant tissues. The data presented in FIG. 13A are generated from transgenic plants having one of two events and wild type control plants having one of two germplasms, with each bar in FIG. 13A representing one of the two transgenic events or germplasms, respectively. For these experiments, individual vascular bundles were separated from the remaining stem/stalk tissue of the samples and subjected to separate analysis. As shown in FIG. 13A, the miRNA expressed by the suppression construct was detected in bulk plant stem tissue ("bulk"; i.e., without separation of vascular and non-vascular tissues), as well as in separated vascular ("Vasc") and non-vascular ("Non-Vasc") tissues from the bulk stem/stalk sample. However, the expression level of the miRNA was much higher in vascular tissue than in non-vascular tissue indicating the vascular expression pattern of the RTBV promoter.

The bulk stem/stalk samples and the separated vascular and non-vascular samples were also analyzed in a similar RNA-Seq experiment to measure and compare the levels of GA20 oxidase_3 and GA20 oxidase_5 gene transcripts in transgenic versus wild-type control plants (along with other GA20 oxidase genes), although only one wild-type sample is shown for each tissue type. For these experiments, stalk tissue from control or transgenic plants (two events) were sectioned to separate vascular bundles and non-vascular tissues as described above. Total sRNA and mRNA were sequenced for each sample, and data was analyzed and compared using principle component analysis.

Figure 13B:
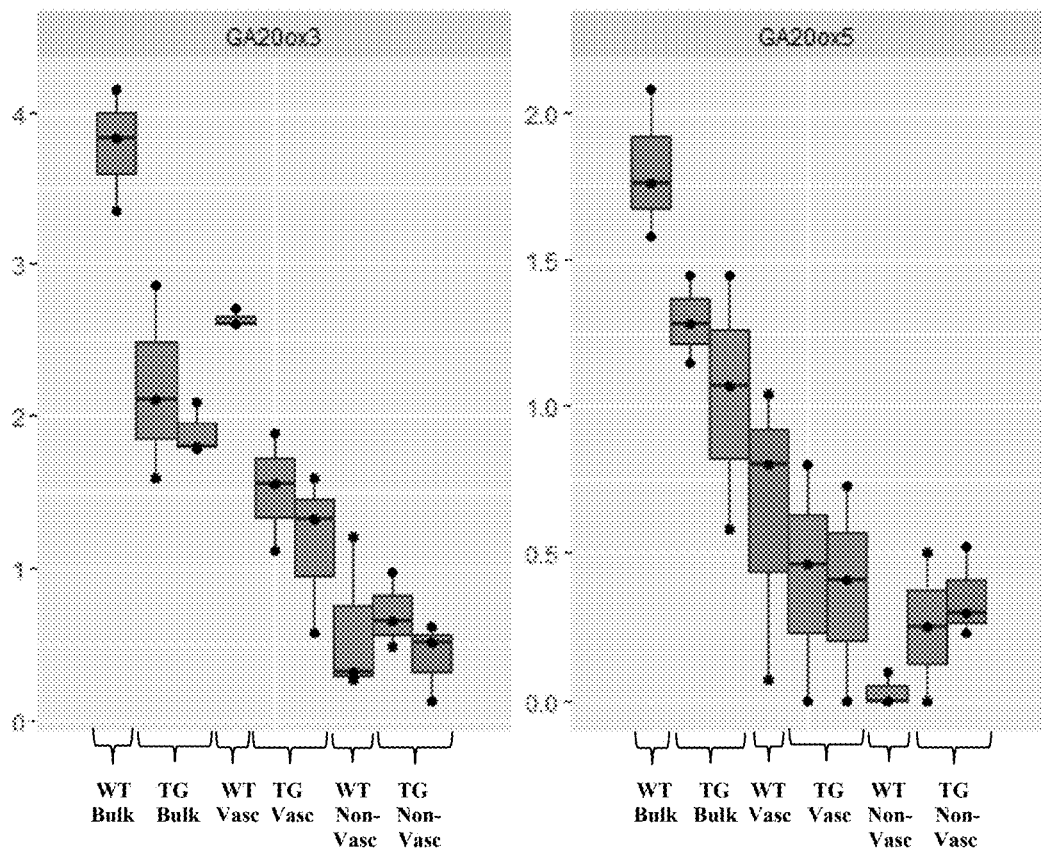
FIG. 13B shows differences in GA20 oxidase_3 and GA20 oxidase_5 mRNA transcript expression levels in bulk stem tissue, or separated vascular and non-vascular stem tissues, of transgenic corn plants versus control.

As shown in FIG. 13B, transcript levels of the GA20 oxidase_3 gene were significantly reduced in bulk stem tissue (Bulk) and separated stem vascular tissues (Vasc) of transgenic plants (TG) relative to wild-type controls (WT), but appeared unchanged in separated non-vascular (Non-Vasc) tissue. However, transcript levels of the GA20 oxidase_5 gene were significantly reduced in bulk stem tissue (Bulk), but relatively unchanged in separated vascular (Vasc) and non-vascular (Non-Vasc) tissues of transgenic plants, although there was a downward trend line for the GA20 oxidase_5 transcript in vascular (Vasc) tissue samples from transgenic plants. The level of expression of the GA20 oxidase_5 gene was low, particularly in non-vascular tissues. All other GA20 oxidase genes did not show a significant reduction in their transcript levels in the transgenic plant tissues analyzed, although a couple GA20 oxidase genes did show a slight upward trend in their level of expression. This data further demonstrates that the expression levels of the GA20 oxidase_3 and GA20 oxidase_5 genes are decreased to varying extents in one or more tissues of transgenic plants having the suppression construct relative to controls. Indeed, the higher expression of the miRNA and greater suppression of the endogenous GA20 oxidase_3 gene in vascular tissues is consistent with the vascular pattern of expression of the RTBV promoter, and perhaps the higher levels of GA20 oxidase_3 gene expression in vascular versus non-vascular tissues of wild-type plants. A similar pattern is also observed for the GA20 oxidase_5 gene, although not as pronounced as the GA20 oxidase_3 gene between vascular and non-vascular tissues.

The short stature, semi-dwarf phenotype observed with GA20 oxidase suppression in transgenic plants is likely mediated by a reduction in the level of active GAs present in the stem or internode tissues and/or in plant tissues that produce active GAs. To determine the levels of active GAs (particularly G1, G3 and G4) relative to other inactive forms of the hormone, GA levels were measured in different tissue samples taken from transgenic and wild-type control plants at different stages of development. For these experiments, fresh frozen samples for each tissue were milled and dispensed into 96 well glass tubes along with internal standards. Samples were extracted using methanol:water:acetic acid (80:19:1 v/v/v) solvent two times for 4 hours at 4° C. Solvent was evaporated from the extract to near dryness using multi-channel SPE with nitrogen. Samples were further purified using a SPE cartridge. After purification, samples were run using standard LC-MS/MS method with Shimadzu® Nexera® UPLC and SCIEX® triple quad 5500 mass spec instrumentation. Chromatographs were analyzed and quantified using internal standards.

Two sets of experiments were performed with samples taken from various tissues of vegetative stage plants. As shown in Table 16 for one experiment in the greenhouse, reduced levels of active GAs (GA1, GA3, and GA4) were observed in various tissues of transgenic plants at different vegetative stages. The data in Table 16 is displayed as the number of transgenic plants having a significant change in the amount of each GA hormone for a given tissue ("U"=up or increased; "D"=down or decreased; "N"=neutral or no change; and "T"=total number of plants). The GAs that showed at least a partial reduction in tissue samples are presented in bold. Active GA1 was reduced in leaf and internode tissues at V8 stage and internode tissue at V14 stage, and active GA4 was reduced in V3 stem and V8 and V14 internode. However, active GA3 was not observably reduced in this experiment. Other inactive forms of GAs were altered in various tissues of transgenic plants as shown in Table 16. In general, GAs that are downstream of GA20 oxidase genes in the gibberellic acid pathway (e.g., GA9, GA20, and GA34) tended to be reduced, whereas GAs that are upstream of GA20 oxidase genes tended to be higher (e.g., GA12 and GA53), which may be due to the lower activity of GA oxidase genes causing the precursor GAs upstream to accumulate. This data is consistent with suppression of GA20 oxidase activity in these tissues and lower levels of active GA hormones in the stem and leaf of transgenic plants.

In a separate experiment, similar measurements of GA hormones were taken from various plant tissues during vegetative stages of development. As shown in in Table 17 for an experiment using tissues taken from plants in the greenhouse and field, reduced levels of one or more active GAs (GA1, GA3, and GA4) were observed in the leaf and internode of transgenic plants at V3 and V8 stages. The leaf samples at V8 stage for this experiment were taken from plants in the field, unlike the other samples taken from plants in the greenhouse. The data in Table 17 is displayed in a similar manner as described for Table 16. Other inactive forms of GAs were altered in various tissues of transgenic plants as shown in Table 17. Similar to the observations above, GAs that are downstream of GA20 oxidase genes in the gibberellic acid pathway (e.g., GA9, GA20, and GA34) tended to be reduced, whereas GAs that are upstream of GA20 oxidase genes tended to be higher (e.g., GA12 and GA53). This data is again consistent with suppression of GA20 oxidase activity in these tissues and lower levels of active GA hormones in the stem and leaf of transgenic plants.

TABLE 16

Change in GA hormone levels in tissues of transgenic corn plants expressing a GA20 oxidase suppression construct in the greenhouse.

| Stage: | V3 | | | V8 | | V14 | | |
|---|---|---|---|---|---|---|---|---|
| Tissue: | Leaf | Stem | Root | Leaf | Internode | Leaf | Internode | Tassel |
| GA1 | 2N/2T | 2N/2T | 2N/2T | 2D/2T | 1D/1N/2T | 2N/2T | 2D/2T | 2N/2T |
| GA3 | 2N/2T | 2N/2T | 2N/2T | 2N/2T | 2N /2T | 2N/2T | 2N/2T | 2N/2T |
| GA4 | 2N/2T | 2D/2T | 2N /2T | 2N/2T | 2D/2T | 2U/2T | 2D/2T | 2N /2T |
| GA8 | 1U/1N/2T | 2N/2T | 1U/1N/2T | 2N/2T | 2D/2T | 1D/1N/2T | 1D/1N/2T | 1U/1N/2T |
| GA9 | 2N/2T | 2D/2T | 2N/2T | 2N/2T | 2D/2T | 2U/2T | 2D/2T | 1D/1N/2T |
| GA12 | 1D/1N/2T | 2U/2T | 2N/2T | 2U/2T | 2N/2T | 1U/1N/2T | 2N/2T | 2N/2T |
| GA20 | 2D/2T | 2N/2T | 2N/2T | 2D/2T | 2D/2T | 2D/2T | 1D/1N/2T | 2N/2T |
| GA34 | 2N/2T | 2D/2T | 2N/2T | 2N/2T | 2D/2T | 2N/2T | 2D/2T | 2N/2T |
| GA53 | 2U/2T | 2U/2T | 2N/2T | 2U/2T | 2N/2T | 2U/2T | 1U/1N/2T | 1U/1N/2T |

TABLE 17

Change in GA hormone levels in tissues of transgenic corn plants expressing a GA20 oxidase suppression construct in the greenhouse (GH) or field.

| | Stage: | | | |
|---|---|---|---|---|
| | V3 | | V8 | |
| Tissue: | Leaf (GH) | Root (GH) | Internode (GH) | Leaf (Field) |
| GA1 | 3D/1N/4T | 2D/1U/1N/4T | 3D/1N/4T | 7D/1N/8T |
| GA3 | 3D/1N/4T | 4N/4T | 3D/1N/4T | 7D/1N/8T |
| GA4 | 4N/4T | 4N/4T | 4D/4T | 8D/8T |
| GA8 | 4N/4T | 4N/4T | 4N/4T | 4N/4T |
| GA9 | 4D/4T | 4N/4T | 4D/4T | 5U/3N/8T |
| GA12 | ND | ND | ND | 7U/1N/8T |
| GA20 | 4D/4T | 1D/3N/4T | 4D/4T | 8D/8T |
| GA34 | 1U/3N/4T | 4D/4T | 4D/4T | 4U/4N/8T |
| GA53 | 4U/4T | 2U/2N/4T | 1D/3N/4T | 8U/8T |

Suppression of the GA20 oxidase_3 and GA20 oxidase_5 genes in transgenic corn plants reduces the levels of targeted GA oxidase transcripts in various tissues including the stem, internode, vascular tissues and leaves, and suppression of these GA20 oxidase genes is further associated with reduced levels of active GAs in tissues of the transgenic plant including the stem and internode, which is the site of action for affecting plant growth during vegetative stages and ultimately plant height by later vegetative and reproductive stages. Similar to observations that GA20 oxidase transcript levels are mostly unchanged or mixed in reproductive stage tissues, the levels of GA hormones including active GAs are also mostly unchanged or mixed in reproductive stage tissues (data not shown).

Having described the present disclosure in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

What is claimed is:

1. A recombinant DNA construct comprising a transcribable DNA sequence encoding a non-coding RNA molecule, wherein the non-coding RNA molecule comprises a targeting sequence that is:
   (a) at least 80% complementary to at least 19 consecutive nucleotides of a first mRNA molecule encoding a first endogenous gibberellin (GA) oxidase protein in a corn plant, the first endogenous GA oxidase protein being at least 90% identical to SEQ ID NO: 9; and
   (b) at least 80% complementary to at least 19 consecutive nucleotides of a second mRNA molecule encoding a second endogenous GA oxidase protein in a corn plant, the second endogenous GA oxidase protein being at least 90% identical to SEQ ID NO: 15;
wherein the transcribable DNA sequence is operably linked to a leaf promoter.

2. The recombinant DNA construct of claim 1, wherein the non-coding RNA molecule reduces the expression levels of the first and second mRNA molecules in at least one tissue of a transgenic corn plant comprising the recombinant DNA construct, relative to a control plant, when the non-coding RNA molecule is expressed in the transgenic corn plant.

3. The recombinant DNA construct of claim 1, wherein the non-coding RNA molecule reduces the expression levels of the first and second endogenous GA oxidase proteins in at least one tissue of a transgenic corn plant comprising the recombinant DNA construct, relative to a control plant, when the non-coding RNA molecule is expressed in the transgenic corn plant.

4. The recombinant DNA construct of claim 1, wherein the targeting sequence of the non-coding RNA molecule is at least 90% complementary to at least 19 consecutive nucleotides of a sequence selected from the group consisting of SEQ ID NOs: 7, 8, 13, and 14.

5. The recombinant DNA construct of claim 1, wherein the targeting sequence of the non-coding RNA molecule is at least 90% complementary to at least 19 consecutive nucleotides of the first mRNA molecule encoding the first endogenous GA20 oxidase protein.

6. The recombinant DNA construct of claim 3, wherein the targeting sequence of the non-coding RNA molecule is 100% complementary to at least 19 consecutive nucleotides of the first mRNA molecule encoding the first endogenous GA20 oxidase protein.

7. The recombinant DNA construct of claim 3, wherein the targeting sequence of the non-coding RNA molecule is at least 90% complementary to at least 19 consecutive nucleotides of SEQ ID NO: 7 or 8.

8. The recombinant DNA construct of claim 1, wherein the targeting sequence of the non-coding RNA molecule is at least 90% complementary to at least 19 consecutive nucleotides of the second mRNA molecule encoding the second endogenous GA20 oxidase protein.

9. The recombinant DNA construct of claim 6, wherein the targeting sequence of the non-coding RNA molecule is 100% complementary to at least 19 consecutive nucleotides of the second mRNA molecule encoding the second endogenous GA20 oxidase protein.

10. The recombinant DNA construct of claim 6, wherein the targeting sequence of the non-coding RNA molecule is at least 90% complementary to at least 19 consecutive nucleotides of SEQ ID NO: 13 or 14.

11. The recombinant DNA construct of claim 1, wherein the targeting sequence of the non-coding RNA molecule is at least 90% complementary to at least 21 consecutive nucleotides of the first mRNA molecule encoding the first endogenous GA20 oxidase protein, and is at least 90% complementary to at least 21 consecutive nucleotides of the second mRNA molecule encoding the second GA20 oxidase protein.

12. The recombinant DNA construct of claim 1, wherein the targeting sequence of the non-coding RNA molecule is 100% complementary to at least 21 consecutive nucleotides of the first mRNA molecule encoding the first endogenous GA20 oxidase protein, and is 100% complementary to at least 21 consecutive nucleotides of the second mRNA molecule encoding the second GA20 oxidase protein.

13. The recombinant DNA construct of claim 1, wherein the non-coding RNA molecule encoded by the transcribable DNA sequence is a precursor miRNA or siRNA that is processed or cleaved in a plant cell to form a mature miRNA or siRNA.

14. The recombinant DNA construct of claim 1, wherein the leaf promoter is selected from the group consisting of: a corn pyruvate phosphate dikinase promoter, a corn fructose 1,6 bisphosphate aldolase promoter, a rice Nadh-Gogat promoter, a ribulose biphosphate carboxylase (RuBisCO) promoter, a RuBisCO small subunit promoter, a chlorophyll a/b binding protein gene promoter, a phosphoenolpyruvate carboxylase promoter, and a Myb gene promoter.

15. The recombinant DNA construct of claim 1, wherein the leaf promoter comprises a DNA sequence that is at least 80% identical to SEQ ID NO: 72, SEQ ID NO: 73, or SEQ ID NO: 74.

16. The recombinant DNA construct of claim 1, wherein the leaf promoter comprises a DNA sequence that is at least 90% identical to SEQ ID NO: 72, SEQ ID NO: 73, or SEQ ID NO: 74.

17. The recombinant DNA construct of claim 1, wherein the leaf promoter comprises a DNA sequence that is 100% identical to SEQ ID NO: 72, SEQ ID NO: 73, or SEQ ID NO: 74.

18. A transgenic corn plant comprising a recombinant DNA construct comprising a transcribable DNA sequence encoding a non-coding RNA molecule, wherein the non-coding RNA molecule comprises a targeting sequence that is:
   (a) at least 80% complementary to at least 19 consecutive nucleotides of a first mRNA molecule encoding a first endogenous GA oxidase protein in a corn plant, the first endogenous GA oxidase protein being at least 90% identical to SEQ ID NO: 9; and
   (b) at least 80% complementary to at least 19 consecutive nucleotides of a second mRNA molecule encoding a second endogenous GA oxidase protein in a corn plant, the second endogenous GA oxidase protein being at least 90% identical to SEQ ID NO: 15;
wherein the transcribable DNA sequence is operably linked to a leaf promoter.

19. The transgenic corn plant of claim 18, wherein the expression levels of the first and second mRNA molecules are reduced in at least one tissue of the transgenic corn plant relative to a control plant.

20. The transgenic corn plant of claim 18, wherein the expression levels of the first and second endogenous GA oxidase proteins in at least one tissue of the transgenic corn plant relative to a control plant.

21. The transgenic corn plant of claim 18, wherein the transgenic corn plant has a shorter plant height relative to a control plant.

22. The transgenic corn plant of claim 18, wherein the height of the transgenic plant is at least 10% shorter than a control plant.

23. The transgenic corn plant of claim 18, wherein the height of the transgenic plant is at least 20% shorter than a control plant.

24. The transgenic corn plant of claim 18, wherein the height of the transgenic plant is at least 30% shorter than a control plant.

25. The transgenic corn plant of claim 18, wherein the height of the transgenic plant is at least 40% shorter than a control plant.

26. The transgenic corn plant of claim 18, wherein expression of the non-coding RNA molecule in the corn plant reduces the level of one or more active GAs in the corn plant as compared to a control plant.

27. The transgenic corn plant of claim 18, wherein the level of one or more active GAs in at least one internode tissue of the stem or stalk of the transgenic corn plant is lower than the same internode tissue of a control plant.

28. The transgenic corn plant of claim 18, wherein the transgenic plant has increased lodging resistance relative to a control plant.

29. The transgenic corn plant of claim 18, wherein the transgenic plant has reduced green snap relative to a control plant.

30. The transgenic corn plant of claim 18, wherein the transgenic plant has increased harvest index relative to a control plant.

31. The transgenic corn plant of claim 18, wherein the transgenic plant has deeper roots relative to a control plant.

32. The transgenic corn plant of claim 18, wherein the transgenic plant has one or more of the following traits relative to a control plant: increased leaf area, earlier canopy closure, higher stomatal conductance, lower ear height, increased foliar water content, improved drought tolerance, and reduced anthocyanin content or area in leaves.

33. The transgenic corn plant of claim 18, wherein the transgenic plant has one or more of the following traits relative to a control plant: increased ear weight, increased yield, increased seed number, and increased seed weight.

34. The transgenic corn plant of claim 18, wherein the stalk or stem diameter of the transgenic plant at one or more stem internodes is greater than the stalk or stem diameter at the same one or more internodes of a control plant.

35. The transgenic corn plant of claim 18, wherein the transgenic plant does not have any significant off-types in at least one female organ or ear.

36. The transgenic corn plant of claim 18, wherein the stalk or stem diameter of the transgenic corn plant at one or more of the first, second, third, and/or fourth internode below the ear is at least 5% greater than the same internode of a control plant.

37. The transgenic corn plant of claim 18, wherein the level of one or more active GAs in at least one internode tissue of the stem or stalk of the transgenic plant is lower than the same internode tissue of a control plant.

38. The transgenic corn plant of claim 18, wherein the targeting sequence of the non-coding RNA molecule is at least 90% complementary to at least 19 consecutive nucleotides of the first mRNA molecule encoding the first endogenous GA20 oxidase protein.

39. The transgenic corn plant of claim 18, wherein the targeting sequence of the non-coding RNA molecule is 100% complementary to at least 19 consecutive nucleotides of the first mRNA molecule encoding the first endogenous GA20 oxidase protein.

40. The transgenic corn plant of claim 18, wherein the targeting sequence of the non-coding RNA molecule is at least 90% complementary to at least 19 consecutive nucleotides of SEQ ID NO: 7 or 8.

41. The transgenic corn plant of claim 18, wherein the targeting sequence of the non-coding RNA molecule is at least 90% complementary to at least 19 consecutive nucleotides of the second mRNA molecule encoding the second endogenous GA20 oxidase protein.

42. The transgenic corn plant of claim 18, wherein the targeting sequence of the non-coding RNA molecule is 100% complementary to at least 19 consecutive nucleotides of the second mRNA molecule encoding the second endogenous GA20 oxidase protein.

43. The transgenic corn plant of claim 18, wherein the targeting sequence of the non-coding RNA molecule is at least 90% complementary to at least 19 consecutive nucleotides of SEQ ID NO: 13 or 14.

44. The transgenic corn plant of claim 18, wherein the targeting sequence of the non-coding RNA molecule is at least 90% complementary to at least 21 consecutive nucleotides of the first mRNA molecule encoding the first endogenous GA20 oxidase protein and is at least 90% complementary to at least 21 consecutive nucleotides of the second mRNA molecule encoding the second endogenous GA20 oxidase protein.

45. The transgenic corn plant of claim 18, wherein the targeting sequence of the non-coding RNA molecule is 100% complementary to at least 21 consecutive nucleotides of the first mRNA molecule encoding the first endogenous GA20 oxidase protein and is 100% complementary to at least 21 consecutive nucleotides of the second mRNA molecule encoding the second GA20 oxidase protein.

46. The transgenic corn plant of claim 18, wherein the non-coding RNA molecule encoded by the transcribable DNA sequence is a precursor miRNA or siRNA that is processed or cleaved in the transgenic corn plant to form a mature miRNA or siRNA.

47. The transgenic corn plant of claim 18, wherein the leaf promoter is selected from the group consisting of: a corn pyruvate phosphate dikinase promoter, a corn fructose 1,6 bisphosphate aldolase promoter, a rice Nadh-Gogat promoter, a ribulose biphosphate carboxylase (RuBisCO) promoter, a RuBisCO small subunit promoter, a chlorophyll a/b binding protein gene promoter, a phosphoenolpyruvate carboxylase promoter, and a Myb gene promoter.

48. The transgenic corn plant of claim 18, wherein the leaf promoter comprises a DNA sequence that is at least 80% identical to SEQ ID NO: 72, SEQ ID NO: 73, or SEQ ID NO: 74.

49. The transgenic corn plant of claim 18, wherein the leaf promoter comprises a DNA sequence that is at least 90% identical to SEQ ID NO: 72, SEQ ID NO: 73, or SEQ ID NO: 74.

50. The transgenic corn plant of claim 18, wherein the leaf promoter comprises a DNA sequence that is 100% identical to SEQ ID NO: 72, SEQ ID NO: 73, or SEQ ID NO: 74.

51. The transgenic corn plant of claim 18, wherein the recombinant DNA construct is stably integrated into the genome of the transgenic plant.

52. A transgenic corn plant part or plant cell comprising a recombinant DNA construct comprising a transcribable DNA sequence encoding a non-coding RNA molecule, wherein the non-coding RNA molecule comprises a targeting sequence that is:
(a) at least 80% complementary to at least 19 consecutive nucleotides of a first mRNA molecule encoding a first endogenous GA oxidase protein in a corn plant, the first endogenous GA oxidase protein being at least 90% identical to SEQ ID NO: 9; and (b) at least 80% complementary to at least 19 consecutive nucleotides of a second mRNA molecule encoding a second endogenous GA oxidase protein in a corn plant, the second endogenous GA oxidase protein being at least 90% identical to SEQ ID NO: 15;

wherein the transcribable DNA sequence is operably linked to a leaf promoter.

53. The transgenic corn plant part or plant cell of claim 52, wherein the non-coding RNA molecule reduces the expression levels of the first and second mRNA molecules in at least one tissue of a transgenic corn plant comprising the corn plant part or plant cell comprising the recombinant DNA construct, relative to a control plant, when the non-coding RNA molecule is expressed in the transgenic corn plant.

54. The transgenic corn plant part or plant cell of claim 52, wherein the non-coding RNA molecule reduces the expression levels of the first and second endogenous GA oxidase proteins in at least one tissue of a transgenic corn plant comprising the corn plant part or plant cell comprising the recombinant DNA construct, relative to a control plant, when the non-coding RNA molecule is expressed in the transgenic corn plant.

55. The transgenic corn plant part or plant cell of claim 52, wherein expression of the non-coding RNA molecule in the corn plant part or plant cell reduces the level of one or more active GAs in the corn plant part or plant cell as compared to a control plant part or plant cell.

56. The transgenic corn plant part or plant cell of claim 52, wherein the targeting sequence of the non-coding RNA molecule is at least 90% complementary to at least 19 consecutive nucleotides of the first mRNA molecule encoding the first endogenous GA20 oxidase protein.

57. The transgenic corn plant part or plant cell of claim 56, wherein the targeting sequence of the non-coding RNA molecule is 100% complementary to at least 19 consecutive nucleotides of the first mRNA molecule encoding the first endogenous GA20 oxidase protein.

58. The transgenic corn plant part or plant cell of claim 56, wherein the targeting sequence of the non-coding RNA molecule is at least 90% complementary to at least 19 consecutive nucleotides of SEQ ID NO: 7 or 8.

59. The transgenic corn plant part or plant cell of claim 52, wherein the targeting sequence of the non-coding RNA molecule is at least 90% complementary to at least 19 consecutive nucleotides of the second mRNA molecule encoding the second endogenous GA20 oxidase protein.

60. The transgenic corn plant part or plant cell of claim 59, wherein the targeting sequence of the non-coding RNA molecule is 100% complementary to at least 19 consecutive nucleotides of the second mRNA molecule encoding the second endogenous GA20 oxidase protein.

61. The transgenic corn plant part or plant cell of claim 59, wherein the targeting sequence of the non-coding RNA molecule is at least 90% complementary to at least 19 consecutive nucleotides of SEQ ID NO: 13 or 14.

62. The transgenic corn plant part or plant cell of claim 52, wherein the targeting sequence of the non-coding RNA molecule is at least 90% complementary to at least 21 consecutive nucleotides of the first mRNA molecule encoding the first endogenous GA20 oxidase protein, and is at least 90% complementary to at least 21 consecutive nucleotides of the second mRNA molecule encoding the second GA20 oxidase protein.

63. The transgenic corn plant part or plant cell of claim 52, wherein the targeting sequence of the non-coding RNA molecule is 100% complementary to at least 21 consecutive nucleotides of the first mRNA molecule encoding the first endogenous GA20 oxidase protein and is 100% complementary to at least 21 consecutive nucleotides of the second mRNA molecule encoding the second GA20 oxidase protein.

64. The transgenic corn plant part or plant cell of claim 52, wherein the non-coding RNA molecule encoded by the transcribable DNA sequence is a precursor miRNA or siRNA that is processed or cleaved in the corn plant part or plant cell to form a mature miRNA or siRNA.

65. The transgenic corn plant part or plant cell of claim 52, wherein the leaf promoter is selected from the group consisting of: a corn pyruvate phosphate dikinase promoter, a corn fructose 1,6 bisphosphate aldolase promoter, a rice Nadh-Gogat promoter, a ribulose biphosphate carboxylase (RuBisCO) promoter, a RuBisCO small subunit promoter, a chlorophyll a/b binding protein gene promoter, a phosphoenolpyruvate carboxylase promoter, and a Myb gene promoter.

66. The transgenic corn plant part or plant cell of claim 52, wherein the leaf promoter comprises a DNA sequence that is at least 80% identical to SEQ ID NO: 72, SEQ ID NO: 73, or SEQ ID NO: 74.

67. The transgenic corn plant part or plant cell of claim 52, wherein the leaf promoter comprises a DNA sequence that is at least 90% identical to SEQ ID NO: 72, SEQ ID NO: 73, or SEQ ID NO: 74.

68. The transgenic corn plant part or plant cell of claim 52, wherein the leaf promoter comprises a DNA sequence that is 100% identical to SEQ ID NO: 72, SEQ ID NO: 73, or SEQ ID NO: 74.

69. The transgenic corn plant part or plant cell of claim 52, wherein the recombinant DNA construct is stably integrated into the genome of the transgenic corn plant part or plant cell.

70. A transformation vector comprising the recombinant DNA construct of claim 1.

71. A DNA molecule comprising the recombinant DNA construct of claim 1.

72. A modified plant product made from the transgenic corn plant of claim 18, wherein the modified plant product comprises the recombinant DNA construct.

73. A modified plant product made from the transgenic corn plant part of claim 52, wherein the modified plant product comprises the recombinant DNA construct.

74. The modified plant product of claim 73, wherein the transgenic corn plant part is a seed.

75. A modified plant product comprising the recombinant DNA construct of claim 1.

76. A composition comprising the recombinant DNA construct of claim 1.

77. A nonviable corn plant part comprising the recombinant DNA construct of claim 1.

78. A non-regenerable corn plant part comprising the recombinant DNA construct of claim 1.

79. A nonviable and non-regenerable corn plant part comprising the recombinant DNA construct of claim 1.

80. A modified plant product comprising a nonviable or non-regenerable corn plant part and the recombinant DNA construct of claim 1.

81. A modified corn protoplast comprising the recombinant DNA construct of claim 1.

82. A modified seed comprising the recombinant DNA construct of claim 1.

83. The transgenic corn plant part or plant cell of claim 52, wherein the transgenic corn plant part is a seed.

* * * * *

UNITED STATES PATENT AND TRADEMARK OFFICE
CERTIFICATE OF CORRECTION

| | | |
|---|---|---|
| PATENT NO. | : 12,319,922 B2 | Page 1 of 1 |
| APPLICATION NO. | : 17/713344 | |
| DATED | : June 3, 2025 | |
| INVENTOR(S) | : Edwards M. Allen et al. | |

It is certified that error appears in the above-identified patent and that said Letters Patent is hereby corrected as shown below:

In the Claims

Claim 20, Column 344, Line 60, should read: "The transgenic corn plant of claim 18, wherein the expression levels of the first and second endogenous GA oxidase proteins are reduced in at least one tissue of the transgenic corn plant relative to a control plant."

Signed and Sealed this
Fourth Day of November, 2025

John A. Squires
*Director of the United States Patent and Trademark Office*

SEQUENCE LISTING

<160> NUMBER OF SEQ ID NOS: 167

<210> SEQ ID NO 1
<211> LENGTH: 1741
<212> TYPE: DNA
<213> ORGANISM: Zea mays

<400> SEQUENCE: 1

```
gacggtagtt ttcatctaaa gtttattctt cgtcacatgg gatggccgtt tgcttgtttg      60
ttgcttccgg gaggcggtgg tgaattgaag cagatcgaca agcatggctg cccactggtc     120
tcgatcgatc ggcctgccat gccatgccat gccactagag tccgtcctga ctggccgccc     180 gttccccgt ataaaaaggc aggcaggcag gcagagcggg gacgagcaag caagcagttg     240
cagttgcagc ggcctcctcc tctgcttcct ccctcctcct cctcaccatg gtgctggctg     300
cgcacgatcc ccctcccctt gtgttcgacg ctgcccgcct gagcggcctc tccgacatcc     360
cgcagcagtt catctggccg gcggacgaga gccccacccc ggactccgcc gaggagctgg     420
ccgtgccgct catcgacctc tccggggacg ccgccgaggt ggtccggcag gtccggcgcg     480
cctgcgacct gcacggcttc ttccaggtgg tggggcacgg catcgacgcg gcgctgacgg     540
cggaggccca ccgctgcatg gacgccttct tcacgctgcc gctcccggac aagcagcgcg     600
cgcagcgccg ccaggggac agctgcggct acgccagcag cttcacgggc cggttcgcgt      660
```

```
ccaagctgcc ctggaaggag acgctgtcgt tccgctacac cgacgacgac gacggcgaca      720
agtccaagga cgtcgtggcg tcctacttcg tggacaagct gggcgagggg taccggcacc      780
acggggaggt gtacgggcgc tactgctctg agatgagccg tctgtcgctg gagctcatgg      840
aggtgctagg cgagagcctg ggcgtgggcc ggcgccactt ccggcgcttc ttccagggga      900
acgactccat catgcgcctc aactactacc cgccgtgcca gcggccctac gacacgctgg      960
gcacggggcc gcattgcgac cccacgtcgc tcaccatcct gcaccaggac gacgtgggcg     1020
gactccaggt gttcgacgcc gccacgctcg cgtggcgctc catcaggccc cgcccgggcg     1080
ccttcgtcgt caacatcggc gacaccttca tggcgctctc caacgggcgc tacaggagct     1140
gcctccaccg cgccgtcgtc aacagccggg tggcacgccg ctcgctcgcc ttcttcctgt     1200
gcccggagat ggacaaggtg gtcaggccgc ccaaggagct ggtggacgac gccaacccga     1260
gggcgtaccc ggacttcacg tggaggacgc tgctggactt caccatgagg cactacaggt     1320
cggacatgag gacgctcgag gccttctcca actggctcag caccagtagc aatggcggac     1380
agcacctgct ggagaagaag taggcatgct atttgggtat ggaagatggt ggatgtaagc     1440
aaacaaagcc aaattaagca gagtaggtta attaaggttg gctgatgatc catttaggga     1500
aggagctgat ctccctgact ccctcctcca attttctcaa ccaaatttat atagtataat     1560
aataataata aaatagcaag taatagttgt atcgtattat tattaattaa tttattagct     1620
ggtaggcaag tagtattaaa taccatttgt agtacgatgg gcgtatttct attttggcgt     1680
tttgctctgt gttttttgac gttccttttg gatttggggg gacctcagat cagctcggcc     1740
t                                                                   1741
```

<210> SEQ ID NO 2
<211> LENGTH: 1116
<212> TYPE: DNA
<213> ORGANISM: Zea mays

<400> SEQUENCE: 2

```
atggtgctgg ctgcgcacga tccccctccc cttgtgttcg acgctgcccg cctgagcggc       60
ctctccgaca tcccgcagca gttcatctgg ccggcggacg agagccccac cccggactcc      120
gccgaggagc tggccgtgcc gctcatcgac ctctccgggg acgccgccga ggtggtccgg      180
caggtccggc gcgcctgcga cctgcacggc ttcttccagg tggtggggca cggcatcgac      240
gcggcgctga cggcggaggc ccaccgctgc atggacgcct tcttcacgct gccgctcccg      300
gacaagcagc gcgcgcagcg ccgccagggg gacagctgcg gctacgccag cagcttcacg      360
ggccggttcg cgtccaagct gccctggaag gagacgctgt cgttccgcta caccgacgac      420
gacgacggcg acaagtccaa ggacgtcgtg gcgtcctact tcgtggacaa gctgggcgag      480
gggtaccggc accacgggga ggtgtacggg cgctactgct ctgagatgag ccgtctgtcg      540
ctggagctca tggaggtgct aggcgagagc ctgggcgtgg gccggcgcca cttccggcgc      600
ttcttccagg ggaacgactc catcatgcgc ctcaactact acccgccgtg ccagcggccc      660
tacgacacgc tgggcacggg gccgcattgc gaccccacgt cgctcaccat cctgcaccag      720
gacgacgtgg gcggactcca ggtgttcgac gccgccacgc tcgcgtggcg ctccatcagg      780
ccccgcccgg gcgccttcgt cgtcaacatc ggcgacacct tcatggcgct ctccaacggg      840
cgctacagga gctgcctcca ccgcgccgtc gtcaacagcc gggtggcacg ccgctcgctc      900
gccttcttcc tgtgcccgga gatggacaag gtggtcaggc cgcccaagga gctggtggac      960
```

```
gacgccaacc cgagggcgta cccggacttc acgtggagga cgctgctgga cttcaccatg    1020
aggcactaca ggtcggacat gaggacgctc gaggccttct ccaactggct cagcaccagt    1080
agcaatggcg gacagcacct gctggagaag aagtag                              1116
```

<210> SEQ ID NO 3
<211> LENGTH: 371
<212> TYPE: PRT
<213> ORGANISM: Zea mays

<400> SEQUENCE: 3

```
Met Val Leu Ala Ala His Asp Pro Pro Leu Val Phe Asp Ala Ala
1               5                   10                  15

Arg Leu Ser Gly Leu Ser Asp Ile Pro Gln Gln Phe Ile Trp Pro Ala
                20                  25                  30

Asp Glu Ser Pro Thr Pro Asp Ser Ala Glu Glu Leu Ala Val Pro Leu
            35                  40                  45

Ile Asp Leu Ser Gly Asp Ala Ala Glu Val Val Arg Gln Val Arg Arg
50                  55                  60

Ala Cys Asp Leu His Gly Phe Phe Gln Val Val Gly His Gly Ile Asp
65                  70                  75                  80

Ala Ala Leu Thr Ala Glu Ala His Arg Cys Met Asp Ala Phe Phe Thr
                85                  90                  95

Leu Pro Leu Pro Asp Lys Gln Arg Ala Gln Arg Gln Gly Asp Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Tyr Thr Asp Asp Asp Gly Asp
    130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
            180                 185                 190

Val Gly Arg Arg His Phe Arg Phe Phe Gln Gly Asn Asp Ser Ile
        195                 200                 205

Met Arg Leu Asn Tyr Tyr Pro Pro Cys Gln Arg Pro Tyr Asp Thr Leu
210                 215                 220

Gly Thr Gly Pro His Cys Asp Pro Thr Ser Leu Thr Ile Leu His Gln
225                 230                 235                 240

Asp Asp Val Gly Gly Leu Gln Val Phe Asp Ala Ala Thr Leu Ala Trp
                245                 250                 255

Arg Ser Ile Arg Pro Arg Pro Gly Ala Phe Val Val Asn Ile Gly Asp
            260                 265                 270

Thr Phe Met Ala Leu Ser Asn Gly Arg Tyr Arg Ser Cys Leu His Arg
        275                 280                 285

Ala Val Val Asn Ser Arg Val Ala Arg Arg Ser Leu Ala Phe Phe Leu
    290                 295                 300

Cys Pro Glu Met Asp Lys Val Val Arg Pro Pro Lys Glu Leu Val Asp
305                 310                 315                 320

Asp Ala Asn Pro Arg Ala Tyr Pro Asp Phe Thr Trp Arg Thr Leu Leu
                325                 330                 335

Asp Phe Thr Met Arg His Tyr Arg Ser Asp Met Arg Thr Leu Glu Ala
            340                 345                 350
```

Phe Ser Asn Trp Leu Ser Thr Ser Ser Asn Gly Gly Gln His Leu Leu
        355                 360                 365
Glu Lys Lys
    370

<210> SEQ ID NO 4
<211> LENGTH: 1517
<212> TYPE: DNA
<213> ORGANISM: Zea mays

<400> SEQUENCE: 4

| | | | | | |
|---|---|---|---|---|---|
| caggaataaa | ataagcctcc | gcccggcttc | gttgcatcca | cgcacgcagc | aagcgatcgg | 60 |
| atttcgccag | catggcggcg | gcggccgtgg | tgttcgacgc | cgaggcgctg | agccgggagg | 120 |
| agcacatccc | ggcgcagttc | gtgtggccca | ccgaggagcg | ggcgccggcg | ggcggcgtgg | 180 |
| aggaggtcgc | catccccgtg | gtcgacctcg | gcgagttcct | ccgccgcggg | gtgctcccgc | 240 |
| gcggcgtggc | ggaggcgtgc | gagcgccacg | gcgtcttcca | ggtggtgaac | cacggcgtgg | 300 |
| gcgccgcgct | gctcgccgag | gcctaccgct | gttgcgacgc | cttttacgcg | ctcccgctcg | 360 |
| cggacaagca | gcgcgcgcag | cgccggcacg | gggagaacca | cggctacgcc | agcagcttca | 420 |
| cgggccgctt | ccactgctgc | ctgccgtgga | aggagacgct | gtccttcaac | tgccccgccg | 480 |
| gtgccgggac | tgcgcgcgcc | gtcgtcggct | acttcgtcga | cgtcctcggc | gaggactacc | 540 |
| gccacatggg | ggaggtgtac | caggagtact | gcgacgcgat | gacgcgtctg | gcgctggacg | 600 |
| tgacggaggt | gctggcggca | gcgctggggc | tggaccgcgg | cgcactgcgc | ggcttcttcg | 660 |
| agggcggcga | ctccgtcatg | cggctgaacc | actacccggc | gtgccggcag | ccgcacctga | 720 |
| cgctggggac | gggcccgcac | cgggacccga | cgtcgctgac | gctgctgcac | caggacgacg | 780 |
| tgggcgggct | gcaggtgcgc | gccggcggcg | ggccgtggcg | cgcggtgcgg | ccccgcgcgg | 840 |
| acgcgttcgt | ggtcaacatt | ggcgacacct | tcgccgcgct | caccgacggg | cgtcacacca | 900 |
| gctgcctgca | ccgcgccgtg | gtgaccggcg | gcggctcccg | ccggtcgctc | gccttcttcc | 960 |
| tcaacccgcc | gctggaccgc | gtcgtccgcc | cgccggcgc | gctcctccag | gagaacaagc | 1020 |
| aggcgggccg | cccgcgcgcg | ttcccggact | tcacgtggcg | cgagttcctc | gagttcacgc | 1080 |
| agaagcacta | ccggtcggac | gcgggcacca | tggacgcctt | cgtgtcgtgg | atcgcgggag | 1140 |
| gccgccgcca | ccatggcgga | caggaggagg | gcaactgaga | tcgatgcatc | tctagctgta | 1200 |
| ggcagcagcg | cagcagctac | caagaataat | ggccggcgac | ggagatgcag | ctacgacgca | 1260 |
| caaataaatt | gagtgtttgt | ggtacaataa | ggacgaggac | gatcaatggc | gacctgtaac | 1320 |
| cggtgcagtt | ttagttaatc | tttcatggcg | atatggcatt | aaccaatcgt | tggtgtaaaa | 1380 |
| tgcgtgcatg | ctttgcatgc | caatgttggc | catgtgatgg | cacagcgtga | gtgtagctca | 1440 |
| cccaccgtga | caacgtgcta | atttcgtgtg | gtcctagata | ccaaggtcgt | ctaatgaact | 1500 |
| tgatggattg | atgattt | | | | | 1517 |

<210> SEQ ID NO 5
<211> LENGTH: 1107
<212> TYPE: DNA
<213> ORGANISM: Zea mays

<400> SEQUENCE: 5

| | | | | | |
|---|---|---|---|---|---|
| atggcggcgg | cggccgtggt | gttcgacgcc | gaggcgctga | gccggagga | gcacatcccg | 60 |
| gcgcagttcg | tgtggcccac | cgaggagcgg | gcgccggcgg | gcggcgtgga | ggaggtcgcc | 120 |

```
atccccgtgg tcgacctcgg cgagttcctc cgccgcgggg tgctcccgcg cggcgtggcg    180
gaggcgtgcg agcgccacgg cgtcttccag gtggtgaacc acggcgtggg cgccgcgctg    240
ctcgccgagg cctaccgctg ttgcgacgcc ttttacgcgc tcccgctcgc ggacaagcag    300
cgcgcgcagc gccggcacgg ggagaaccac ggctacgcca gcagcttcac gggccgcttc    360
cactgctgcc tgccgtggaa ggagacgctg tccttcaact gccccgccgg tgccgggact    420
gcgcgcgccg tcgtcggcta cttcgtcgac gtcctcggcg aggactaccg ccacatgggg    480
gaggtgtacc aggagtactg cgacgcgatg acgcgtctgg cgctggacgt gacggaggtg    540
ctggcggcag cgctggggct ggaccgcggc gcactgcgcg gcttcttcga gggcggcgac    600
tccgtcatgc ggctgaacca ctacccggcg tgccggcagc cgcacctgac gctggggacg    660
ggcccgcacc gggaccccga cgtcgctgac ctgctgcacc aggacgacgt gggcgggctg    720
caggtgcgcg ccggcggcgg gccgtggcgc gcggtgcggc cccgcgcgga cgcgttcgtg    780
gtcaacattg cgacaccttt cgccgcgctc accgacgggc gtcacaccag ctgcctgcac    840
cgcgccgtgg tgaccggcgg cggctcccgc cggtcgctcg ccttcttcct caacccgccg    900
ctggaccgcg tcgtccgccc gccgggcgcg ctcctccagg agaacaagca ggcgggccgc    960
ccgcgcgcgt tccggacttt cacgtggcgc gagttcctcg agttcacgca gaagcactac   1020
cggtcggacg cgggcaccat ggacgccttc gtgtcgtgga tcgcgggagg ccgccgccac   1080
catggcggac aggaggaggg caactga                                       1107
```

<210> SEQ ID NO 6
<211> LENGTH: 368
<212> TYPE: PRT
<213> ORGANISM: Zea mays

<400> SEQUENCE: 6

```
Met Ala Ala Ala Val Val Phe Asp Ala Glu Ala Leu Ser Arg Glu
1               5                   10                  15

Glu His Ile Pro Ala Gln Phe Val Trp Pro Thr Glu Glu Arg Ala Pro
            20                  25                  30

Ala Gly Gly Val Glu Glu Val Ala Ile Pro Val Val Asp Leu Gly Glu
        35                  40                  45

Phe Leu Arg Arg Gly Val Leu Pro Arg Gly Val Ala Glu Ala Cys Glu
    50                  55                  60

Arg His Gly Val Phe Gln Val Val Asn His Gly Val Gly Ala Ala Leu
65                  70                  75                  80

Leu Ala Glu Ala Tyr Arg Cys Cys Asp Ala Phe Tyr Ala Leu Pro Leu
                85                  90                  95

Ala Asp Lys Gln Arg Ala Gln Arg Arg His Gly Glu Asn His Gly Tyr
            100                 105                 110

Ala Ser Ser Phe Thr Gly Arg Phe His Cys Cys Leu Pro Trp Lys Glu
        115                 120                 125

Thr Leu Ser Phe Asn Cys Pro Ala Gly Ala Gly Thr Ala Arg Ala Val
    130                 135                 140

Val Gly Tyr Phe Val Asp Val Leu Gly Glu Asp Tyr Arg His Met Gly
145                 150                 155                 160

Glu Val Tyr Gln Glu Tyr Cys Asp Ala Met Thr Arg Leu Ala Leu Asp
                165                 170                 175

Val Thr Glu Val Leu Ala Ala Ala Leu Gly Leu Asp Arg Gly Ala Leu
            180                 185                 190

Arg Gly Phe Phe Glu Gly Gly Asp Ser Val Met Arg Leu Asn His Tyr
```

```
                195                 200                 205
    Pro Ala Cys Arg Gln Pro His Leu Thr Leu Gly Thr Gly Pro His Arg
        210                 215                 220
    Asp Pro Thr Ser Leu Thr Leu Leu His Gln Asp Asp Val Gly Gly Leu
    225                 230                 235                 240
    Gln Val Arg Ala Gly Gly Pro Trp Arg Ala Val Arg Pro Arg Ala
                    245                 250                 255
    Asp Ala Phe Val Val Asn Ile Gly Asp Thr Phe Ala Ala Leu Thr Asp
                260                 265                 270
    Gly Arg His Thr Ser Cys Leu His Arg Ala Val Val Thr Gly Gly Gly
                275                 280                 285
    Ser Arg Arg Ser Leu Ala Phe Phe Leu Asn Pro Pro Leu Asp Arg Val
        290                 295                 300
    Val Arg Pro Pro Gly Ala Leu Leu Gln Glu Asn Lys Gln Ala Gly Arg
    305                 310                 315                 320
    Pro Arg Ala Phe Pro Asp Phe Thr Trp Arg Glu Phe Leu Glu Phe Thr
                    325                 330                 335
    Gln Lys His Tyr Arg Ser Asp Ala Gly Thr Met Asp Ala Phe Val Ser
                340                 345                 350
    Trp Ile Ala Gly Gly Arg Arg His His Gly Gly Gln Glu Glu Gly Asn
                355                 360                 365
```

<210> SEQ ID NO 7
<211> LENGTH: 1522
<212> TYPE: DNA
<213> ORGANISM: Zea mays

<400> SEQUENCE: 7

```
gcacactcgc agctcgcaca tctcatggtg tcctaagaac ggcaagagcc agctctgcct      60
agcagcagcg cacagccaca tccatggacg ccagcccgac ccaccgctc  cccctccgcg     120
ccccaactcc cagcattgac ctccccgctg caaggacag  ggccgacgcg gcggctaaca    180
aggccgcggc tgtgttcgac ctgcgccggg agcccaagat cccggagcca ttcctgtggc    240
cgcacgaaga ggcgcggccg acctcggccg cggagctgga ggtgccggtg gtggacgtgg    300
gcgtgctgcg caatggcgac ggcgcgggc  tccgccgcgc gcggcgcaa  gtggcggcgg    360
cgtgcgcgac gcacgggttc ttccaggtgt gcgggcacgg cgtggacgcg cgctggggc     420
gcgccgcgct ggacggcgcc agcgacttct  ccggctgcc  gctggctgag aagcagcggg   480
cccggcgcgt cccccggcacc gtgtccgggt acacgagcgc gcacgccgac cggttcgcgt   540
ccaagctccc ctggaaggag accctgtcct tcggcttcca cgacggcgcc gcggcgcccg   600
tcgtcgtgga ctacttcacc ggcaccctcg gccaagattt cgagccagtg gggcgggtgt    660
accagaggta ctgcgaggag atgaaggagc tgtcgctgac gatcatggag ctgctggagc   720
tgagcctggg cgtggagcgc ggctactacc gggagttctt cgaggacagc cgctccatca    780
tgcggtgcaa ctactacccg ccgtgcccgg tgccggagcg cacgctgggc acgggccgc     840
actgcgaccc cacggcgctg accatcctcc tgcaggacga cgtcggcggg ctggaggtcc    900
tggtggacgg cgagtggcgc cccgtccggc cgtcccagg  cgccatggtc atcaacatcg    960
gcgacaccct tcatggcgctg tccaacgggc ggtacaagag ctgcctgcac cgcgcggtgg   1020
tgaaccggcg gcaggagcgg caatcgctgg ccttcttcct gtgcccgcgc gaggaccggg   1080
tggtgcgccc gccggccagc gccgcgccgc ggcagtaccc ggacttcacc tgggccgacc    1140
tcatgcgctt cacgcagcgc cactaccgcg ccgacacccg cacgctggac gccttcaccc   1200
```

```
gctggctctc ccacggcccg gcggcggcgg ctccctgcac ctaacgagcc ggccgtctct      1260
ttcgccgggg cccgcgcggg gttcgcccac gtggtgatca ggtggcagac atgtggccca      1320
cgggccccgc gccgccttcc ccattttttgg acgaccctac tgctactact actagtgtac      1380
atatgcaaaa aaatacatat atatataggt actttctcta atattttat atataagcaa       1440 ggcggcctgg tgttctttttc tttgttttgt cgacaactgt ttgatcccat cctatggacg      1500
atggatagtt caatgtttgt ac                                                1522

<210> SEQ ID NO 8
<211> LENGTH: 1161
<212> TYPE: DNA
<213> ORGANISM: Zea mays

<400> SEQUENCE: 8
atggacgcca gcccgacccc accgctcccc ctccgcgccc caactcccag cattgacctc       60
cccgctggca aggacagggc cgacgcggcg gctaacaagg ccgcggctgt gttcgacctg      120
cgccgggagc ccaagatccc ggagccattc ctgtggccgc acgaagaggc gcggccgacc      180
tcggccgcgg agctggaggt gccggtggtg acgtgggcg tgctgcgcaa tggcgacggc       240
gcggggctcc gccgcgccgc ggcgcaagtg gcggcggcgt gcgcgacgca cgggttcttc       300
caggtgtgcg gcacggcgt ggacgcggcg ctggggcgcg ccgcgctgga cggcgccagc       360
gacttcttcc ggctgccgct ggctgagaag cagcgggccc ggcgcgtccc cggcaccgtg       420
tccgggtaca cgagcgcgca cgccgaccgg ttcgcgtcca agctcccctg gaaggagacc       480
ctgtccttcg gcttccacga cggcgccgcg gcgcccgtcg tcgtggacta cttcaccggc       540
accctcggcc aagatttcga gccagtgggg cgggtgtacc agaggtactg cgaggagatg       600
aaggagctgt cgctgacgat catggagctg ctggagctga gctgggcgt ggagcgcggc        660 tactaccggg agttcttcga ggacagccgc tccatcatgc ggtgcaacta ctacccgccg       720
tgcccggtgc cggagcgcac gctgggcacg ggcccgcact gcgaccccac ggcgctgacc       780
atcctcctgc aggacgacgt cggcgggctg gaggtcctgg tggacggcga gtggcgcccc      840
gtccggcccg tcccaggcgc catggtcatc aacatcggcg acaccttcat ggcgctgtcc       900
aacgggcggt acaagagctg cctgcaccgc gcggtggtga accggcggca ggagcggcaa       960
tcgctggcct tcttcctgtg cccgcgcgag accggggtgg tgcgcccgcc ggccagcgcc      1020
gcgccgcggc agtacccgga cttcacctgg gccgacctca tgcgcttcac gcagcgccac      1080
taccgcgcca caccccgcac gctggacgcc ttcacccgct ggctctccca cggcccggcg       1140
gcggcggctc cctgcaccta a                                                1161

<210> SEQ ID NO 9
<211> LENGTH: 386
<212> TYPE: PRT
<213> ORGANISM: Zea mays

<400> SEQUENCE: 9

Met Asp Ala Ser Pro Thr Pro Pro Leu Pro Leu Arg Ala Pro Thr Pro
1               5                   10                  15

Ser Ile Asp Leu Pro Ala Gly Lys Asp Arg Ala Asp Ala Ala Ala Asn
            20                  25                  30

Lys Ala Ala Ala Val Phe Asp Leu Arg Arg Glu Pro Lys Ile Pro Glu
        35                  40                  45

Pro Phe Leu Trp Pro His Glu Glu Ala Arg Pro Thr Ser Ala Ala Glu
```

```
                 50                  55                  60
Leu Glu Val Pro Val Val Asp Val Gly Val Leu Arg Asn Gly Asp Gly
 65                  70                  75                  80

Ala Gly Leu Arg Arg Ala Ala Gln Val Ala Ala Cys Ala Thr
                 85                  90                  95

His Gly Phe Phe Gln Val Cys Gly His Gly Val Asp Ala Ala Leu Gly
                100                 105                 110

Arg Ala Ala Leu Asp Gly Ala Ser Asp Phe Phe Arg Leu Pro Leu Ala
                115                 120                 125

Glu Lys Gln Arg Ala Arg Arg Val Pro Gly Thr Val Ser Gly Tyr Thr
130                 135                 140

Ser Ala His Ala Asp Arg Phe Ala Ser Lys Leu Pro Trp Lys Glu Thr
145                 150                 155                 160

Leu Ser Phe Gly Phe His Asp Gly Ala Ala Pro Val Val Val Asp
                165                 170                 175

Tyr Phe Thr Gly Thr Leu Gly Gln Asp Phe Glu Pro Val Gly Arg Val
                180                 185                 190

Tyr Gln Arg Tyr Cys Glu Glu Met Lys Glu Leu Ser Leu Thr Ile Met
                195                 200                 205

Glu Leu Leu Glu Leu Ser Leu Gly Val Glu Arg Gly Tyr Tyr Arg Glu
210                 215                 220

Phe Phe Glu Asp Ser Arg Ser Ile Met Arg Cys Asn Tyr Tyr Pro Pro
225                 230                 235                 240

Cys Pro Val Pro Glu Arg Thr Leu Gly Thr Gly Pro His Cys Asp Pro
                245                 250                 255

Thr Ala Leu Thr Ile Leu Leu Gln Asp Asp Val Gly Gly Leu Glu Val
                260                 265                 270

Leu Val Asp Gly Glu Trp Arg Pro Val Arg Pro Val Pro Gly Ala Met
                275                 280                 285

Val Ile Asn Ile Gly Asp Thr Phe Met Ala Leu Ser Asn Gly Arg Tyr
                290                 295                 300

Lys Ser Cys Leu His Arg Ala Val Val Asn Arg Arg Gln Glu Arg Gln
305                 310                 315                 320

Ser Leu Ala Phe Phe Leu Cys Pro Arg Glu Asp Arg Val Val Arg Pro
                325                 330                 335

Pro Ala Ser Ala Ala Pro Arg Gln Tyr Pro Asp Phe Thr Trp Ala Asp
                340                 345                 350

Leu Met Arg Phe Thr Gln Arg His Tyr Arg Ala Asp Thr Arg Thr Leu
                355                 360                 365

Asp Ala Phe Thr Arg Trp Leu Ser His Gly Pro Ala Ala Ala Pro
370                 375                 380

Cys Thr
385

<210> SEQ ID NO 10
<211> LENGTH: 1457
<212> TYPE: DNA
<213> ORGANISM: Zea mays

<400> SEQUENCE: 10
taatcacctc atcacaggtc cccccagcct cactctcgcg ccggctcaag gtacattgcg    60
tgtcctagcc aagacacgca gctcatctca gcctcacacg cacagcaaga gcgaggcgtg   120
attcgccatg ggcggcctca ctatggacca ggccttcgtg caggcccccg agcaccgccc   180
```

```
caagcccatc gtcaccgagg ccaccggcat ccctctcatc gacctctcgc ctctggccgc        240
cagcggcggc gccgtggacg cgctggccgc cgaggtgggc gcggcgagcc gggactgggg        300
cttcttcgtg gtcgtgggcc acggcgtgcc cgcagagacc gtggcgcgcg cgacggaggc        360
gcagcgagcg ttcttcgcgc tgccggcaga gcggaaggcc gccgtgcgga ggaacgaggc        420
ggagccgctc gggtactacg agtcggagca caccaagaac gtgagggact ggaaggaggt        480
gtacgacctc gtgccgcgcg agccgccgcc gccggcagcc gtggccgacg gcgagcttgt        540
gttcgataac aagtggcccc aggatctacc gggcttcaga gaggcgctgg aggagtacgc        600
gaaagcgatg gaagagctgg cgttcaagct gctggagctg atcgcccgga gcctgaagct        660
gaggcccgac cggctgcacg gcttcttcaa ggaccagacg accttcatcc ggctgaacca        720
ctaccctcct tgcccgagcc ccgacctggc cctcggcgtg gggcggcaca aggacgccgg        780
cgccctgacc atcctgtacc aggacgacgt cggggggctc gacgtccggc ggcgctccga        840
cggcgagtgg gtccgcgtca ggcccgtgcc cgactcgttc atcatcaacg tcggcgacct        900
catccaggta cgagagcgcg gagcaccggg tgtcggtgaa ctcggcgagg agaggttct         960 ccatgcccta cttcttcaac ccggcgacct acaccatggt ggagccggtg gaggagctgg       1020
tgagcaagga cgatccgccc aggtacgacg cctacaactg ggcgacttc ttcagcacca       1080 ggaagaacag caacttcaag aagctcaacg tggagaacat tcagatcgcg catttcaaga       1140
agagcctcgt cctcgcctaa ctactgctac tgctaggatc catgccattg ccatgtcgtc       1200
ttcagattca gagcacgcca tgtcgtcgct agcttcgtgg tagaacaaat aatgatgtgc       1260
gtgctgtgtg taagcatgga tatggatgtg aatatgtaat atgatgagca ctcctacttt       1320
ggtatgtttg ggaataacag acttgtgttg gtctggttca ttatttgtaa gaaaatcaaa       1380
aagagttagt agggcaggag gctaaccaca gtcatgctgc accacatccc tggtggaaag       1440
ctggccgggt tacgcta                                                      1457

<210> SEQ ID NO 11
<211> LENGTH: 1116
<212> TYPE: DNA
<213> ORGANISM: Zea mays

<400> SEQUENCE: 11
atgggcggcc tcactatgga ccaggccttc gtgcaggccc ccgagcaccg ccccaagccc         60
atcgtcaccg aggccaccgg catccctctc atcgacctct cgcctctggc cgccagcggc        120
ggcgccgtgg acgcgctggc cgccgaggtg gcgcgggcga ccgggactg gggcttcttc         180 gtggtcgtgg gccacggcgt gccgcagag accgtggcgc gcgcgacgga ggcgcagcga        240
gcgttcttcg cgctgccggc agagcggaag gccgccgtgc ggaggaacga ggcggagccg        300
ctcgggtact acgagtcgga gcacaccaag aacgtgaggg actggaagga ggtgtacgac        360
ctcgtgccgc gcgagccgcc gccgccggca gccgtggccg acggcgagct tgtgttcgat        420
aacaagtggc cccaggatct accgggcttc agagaggcgc tggaggagta cgcgaaagcg        480
atggaagagc tggcgttcaa gctgctggag ctgatcgccc ggagcctgaa gctgaggccc        540
gaccggctgc acggcttctt caaggaccag acgaccttca tccggctgaa ccactaccct        600
ccttgcccga gccccgacct ggccctcggc gtggggcggc acaaggacgc cggcgccctg        660
accatcctgt accaggacga cgtcgggggg ctcgacgtcc ggcggcgctc cgacggcgag        720
tgggtccgcg tcaggcccgt gcccgactcg ttcatcatca acgtcggcga cctcatccag        780
gtacgagagc gcggagcacc gggtgtcggt gaactcggcg agggagaggt tctccatgcc        840
```

```
ctacttcttc aacccggcga cctacaccat ggtggagccg gtggaggagc tggtgagcaa      900
ggacgatccg cccaggtacg acgcctacaa ctggggcgac ttcttcagca ccaggaagaa      960
cagcaacttc aagaagctca acgtggagaa cattcagatc gcgcatttca agaagagcct     1020
cgtcctcgcc taactactgc tactgctagg atccatgcca ttgccatgtc gtcttcagat     1080
tcagagcacg ccatgtcgtc gctagcttcg tggtag                               1116
```

<210> SEQ ID NO 12
<211> LENGTH: 371
<212> TYPE: PRT
<213> ORGANISM: Zea mays

<400> SEQUENCE: 12

```
Met Gly Gly Leu Thr Met Asp Gln Ala Phe Val Gln Ala Pro Glu His
1               5                   10                  15

Arg Pro Lys Pro Ile Val Thr Glu Ala Thr Gly Ile Pro Leu Ile Asp
                20                  25                  30

Leu Ser Pro Leu Ala Ala Ser Gly Ala Val Asp Ala Leu Ala Ala
            35                  40                  45

Glu Val Gly Ala Ala Ser Arg Asp Trp Gly Phe Phe Val Val Gly
50                  55                  60

His Gly Val Pro Ala Glu Thr Val Ala Arg Ala Thr Glu Ala Gln Arg
65                  70                  75                  80

Ala Phe Phe Ala Leu Pro Ala Glu Arg Lys Ala Ala Val Arg Arg Asn
                85                  90                  95

Glu Ala Glu Pro Leu Gly Tyr Tyr Glu Ser Glu His Thr Lys Asn Val
            100                 105                 110

Arg Asp Trp Lys Glu Val Tyr Asp Leu Val Pro Arg Glu Pro Pro Pro
        115                 120                 125

Pro Ala Ala Val Ala Asp Gly Glu Leu Val Phe Asp Asn Lys Trp Pro
130                 135                 140

Gln Asp Leu Pro Gly Phe Arg Glu Ala Leu Glu Glu Tyr Ala Lys Ala
145                 150                 155                 160

Met Glu Glu Leu Ala Phe Lys Leu Leu Glu Leu Ile Ala Arg Ser Leu
                165                 170                 175

Lys Leu Arg Pro Asp Arg Leu His Gly Phe Phe Lys Asp Gln Thr Thr
            180                 185                 190

Phe Ile Arg Leu Asn His Tyr Pro Pro Cys Pro Ser Pro Asp Leu Ala
        195                 200                 205

Leu Gly Val Gly Arg His Lys Asp Ala Gly Ala Leu Thr Ile Leu Tyr
210                 215                 220

Gln Asp Asp Val Gly Gly Leu Asp Val Arg Arg Ser Asp Gly Glu
225                 230                 235                 240

Trp Val Arg Val Arg Pro Val Pro Asp Ser Phe Ile Ile Asn Val Gly
                245                 250                 255

Asp Leu Ile Gln Val Arg Glu Arg Gly Ala Pro Val Gly Glu Leu
            260                 265                 270

Gly Glu Gly Glu Val Leu His Ala Leu Leu Leu Gln Pro Gly Asp Leu
        275                 280                 285

His His Gly Gly Ala Gly Gly Ala Gly Glu Gln Gly Arg Ser Ala
290                 295                 300

Gln Val Arg Arg Leu Gln Leu Gly Arg Leu Leu Gln His Gln Glu Glu
305                 310                 315                 320
```

| Gln | Gln | Leu | Gln | Glu | Ala | Gln | Arg | Gly | Glu | His | Ser | Asp | Arg | Ala | Phe |
| | | | | 325 | | | | | 330 | | | | | 335 | |

| Gln | Glu | Glu | Pro | Arg | Pro | Arg | Leu | Thr | Thr | Ala | Thr | Ala | Arg | Ile | His |
| | | | | 340 | | | | | 345 | | | | | 350 | |

| Ala | Ile | Ala | Met | Ser | Ser | Ser | Asp | Ser | Glu | His | Ala | Met | Ser | Ser | Leu |
| | | | | 355 | | | | | 360 | | | | | 365 | |

| Ala | Ser | Trp |
| | | 370 |

<210> SEQ ID NO 13
<211> LENGTH: 1733
<212> TYPE: DNA
<213> ORGANISM: Zea mays

<400> SEQUENCE: 13

| atgaggccgc | gcctccctcc | aaatgttccc | tccctgcctt | cgtctttgtc | gttgctcgca | 60 |
| aactccctgt | cctcccctgt | tacaaatacc | cccacccgcc | cggacagctt | ccctgcatac | 120 |
| ttgcagctcg | cacatctcat | ggtgtcgcag | gaacgacaag | agccagctgt | gcctagcagc | 180 |
| agcagcagca | gcgccaagcg | cgcagccacg | tccatggacg | ccagcccggc | cccgccgctc | 240 |
| ctcctccgcg | ccccactcc | cagccccagc | attgacctcc | ccgctggcaa | ggacaaggcc | 300 |
| gacgcggcgg | ccagcaaggc | cggcgcggcc | gtgttcgacc | tgcgccggga | gcccaagatc | 360 |
| cccgcgccat | tcctgtggcc | gcaggaagag | gcgcggccgt | cctcggccgc | ggagctggag | 420 |
| gtgccgatgg | tggacgtggg | cgtgctgcgc | aatggcgacc | gcgcggggct | gcggcgcgcc | 480 |
| gcggcgcagg | tggccgcggc | gtgcgcgacg | cacgggttct | tccaggtgtg | cgggcacggc | 540 |
| gtggacgcgg | cgctggggcg | cgccgcgctg | gacggcgcca | gcgacttctt | ccggctgccg | 600 |
| ctcgccgaga | agcagcgcgc | ccggcgcgtc | ccggcaccg | tgtccgggta | cacgagcgcg | 660 |
| cacgccgacc | ggttcgcggc | caagctcccc | tggaaggaga | ccctgtcgtt | cggctaccac | 720 |
| gacggcgccg | cgtcgcctgt | cgtcgtggac | tacttcgtcg | gcaccctcgg | ccaggatttc | 780 |
| gagccaatgg | ggtgggtgta | ccagaggtac | tgcgaggaga | tgaaggagct | gtcgctgacg | 840 |
| atcatggagc | tgctggagct | gagcctgggc | gtggagctgc | gcggctacta | ccggagttc | 900 |
| ttcgaggaca | gccggtccat | catgcggtgc | aactactacc | cgccgtgccc | ggagccggag | 960 |
| cgcacgctgg | gcacgggccc | gcactgcgac | cccacggcgc | tcaccatcct | cctgcaggac | 1020 |
| gacgtgggcg | gctggaggt | gctggtggac | ggtgagtggc | gccccgtccg | gcccgtcccg | 1080 |
| ggcgccatgg | tcatcaacat | cggcgacacc | ttcatggcgc | tgtcgaacgg | gaggtacaag | 1140 |
| agctgcctgc | accgcgcggt | ggtgaaccag | cggcgggcgc | ggcggtcgct | ggccttcttc | 1200 |
| ctgtgcccgc | gcgaggaccg | ggtggtgcgc | ccgccggcca | gtgctgcgcc | gcggcgctac | 1260 |
| ccggacttca | cctgggccga | cctcatgcgc | ttcacgcagc | gccactaccg | cgccgacacc | 1320 |
| cgcacgctgg | acgccttcac | ccgctggctc | tcccacggcc | cggcccaggc | ggcggcgcct | 1380 |
| ccctgcacct | agcgagccgg | gccaaggccg | tctctttcgc | cccacgtgcg | cgcccagctg | 1440 |
| ggcaggtggc | cagacacgcg | gcccgcgggc | cccgcgccgc | cttgccattt | tttgacgctg | 1500 |
| gccctactgc | tgtgctacta | gtgtacatat | gcaagagtac | atatatatat | atatatatac | 1560 |
| gtattttcta | tatattatat | ataaaagcaa | ggcggcccgg | tgcccttctc | ttgttttgtc | 1620 |
| cacaactgtt | tgatcccatt | attctatgga | ccatggatac | ttcaatgttt | gtactaagac | 1680 |
| cgtgaacgtg | ggattctttt | ccttcctctg | tgttttttct | gagaaaaatt | aaa | 1733 |

<210> SEQ ID NO 14
<211> LENGTH: 1392
<212> TYPE: DNA
<213> ORGANISM: Zea mays

<400> SEQUENCE: 14

| | | | | | |
|---|---|---|---|---|---|
| atgaggccgc | gcctccctcc | aaatgttccc | tccctgcctt | cgtctttgtc | gttgctcgca | 60 |
| aactccctgt | cctccctgt | tacaaatacc | cccacccgcc | cggacagctt | ccctgcatac | 120 |
| ttgcagctcg | cacatctcat | ggtgtcgcag | gaacgacaag | agccagctgt | gcctagcagc | 180 |
| agcagcagca | gcgccaagcg | cgcagccacg | tccatggacg | ccagcccggc | ccgccgctc | 240 |
| ctcctccgcg | ccccactcc | cagcccagc | attgacctcc | ccgctggcaa | ggacaaggcc | 300 |
| gacgcggcgg | ccagcaaggc | cggcgcggcc | gtgttcgacc | tgcgccggga | gcccaagatc | 360 |
| cccgcgccat | tcctgtggcc | gcaggaagag | gcgcggccgt | cctcggccgc | ggagctggag | 420 |
| gtgccgatgg | tggacgtggg | cgtgctgcgc | aatggcgacc | gcgcggggct | gcggcgcgcc | 480 |
| gcggcgcagg | tggccgcggc | gtgcgcgacg | cacgggttct | tccaggtgtg | cgggcacggc | 540 |
| gtggacgcgg | cgctggggcg | cgccgcgctg | gacgcgccca | gcgacttctt | ccggctgccg | 600 |
| ctcgccgaga | agcagcgcgc | ccggcgcgtc | ccggcaccg | tgtccgggta | cacgagcgcg | 660 |
| cacgccgacc | ggttcgcggc | caagctcccc | tggaaggaga | ccctgtcgtt | cggctaccac | 720 |
| gacggcgccg | cgtcgcctgt | cgtcgtggac | tacttcgtcg | gcaccctcgg | ccaggatttc | 780 |
| gagccaatgg | ggtgggtgta | ccagaggtac | tgcgaggaga | tgaaggagct | gtcgctgacg | 840 |
| atcatggagc | tgctggagct | gagcctgggc | gtggagctgc | gcggctacta | ccgggagttc | 900 |
| ttcgaggaca | gccggtccat | catgcggtgc | aactactacc | gccgtgccc | ggagccggag | 960 |
| cgcacgctgg | gcacgggccc | gcactgcgac | cccacggcgc | tcaccatcct | cctgcaggac | 1020 |
| gacgtgggcg | ggctggaggt | gctggtgac | ggtgagtggc | gccccgtccg | gcccgtcccg | 1080 |
| ggcgccatgg | tcatcaacat | cggcgacacc | ttcatggcgc | tgtcgaacgg | gaggtacaag | 1140 |
| agctgcctgc | accgcgcggt | ggtgaaccag | cggcgggcgc | ggcggtcgct | ggccttcttc | 1200 |
| ctgtgcccgc | gcgaggaccg | ggtggtgcgc | ccgccggcca | gtgctgcgcc | gcggcgctac | 1260 |
| ccggacttca | cctgggccga | cctcatgcgc | ttcacgcagc | gccactaccg | cgccgacacc | 1320 |
| cgcacgctgg | acgccttcac | ccgctggctc | tcccacggcc | cggcccaggc | ggcggcgcct | 1380 |
| ccctgcacct | ag | | | | | 1392 |

<210> SEQ ID NO 15
<211> LENGTH: 463
<212> TYPE: PRT
<213> ORGANISM: Zea mays

<400> SEQUENCE: 15

Met Arg Pro Arg Leu Pro Pro Asn Val Pro Ser Leu Pro Ser Ser Leu
1               5                   10                  15

Ser Leu Leu Ala Asn Ser Leu Ser Pro Val Thr Asn Thr Pro Thr
            20                  25                  30

Arg Pro Asp Ser Phe Pro Ala Tyr Leu Gln Leu Ala His Leu Met Val
        35                  40                  45

Ser Gln Glu Arg Gln Glu Pro Ala Val Pro Ser Ser Ser Ser Ser Ser
    50                  55                  60

Ala Lys Arg Ala Ala Thr Ser Met Asp Ala Ser Pro Ala Pro Pro Leu
65                  70                  75                  80

Leu Leu Arg Ala Pro Thr Pro Ser Pro Ser Ile Asp Leu Pro Ala Gly 85                  90                  95
Lys Asp Lys Ala Asp Ala Ala Ser Lys Ala Gly Ala Ala Val Phe
                100                 105                 110

Asp Leu Arg Arg Glu Pro Lys Ile Pro Ala Pro Phe Leu Trp Pro Gln
            115                 120                 125

Glu Glu Ala Arg Pro Ser Ser Ala Ala Glu Leu Glu Val Pro Met Val
        130                 135                 140

Asp Val Gly Val Leu Arg Asn Gly Asp Arg Ala Gly Leu Arg Arg Ala
145                 150                 155                 160

Ala Ala Gln Val Ala Ala Cys Ala Thr His Gly Phe Phe Gln Val
                165                 170                 175

Cys Gly His Gly Val Asp Ala Ala Leu Gly Arg Ala Ala Leu Asp Gly
                180                 185                 190

Ala Ser Asp Phe Phe Arg Leu Pro Leu Ala Glu Lys Gln Arg Ala Arg
                195                 200                 205

Arg Val Pro Gly Thr Val Ser Gly Tyr Thr Ser Ala His Ala Asp Arg
            210                 215                 220

Phe Ala Ala Lys Leu Pro Trp Lys Glu Thr Leu Ser Phe Gly Tyr His
225                 230                 235                 240

Asp Gly Ala Ala Ser Pro Val Val Asp Tyr Phe Val Gly Thr Leu
                245                 250                 255

Gly Gln Asp Phe Glu Pro Met Gly Trp Val Tyr Gln Arg Tyr Cys Glu
            260                 265                 270

Glu Met Lys Glu Leu Ser Leu Thr Ile Met Glu Leu Leu Glu Leu Ser
            275                 280                 285

Leu Gly Val Glu Leu Arg Gly Tyr Tyr Arg Glu Phe Phe Glu Asp Ser
    290                 295                 300

Arg Ser Ile Met Arg Cys Asn Tyr Tyr Pro Pro Cys Pro Glu Pro Glu
305                 310                 315                 320

Arg Thr Leu Gly Thr Gly Pro His Cys Asp Pro Thr Ala Leu Thr Ile
                325                 330                 335

Leu Leu Gln Asp Asp Val Gly Gly Leu Glu Val Leu Val Asp Gly Glu
                340                 345                 350

Trp Arg Pro Val Arg Pro Val Pro Gly Ala Met Val Ile Asn Ile Gly
                355                 360                 365

Asp Thr Phe Met Ala Leu Ser Asn Gly Arg Tyr Lys Ser Cys Leu His
                370                 375                 380

Arg Ala Val Val Asn Gln Arg Ala Arg Ser Leu Ala Phe Phe
385                 390                 395                 400

Leu Cys Pro Arg Glu Asp Arg Val Val Arg Pro Ala Ser Ala Ala
                405                 410                 415

Pro Arg Tyr Pro Asp Phe Thr Trp Ala Asp Leu Met Arg Phe Thr
                420                 425                 430

Gln Arg His Tyr Arg Ala Asp Thr Arg Thr Leu Asp Ala Phe Thr Arg
                435                 440                 445

Trp Leu Ser His Gly Pro Ala Gln Ala Ala Ala Pro Pro Cys Thr
450                 455                 460

<210> SEQ ID NO 16
<211> LENGTH: 1510
<212> TYPE: DNA
<213> ORGANISM: Zea mays

<400> SEQUENCE: 16

```
aaagagcgcg cgacggcggc ccctgggaga gccatgcgag actggaggcg gaaccgcgca      60
cgacaccaag ctgccgcgcc ggactgctgc acgcaagcgc agcgcaggac cgaccgacct     120
ccgtaggcac gcacggcgcc ggcggcatgg cggagcacct cctgtcgacg gccgtgcacg     180
acacgctgcc ggggagctac gtgcggccgg agcggagcg cccgcgcctc gcggaggtcg      240
tgaccggcgc gcgcatcccc gtcgtggacc tgggcagccc cgaccgcggc gcggtcgtgg     300
ccgccgtcgg cgacgcctgc cgctcgcacg gcttcttcca ggtcgtcaac cacgggatac     360
acgccgccct ggtcgcggcg gtgatggccg cggggcgcgg cttcttccgg ctgcccccg      420 aggagaaggc caagctctac tccgacgacc ccgccaggaa gatccggctg tccaccagct     480
tcaacgtgcg caaggagacg gtgcacaact ggcgcgacta cctccgcctg cactgccatc     540
ccctcgacga gttcctgccc gattggccgt ccaacccgcc cgatttcaag agaccatgg      600 gcacctactg caaggaggtc cgggagctcg ggttcaggct gtacgccgcg atctcggaga     660
gcctgggcct agaggcgagc tacatgaagg aagcgctggg ggagcaggag cagcacatgg     720
cggtcaactt ctacccgccg tgcccggagc cggagctcac ctacgcctc ccggcgcaca     780 ccgaccccaa cgcgctcacc atcctgctca tggacccgga cgtcgccggc ctgcaggtgc     840
tccacgccgg ccagtgggtc gccgtcaacc cgcagcccgg cgcgctcatc atcaacatcg     900
gcgaccagct gcaggcgctg agcaacgggc agtaccggag cgtgtggcac cgcgcggtgg     960
tgaactcgga ccgggagcgc atgtccgtgg cgtcgttcct gtgcccgtgc aaccacgtcg    1020
tgctcggccc cgcgcggaag ctcgtcaccg aggacacccc ggccgtgtac aggaactaca    1080
cgtacgacaa gtactacgcc aagttctgga gcaggaacct ggaccaggag cactgcctcg    1140
agctcttcag aacctagcga atcggatacg gatggatgga tacattacat acgcgccctc    1200 tgttttctc catgacgtta gaagaacacg ttctgcaatg tttgtccatt caaggtggta     1260
tcaatcaagg ctgtggtcgt tgcaattctt ccgctccata tacatgatta aatgctttga    1320
aagaaaaaga aaaaaagaa acacaagtat tatggcacta ctagtgtttt taggaacaag    1380
gaaagagggg ttgcccctgc tggctatata tattaaatat aaataaaggt aaggctgtag    1440
acattggtga ataagagaaa gtatttgagt ttctctattg tcactccaga acagactcct    1500
ttgcctcgat                                                           1510
```

<210> SEQ ID NO 17
<211> LENGTH: 1011
<212> TYPE: DNA
<213> ORGANISM: Zea mays

<400> SEQUENCE: 17

```
atggcggagc acctcctgtc gacggccgtg cacgacacgc tgccggggag ctacgtgcgg     60
ccggagccgg agcgcccgcg cctcgcggag gtcgtgaccg gcgcgcgcat ccccgtcgtg    120
gacctgggca gccccgaccg cggcgcggtc gtggccgccg tcggcgacgc ctgccgctcg    180
cacggcttct tccaggtcgt caaccacggg atacacgccg ccctggtcgc ggcggtgatg    240
gccgcggggc gcggcttctt ccggctgccc ccgaggagaa aggccaagct ctactccgac    300
gaccccgcca ggaagatccg gctgtccacc agcttcaacg tgcgcaagga gacggtgcac    360
aactggcgcg actacctccg cctgcactgc catcccctcg acgagttcct gcccgattgg    420
ccgtccaacc cgcccgattt caaggagacc atgggcacct actgcaagga ggtccgggag    480
ctcgggttca ggctgtacgc cgcgatctcg gagagcctgg gcctagaggc gagctacatg    540
aaggaagcgc tgggggagca ggagcagcac atggcggtca acttctaccc gccgtgcccg    600
```

```
gagccggagc tcacctacgg cctcccggcg cacaccgacc ccaacgcgct caccatcctg    660
ctcatggacc cggacgtcgc cggcctgcag gtgctccacg ccggccagtg ggtcgccgtc    720
aacccgcagc ccggcgcgct catcatcaac atcggcgacc agctgcaggc gctgagcaac    780
gggcagtacc ggagcgtgtg gcaccgcgcg gtggtgaact cggaccggga gcgcatgtcc    840
gtggcgtcgt tcctgtgccc gtgcaaccac gtcgtgctcg ccccgcgcg aagctcgtc     900 accgaggaca ccccggccgt gtacaggaac tacacgtacg acaagtacta cgccaagttc    960
tggagcagga acctggacca ggagcactgc ctcgagctct tcagaaccta g           1011
```

<210> SEQ ID NO 18
<211> LENGTH: 336
<212> TYPE: PRT
<213> ORGANISM: Zea mays

<400> SEQUENCE: 18

```
Met Ala Glu His Leu Leu Ser Thr Ala Val His Asp Thr Leu Pro Gly
1               5                   10                  15

Ser Tyr Val Arg Pro Glu Pro Glu Arg Pro Arg Leu Ala Glu Val Val
            20                  25                  30

Thr Gly Ala Arg Ile Pro Val Asp Leu Gly Ser Pro Asp Arg Gly
        35                  40                  45

Ala Val Val Ala Ala Val Gly Asp Ala Cys Arg Ser His Gly Phe Phe
    50                  55                  60

Gln Val Val Asn His Gly Ile His Ala Ala Leu Val Ala Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
            100                 105                 110

Asn Val Arg Lys Glu Thr Val His Asn Trp Arg Asp Tyr Leu Arg Leu
        115                 120                 125

His Cys His Pro Leu Asp Glu Phe Leu Pro Asp Trp Pro Ser Asn Pro
    130                 135                 140

Pro Asp Phe Lys Glu Thr Met Gly Thr Tyr Cys Lys Glu Val Arg Glu
145                 150                 155                 160

Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
            180                 185                 190

Val Asn Phe Tyr Pro Pro Cys Pro Glu Pro Glu Leu Thr Tyr Gly Leu
        195                 200                 205

Pro Ala His Thr Asp Pro Asn Ala Leu Thr Ile Leu Leu Met Asp Pro
    210                 215                 220

Asp Val Ala Gly Leu Gln Val Leu His Ala Gly Gln Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
        275                 280                 285

Asn His Val Val Leu Gly Pro Ala Arg Lys Leu Val Thr Glu Asp Thr
    290                 295                 300
```

```
        Pro Ala Val Tyr Arg Asn Tyr Thr Tyr Asp Lys Tyr Ala Lys Phe
        305                 310                 315                 320

Trp Ser Arg Asn Leu Asp Gln Glu His Cys Leu Glu Leu Phe Arg Thr
                        325                 330                 335

<210> SEQ ID NO 19
<211> LENGTH: 1387
<212> TYPE: DNA
<213> ORGANISM: Zea mays

<400> SEQUENCE: 19
gttttctttt tgaacgtaac tgacagaagc tatctgccta gctacggcgt gtcggttgct      60
tgtctcacca agcagcgac atggaagcct acagctcgt cgcgtcgcgc catttccacc      120
caacaaagcg gcggcgccag cacgcactgc ttctgcttgt gcgtgctcct ccgttccggg      180
cacgcctcta aagtctatac agcctcgaat ccatcccggc cgccgctcct ggggatact      240 acagcgagcc gaagcgggga tggcggagat ccctgtgatc gacctgcgcg tcgccggctc      300
ggcggccgag gagtccgcgc ggctgcgggc cgcgtgcgag cgcctgggct gcttccgggt      360
gaccggccac ggcgtgccct cggtgctcct ggcagagatg aaggccgccg tgcgcgcgct      420
cttcgacctc cccgacgacg ccaagcgccg caacgccgac gtcatcaccg gcagcggcta      480
cgtcgccccc agcccgacca acccgctcta cgaggccttc gggctcctcg acgccgccgt      540
gcccaccgac gtcgacgcct tttgcgcgct cctcgacgcg ccgcccaaca tcagggagac      600
cgtcaaggcc tacgcggaga agatgcacga tgtgatcgtt ggcgtcgccc gcgagctggc      660
gtctagcctg gggctagtcg aggagcactc gttccaggac tggccgtgcc agttccgcat      720
caacaggtac aactacacgc gggagacggt gggctcctcc ggcgtgcaga cccacacgga      780
ctcgggcttc ctcaccgtgc tccatgagga cgagtgtgtc ggcggcctcg aggtcctgga      840
cccgggcacc ggcgagttcg tgcccgtgga ccccgtcgcg ggctcctttc tcgtaaacat      900
cggcgacgtc ggcacggcgt ggagcaacgg gaggctgcac aacgtgaagc accgggtgcg      960
gtgcgtcgca cccgtgccgc gcatctccat cgccatgttc ctgctcgcac ccaaggacga      1020
cagcgtgagc gcaccggcgg cgttcgtgga cgcggaccac ccgcgcaggt acaaggtgtt      1080
caactacaac gactatcgga ggctcagact gtccaccggc gagcacgcag gcgaggcgct      1140
cgcacggatg gcggcgtgac gtggctggag ctgcaaattg gattggaagc cgagacaagc      1200
cgttagttat ttaccatgcc gtgcgttca ccgcacacaa tcatattcaa aagccataaa      1260
ataaaaaata atttttaatat cagtcaacat atggtttaaa tatcatatgg agtacaatat      1320
tccgaatttt ttttttgtaat ttagtctgtc ttttgaaaaa aatgcacatc tagacctccg      1380
gatgact                                                                1387

<210> SEQ ID NO 20
<211> LENGTH: 900
<212> TYPE: DNA
<213> ORGANISM: Zea mays

<400> SEQUENCE: 20
atggcggaga tccctgtgat cgacctgcgc gtcgccggct cggcggccga ggagtccgcg      60
cggctgcggg ccgcgtgcga gcgcctgggc tgcttccggg tgaccggcca cggcgtgccc      120
tcggtgctcc tggcagagat gaaggccgcc gtgcgcgcgc tcttcgacct ccccgacgac      180
gccaagcgcc gcaacgccga cgtcatcacc ggcagcggct acgtcgcccc cagcccgacc      240
```

```
aacccgctct acgaggcctt cgggctcctc gacgccgccg tgcccaccga cgtcgacgcc      300
ttttgcgcgc tcctcgacgc gccgcccaac atcaggagga ccgtcaaggc ctacgcggag      360
aagatgcacg atgtgatcgt tggcgtcgcc cgcgagctgg cgtctagcct ggggctagtc      420
gaggagcact cgttccagga ctggccgtgc cagttccgca tcaacaggta caactcacg       480 cgggagacgg tgggctcctc cggcgtgcag acccacacgg actcgggctt cctcaccgtg      540
ctccatgagg acgagtgtgt cggcggcctc gaggtcctgg acccgggcac cggcgagttc      600
gtgcccgtgg acccgtcgc gggctccttt ctcgtaaaca tcggcgacgt cggcacggcg       660
tggagcaacg ggaggctgca caacgtgaag caccgggtgc ggtgcgtcgc acccgtgccg      720
cgcatctcca tcgccatgtt cctgctcgca cccaaggacg acagcgtgag cgcaccggcg      780
gcgttcgtgg acgcggacca cccgcgcagg tacaaggtgt tcaactacaa cgactatcgg      840
aggctcagac tgtccaccgg cgagcacgca ggcgaggcgc tcgcacggat ggcggcgtga      900
```

<210> SEQ ID NO 21
<211> LENGTH: 299
<212> TYPE: PRT
<213> ORGANISM: Zea mays

<400> SEQUENCE: 21

```
Met Ala Glu Ile Pro Val Ile Asp Leu Arg Val Ala Gly Ser Ala Ala
1               5                   10                  15

Glu Glu Ser Ala Arg Leu Arg Ala Ala Cys Glu Arg Leu Gly Cys Phe
            20                  25                  30

Arg Val Thr Gly His Gly Val Pro Ser Val Leu Leu Ala Glu Met Lys
        35                  40                  45

Ala Ala Val Arg Ala Leu Phe Asp Leu Pro Asp Asp Ala Lys Arg Arg
    50                  55                  60

Asn Ala Asp Val Ile Thr Gly Ser Gly Tyr Val Ala Pro Ser Pro Thr
65                  70                  75                  80

Asn Pro Leu Tyr Glu Ala Phe Gly Leu Leu Asp Ala Ala Val Pro Thr
                85                  90                  95

Asp Val Asp Ala Phe Cys Ala Leu Leu Asp Ala Pro Pro Asn Ile Arg
            100                 105                 110

Glu Thr Val Lys Ala Tyr Ala Glu Lys Met His Asp Val Ile Val Gly
        115                 120                 125

Val Ala Arg Glu Leu Ala Ser Ser Leu Gly Leu Val Glu Glu His Ser
    130                 135                 140

Phe Gln Asp Trp Pro Cys Gln Phe Arg Ile Asn Arg Tyr Asn Tyr Thr
145                 150                 155                 160

Arg Glu Thr Val Gly Ser Ser Gly Val Gln Thr His Thr Asp Ser Gly
                165                 170                 175

Phe Leu Thr Val Leu His Glu Asp Glu Cys Val Gly Gly Leu Glu Val
            180                 185                 190

Leu Asp Pro Gly Thr Gly Glu Phe Val Pro Val Asp Pro Val Ala Gly
        195                 200                 205

Ser Phe Leu Val Asn Ile Gly Asp Val Gly Thr Ala Trp Ser Asn Gly
    210                 215                 220

Arg Leu His Asn Val Lys His Arg Val Arg Cys Val Ala Pro Val Pro
225                 230                 235                 240

Arg Ile Ser Ile Ala Met Phe Leu Leu Ala Pro Lys Asp Asp Ser Val
                245                 250                 255

Ser Ala Pro Ala Ala Phe Val Asp Ala Asp His Pro Arg Arg Tyr Lys
```

```
                 260                 265                 270
Val Phe Asn Tyr Asn Asp Tyr Arg Arg Leu Arg Leu Ser Thr Gly Glu
            275                 280                 285

His Ala Gly Glu Ala Leu Ala Arg Met Ala Ala
            290                 295

<210> SEQ ID NO 22
<211> LENGTH: 1496
<212> TYPE: DNA
<213> ORGANISM: Zea mays

<400> SEQUENCE: 22
gtcggtctct tgtctcacca aaccggcgac atggtacatg gaggccagcc cgtcgcttgg      60
cgccacaagt ctcggtgccg tccgtccgac aagcggcgcc agcgcacgct ggctgctcgt     120
gcacgcctct aaatacggcc ccggacccgc caccaagcga aggccaatcc cgtccgccgc     180
cccccaccaa ccacgaacca cgcaagcgaa cccggccggc gcggggcagc ggcgatggcg     240
gagatcccgg tgatcgacct cgcctcgccc ggctcgtcgc ccgacgagtc ggcgcggctg     300
cgcgacgcgt gcgagcgcct gggctgcttt cgggtgaccg gccacggcgc gcccgcgggg     360
ctcctggccg acatgaaggc cgccgtgcgc gcgctcttcg acctccccga cgacgccaag     420
cgccgcaacg ccgacgtcat ccccggcagc ggctacgtcg cgccctgccc cgccaacccg     480
ctctacgagg ccttcgggct cctcgacgcc gccgcgcccg ccgacgtcga cgccttctgc     540
gcgcgcctcg acgcgccgcc caaagtcagg gagaccgtca agacctacgc ggagaagatg     600
cacgacgtga tcgtcggcgt cgccggcgag ctggccacca gcctggggct gggcctggag     660
gagcactcgt tccaggactg gccgtgccag ttccgcatca acaggtacaa ctacacgcag     720
gagacggtgg gctcctccgg cgtgcagacc cacacggact cgggcttcct caccgtgctc     780
caggaggacg agtgcgtcgg cggcctcgag gtgctggacc ccgccgccgg tgagttcgtg     840
cccgtggacc ccgtcgccgg ctccttcctc gtcaacatcg cgacgtcgg cacggcgtgg     900 agcaacggga ggctccacaa cgtgaagcac cgggtgcggt gcgtcgcgcc cgtgccgcgc     960
atctccatcg ccatgttcct gctggcgccc aaggacgacc gcgtgagcgc cccggaggcg    1020
ttggtcgacg cgggccaccc cgtcggtac aagccgttca actacgacga ctaccggagg    1080
ctccggctgt ccaccggcga gcgcgcagg gaggcgctcg cgcggatggc ggcgtgatgt    1140
cgtcacgcac gtgcaagccg ttaattatag gctcgcgcat gcatacgcct acacgagagg    1200
ttgtctcgtt aagccgttct attaaaatgt gtggggagaa aagatgacta ccgtggtgcc    1260
atgtggattg ctatcgggtc tgatcaataa aatcttgcaa cacttgcacg tgcgattcca    1320
tatcctagca cgggtgggcg ccacgctagt aggtagagac cggagcggcc aaaaaatggc    1380
tacagcacca gtaggtgaac tctcaagcaa cactggctat cccacttctg acgttgtctc    1440
tctcatcact atgtatgacc agcgaatgaa gtgtttaaaa atctgacgcc gtgaaa        1496

<210> SEQ ID NO 23
<211> LENGTH: 903
<212> TYPE: DNA
<213> ORGANISM: Zea mays

<400> SEQUENCE: 23
atggcggaga tcccggtgat cgacctgcgc ctcgccggct cgtcgcccga cgagtcggcg      60
cggctgcgcg acgcgtgcga gcgcctgggc tgctttcggg tgaccggcca cggcgcgccc     120
gcggggctcc tggccgacat gaaggccgcc gtgcgcgcgc tcttcgacct ccccgacgac     180
```

```
gccaagcgcc gcaacgccga cgtcatcccc ggcagcggct acgtcgcgcc ctgccccgcc    240
aacccgctct acgaggcctt cgggctcctc gacgccgccg cgcccgccga cgtcgacgcc    300
ttctgcgcgc gcctcgacgc gccgcccaaa gtcaggagga ccgtcaagac ctacgcggag    360
aagatgcacg acgtgatcgt cggcgtcgcc ggcgagctgg ccaccagcct ggggctgggc    420
ctggaggagc actcgttcca ggactggccg tgccagttcc gcatcaacag gtacaactac    480
acgcaggaga cggtgggctc ctccggcgtg cagacccaca cggactcggg cttcctcacc    540
gtgctccagg aggacgagtg cgtcggcggc ctcgaggtgc tggaccccgc cgccggtgag    600
ttcgtgcccg tggaccccgt cgccggctcc ttcctcgtca acatcggcga cgtcggcacg    660
gcgtggagca acgggaggct ccacaacgtg aagcaccggg tgcggtgcgt cgcgcccgtg    720
ccgcgcatct ccatcgccat gttcctgctg gcgcccaagg acgaccgcgt gagcgccccg    780
gaggcgttgg tcgacgcggg ccacccgcgt cggtacaagc cgttcaacta cgacgactac    840
cggaggctcc ggctgtccac cggcgagcgc gcaggcgagg cgctcgcgcg gatggcggcg    900
tga                                                                  903
```

<210> SEQ ID NO 24
<211> LENGTH: 300
<212> TYPE: PRT
<213> ORGANISM: Zea mays

<400> SEQUENCE: 24

```
Met Ala Glu Ile Pro Val Ile Asp Leu Arg Leu Ala Gly Ser Pro
1               5                   10                  15

Asp Glu Ser Ala Arg Leu Arg Asp Ala Cys Glu Arg Leu Gly Cys Phe
            20                  25                  30

Arg Val Thr Gly His Gly Ala Pro Ala Gly Leu Leu Ala Asp Met Lys
        35                  40                  45

Ala Ala Val Arg Ala Leu Phe Asp Leu Pro Asp Asp Ala Lys Arg Arg
    50                  55                  60

Asn Ala Asp Val Ile Pro Gly Ser Gly Tyr Val Ala Pro Cys Pro Ala
65                  70                  75                  80

Asn Pro Leu Tyr Glu Ala Phe Gly Leu Leu Asp Ala Ala Pro Ala
                85                  90                  95

Asp Val Asp Ala Phe Cys Ala Arg Leu Asp Ala Pro Pro Lys Val Arg
            100                 105                 110

Glu Thr Val Lys Thr Tyr Ala Glu Lys Met His Asp Val Ile Val Gly
        115                 120                 125

Val Ala Gly Glu Leu Ala Thr Ser Leu Gly Leu Gly Leu Glu Glu His
    130                 135                 140

Ser Phe Gln Asp Trp Pro Cys Gln Phe Arg Ile Asn Arg Tyr Asn Tyr
145                 150                 155                 160

Thr Gln Glu Thr Val Gly Ser Ser Gly Val Gln Thr His Thr Asp Ser
                165                 170                 175

Gly Phe Leu Thr Val Leu Gln Glu Asp Glu Cys Val Gly Gly Leu Glu
            180                 185                 190

Val Leu Asp Pro Ala Ala Gly Glu Phe Val Pro Val Asp Pro Val Ala
        195                 200                 205

Gly Ser Phe Leu Val Asn Ile Gly Asp Val Gly Thr Ala Trp Ser Asn
    210                 215                 220

Gly Arg Leu His Asn Val Lys His Arg Val Arg Cys Val Ala Pro Val
225                 230                 235                 240
```

```
Pro Arg Ile Ser Ile Ala Met Phe Leu Leu Ala Pro Lys Asp Asp Arg
                245                 250                 255

Val Ser Ala Pro Glu Ala Leu Val Asp Ala Gly His Pro Arg Arg Tyr
            260                 265                 270

Lys Pro Phe Asn Tyr Asp Asp Tyr Arg Arg Leu Arg Leu Ser Thr Gly
        275                 280                 285

Glu Arg Ala Gly Glu Ala Leu Ala Arg Met Ala Ala
    290                 295                 300

<210> SEQ ID NO 25
<211> LENGTH: 1614
<212> TYPE: DNA
<213> ORGANISM: Zea mays

<400> SEQUENCE: 25
accacacgaa ttgcacatct ccacagctca cgattccaac actagctaca tatatatgta      60
gctttctagg ctactatata cactcaccac caagtgtgaa gtgtgtatat atagtgacag     120
ctactgcaat atatacatac gcgtcaccta tatattagcc aagctagcta tatgagcttg     180
gttgcggcgc caatggcgat cgtcgacgtg gccaacgccc agctgcagca agcagcagca     240
gcagctgcca agaaagacga ggacggccat gagcagcagg agtcgtccta cgactacggc     300
gcgctgatga aggcgtgag gcacctgtcg gacagcggca ttaccaggct gcccgacagg      360
tacgtcctgc ccgcgtccga ccgccccggc gtccttgccg tctcgtcgtc cgtggcgggc     420
agcggcaggg tcaagctccc tgtcgtcaac ctcgccggcc tccgcgaccc ctgccagcgc     480
gccgccgtgc tggccacgct cgacgccgcg tgccgggagt acggcttctt tcaggtggta     540
aaccacgggt tcgggagcga cgtgagcggc gggatgctgg acgtggcgca gcgcttcttc     600
gagctgccgc tggccgagcg agcgcggcac atgtcggcgg acgtgcgggc gccggtgcgc     660
tacggcacca gcttcaacca ggccaaggac gacgtgctct gctggcgcga cttcctcaag     720
ctcgtctgcc agccgctgca ggcggtgctc ccgtactggc cccagcagcc ggcggacctc     780
agggacgtgg ccaccaggta cgccacggcg agccaccggc tgttcatgga ggtcatggag     840
gcggcgctgg aggccctggg catccccacg gccggcggcg tgctcgggga gctggcagcg     900
tcgtcgtcgc acatgatgac ggtgaactgc tacccggcgt gcccgcagcc tgagctcacg     960
ctggggatgc cctcgcactc ggactacggc ctcttcacgt tcgtcctgca ggaccacgtc    1020
gagggcctcc aggtcatgca cgacggccgc tggctcacca tcgacccccat cccgggatcg    1080 ttcgtcgtca acgtcggcga ccacctagag atctacagca acgggcggta caagagcgcg    1140
ctgcaccggg tgcacgtgaa ctccacgcgg ccgcgcatct cggtggcgtc gttccacagc    1200
ctgccggcgg agcgagtgat cgggccggcg ccggagctgg tggacgacga ggccggcaac    1260
ccgcggcggt acatggacac cgacttcgct accttcctcg cctacctcgc atccgcggac    1320
ggcaagaaca agaccttcct ccagtcaagg aagctgcctg ctgctgctcc tccatgcctc    1380
tagctaacta gatagctgct tattaatctg acagaataaa attaatcagt tcagcgcaca    1440
attccacaag cgaaaacaaa cctggatttg ttttaattag ctctgcccct cattattaca    1500
ttcaagctag ctcttggtca acgcatgcac acaagcttga gcattgactg gtccctttc    1560 aatcggttgc attgtactcc ctccgtacca aaattggttg tcgctatagt attt         1614

<210> SEQ ID NO 26
<211> LENGTH: 1212
<212> TYPE: DNA
```

<213> ORGANISM: Zea mays

<400> SEQUENCE: 26

```
atgagcttgg ttgcggcgcc aatggcgatc gtcgacgtgg ccaacgccca gctgcagcaa      60
gcagcagcag cagctgccaa gaaagacgag gacggccatg agcagcagga gtcgtcctac     120
gactacggcg cgctgatgaa aggcgtgagg cacctgtcgg acagcggcat taccaggctg     180
cccgacaggt acgtcctgcc cgcgtccgac cgccccggcg tccttgccgt ctcgtcgtcc     240
gtggcgggca gcggcagggt caagctccct gtcgtcaacc tcgccggcct ccgcgacccc     300
tgccagcgcg ccgccgtgct ggccacgctc gacgccgcgt gccgggagta cggcttcttt     360
caggtggtaa accacgggtt cgggagcgac gtgagcggcg ggatgctgga cgtggcgcag     420
cgcttcttcg agctgccgct ggccgagcga gcgcggcaca tgtcggcgga cgtgcgggcg     480
ccggtgcgct acggcaccag cttcaaccag gccaaggacg acgtgctctg ctggcgcgac     540
ttcctcaagc tcgtctgcca gccgctgcag gcggtgctcc cgtactggcc ccagcagccg     600
gcggacctca gggacgtggc caccaggtac gccacggcga ccaccggct gttcatggag      660
gtcatggagg cggcgctgga ggccctgggc atccccacgg ccggcggcgt gctcggggag     720
ctggcagcgt cgtcgtcgca catgatgacg gtgaactgct acccggcgtg cccgcagcct     780
gagctcacgc tggggatgcc ctcgcactcg gactacggcc tcttcacgtt cgtcctgcag     840
gaccacgtcg agggcctcca ggtcatgcac gacggccgct ggctcaccat cgaccccatc     900
ccgggatcgt tcgtcgtcaa cgtcggcgac cacctagaga tctacagcaa cgggcggtac     960
aagagcgcgc tgcaccgggt gcacgtgaac tccacgcggc cgcgcatctc ggtggcgtcg    1020
ttccacagcc tgccggcgga gcgagtgatc gggccggcgc cggagctggt ggacgacgag    1080
gccggcaacc cgcggcggta catggacacc gacttcgcta ccttcctcgc ctacctcgca    1140
tccgcggacg gcaagaacaa gaccttcctc cagtcaagga agctgcctgc tgctgctcct    1200
ccatgcctct ag                                                       1212
```

<210> SEQ ID NO 27
<211> LENGTH: 403
<212> TYPE: PRT
<213> ORGANISM: Zea mays

<400> SEQUENCE: 27

```
Met Ser Leu Val Ala Ala Pro Met Ala Ile Val Asp Val Ala Asn Ala
1               5                   10                  15

Gln Leu Gln Gln Ala Ala Ala Ala Ala Lys Lys Asp Glu Asp Gly
            20                  25                  30

His Glu Gln Gln Glu Ser Ser Tyr Asp Tyr Gly Ala Leu Met Lys Gly
        35                  40                  45

Val Arg His Leu Ser Asp Ser Gly Ile Thr Arg Leu Pro Asp Arg Tyr
    50                  55                  60

Val Leu Pro Ala Ser Asp Arg Pro Gly Val Leu Ala Val Ser Ser Ser
65                  70                  75                  80

Val Ala Gly Ser Gly Arg Val Lys Leu Pro Val Val Asn Leu Ala Gly
                85                  90                  95

Leu Arg Asp Pro Cys Gln Arg Ala Ala Val Leu Ala Thr Leu Asp Ala
            100                 105                 110

Ala Cys Arg Glu Tyr Gly Phe Phe Gln Val Val Asn His Gly Phe Gly
        115                 120                 125

Ser Asp Val Ser Gly Gly Met Leu Asp Val Ala Gln Arg Phe Phe Glu
```

```
                    130                 135                 140
Leu Pro Leu Ala Glu Arg Ala Arg His Met Ser Ala Asp Val Arg Ala
145                 150                 155                 160

Pro Val Arg Tyr Gly Thr Ser Phe Asn Gln Ala Lys Asp Asp Val Leu
                165                 170                 175

Cys Trp Arg Asp Phe Leu Lys Leu Val Cys Gln Pro Leu Gln Ala Val
            180                 185                 190

Leu Pro Tyr Trp Pro Gln Gln Pro Ala Asp Leu Arg Asp Val Ala Thr
        195                 200                 205

Arg Tyr Ala Thr Ala Ser His Arg Leu Phe Met Glu Val Met Glu Ala
    210                 215                 220

Ala Leu Glu Ala Leu Gly Ile Pro Thr Ala Gly Val Leu Gly Glu
225                 230                 235                 240

Leu Ala Ala Ser Ser Ser His Met Met Thr Val Asn Cys Tyr Pro Ala
                245                 250                 255

Cys Pro Gln Pro Glu Leu Thr Leu Gly Met Pro Ser His Ser Asp Tyr
            260                 265                 270

Gly Leu Phe Thr Phe Val Leu Gln Asp His Val Glu Gly Leu Gln Val
        275                 280                 285

Met His Asp Gly Arg Trp Leu Thr Ile Asp Pro Ile Pro Gly Ser Phe
    290                 295                 300

Val Val Asn Val Gly Asp His Leu Glu Ile Tyr Ser Asn Gly Arg Tyr
305                 310                 315                 320

Lys Ser Ala Leu His Arg Val His Val Asn Ser Thr Arg Pro Arg Ile
                325                 330                 335

Ser Val Ala Ser Phe His Ser Leu Pro Ala Glu Arg Val Ile Gly Pro
            340                 345                 350

Ala Pro Glu Leu Val Asp Asp Glu Ala Gly Asn Pro Arg Arg Tyr Met
        355                 360                 365

Asp Thr Asp Phe Ala Thr Phe Leu Ala Tyr Leu Ala Ser Ala Asp Gly
    370                 375                 380

Lys Asn Lys Thr Phe Leu Gln Ser Arg Lys Leu Pro Ala Ala Ala Pro
385                 390                 395                 400

Pro Cys Leu

<210> SEQ ID NO 28
<211> LENGTH: 1863
<212> TYPE: DNA
<213> ORGANISM: Zea mays

<400> SEQUENCE: 28
tgccaccata ccactagtgc aaggtcctag atttacactt ggtgctacac cttgcttcgc      60
cccctccctt ccttccttcc ttccttccct ccttccttgg tctctaggca gctagcagtg    120
tggtgctgct gccggccgcc tattggccgc ctgggactgg gatccattaa ttactgcgcg    180
cgcgcggcta accaacccaat cccagcgtgc gtaatctatt gcccacatgc cgacgccgtc    240
gcacctcaac aagaacccgc gctacctgga cttccgggcg gcgcggcggg tgccggagtc    300
gcacgcctgg ccgggcctgc acgaccaccc cgtcgtggac ggcggcgcgc cgggccccga    360
cgccgtgccg gtggtggacc tgggcgccgc ggacccggcg ccggcgccgg cggcggcggt    420
ggcccgcgcc gccgagcaat ggggcgcgtt cctgctcacg ggccacggcg tccccgcgga    480
cctgctggcg cgcgtggagg accggatcgc caccatgttc gcgctgccgg ccgacgacaa    540
gatgcgcgcc gtgcgcgggc ccggcgacgc ctgcggctac ggctccccgc ccatctcctc    600
```

```
cttcttctcc aagtgcatgt ggtccgaggg ctacaccttc tcgccggcct ccctccgcgc    660
cgacctccgc aagctctggc ccaaggccgg cgacgactac accagcttct gtgatgtgat    720
ggaggagttc cacaagcaca tgcgcgccct cgcggacaag ctgctggagc tgttcctcat    780
ggcgctgggg ctcaccgacg agcaggccag cgccgtcgag gccgagcgga ggatcgccga    840
gacgatgacc gccaccatgc atctcaactg gtacccgagg tgcccggacc cgcggcgcgc    900
gctggggctg atcgcgcaca ccgactcggg cttcttcacc ttcgtgatgc agagcctcgt    960
gcccgggctg cagctcttcc gccacgcccc ggaccggtgg gtggcggtgc cggccgtgcc   1020
gggcgccttc gtcgtcaacg tgggcgacct cttccacatc ctcaccaacg gccggttcca   1080
cagcgtgtac caccgcgccg tcgtgaaccg ggacctcgac aggatctcgc tcggctactt   1140
cctcggcccg ccgccgcacg ccaaggtggc gccgctgcgc gaggccgtgc cgcccggccg   1200
ggcccccgcg taccgcgccg tcacgtggcc cgagtacatg ggcgtccgca agaaggcctt   1260
caccaccggc gcctccgcgc tcaagatggt cgccctcgcc gccgccgccg acctcgacga   1320
cgacggcgac gccgccgtcg tccatcagca gcagcagcta gtcgtctcgt cgtagccgag   1380
accgatcgcc ggagactgat gctgatgatg atgcatatat acatgagaga aatcgtcgag   1440
tagactagcc gattgcaaaa gcaaccccag ctgccgaaac ctggcatatc gatcccattc   1500
tctgctgcgc acatgtatgc atgcatgcgc ttcgtccgtt cgactcgtgt gtgcttgctt   1560
gcttgcgcgt gcagcagaac taattccgtt ccgcagctag ctgctctgct ctgctctgct   1620
ggaatgtaat taagtagtag tatatggtag tagagaaaag attagctagg cgatcgatat   1680
agatgacggg ccggggaaga agacgaatta attaagatcg atcgacgacg acgagctgtg   1740
cgtggctggc tgtgttcttc tctagcctag ttacagaggc cggctgctgc tgcttccaat   1800
cgggctgctt gtcgctactg acgatcgtta gtggatccat taactaatct ggaattctgg   1860
att                                                                 1863
```

<210> SEQ ID NO 29
<211> LENGTH: 1149
<212> TYPE: DNA
<213> ORGANISM: Zea mays

<400> SEQUENCE: 29

```
atgccgacgc cgtcgcacct caacaagaac ccgcgctacc tggacttccg ggcggcgcgg     60
cgggtgccgg agtcgcacgc ctggccgggc ctgcacgacc accccgtcgt ggacggcggc    120
gcgccgggcc ccgacgccgt gccggtggtg gacctgggcg ccgcggaccc ggcgccggcg    180
ccggcggcgg cggtgccccg cgccgccgag caatggggcg cgttcctgct cacgggccac    240
ggcgtccccg cggacctgct ggcgcgcgtg gaggaccgga tcgccaccat gttcgcgctg    300
ccggccgacg acaagatgcg cgccgtgcgc gggcccggcg acgcctgcgg ctacggctcc    360
ccgcccatct cctccttctt ctccaagtgc atgtggtccg agggctacac cttctcgccg    420
gcctccctcc gcgccgacct ccgcaagctc tggcccaagg ccggcgacga ctacaccagc    480
ttctgtgatg tgatggagga gttccacaag cacatgcgcg ccctcgcgga caagctgctg    540
gagctgttcc tcatggcgct ggggctcacc gacgagcagg ccagcgccgt cgaggccgag    600
cggaggatcg ccgagacgat gaccgccacc atgcatctca actggtaccc gaggtgcccg    660
gacccgcggc gcgctgggg ctgatcgcg cacaccgact cgggcttctt caccttcgtg    720
atgcagagcc tcgtgcccgg gctgcagctc ttccgccacg ccccggaccg gtgggtggcg    780
```

```
gtgccggccg tgccgggcgc cttcgtcgtc aacgtgggcg acctcttcca catcctcacc    840
aacggccggt tccacagcgt gtaccaccgc gccgtcgtga accgggacct cgacaggatc    900
tcgctcggct acttcctcgg cccgccgccg cacgccaagg tggcgccgct gcgcgaggcc    960
gtgccgcccg gccgggcccc cgcgtaccgc gccgtcacgt ggcccgagta catgggcgtc   1020
cgcaagaagg ccttcaccac cggcgcctcc gcgctcaaga tggtcgccct cgccgccgcc   1080
gccgacctcg acgacgacgg cgacgccgcc gtcgtccatc agcagcagca gctagtcgtc   1140
tcgtcgtag                                                           1149
```

<210> SEQ ID NO 30
<211> LENGTH: 382
<212> TYPE: PRT
<213> ORGANISM: Zea mays

<400> SEQUENCE: 30

```
Met Pro Thr Pro Ser His Leu Asn Lys Asn Pro Arg Tyr Leu Asp Phe
1               5                   10                  15

Arg Ala Ala Arg Arg Val Pro Glu Ser His Ala Trp Pro Gly Leu His
            20                  25                  30

Asp His Pro Val Val Asp Gly Gly Ala Pro Gly Pro Asp Ala Val Pro
        35                  40                  45

Val Val Asp Leu Gly Ala Ala Asp Pro Ala Pro Ala Pro Ala Ala Ala
    50                  55                  60

Val Ala Arg Ala Ala Glu Gln Trp Gly Ala Phe Leu Leu Thr Gly His
65                  70                  75                  80

Gly Val Pro Ala Asp Leu Leu Ala Arg Val Glu Asp Arg Ile Ala Thr
                85                  90                  95

Met Phe Ala Leu Pro Ala Asp Asp Lys Met Arg Ala Val Arg Gly Pro
            100                 105                 110

Gly Asp Ala Cys Gly Tyr Gly Ser Pro Pro Ile Ser Ser Phe Phe Ser
        115                 120                 125

Lys Cys Met Trp Ser Glu Gly Tyr Thr Phe Ser Pro Ala Ser Leu Arg
    130                 135                 140

Ala Asp Leu Arg Lys Leu Trp Pro Lys Ala Gly Asp Asp Tyr Thr Ser
145                 150                 155                 160

Phe Cys Asp Val Met Glu Glu Phe His Lys His Met Arg Ala Leu Ala
                165                 170                 175

Asp Lys Leu Leu Glu Leu Phe Leu Met Ala Leu Gly Leu Thr Asp Glu
            180                 185                 190

Gln Ala Ser Ala Val Glu Ala Glu Arg Arg Ile Ala Glu Thr Met Thr
        195                 200                 205

Ala Thr Met His Leu Asn Trp Tyr Pro Arg Cys Pro Asp Pro Arg Arg
    210                 215                 220

Ala Leu Gly Leu Ile Ala His Thr Asp Ser Gly Phe Phe Thr Phe Val
225                 230                 235                 240

Met Gln Ser Leu Val Pro Gly Leu Gln Leu Phe Arg His Ala Pro Asp
                245                 250                 255

Arg Trp Val Ala Val Pro Ala Val Pro Gly Ala Phe Val Val Asn Val
            260                 265                 270

Gly Asp Leu Phe His Ile Leu Thr Asn Gly Arg Phe His Ser Val Tyr
        275                 280                 285

His Arg Ala Val Val Asn Arg Asp Leu Asp Arg Ile Ser Leu Gly Tyr
    290                 295                 300
```

Phe Leu Gly Pro Pro Pro His Ala Lys Val Ala Pro Leu Arg Glu Ala
305                 310                 315                 320

Val Pro Pro Gly Arg Ala Pro Ala Tyr Arg Ala Val Thr Trp Pro Glu
            325                 330                 335

Tyr Met Gly Val Arg Lys Lys Ala Phe Thr Thr Gly Ala Ser Ala Leu
        340                 345                 350

Lys Met Val Ala Leu Ala Ala Ala Asp Leu Asp Asp Asp Gly Asp
    355                 360                 365

Ala Ala Val Val His Gln Gln Gln Gln Leu Val Val Ser Ser
    370                 375                 380

<210> SEQ ID NO 31
<211> LENGTH: 1439
<212> TYPE: DNA
<213> ORGANISM: Zea mays

<400> SEQUENCE: 31

| | | | |
|---|---|---|---|
| gacctccatt ttgattatct ctatcctgta cgtgccgaga gtccttcaaa gccgacgacg | | | 60 |
| agacgacgat gcagtcgtcg tcgtcatcag cctcgacgcc ggctgccgct tccggcctcg | | | 120 |
| tcttcgatct cgggtctgcg gcgggcgtgc cggagacaca cgcgtggccg ggggtgaacg | | | 180 |
| agtacccgtc ggtggagtcc gctggccgcg acgtggtccc ggtggtggac atggggtgg | | | 240 |
| cctgccggga cgcgacgcgg gcgttggcgc gcgccgcaga cgagtggggc gtgtttctgc | | | 300 |
| tcgtcggcca cggcgtgccc cgggaagtgg cggcgcgtgc cgaggagcag gtcgcgcgcc | | | 360 |
| tgttcgtgct cccggctcct gacaaggccc gcgcggggcg ccgccccggg gagcccacgg | | | 420 |
| ccaccggcta cggcaggccg ccctggcac tccgcttctc caagctcatg tggtccgagg | | | 480 |
| ggtacacgtt ccgcgccgcc accgtccgcg aagagttccg ccgcgtctgg cccgacggcg | | | 540 |
| gcgacgacta cctccgcttc tgcgacgtga tggaggagta cgacagagag atgagggctc | | | 600 |
| tcggtggcag gctgctcgac ctcttcttca tggcgctcgg cctcaccgac gtccagttcg | | | 660 |
| ccaccggcga gacggagcgg aggatccgcg agacctggac ggcgacgatg cacccaatcc | | | 720 |
| tgtgtccgga accggagcgc gccatcgggc tgacggcgca cacgactcg ggcttcatca | | | 780 |
| cgctcatcat gcagagcccc gtgcccgggc tgcagctgct ccgccgcggg ccggaccggt | | | 840 |
| gggtgacggt gccggcgccg ccgggcgcgc tcatcgtcat gctcggcgac ctgttccagg | | | 900 |
| tgctcacgaa cggccgcttc cggagcccta tccaccgcgc cgtcgtaagc cgagagcgcg | | | 960 |
| agcggatctc cgtgccctac ttcctctgcc cgccggagga catgacggtg gcgccgctcg | | | 1020 |
| cgtccgctct gctgccgggg aggaaggccg tgttccgggc cgtgacgtgg ccagagtaca | | | 1080 |
| tggaggtcaa gcacaaggtg ttcggcacgg atgcgccggc cctggagatg ctgcagctgc | | | 1140 |
| aggtggatga ggaagaacaa ggtgaaaggg ccgccaccac ctaagcccta aggaactact | | | 1200 |
| agctgaatcc ataaactaat aaagaattcg tgaataaggg cgttggaaga ctggacacaa | | | 1260 |
| cacaagagag ttgctatata tcgtatttct gaaatttaag gcaaatatct tagttaaaaa | | | 1320 |
| actggtatat ttaaatagac aatatatatc taaaataaag atagttcacc attttacgg | | | 1380 |
| tcgaacaatg ataaagttat atattgtctg aatagtaaca aattaaagat ttccaggag | | | 1439 |

<210> SEQ ID NO 32
<211> LENGTH: 1116
<212> TYPE: DNA
<213> ORGANISM: Zea mays

<400> SEQUENCE: 32

```
atgcagtcgt cgtcgtcatc agcctcgacg ccggctgccg cttccggcct cgtcttcgat      60
ctcgggtctg cggcgggcgt gccggagaca cacgcgtggc cgggggtgaa cgagtacccg     120
tcggtggagt ccgctggccg cgacgtggtc ccggtggtgg acatgggggt ggcctgcccg     180
gacgcgacgc gggcgttggc gcgcgccgca gacgagtggg gcgtgttcct gctcgtcggc     240
cacggcgtgc cccgggaagt ggcggcgcgt gccgaggagc aggtcgcgcg cctgttcgtg     300
ctccggctc ctgacaaggc ccgcgcgggg cgccgccccg gggagcccac ggccaccggc      360
tacggcaggc cgcccctggc actccgcttc tccaagctca tgtggtccga ggggtacacg     420
ttccgcgccg ccaccgtccg cgaagagttc cgccgcgtct ggcccgacgg cggcgacgac     480
tacctccgct tctgcgacgt gatggaggag tacgacagag agatgagggc tctcggtggc     540
aggctgctcg acctcttctt catggcgctc ggcctcaccg acgtccagtt cgccaccggc     600
gagacggagc ggaggatccg cgagacctgg acggcgacga tgcacccaat cctgtgtccg     660
gaaccggagc gcgccatcgg gctgacggcg cacacggact cgggcttcat cacgctcatc     720
atgcagagcc ccgtgcccgg gctgcagctg ctccgccgcg gccggaccg vtgggtgacg     780
gtgccggcgc cgccgggcgc gctcatcgtc atgctcggcg acctgttcca ggtgctcacg     840
aacgccgct tccggagccc tatccaccgc gccgtcgtaa gccgagagcg cgagcggatc     900
tccgtgccct acttcctctg cccgccggag acatgacgg tggcgccgct cgcgtccgct     960
ctgctgccgg ggaggaaggc cgtgttccgg gccgtgacgt ggccagagta catggaggtc    1020
aagcacaagg tgttcggcac ggatgcgccg gccctggaga tgctgcagct gcaggtggat    1080
gaggaagaac aaggtgaaag gccgccacc acctaa                              1116
```

<210> SEQ ID NO 33
<211> LENGTH: 371
<212> TYPE: PRT
<213> ORGANISM: Zea mays

<400> SEQUENCE: 33

```
Met Gln Ser Ser Ser Ser Ala Ser Thr Pro Ala Ala Ala Ser Gly
1               5                   10                  15

Leu Val Phe Asp Leu Gly Ser Ala Ala Gly Val Pro Glu Thr His Ala
            20                  25                  30

Trp Pro Gly Val Asn Glu Tyr Pro Ser Val Glu Ser Ala Gly Arg Asp
        35                  40                  45

Val Val Pro Val Val Asp Met Gly Val Ala Cys Pro Asp Ala Thr Arg
    50                  55                  60

Ala Leu Ala Arg Ala Ala Asp Glu Trp Gly Val Phe Leu Leu Val Gly
65                  70                  75                  80

His Gly Val Pro Arg Glu Val Ala Ala Arg Ala Glu Glu Gln Val Ala
                85                  90                  95

Arg Leu Phe Val Leu Pro Ala Pro Asp Lys Ala Arg Ala Gly Arg Arg
            100                 105                 110

Pro Gly Glu Pro Thr Ala Thr Gly Tyr Gly Arg Pro Pro Leu Ala Leu
        115                 120                 125

Arg Phe Ser Lys Leu Met Trp Ser Glu Gly Tyr Thr Phe Arg Ala Ala
    130                 135                 140

Thr Val Arg Glu Glu Phe Arg Arg Val Trp Pro Asp Gly Gly Asp Asp
145                 150                 155                 160

Tyr Leu Arg Phe Cys Asp Val Met Glu Glu Tyr Asp Arg Glu Met Arg
                165                 170                 175
```

```
Ala Leu Gly Gly Arg Leu Leu Asp Leu Phe Phe Met Ala Leu Gly Leu
            180                 185                 190

Thr Asp Val Gln Phe Ala Thr Gly Glu Thr Glu Arg Arg Ile Arg Glu
        195                 200                 205

Thr Trp Thr Ala Thr Met His Pro Ile Leu Cys Pro Glu Pro Glu Arg
    210                 215                 220

Ala Ile Gly Leu Thr Ala His Thr Asp Ser Gly Phe Ile Thr Leu Ile
225                 230                 235                 240

Met Gln Ser Pro Val Pro Gly Leu Gln Leu Leu Arg Arg Gly Pro Asp
                245                 250                 255

Arg Trp Val Thr Val Pro Ala Pro Pro Gly Ala Leu Ile Val Met Leu
            260                 265                 270

Gly Asp Leu Phe Gln Val Leu Thr Asn Gly Arg Phe Arg Ser Pro Ile
        275                 280                 285

His Arg Ala Val Val Ser Arg Glu Arg Glu Arg Ile Ser Val Pro Tyr
    290                 295                 300

Phe Leu Cys Pro Pro Glu Asp Met Thr Val Ala Pro Leu Ala Ser Ala
305                 310                 315                 320

Leu Leu Pro Gly Arg Lys Ala Val Phe Arg Ala Val Thr Trp Pro Glu
                325                 330                 335

Tyr Met Glu Val Lys His Lys Val Phe Gly Thr Asp Ala Pro Ala Leu
            340                 345                 350

Glu Met Leu Gln Leu Gln Val Asp Glu Glu Gln Gly Glu Arg Ala
        355                 360                 365

Ala Thr Thr
    370

<210> SEQ ID NO 34
<211> LENGTH: 4095
<212> TYPE: DNA
<213> ORGANISM: Zea mays

<400> SEQUENCE: 34
taaatttgtg atccttgtga agttgttata tcatgaattg tgaacttgtt gcatttgtga      60
tcttttgtca actttgttgt attgtgaagt ttgatatgtt taccgatcgt attttagatt     120
tcgatcgtta ccggtgtatt ttccgcacca aacttttgtt tccgatgttt tcgaaatacc     180
gatatcgttt ccgtttctat agttacccct ttcaatttta tttccgatta aaaatatgaa     240
aacggtaatg gttttagtgt ttatcgaccg ttttcatctc taatcatccc tgccggtgaa     300 gtttaattttt tcccttggct aaagagatgc aagctgctgt aaaatacgtt aaaacaggca     360
aggcagcccc agcagccagc atcgcgtgcc cgtctatgta catcagtgga tacgtagcat     420
ctctagtgag taatataacg attgcatttg gctggaggac gtatgttata taagtatgtc     480
atttaccagt tgcattagta tcttccctaa ctcctataat aactctcttc gtggaatgga     540
cgtagacgta tgctatataa gtattaaaaa atagtttttt aagctggtgt cctcaatttt     600
gctattgttc tcgtttttat ctttagttgt gtcacaaatt taatccgtac aacaaatcaa     660
aaataccata cccttcttat attaattttc taacataaca tttgtttaga tattttcagt     720
cgtgaaaata caattctaat tctaacgtcg tagtatcaaa tcaaaccatc cagaatttga     780
ccaagcttaa ttataaaaaa tataaaattt atgatactga atagatagca ttagatttgt     840 tatataaatat attttataa aataccattt ttatggtata aatattggta ctcctttact     900
ttaaactata gatagttttg actaaggatg caactagaat tgcatcctct tttcactgca     960
```

```
ccttcattag ttttaatatt tatttagatg ggcccttgca aactgtagat atcatctctt    1020
gcaacattct ttctatagca ccacgaaaat gtattgcggc tttgaaatta taattgaatt    1080
agttgtatca tttctttcac cgatgcgtta aattcaaaat taagtgttat atttcttcat    1140
aatttgttaa atatatagac cctataatcc accattattt actataatag catacattaa    1200
cattggtttt agcctacact acgacactcg aggcattgaa ttttcctcta tcaaagaatt    1260
atatgtgtag tagtattgtt cttgacaaaa aggggatta aaattaaact accaatattg    1320
atacttatct tatcacatcc atgaatacaa tcaacactct tacaaaagat aagatacaag    1380
attaaaaagt accatgataa tacattaaga ttattagcaa tgcattaaat taaataaatg    1440
tgcaagtgaa tcatgatttt agttttatct attttacttt taaaatatga tattctctga    1500
ctacttctaa gcataaatgt gattctaagt catgaccgat cgtgcttatt cagaaaaatg    1560
aaggagacac agatttctat aaaaaaaggt tgtcatggga ctattgggtc aaccatctta    1620
ttcatttggg aaaataagtt tagaacacat caacccattt tagatgttga gtttggccct    1680
aatggtccat tgaccttact tttgtgggtt gacatagacc atctatccca agttattgtt    1740
gtgtcacatt ccctgatatc atgaatctat attttagctt tccgttttca tattttagt     1800 cgttacatat tttttatccg cgtactagat taaaactcta gttgttgcaa tacattttgt    1860
tcattttttt ctatttcttc tttactaaca acatattcta gttcctagct acattcttaa    1920
gtaccatagt gctataaaca ttttttatcc tacattattc cacttaagaa attgaatttt    1980
ctgcataaaa aaattatatg tccagtagtg ttgtcttata aaagcataaa gtgattaaaa    2040
ttaaaaccat tattgatatc ttattttca aaaaaaata taagcttata gaaagtgaat     2100
taatttcatg gtaaattaat atagtttaaa ttgaattatt agtgttatta ctatgtttat    2160
tatcaatgaa acatttttca tggttgatat aacttagtgt tacttatttt agtatttttt    2220
atataattct agttaacttt tagtttttga tttaaaaaaa cgagaattgt gtccttttgt    2280
ggagtgagta taaagaaagt aatatctgtt catcataatt tggtttttta aggtacgtga    2340
aacttgcttt atatttggac tcaagctatg tctaaataca tagtaaaaaa gcaatatttc    2400
tagaaaagac aaaacatctt ataatttaga atcaaggaaa tatatagatt ttatgtgcag    2460
tgagaagcca tttacaatgg aacgttcaac gttgggccaa tagatatttt gcgatatgat    2520
gatgggcata tttttgcatg gttgtccctc cactagctat agtttgatga tacgatacgc    2580
tgcacacacc attgggttgt accatgttag tgtagcaaca gtagaaaccc aattgtggcc    2640
gtgaaccatg ataatactag gtagagtgct agctagaggt ttcaggctat tgatgcgtga    2700
attaaacttt ctgttgtgtt gcgaggaaac gagtattgtg aaatatttga aacggttttt    2760
tttgtgaaag atttgaaacg gtattttgt tgtgaaataa agatcaaggc taaataaatt     2820
caaactaata aaacatatta attgacggcc tgaagccccc gccccatgg cccatgcca      2880 tagcatcagg tcccacatga catgaggccg cgcctccctc tatgttggct ccctgccttc    2940
gccgttgtcg tcgctcccga actccctctc ctccctgtt acaaatacc caccgccc       3000 ggacagcttc cctgcacact cgcagctcgc acatctcatg gtgtcctaag aacggcaaga    3060
gccagctctg cctagcagca gcgcacagcc acatccatgg acgccagccc gaccccaccg    3120
ctccccctcc gcgccccaac tcccagcatt gacctccccg ctggcaagga cagggccgac    3180
gcggcggcta acaaggccgc ggctgtgttc gacctgcgcc gggagcccaa gatcccggag    3240
ccattcctgt ggccgcacga agaggcgcgg ccgacctcgg ccgcggagct ggaggtgccg    3300
gtggtggacg tgggcgtgct gcgcaatggc gacggcgcgg ggctccgccg cgccgcggcg    3360
```

```
caagtggcgg cggcgtgcgc gacgcacggg ttcttccagg tgtgcgggca cggcgtggac   3420
gcggcgctgg ggcgcgccgc gctggacggc gccagcgact tcttccggct gccgctggct   3480
gagaagcagc gggcccggcg cgtccccggc accgtgtccg ggtacacgag cgcgcacgcc   3540
gaccggttcg cgtccaagct cccctggaag gagaccctgt ccttcggctt ccacgacggc   3600
gccgcggcgc ccgtcgtcgt ggactacttc accggcaccc tcggccaaga tttcgagcca   3660
gtggggtgag taaagaagaa gatggcgccg aatttacatt tataagtagg accagcagaa   3720 gccctgccc ctgggggcct tagcattgca ttcgactgat gaatacgcat ggcaggcggg   3780
tgtaccagag gtactgcgag gagatgaagg agctgtcgct gacgatcatg gagctgctgg   3840
agctgagcct gggcgtggag cgcggctact accgggagtt cttcgaggac agccgctcca   3900
tcatgcggtg caactactac ccgccgtgcc cggtgccgga gcgcacgctg gcacgggcc    3960 cgcactgcga ccccacggcg ctgaccatcc tcctgcagga cgacgtcggc gggctggagg   4020
tcctggtgga cggcgagtgg cgccccgtcc ggcccgtccc aggcgccatg gtcatcaaca   4080
tcggcgacac cttca                                                    4095
```

<210> SEQ ID NO 35
<211> LENGTH: 7404
<212> TYPE: DNA
<213> ORGANISM: Zea mays

<400> SEQUENCE: 35

```
cctattttgt gtctaatact cttcttatat taattgtttg gtcaaacttt agataaattt     60
gactaatgat gcaattaaaa ctgcatcacc tttactaagg tactgcttta tatgtttcga    120
caaaattttc aattattctc tatgtgtttt aatctttgcg ctacacctcc attgatttaa    180
atactcattt attttaaacc ataacttaaa ttatatcgga tctttgcatc ctttctatgg    240
caccatacat gaatcgatat tttggctgca aattttaat catgttagtt ttagcatttt     300
ttcatatcca tgtgttaagt ttgaatcatg tgttgttttt atataattta ttgaaaatat    360
agatcctaaa cttcactaat acttacaaca atagcatcat catgtgtttt aatccacgcc    420
acaacactca aggcattgaa ttttcttcta ccaaagagtt gtatgtgtgt attgttcttt    480
aaaaaataga gtgattataa ttaaactacc agtattcata tgtaaaatgt atagacatct    540
aaaataaaat ttgcaaaaaa cattgttgca gactttcaat ataattaaga atgggtttta    600
gggtcatgat atatggtttg ttaaagaaac ttgtttttttt ttgcaattga taaactataa    660
aatacatttt cactattgtg tgcatatgta cttggtatac atagtggcat atatcattt     720 tgtttacttt gaggtttgaa ttatctatgt taaaattgga taacatagat acattggtgt    780
gcgtcctttg gcccatttac ttgactgagg agcaatacta taaagtaaaa catatttgga    840 tatttttatct taaactccta gcataatatt gatttaatta tgaacaaata tatgtttagg   900
tgatagtttc atgggtggta aactatataa gaaggcttac catgatcttt gcaaactcta    960
ggctatgaaa gagttccatg atttgtctta gaagcataga caaaacagtg ataatgatct   1020
aaatcacact tatggcactg atgaccatat atgcaaagct aaatgcatgt taagttgtat   1080
tatatcatat gtttacaatg actatcgcat ataacgagga atacattgtc tatatagata   1140
gctattactg tagtagtgcc aaatgttgga caacatgaat cataatcttc aaacctagag   1200
aaattgtagt cagtcgtaca catatcgtct agtaagttgt ctatactttt tatttattgt   1260
atcaaatttt attgttatct tgcttgcttg tttgtttgta ccatagacac aatatggtca   1320
```

```
aaaagtggtc aatcgattcg aagaagattg caattgacga gtgctaacag ttgatccttt    1380
tgttgtgcac gctagcggag tagcatgaaa agagtaaaat atgaaattag cgttctaaac    1440
tgtttgtgct ataggtactt cgtatttaat ggagtgacta actataggaa ggtgagagct    1500
cagaagtcag caccctcaca cagagttcta gagttagtgg tcatcgaacc acgacaaact    1560
acatgatgag cagaagaggc aacatcaaga ctatgatcaa tagtttcggg tcaatgaatg    1620
acatcgtgat gagtatttat ctaactatat agaacaacaa cacatgatgt tttaagtaag    1680
ttcaactgat cttctattgc tatctttaag tatttaacgt agcgaataat gttttatcta    1740
tttcattcat aaataatgtt gtgacaaaag gggataacca tcacttttac catgttctag    1800
ataccacaac catctccacc atcataatgg gttcttcatt ggtgcttgga cctcaaataa    1860
tcatatctat agccaactta gctcaattct aataaaatta ggcaacttgg cttcattgta    1920
gcaaaaatag ccaacttagc tcaattttat ctaaacttag ctaatctagc acaacttaga    1980
tcaatattag gaaaaactaa tcaatctaat ctagctcaac tatagcgaaa gatagatatt    2040
gtagcataac ttagtagatc tatctcaaat tttagcaaaa actaatcaat ttagataaac    2100
tctataaaat tttaatcatt atgacttatt ccaactaat tgtaacttgc atgatttta     2160 tgttccttct ttataattag caacacctaa agacacgaat gatgagggt ctaacgcatt     2220 cattaaccag ttgttaaata atactctagg tagatgataa gaactctaat tattctatga    2280
atctaagcta aaagatgttt aatatttaag tattggtgtt tattatgtta tttagaacga    2340
ttcatgttac ttaaagattt gttatgattt ttaaatatga ttatgataat ttatgtggtg    2400
tggattaact tgtgaacata tgtgatgtag atgaatatgt atgttgtgga tggaaccata    2460
tgaatatata tacacactca tatactattc gttggtgtag gtaaagcttc atccatcggt    2520
aattactaaa tggtcttcag tcattaccac taggtgaagc ttcacacgac cgataattat    2580
tgaagaacgc tcattaattt ccggtaatgg cttattggcc ttcactagtc ggtgaaaatt    2640
agctattttt ataccaataa aaattagcta atatatgtaa accaggtcta attttatgg     2700 gcctcttacc gaccaaaatt gattagatta ttgttacaat agttttagtc aaaagctagc    2760
tatgctataa aaattttgaa ttaaagtgag tttcgtaata aaaattgcat acttttaaaa    2820
taaaataatt aaaaaacagt ttttagaaat acaatcaaac accttatgct ataaaaaat    2880 tgtaatgtac ctacaaatat ataatacttt actttaaaat aggcctgtgc cttctcggct    2940
ctatatgggc tgcctccaac gaagcgccat ggccatgggc tccactgtgt cgggtccac     3000 atgaggccgc gcctccctcc aaatgttccc tccctgcctt cgtctttgtc gttgctcgca    3060
aactccctgt cctcccctgt tacaaatacc cccacccgcc cggacagctt ccctgcatac    3120
ttgcagctcg cacatctcat ggtgtcgcag gaacgacaag agccagctgt gcctagcagc    3180
agcagcagca gcgccaagcg cgcagccacg tccatggacg ccagcccggc ccgccgctc    3240 ctcctccgcg cccccactcc cagccccagc attgacctcc ccgctggcaa ggacaaggcc    3300
gacgcggcgg ccagcaaggc cggcgcggcc gtgttcgacc tgcgccggga gcccaagatc    3360
cccgcgccat tcctgtggcc gcaggaagag gcgcggccgt cctcggccgc ggagctggag    3420
gtgccgatgg tggacgtggg cgtgctgcgc aatggcgacc gcgcggggct gcggcgcgcc    3480
gcggcgcagg tggccgcggc gtgcgcgacg cacgggttct tccaggtgtg cgggcacggc    3540
gtggacgcgg cgctggggcg cgccgcgctg gacggcgcca gcgacttctt ccggctgccg    3600
ctcgccgaga agcagcgcgc ccggcgcgtc cccggcaccg tgtccgggta cacgagcgcg    3660
cacgccgacc ggttcgcggc caagctcccc tggaaggaga ccctgtcgtt cggctaccac    3720
```

```
gacggcgccg cgtcgcctgt cgtcgtggac tacttcgtcg gcaccctcgg ccaggatttc    3780
gagccaatgg ggtaagtaag gtagtaagaa ggagcgccgg tttacattta ccgcacgtcg    3840
gcgtgcggtc gagtcgggac tcgggagacg tatgaaccc cgtcccgtcc catgcatgtg    3900
tggcaggtgg gtgtaccaga ggtactgcga ggagatgaag gagctgtcgc tgacgatcat    3960
ggagctgctg gagctgagcc tgggcgtgga gctgcgcggc tactaccggg agttcttcga    4020
ggacagccgt tccatcatgc ggtgcaacta ctacccgccg tgcccggagc cggagcgcac    4080
gctgggcacg ggcccgcact gcgaccccac ggcgctcacc atcctcctgc aggacgacgt    4140
gggcgggctg gaggtgctgg tggacggtga gtggcgcccc gtccggcccg tcccgggcgc    4200
catggtcatc aacatcggcg acaccttcat ggtaacgaaa cgaaagcgct cgctcctctg    4260
tttccttgg ccgctcttgt cctgtgtgta tattcagttg agctctctct gtgctgttat    4320
ttcccgaatc ctagtggacc taaacgggca ggttattaca gcacgcacac gtaggcatgt    4380
catgtagcta gtacatacat agcgatgccg atgcaaatgc aatagagaca tgcgttcgag    4440
ttggttccta tctcggcggg ctacggcagg tacacgcggc cgcggcgcgc tctctctagt    4500
ctatccgcgg ccgcgcccag gccgatcgag gcttccgggg gagagttgcg acaagagaac    4560
ggaccgaggg ggtcggctag cggtagcaag ttccctgttg gtttgtggcg ttggagcgtt    4620
gcggagaggc ttgcgcggcg gcggggacgt cgacggggac gtggcgggga gacgatacga    4680
tgggtgccgg gcaggtttcc gaattccaaa cgttttgtg gcgtgcgtcc atgggcgcc     4740
cccaaacttc ggacgtttcc ggcgctccaa caaatcttct cgcttcacac gtcaccgtcg    4800
tcccggattc atttgcctcg tcgctccacc attcgctgct ctcctctcca cgtactctta    4860
ccctgacctt tgggaaagaa ctgaacattc gagatgcaca acagttcaaa tataacatat    4920
gcagcacaag atcgttcgac tgctatccga caagccaaca acgtgcccag tagaactgaa    4980
tgtacctgtg atttccagca ctaacttaca gcaacgttgt gaaaaaacaa aaacgaaaac    5040
aaacggcaga aaaaacagat gtattgttct acagttacac caaatatttt ctggtccttt    5100
cagcaccaac aagagccata cgcatatcta gaagacaaaa ttcctctaat ttcaccccta    5160
cgtggtagca gttcctcctc aacacagttc acgtgctagc gtcgagttct ttgggccgcc    5220
acatcgactt ctcgacgcag agcaggccct cgctgccctt ggtgtaggtc atccgcacct    5280
cccactgcac ggacttggcc atgctctcca gctcatttat cgtgtccgcg gtgtccctca    5340
cgatcagctt gccctgtggc ctcagtacac ggtcgacctc ggcgaaaact gcagccagtt    5400
tgcatctgta aacaggcaac acagattttt agtatctaaa acactgcagg caaacgccac    5460
aggttttagt cgcaagaagc aataaaagca tgcaaacaat gctacgtgta cgtatcaaag    5520
gaacatgtca aaactcgttg catgaacgat cattgatgtt tccttgctga actagtcaca    5580
tcagtctgct tcaacttctg ggtttcacta gtagatatac cagaagggta gaataatgtg    5640
aagagcaaga aatacagacc tctttctgag cttttgagaac agatggtccg cgtgcagaag    5700
gtcatacgtt cttgggtaag tgctgaaaga ctcgcaccag tcatggtaca tgccaaacaa    5760
accgcgctcg tagatgatgg gcagcgtgtc tggtgaatcg atcggcacga tattcatgac    5820
ccagaccttt tggtccctca gagctgcagc aaaactgcca tgcaacaatg taaagcatta    5880
gtcaagaaga aggtgtacag tgcatttctc cttgtcaaca gtcttcagta acaaaaaaaa    5940
agtgttatgc ttgactgaat cttttcaaaga aaatatgcttg atgacttatg gtggacaagt    6000
tgcctgttat agtgttatgt tttaattaac tatgtgccag cttgggtaac tagtagttat    6060
```

```
gtagtgtgat ctgaattacc aaaatataaa taaataaata aacatgccca agaaactacg    6120
aaaaccattt acttaccctc catagacagc tctcatgtcc atgacatttc tcactttgga    6180
ccagtcaatt cccatgccat tcacatacga tttacttaca acccgttttcc agtgggcatt   6240 atctgcctca aaatcttcat ttgcaggctt tccatagaca ccaaccttgg aaccatcaat    6300
ccagaaaggg gtcttctcaa gcctttgcgg ccataactct ggccattttg atcctcggac    6360
ttttgagcca ccaggcagtt tgtgcatgca tgcttccaac ggtacattcc tgcaaatcaa    6420
aaggctgtgt aagcaaagca gagaagcact tttctccatt gaaaatatac tcttctcaaa    6480
gaaccgaaac cataccaagc agcatctgca tcatcagatt ccttgcacaa tggcgggctg    6540
ttttcagatc ttttctcata gcaaatattg tccattggtt tctgatatat gaccatacca    6600
acttggttta acttatcctt agtcttgttg accatcttcc agcacatgga ctttgtcaaa    6660
gtagacatgg ctgaaaaggg tatgtggcca catgttatgt tagaaataaa attcaatttt    6720
gaacagttgg tccatagcat gtattttgaa caaatgcaat ccttctccat ccatgaaaga    6780
agttgaccct tcatacttag gattattcag tactttcact catgtctgct gaatttgttc    6840
tcttggtagt tgctatacaa gaaaggggga agtacagagt agctaaactt atacaagcta    6900
tagtctgata tttgtatgaa acataaattt tggtatggat gtcttattaa aatgggaggt    6960
tgtataatat ttttctagcc tacctcaact tgcttgagac taaaaggctt tgttgttgtt    7020
gttgaggctg tatggtgctt tgactttaca aatcaagtta tcagctaccc tacttatgga    7080
tatacacctc tcataaaatg atggtaagaa gtttcgatat gtcacattaa cataagaact    7140
tcattcagtt agggtacaac gaagttaagt agttacggaa ataccattcc aaatctcaac    7200
atcctctggg agcttttggt aaacaggagt ggcagaccag acaaagtaac caccagggcg    7260
taacaagcgg ttcaattcca gcaaaagcat gccacctaaa agtagcgagc cagcaataag    7320
attcagttct atagcaaatc aataaatgaa aggaggacat gtcaatatgt aaccagcagg    7380
acaaaccttc gatgtgccaa ggga                                         7404

<210> SEQ ID NO 36
<211> LENGTH: 1788
<212> TYPE: DNA
<213> ORGANISM: Zea mays

<400> SEQUENCE: 36
aatcccagcg tgcgtaatct attgcccaca tgccgacgcc gtcgcacctc aacaagaacc      60
cgcgctacct ggacttccgg gcggcgcggc gggtgccgga gtcgcacgcc tggccgggcc     120
tgcacgacca ccccgtcgtg gacggcggcg cgccgggccc cgacgccgtg ccggtggtgg     180
acctgggcgc cgcggacccg gcgccggcgc cggcggcggc ggtggcccgc gccgccgagc     240
aatggggcgc gttcctgctc acgggccacg gcgtccccgc ggacctgctg gcgcgcgtgg     300
aggaccggat cgccaccatg ttcgcgctgc cggccgacga caagatgcgc gccgtgcgcg     360
ggcccggcga cgcctgcggc tacggctccc cgcccatctc ctccttcttc tccaagtgca     420
tgtggtccga gggctacacc ttctcgccgg cctccctccg cgccgacctc cgcaagctct     480
ggcccaaggc cggcgacgac tacaccagct tctggtacgt tgcgttgcgt gcttgtgtgc     540
gcgcacacct gccgaccgcg gccacaccgt acgcaaccca cgcgtacgta cgtgcgctag     600
ctacctgctt cgctcgcttc gctcctctcg cctcgccatg catatgcacg tacggccgta     660
caggtacagc agcaggtcac acgcacgaac gcacgcacgc accagcaccg atatgataca    720
tcatcgacgt gtcgtccccc cgtctaaggc catgcatgca tgcaagcacg cctagctagc    780
```

-continued

| | |
|---|---|
| ccttttggct tgctagctga cgaggggagc taggacgagc atacttactg tgcgcgtcat | 840 |
| gctcaattgc tcacactata ctactacttg ttactacagt gatgtgatgg aggagttcca | 900 |
| caagcacatg cgcgccctcg cggacaagct gctggagctg ttcctcatgg cgctggggct | 960 |
| caccgacgag caggccagcg ccgtcgaggc cgagcggagg atcgccgaga cgatgaccgc | 1020 |
| caccatgcat ctcaactggt gggtatatat tattgtctgt catgttgtcg tcgtcgtacg | 1080 |
| cgttgcggtt gggtgtacat gtatataaca caaacaacaa aaaactaacg ccgtgccgac | 1140 |
| gacgacgacg atcatcaggt acccgaggtg cccggacccg cggcgcgcgc tggggctgat | 1200 |
| cgcgcacacc gactcgggct tcttcacctt cgtgatgcag agcctcgtgc ccgggctgca | 1260 |
| gctcttccgc cacgcccgg accggtgggt ggcggtgccg gccgtgccgg gcgccttcgt | 1320 |
| cgtcaacgtg ggcgacctct tccacatcct caccaacggc cggttccaca gcgtgtacca | 1380 |
| ccgcgccgtc gtgaaccggg acctcgacag gatctcgctc ggctacttcc tcggcccgcc | 1440 |
| gccgcacgcg aaggtggcgc cgctgcgcga ggccgtgccg cccggccggg cccccgcgta | 1500 |
| ccgcgccgtc acgtggcccg agtacatggg cgtccgcaag aaggccttca ccaccggcgc | 1560 |
| ctccgcgctc aagatggtcg ccctcgccgc cgccgccgac ctcgacgacg acggcgacgc | 1620 |
| cgccgtcgtc catcagcagc agcagctagt cgtctcgtcg tagccgagac cgatcgccgg | 1680 |
| agactgatgc tgatgatgat gcatatatac atgagagaaa tcgtcgagta gactagccga | 1740 |
| ttgcaaaagc aaccccagct gccgaaacct ggcatatcga tcccattc | 1788 |

<210> SEQ ID NO 37
<211> LENGTH: 1698
<212> TYPE: DNA
<213> ORGANISM: Zea mays

<400> SEQUENCE: 37

| | |
|---|---|
| cgtgccgaga gtccttcaaa gccgacgacg agacgacgat gcagtcgtcg tcgtcatcag | 60 |
| cctcgacgcc ggctgccgct tccggcctcg tcttcgatct cgggtctgcg gcgggcgtgc | 120 |
| cggagacaca cgcgtggccg ggggtgaacg agtacccgtc ggtggagtcc gctggccgcg | 180 |
| acgtggtccc ggtggtggac atggggggtgg cctgcccgga cgcgacgcgg gcgttggcgc | 240 |
| gcgccgcaga cgagtggggc gtgtttctgc tcgtcggcca cggcgtgccc gggaagtgg | 300 |
| cggcgcgtgc cgaggagcag gtcgcgcgcc tgttcgtgct cccggctcct gacaaggccc | 360 |
| gcgcggggcg ccgccccggg gagcccacgg ccaccggcta cggcaggccg cccctggcac | 420 |
| tccgcttctc caagctcatg tggtccgagg gtacacgtt ccgcgccgcc accgtccgcg | 480 |
| aagagttccg ccgcgtctgg cccgacggcg gcgacgacta cctccgcttc tggtacgtac | 540 |
| gagcgccatg tcacgtgctt gtgctttcat gcctcgtacc gtcgtcgtgc tgtacgtgtt | 600 |
| atgtttatcg gccggtacgt cacgcgtgct acactggtta acgacgtgag cgtgcccacg | 660 |
| ttgactgcat gcatgcat gcgcgcgccc agcgacgtga tggaggagta cgacagagag | 720 |
| atgagggctc tcggtggcag gctgctcgac ctcttcttca tggcgctcgg cctcaccgac | 780 |
| gtccagttcg ccaccggcga acggagcgg aggatccgcg agacctggac ggcgacgatg | 840 |
| cacccaatcc tgtacgtacg tcaaaaacga atatctgacc aatgcaaacg ttttctgca | 900 |
| atgccagtca tccactcatc ctgtacgtac ctctggactc tgcttgtcca tctactgatg | 960 |
| acacgtatgg taggtacccc aggtgtccgg aaccggagcg cgccatcggg ctgacggcgc | 1020 |
| acacggactc gggcttcatc acgctcatca tgcagagccc cgtgcccggg ctgcagctgc | 1080 |

```
tccgccgcgg gccggaccgg tgggtgacgg tgccggcgcc gccgggcgcg ctcatcgtca    1140
tgctcggcga cctgttccag gtgctcacga acggccgctt ccggagccct atccaccgcg    1200
ccgtcgtaag ccgagagcgc gagcggatct ccgtgcccta cttcctctgc ccgccggagg    1260
acatgacggt ggcgccgctc gcgtccgctc tgctgccggg gaggaaggcc gtgttccggg    1320
ccgtgacgtg gccagagtac atggaggtca agcacaaggt gttcggcacg gatgcgccgg    1380
ccctggagat gctgcagctg caggtggatg aggaagaaca aggtgaaagg gccgccacca    1440
cctaagccct aaggaactac tagctgaatc cataaactaa taaagaattc gtgaataagg    1500
gcgttggaag actggacaca acacaagaga gttgctatat atcgtatttc tgaaatttaa    1560
ggcaaatatc ttagttaaaa aactggtata tttaaataga caatatatat ctaaaataaa    1620
gatagttcac cattttttacg gtcgaacaat gataaagtta tatattgtct gaatagtaac    1680
aaattaaaga tttccagg                                                  1698

<210> SEQ ID NO 38
<211> LENGTH: 4095
<212> TYPE: DNA
<213> ORGANISM: Zea mays

<400> SEQUENCE: 38
cggtctaagt gaccgtttga gagaggaaaa gggttgaaag agacccggtc tttgtgacca      60
cctcaacggg gagtaggttt ataagaaccg aacctcggta aaacgaatca ccgtgtcatc     120
cgccttattt gcttgtgatt tgttttcgcc ctctctttcg gactcgttta tatttctaac     180
gctaaccccg acttgtagtt gtgcttaaag tttgtaaatt tcagattcgc cctattcacc     240
ccctctaggc gactttcata taaatattgg gagaaatatg aaaaacaaat gaaggtcgaa     300
cgagtcagag acaccataaa aaagaggtcg tcttaactag ggtgctaaac ctcaacattg     360
tagtagatct tagtactgag tttgacatct ttgacaccaa caagatggtg atacgttact     420
ttctacgtta acttgggtag gtatatcgac tatagtggcc tataacacta ggctatgtaa     480
tatgatattg tgttgagtct ttataaacat gattttttt aaaaaaaga gctaaaataa      540 aaaatagaaa tcgacggtac gatgcaagtt cttctcaaga caaccaaacg caccccttgcc    600 cctttattga aattgaagta tgtgctttat caaatgttta aatactaatt ataagtatta     660
aatataattt aattataata ctaattatat agataaagac taaataacaa gacaaattta     720
ttaaatataa ttaattcatt attaacaaat acttaatgta gcacgatcga atcatggact     780
aattagtctt gatagactcg tcttaccatt taatcataat tagttttgta tactgtttat     840
aatatttcta actagctagt attaaacttt tgatgtaacc taactaaagt ttagtcacgc     900
caatacataa ggactcggat cgttcgatca cccatgacat cacgtatact aagagcatct     960
ccaaaagctc tccagaagtc tcccctaaat ctatttttt gggaaaaaca caaaaacatg     1020
tctccaacag ttcccttaaa gcgccccaa ctttttcata gccctaaaaa ctccctcatt     1080
tgtagctaca aatgagggt ttttgggct ccccagaaac aaactgttga tttaagggat      1140
ctgttggaga aaggattaaa atttaccctc acttattatt tagatgtccc ttaaaactga    1200
ttttgaggag tcgttttatg tagagctctt ggagatgctc taacacaccg agcacaaccg    1260
catcatcaat caaaacaacc caaagtttgt tcggtacaag tcatcagcct gtgtacacac    1320
atcagcctcg gccccgggag aagcgctagc aaacaaggtt cacctaaaaa tccatccaga    1380
ttcattgaat ccaaccagca caaacgtccc atttattaat caccctcatca caggtccccc    1440 cagcctcact ctcgcgccgg ctcaaggtac attgcgtgtc ctagccaaga cacgcagctc    1500
```

```
atctcagcct cacacgcaca gcaagagcga ggcgtgattc gccatgggcg gcctcactat    1560
ggaccaggcc ttcgtgcagg cccccgagca ccgccccaag cccatcgtca ccgaggccac    1620
cggcatccct ctcatcgacc tctcgcctct ggccgccagc ggcggcgccg tggacgcgct    1680
ggccgccgag gtgggcgcgg cgagccggga ctggggcttc ttcgtggtcg tgggccacgg    1740
cgtgcccgca gagaccgtgg cgcgcgcgac ggaggcgcag cgagcgttct tcgcgctgcc    1800
ggcagagcgg aaggccgccg tgcggaggaa cgaggcggag ccgctcgggt actacgagtc    1860
ggagcacacc aagaacgtga gggactggaa ggaggtgtac gacctcgtgc gcgcgcgagcc   1920 gccgccgccg gcagccgtgg ccgacggcga gcttgtgttc gataacaagt ggccccagga    1980
tctaccgggc ttcaggtgac gaaattaact atatatccct ttcgatcata gttgcgttaa    2040
taaattaagg gaatcgtgag cgtacgtacg taagtttccg cagagaggcg ctggaggagt    2100
acgcgaaagc gatggaagag ctggcgttca agctgctgga gctgatcgcc cggagcctga    2160
agctgaggcc cgaccggctg cacggcttct tcaaggacca gacgaccttc atccggctga    2220
accactaccc tccttgcccg agcccgacc tggccctcgg cgtggggcgg cacaaggacg     2280
ccggcgccct gaccatcctg taccaggacg acgtcggggg gctcgacgtc cggcggcgct    2340
ccgacggcga gtgggtccgc gtcaggcccg tgcccgactc gttcatcatc aacgtcggcg    2400
acctcatcca ggtacgtgcc cacctgatga actgagctga acgtaggttg catgcactgc    2460
atgtgtatag gcttctcaga tcgcttcgtg tggcgtaagg tgtggagcaa cgacaggtac    2520
gagagcgcgg agcaccgggt gtcggtgaac tcggcgaggg agaggttctc catgccctac    2580
ttcttcaacc cggcgaccta caccatggtg gagccggtgg aggagctggt gagcaaggac    2640
gatccgccca ggtacgacgc ctacaactgg ggcgacttct tcagcaccag gaagaacagc    2700
aacttcaaga agctcaacgt ggagaacatt cagatcgcgc atttcaagaa gagcctcgtc    2760
ctcgcctaac tactgctact gctaggatcc atgccattgc catgtcgtct tcagattcag    2820
agcacgccat gtcgtcgcta gcttcgtggt agaacaaata atgatgtgcg tgctgtgtgt    2880
aagcatggat atggatgtga atatgtaata tgatgagcac tcctactttg gtatgtttgg    2940
gaataacaga cttgtgttgg tctggttcat tatttgtaag aaaatcaaaa agagttagta    3000
gggcaggagg ctaaccacag tcatgctgca ccacatccct ggtggaaagc tggccgggtt    3060
acgctacgct cgtgcagcca gattactgca gggccgggat atgcttccgg tggaaggaag    3120
gggacggtgg ctgaggacca tggggctgga gcctgggaga gaggtcgagc tagaagaaag    3180
ggggagagag aagacgcaca acgaagatgg gtcagccagg gatttcgacc caaggggggag   3240 ctagtggatt ttgggagaaa acagaaaaga gaaagagaa aagaagaaaa atttgttggt     3300
gtgaacacaa ggttgatttg tcttttctta tttggattga tgatgagtcg tggactaacc    3360
gacccgtgag ctattgtgtc gtataatcat gtctctcggt ttctggtgtg caggtttgaa    3420
gcacagagac ggtggtcgac gcaaaggtga acgtcatgca ggttcgtgcc gatgaccgg     3480 gagcagtgaa agacgagcgt tgggacttga caagggacc agagtcgccg gatgactagc     3540
cgcagtggct gacgcctgga acacgcatag acgtgaggac gtggtagagc aggtgaaaat    3600
cgcctagagg ggggggggt gaatagacaa aacctaaaaa ttataaactt tgaacacaaa     3660
ctttacctga ggttaccgtt agaacgagta ttaatgaaat cggagtgcgg aaggcaagtt    3720
cttcttgcta cgagttgctt aatcaatatt gataactttg ggagtcaact caaaatgatc    3780
acaagcaaaa gaactagaga gagaggagag gaagaatcaa ctcgcaaagt aatgatcaac    3840
```

-continued

```
acaaatgaac acaatgattt atttctcgag gtttggttcc gaagaaccta ctccccgttc    3900
aggagtccac ataggacatg tctctttcaa ccctttctct ctctcaaatg gtcacataga    3960
ctggttcagt tgagagcacc tagagggggg tgaataggtg atcttgtaaa atcaaacact    4020
aatagccaca aaacttagtt taaagtgtta gtacggctaa gtagctttga agcgagttat    4080
tgtgaacaca acaat                                                     4095
```

<210> SEQ ID NO 39
<211> LENGTH: 21
<212> TYPE: DNA
<213> ORGANISM: Artificial Sequence
<220> FEATURE:
<223> OTHER INFORMATION: suppression oligo

<400> SEQUENCE: 39
ctccatcatg cggtgcaact a                                              21

<210> SEQ ID NO 40
<211> LENGTH: 21
<212> TYPE: RNA
<213> ORGANISM: Artificial Sequence
<220> FEATURE:
<223> OTHER INFORMATION: suppression oligo

<400> SEQUENCE: 40
uaguugcacc gcaugaugga g                                              21

<210> SEQ ID NO 41
<211> LENGTH: 19
<212> TYPE: DNA
<213> ORGANISM: Artificial Sequence
<220> FEATURE:
<223> OTHER INFORMATION: suppression oligo

<400> SEQUENCE: 41
ggtactgcga ggagatgaa                                                 19

<210> SEQ ID NO 42
<211> LENGTH: 21
<212> TYPE: RNA
<213> ORGANISM: Artificial Sequence
<220> FEATURE:
<223> OTHER INFORMATION: suppression oligo

<400> SEQUENCE: 42 uucaucccu cgcaguaccu a                                               21

<210> SEQ ID NO 43
<211> LENGTH: 19
<212> TYPE: DNA
<213> ORGANISM: Artificial Sequence
<220> FEATURE:
<223> OTHER INFORMATION: suppression oligo

<400> SEQUENCE: 43
caggcgccat ggtcatcaa                                                 19

<210> SEQ ID NO 44
<211> LENGTH: 21
<212> TYPE: RNA
<213> ORGANISM: Artificial Sequence
<220> FEATURE:
<223> OTHER INFORMATION: suppression oligo

<400> SEQUENCE: 44

-continued uugaugacca uggcgccugg a                      21

<210> SEQ ID NO 45
<211> LENGTH: 19
<212> TYPE: DNA
<213> ORGANISM: Artificial Sequence
<220> FEATURE:
<223> OTHER INFORMATION: suppression oligo

<400> SEQUENCE: 45
tcatgcggtg caactacta                         19

<210> SEQ ID NO 46
<211> LENGTH: 21
<212> TYPE: RNA
<213> ORGANISM: Artificial Sequence
<220> FEATURE:
<223> OTHER INFORMATION: suppression oligo

<400> SEQUENCE: 46
uaguaguugc accgcaugau a                      21

<210> SEQ ID NO 47
<211> LENGTH: 19
<212> TYPE: DNA
<213> ORGANISM: Artificial Sequence
<220> FEATURE:
<223> OTHER INFORMATION: suppression oligo

<400> SEQUENCE: 47
tcgctcgcct tcttcctca                         19

<210> SEQ ID NO 48
<211> LENGTH: 21
<212> TYPE: RNA
<213> ORGANISM: Artificial Sequence
<220> FEATURE:
<223> OTHER INFORMATION: suppression oligo

<400> SEQUENCE: 48
ugaggaagaa ggcgagcgac a                      21

<210> SEQ ID NO 49
<211> LENGTH: 19
<212> TYPE: DNA
<213> ORGANISM: Artificial Sequence
<220> FEATURE:
<223> OTHER INFORMATION: suppression oligo

<400> SEQUENCE: 49
tccaacgggc ggtacaaga                         19

<210> SEQ ID NO 50
<211> LENGTH: 21
<212> TYPE: RNA
<213> ORGANISM: Artificial Sequence
<220> FEATURE:
<223> OTHER INFORMATION: suppression oligo

<400> SEQUENCE: 50
ucuuguaccg cccguuggac c                      21

<210> SEQ ID NO 51
<211> LENGTH: 19
<212> TYPE: DNA

```
<213> ORGANISM: Artificial Sequence
<220> FEATURE:
<223> OTHER INFORMATION: suppression oligo

<400> SEQUENCE: 51
gcatcaacag gtacaacta                                            19

<210> SEQ ID NO 52
<211> LENGTH: 21
<212> TYPE: RNA
<213> ORGANISM: Artificial Sequence
<220> FEATURE:
<223> OTHER INFORMATION: suppression oligo

<400> SEQUENCE: 52
uaguuguacc uguugaugcg a                                         21

<210> SEQ ID NO 53
<211> LENGTH: 19
<212> TYPE: DNA
<213> ORGANISM: Artificial Sequence
<220> FEATURE:
<223> OTHER INFORMATION: suppression oligo

<400> SEQUENCE: 53
tggacgatgg atagttcaa                                            19

<210> SEQ ID NO 54
<211> LENGTH: 21
<212> TYPE: RNA
<213> ORGANISM: Artificial Sequence
<220> FEATURE:
<223> OTHER INFORMATION: suppression oligo

<400> SEQUENCE: 54
uugaacuauc caucguccau c                                         21

<210> SEQ ID NO 55
<211> LENGTH: 19
<212> TYPE: DNA
<213> ORGANISM: Artificial Sequence
<220> FEATURE:
<223> OTHER INFORMATION: suppression oligo

<400> SEQUENCE: 55
tggaccatgg atacttcaa                                            19

<210> SEQ ID NO 56
<211> LENGTH: 21
<212> TYPE: RNA
<213> ORGANISM: Artificial Sequence
<220> FEATURE:
<223> OTHER INFORMATION: suppression oligo

<400> SEQUENCE: 56
uugaaguauc caugguccau c                                         21

<210> SEQ ID NO 57
<211> LENGTH: 19
<212> TYPE: DNA
<213> ORGANISM: Artificial Sequence
<220> FEATURE:
<223> OTHER INFORMATION: suppression oligo

<400> SEQUENCE: 57
gcaaggtcct agatttaca                                            19
```

<210> SEQ ID NO 58
<211> LENGTH: 21
<212> TYPE: RNA
<213> ORGANISM: Artificial Sequence
<220> FEATURE:
<223> OTHER INFORMATION: suppression oligo

<400> SEQUENCE: 58
uguaaaucua ggaccuugca a                                              21

<210> SEQ ID NO 59
<211> LENGTH: 19
<212> TYPE: DNA
<213> ORGANISM: Artificial Sequence
<220> FEATURE:
<223> OTHER INFORMATION: suppression oligo

<400> SEQUENCE: 59
cagagtacat ggaggtcaa                                                 19

<210> SEQ ID NO 60
<211> LENGTH: 21
<212> TYPE: RNA
<213> ORGANISM: Artificial Sequence
<220> FEATURE:
<223> OTHER INFORMATION: suppression oligo

<400> SEQUENCE: 60
uugaccucca uguacucugg a                                              21

<210> SEQ ID NO 61
<211> LENGTH: 19
<212> TYPE: DNA
<213> ORGANISM: Artificial Sequence
<220> FEATURE:
<223> OTHER INFORMATION: suppression oligo

<400> SEQUENCE: 61
ccatgcccta cttcttcaa                                                 19

<210> SEQ ID NO 62
<211> LENGTH: 21
<212> TYPE: RNA
<213> ORGANISM: Artificial Sequence
<220> FEATURE:
<223> OTHER INFORMATION: suppression oligo

<400> SEQUENCE: 62
uugaagaagu agggcaugga a                                              21

<210> SEQ ID NO 63
<211> LENGTH: 19
<212> TYPE: DNA
<213> ORGANISM: Artificial Sequence
<220> FEATURE:
<223> OTHER INFORMATION: suppression oligo

<400> SEQUENCE: 63
acatggcggt caacttcta                                                 19

<210> SEQ ID NO 64
<211> LENGTH: 21
<212> TYPE: RNA
<213> ORGANISM: Artificial Sequence
<220> FEATURE:

<223> OTHER INFORMATION: suppression oligo

<400> SEQUENCE: 64
uagaaguuga ccgccaugug a                                               21

<210> SEQ ID NO 65
<211> LENGTH: 726
<212> TYPE: DNA
<213> ORGANISM: Rice tungro bacilliform virus

<400> SEQUENCE: 65
tcctacaaaa gggagtagta atatttaatg agcttgaagg aggatatcaa ctctctccaa     60
ggtttattgg agacctttat gctcatggtt ttattaaaca ataaacttc acaaccaagg    120
ttcctgaagg gctaccgcca atcatagcgg aaaaacttca agactataag ttccctggat   180
caaataccgt cttaatagaa cgagagattc ctcgctggaa cttcaatgaa atgaaaagag   240
aaacacagat gaggaccaac ttatatatct tcaagaatta tcgctgtttc tatggctatt   300
caccattaag gccatacgaa cctataactc ctgaagaatt tgggtttgat tactacagtt   360
gggaaaatat ggttgatgaa gacgaaggag aagttgtata catctccaag tatactaaga   420
ttatcaaagt cactaaagag catgcatggg cttggccaga acatgatgga gacacaatgt   480
cctgcaccac atcaatagaa gatgaatgga tccatcgtat ggacaatgct taaagaagct   540
ttatcaaaag caactttaag tacgaatcaa taaagaagga ccagaagata taaagcggga   600
acatcttcac atgctaccac atggctagca tctttacttt agcatctcta ttattgtaag   660
agtgtataat gaccagtgtg ccctggact ccagtatata aggagcacca gagtagtgta    720
atagat                                                              726

<210> SEQ ID NO 66
<211> LENGTH: 165
<212> TYPE: DNA
<213> ORGANISM: Rice tungro bacilliform virus

<400> SEQUENCE: 66
acgaatcaat aaagaaggac cagaagatat aaagctggaa catcttcaca tgctaccaca     60
tggctagcat ctttactta gcatctctat tattgtaaga gtgtataatg accagtgtgc    120
ccctggactc cagtatataa ggagcaccag agtagtgtaa tagat                   165

<210> SEQ ID NO 67
<211> LENGTH: 2000
<212> TYPE: DNA
<213> ORGANISM: Zea mays

<400> SEQUENCE: 67
ctgcaatata tacaccaaaa gtattataaa ctgtcatata tatgaccaaa acctttttat     60
tttagaaaag tatattaatc atggtatatt aatcaaagtt gttgttgggg ctgcaaaaat   120
catacccttc ttccacaagc tgttccttga actgcaggta ctcaggaact ctcagctcct   180
caacagcgag ctcactgacg ttgaccctca catactccca gacaccaggc ctagggcgga   240
tgcaagtgc aacccatggg gggatgacaa tcgcctcctg taagataata gagctagaat    300
gattaaagaa ggtgcacact acaaaaggaa cagtgctgtc cagcgagatc tgaatctgat   360
gcaaacctga gctgccctca ggacatcctc aaaagcacca tccttgagct tctcgcgctc   420
agcctcaggg atcgcattgt tgtactcggc aatgatctgg tggggctgca gcataccctt   480
tccaaggttt ttcagcctgc gcaaaacgat gtgccaaata acatcagact atgccagatc   540

| | | | |
|---|---|---|---|
| tataaactca | tcaaacatat | acaatttcaa gaaatagttt agacgtatga tcagcagtca | 600 |
| gtagcgtggg | aacatatgca | acatagcgaa gaggcacaac agcaaattca ttcgaaaaaa | 660 |
| tgaaaacaaa | gattcctctc | ttttaactga acttctcgaa accccttca tgcctacaca | 720 |
| tccgatctag | tcagatgcct | atgcgttcat gctgaacaga acgtgtcaga actaagcata | 780 |
| aactggttag | caagcattat | cgtattcgat agacccttta gtaacaagct atacattggg | 840 |
| taagttcaga | ctccaatcat | tctgttcaga aacatcgtat tgaatataaa actaaagaac | 900 |
| acacatgcag | gtgcagccag | atctaacagc agtttacagt cggtactaaa aaaagcatgg | 960 |
| tgtatgtatg | tatcatcagt | atccagtact aggtttcgac aaaatcctgg atgctaatta | 1020 |
| aatactcatc | ttattaggga | acacaggaac attatgtcta cagcattgaa tgatggccac | 1080 |
| atcatgctag | atctaacaat | acataatatg atggaactgg tcttaaaaag tcgcattcgc | 1140 |
| tcaaataata | cccgtagcaa | aataaatgta aacttgcaga cgaagcgggg gaaatgaggg | 1200 |
| cagacctggt | gaagacggcg | acaagctcat tggggtgggc agagagtgag tcgccaatgc | 1260 |
| gctccctgac | gctgtggagg | cggctcagga cacggtcacc tgcaccttcc cccattgctg | 1320 |
| tcctcttcct | ggatcctcag | gcctgcacag cgaaaccgaa acggaagcgg aagcttcagt | 1380 |
| cagcagagaa | aactgaaacc | gaaaaacggt tcagatccgt tgacataaaa gctgcgatga | 1440 |
| catcctaaaa | ctaaaccccc | tccagcaaga cataaaccca actgccaaca accagtcttt | 1500 |
| taagtctcga | cacacccttg | acgctgcgcc acgaaactat attgcaggca agaaaccaac | 1560 |
| agaacctaac | tctggaaggg | gggaaagaaa cggcagacag gagcaagacc caaaaaaaaa | 1620 |
| cgactcagat | cctggtacta | tagtcctagt acctagacca gaaagaagaa acaaccaata | 1680 |
| caacaagagg | catacaagaa | ctgaatcgat gaactgaaac gcttcagagg accgaggaat | 1740 |
| ggcggagaag | ggaggcgcct | atttatacag atctgacgag agaaccgaac aaaaacacat | 1800 |
| cgatgggaac | catggagaag | aaaagggctg gccgcatggc accaatggcc tcggcctcca | 1860 |
| aaaagccgtt | gaatccaaag | caggcgagga cgaagcgtga cgcggcaggg tacttctcta | 1920 |
| gaaaagcacg | gcatcagcaa | ggtgggggg ctggggttcc ttattgcagg caatcacgag | 1980 |
| gtgattagca | caaacggaag | | 2000 |

<210> SEQ ID NO 68
<211> LENGTH: 2000
<212> TYPE: DNA
<213> ORGANISM: Oryza sativa

<400> SEQUENCE: 68

| | | | |
|---|---|---|---|
| ctgaaatata | catcagagat | attacaatga catatatatc gataaaagaa aaataataaa | 60 |
| attaagtttt | aaattttaag | aatatatgtt tttagtatcc caattatgca gatttctatac | 120 |
| ccttcttcca | caagctgttc | cttgaactgc aagtactcgg ggactgtcag caactcaaca | 180 |
| gcgagctcgc | tcacattgac | cctcacatac tcccagacac cgggcctcgg gcggatggca | 240 |
| agggcaaccc | atggggagat | aacaatcccc tcctgcatga taaaaaacaa ttacaagtta | 300 |
| agttagagca | agcggtagag | taaagatgga tctctgtgat gcaatgaaat ctgaatctga | 360 |
| ttcaaacctg | tgcactcctc | aggacatcct caaaagcacc gtccttcagc ttctcacgat | 420 |
| cagcctcaga | gattgcgttg | ttgtactcag caatgatctg gtgggcctga agcattccct | 480 |
| ttccgaggtt | aaccagcctg | cgcaaataac agtgtcaaca aaaatatcag gccagatcta | 540 |
| tcaactcagc | ctataaatat | ctcaataaga taattttagc acttgagcat ttgcgcataa | 600 |

```
taagaaaatt tgctattagc cacttaaaaa gaccatatat gatctgtttg cattgagatg      660
aattaaaaat ttcattgtag atatgaaatg attagttttg accatttaat tggacttaat      720
gaaatatgcg cgataatcag atctacgcgc tcgcgccaat agatctagta agatgtaggt      780
tttttatttt ttttgtgaaa ctttgctacc acaacaagca tctgtaccag tgcagaattc      840
attacttgta ttcagtttgt aaaccgtata tataatataa ataacatgca catgcagtca      900
gatctagcac taccagtcca cagtaatcca aaactacatt tgtatatttc atcattattc      960
agtagtacta ggtttgtaca aaatcttggc tgcagaaggc cgcacttaaa tattcattct     1020
aatcagaaac ttaaaaaaaa agtgactaca aaatgattgc atccaattca gtaaatatga     1080
gccattcctg gccagatcta acaatctcaa caacaaagat cctatatgaa catctccttc     1140
taaaagaaaa tacagtaaca tctgaaggca gtagactaga aaccaacaaa atctaatgct     1200
gggaaatcac taaatcagca cgaacctggt gaagacggcg acgagctcat tggggtgggc     1260
ggagagggag tcgccgatgc gctccctgac gctgtggagg cggctcagga cgcggtcgcc     1320
ggcagcttcc cccattgctc tcctcttcct cttggctcct caagcctgcg tgcacaacca     1380
accaccatca tcagatacat ccagacccag tcaacacaat cactccagga aaaaaaaaag     1440
tcaagccata acccccaacc aaaaaccacg cctttgacaa acactggaag aaaaagaaaa     1500
tcgcagcttt ttcacaagca atctagaaga aagaaaaag aaaagactac atagcagcta     1560
taattgactg agaagcatac aggaatcaaa caatggagaa gggagggag gaagaacaat     1620 gatgctccag gctgaggacc gaggaactgg gtgaagcggg gtaggcgcgt atttatgcag     1680
atctgaggag agaaaccacc aaaacaatcc gatggtttca acgaaaaaga tcgtcgcttc     1740
ttgctgcacc agctcaccca tagccgttga gatcgaagct aagctagcag cagcaaagct     1800
ggaacgaaga gtgacgcatt caagctcctc tcctctcctc tcctctcctc cggagcacga     1860
ggccagcatg ggatggattg gggtttcttg ttggccatgg caaggagga ggtcattaac     1920 gttgacacgg cgtaatttaa ttaaatctta tcttaaaata tgatttaagt ggtagtaaca     1980
aggaagatta atactatgaa                                                 2000
```

<210> SEQ ID NO 69
<211> LENGTH: 2000
<212> TYPE: DNA
<213> ORGANISM: Oryza sativa

<400> SEQUENCE: 69

```
gctgtttaag aaaaacagaa gtaaaattca gtcactgtta ttttgcttca gttataatct      60
gcaaatcgtc gttctggtac ttactgtcca tcaacaagct gttccttgaa tgccaagtac     120
tcagaaacac tcagctcttc cactgccaac tcacttacat tcacccgaat gtagtcccag     180
acaccaggcc ttggcctgat ggccagtgca acccagggcg gcagcacaat ggcttcctac     240
atacagtcaa ggaagtaagt tagaaagact ggtatttgac tttgagttga ctatcataac     300
catcctggct cattgccaaa tttacctgag cagcccggag aatgtcttca aagggagcat     360
atttctcttt gtcagcttcg atcaaggcat cgaactccgc aagcagctgg tgacgctgga     420
gcattccctt tccctggtta acatacctgc atagagtgat atttaagaaa tagaaccaat     480
gcttagatct cacatccttt ctgcggctga actatgttaa tggcactacc acataaacct     540
gatttttact tcttattttt aagaccacat gatctgtact taatctagct atgaacaaac     600
aatatttcaa catcatctaa gattcatgac tcaagacaaa aatgttagag ctcatcacag     660
attattatag ataccatcat taaaactaaa gagatgcata accttgtcag ctaagaattt     720
```

```
gtaacatact aacatgttat cgtttcacat ctgggttgac taagaactaa ccaactgtat      780
ggataaaatc attgaaaact caaaacaatt agtagcaggt tccaagaaga cacaagatat      840
tatattgaga tcttcaccta gagaagagtg caatcaactc attgggatga gacgagaagg      900
tggcaccgag gcgttcgcgg agactgtgga ggcgagctag cttggcagcc atgactcaat      960
ttcaggaact gcaagaaag gttacactta gcaacacgta ccaaaaccac tcacttgcac      1020
aagaataatt agtcaacagc catcactaag cattgcaaga ctatctctga acaggaaagc      1080
catgctaaat caacactaat aacatcacac aaaagcattg gaagatcaaa acataactaa      1140
aaacagctgt ttcatctaca caactgaaag catctatggt ttacgaagca gagtgcgagt      1200
actgattcaa aataaatcaa cctgaaccaa tatactctga caatgttttc aaagggataa      1260
aagaaccagc tttatcaaat ggatttgttg ggttttagta agtatcattg agataccgat      1320
ggcatatctc aaactttgca aaattataat ggcatggttc caaattaccc tttagtatta      1380
gcaccagtta gatcctaatt cctaaatccg ataggacaga gcgaaagatc cctggagata      1440
tgaagatttg gctacagatt aagcagagcc aacatgaagt tccgaatatt atgaatccgc      1500
aagcggggag atcaaagaga agaatacgga aggtcgcgac tccatgaaag aatccaacca      1560
aaaacccaaa gatttttctc agttcaaaaa aaaaaaaccc ttcattttttg gttcgccatc     1620 caccgacagg caccaagaca ttcctcagga agcaaaaaag attaagcaga acaagtgata     1680
agcaagacac agtatcaacg gactacgagt cgagaaaatc actgaggcgc gattcttact      1740
gcaccaagta aaaaaaaatt tggggggcaaa aagaactctg caatggggcg gagcaacgtg      1800
gcagcaaaac taaggtcga ggatttgagg ttttttgccg gttttcctcg aaaccccgaa      1860
tccgctcata gtaaacccac taaactgcag cagaaaccccc cctcttggtt cagatttacc      1920
gaaagcagta aacccaagaa catgtcagca aaaactcctg caagattcag ctgacgaccc      1980
accaaagaat cgcaagaaat                                                  2000
```

<210> SEQ ID NO 70
<211> LENGTH: 2000
<212> TYPE: DNA
<213> ORGANISM: Oryza sativa

<400> SEQUENCE: 70

```
tggcggacgc gccacgcaca aacacaaacc tgcacacccc tgtgtcagag gaggagaggc       60
caagaaagga aatcgagtgg aggaagtgag gagcggcgga gacgtaggag gaggagggggg     120 agatggaaat ggaaagccgc gcgagagagg aggcgcgtgc tggatgggag gaggaggagg     180
aggtggtggg tttgtgtttg gagagacgag cgagagaggc gaagcattta agggaggaa      240 gaggggggaga gagagagaga gagagagaga gagagagaga gagagagaaa ggaggaatat    300
aataaagggt ggtgcacctg ccaactgcta tgctcaccaa cactttgtac acacccagtt     360 acaccccccct gcctttatta tttccagtgc agtaataact tcaacaatta ttgaaatgaa    420
aatggaatta atggagttag tatcggatta gcgacacgct tgccgagctt ctagacggtg     480
cgattatttc agcgggaacg actttctgta ggtgaattta atagaggagt gtttaaatc      540 cactcgacgt tgtaatagct ggtttaattc gtttgtactg tcgagtagtt atccaaaatc     600 aatttggat atttaaaga aaaaaaaaca gatccgaagt attggaccta ctggcaaata      660
ggaattttgc tatatatagg tgtgcgttca tttataatgg agtagcatgg agttttatta      720
atccagtaaa tgttttcatt gatttaatta atataacgaa tttcgcttga ggccatattt      780
```

```
gttaaacgct tttatctcta tcatcattca tcctaccagt aaagagcacc ggagatcgca      840
cttcatttaa atatatgtcc atgttggata aaccatagtt tattatagtg ttcttttata      900
tgttttgtgg ggaatttaga ttgtttaata tggcatacat atccatccat cattattata      960
ttctaacaca actggataag tgttctaaac tattgtagaa taactttgta gtatgatcga     1020
tcttgtggaa taaaaaagt ctgacaataa cctttcataa aggaatatga ataccgtaa      1080 tcaacgcatc aaatcattca cggtgtacgc ctagcgaatt cgttggcgag tgctcgtgcg     1140
gccgtgggct cgctgtgatg catgcatggc tctctggcta cgtcgagata gcgattagta     1200
gcaaaattaa gcaagccact tattaattaa tctttggaga tatcatatga ttaaggcatt     1260
aattcgtacg tactcgtcgt cagcgttttc tgcaaagtcc actacagttt tttctttctt     1320
tgctgaaaat gctgatgtgt tggagatgga gtgacgtgca caacctgccg ccacgtggat     1380
ggttgctgga gcctacgtgt catcttaatt tgaacaaaaa aaaagagga ataatacatc      1440 aatacatttt cgaatttcag ttctgccatt gaccagtaat acacatgtcg gcctcacatt     1500
ttaccctgat cttagtaacg ggtggtcgcc tggtcggtca ctgaaaaaag ttcaggaaat     1560
tatagtcaaa ctgaaacgaa catattcact ccttaaaaaa actaaatctt tttatatatt     1620
tgtgatattg taaaatagct acgggataat gatatagata tatatagtga tagggatag      1680 atggatcgag atatggagtt gtgctttctt taatttccac tacttgggct accatattat     1740
ggtagttggt atgaaaagat acacagcagt atagtgatgt gatcaatgac atgtatatct     1800
cacatgctcc catgttggag tcaaattttg ctagactaaa atccaattcc aagcagtccc     1860
tagccaagaa caaacaaaat tcagtgaggt cactgctgca ccaaggactg catgcatgca     1920
ggagaagggc attttctctt ttttcttttg gagactcgat tcaattcggt cggtcggtcg     1980
caatggtcag cttaattaaa                                                 2000

<210> SEQ ID NO 71
<211> LENGTH: 2000
<212> TYPE: DNA
<213> ORGANISM: Oryza sativa

<400> SEQUENCE: 71
tgtgaaaggt ggcggcacca gcttagccgc agcttctctc gtcgtctccc tgaaacgaga       60
gggaggaagt tggtagcgtg atatatttag gcatgtcatc tcttgtataa gaagtcttat      120
ctgtgctaat tcacacggtt ctctaatctc tctccattct gttttttgtaa attggttcag     180 tagatagcgt agggttatgc ttatatatac tccgtgaagt atatatttaa aaattagtca     240
cacgtaaagt actatacatg ttttatcgtc taataacaat aaaaacacta atcataaaat     300 tttttttaaat aatacgaatg gttaaacgtt gaatatgaac cgtgcaaaac tatatttatt    360
ttgtaacaga gaaaatattt cacattaatt agattgttgt tttatggaag gttggagagc     420
tgcgccgccg ttgcgcagac ctaggaggct gcttataagt tataatcaat caattcacgg     480
atgccggctg ggacgcggcc catcgtccgg gaagacgaca actcaacgca aaaagccgat     540
atgcctccaa attgccattg ccacctctac ggctgtttat actgctccaa atcaaaagcg     600
tccatggaag aatctagtat ttcccgcaaa gacgatgatg atatgcagga ttggatatat     660
agggggttgt tgcatgattg ctagaactcc cgtttccgaa gttgttcgtc cattttttaaa    720 gctgccaaat aggaattttat tttgttttca agtgtaatag agttctgtcc agatgagtga    780
attataattt ggttcacatt ttatttgcta agttcagtt tgaacattct caaataactt      840
ttttcttcac tttttaaccg agtaacttag ttattttttc cgtttggacc acccaacaat     900
```

```
ttgttgctaa gtgcatctca cccgtcaaat aattcctttg aatccaaatt caattatatc    960
ccaaaaataa aaaacttctg aattccacat caattcaaac cccaaccatt ttaatttctc   1020
tccatatttt ccatttctct atttttacct ttctcttttt tccatctatt tattttttc    1080 cttttctatt tctttctttc tccttccttt ctctgtttcc ttcttcttct cctcggctag   1140
gcccgagcca gcccgtgccg cctcgcgcca accctgtgcc gccttacgcc gcgcttgcgt   1200
gcgctcgcgc ccacctcgtg cccaacccgc gcacgccaca cgcacacacg aggacgatcg   1260
acggacgaat gcaatcatat cccttcctt actcagctag aaggctcaag aaccgcaact    1320
ttgatctctt ccaccctctc aaatccgccc caaccctgc tgactcaatc gccattaccg    1380
gaggaaaaat ccccgaaacc ctattaccgg cgccactaac agagctccaa aattcgtcgc   1440
ataattcgaa aatattctga aattgaaggt aaaaatggaa tctacatgcg aagtactccc   1500
tttcccctcc aatccgtcac tggaacgccg ccggcgccgc ctcccgctgc cactgccctg   1560
tttggccgcc gacagccgca cggcgcgccg ctgctccagg ccgccctagc ttcaaccacc   1620
gccacctttg gctccgcctc cctcctctta tgctcaccaa gcccgcctcc ctcgccggag   1680
atcgccggaa ccaccgccgc catggccgcc accgcctcct gcttctggcc gccgccgcca   1740
gcctcgccac cggcgcctat gccaccgccg accacggaaa cggagtccct acaccttggg   1800
gaccacaaaa ccggcggcat ccctcccaaa accggcctcc tccaccgccg gcgttcgtgg   1860
gattccggcc agttctgtgc agagcgagag aagaagagga aaaatagatt ttcctattga   1920
aagataaatc agaaaattcc tttttctttt cctatcaagt tgaccatccg tttgacctca   1980
aaatcaaaat ctgagaccta                                              2000

<210> SEQ ID NO 72
<211> LENGTH: 786
<212> TYPE: DNA
<213> ORGANISM: Zea mays

<400> SEQUENCE: 72
gacatggagg tggaaggcct gacgtagata gagaagatgc tcttagcttt cattgtcttt     60
cttttgtagt catctgattt acctctctcg tttatacaac tggtttttta aacactcctt    120
aacttttcaa attgtctctt tctttacccct agactagata attttaatgg tgattttgct   180
aatgtggcgc catgttagat agaggtaaaa tgaactagtt aaaagctcag agtgataaat    240
caggctctca aaaattcata aactgttttt taaatatcca aatattttta catggaaaat    300
aataaaattt agtttagtat taaaaaattc agttgaatat agttttgtct tcaaaaatta    360
tgaaactgat cttaattatt tttccttaaa accgtgctct atctttgatg tctagtttga    420
gacgattata taatttttt tgtgcttaac tacgacgagc tgaagtacgt agaaatacta    480
gtggagtcgt gccgcgtgtg cctgtagcca ctcgtacgct acagcccaag cgctagagcc    540
caagaggccg gaggtggaag gcgtcgcggc actatagcca ctcgccgcaa gagcccaaga    600
gaccggagct ggaaggatga gggtctgggt gttcacgaat tgcctggagg caggaggctc    660
gtcgtccgga gccacaggcg tggagacgtc cgggataagg tgagcagccg ctgcgatagg    720
ggcgcgtgtg aaccccgtcg cgccccacgg atggtataag aataaaggca ttccgcgtgc    780
aggatt                                                              786

<210> SEQ ID NO 73
<211> LENGTH: 1160
<212> TYPE: DNA
```

<213> ORGANISM: Zea mays

<400> SEQUENCE: 73

```
atgtgctggt gccccataag gtaggcacct aggtctgtgt ttgaagcatc gacagatttg      60
taaacatgtt cctatgaacc tatttctgat tgataatttg tcaaaactca tcatttgtct     120
tcatccttgc ctgcttgcgt tcacgtgaca agtacgtgt atgtcttcgg cctttgctgt      180
gtatgtttcg cattgcttag atgtggtgaa agaacatcag aagatgcatt gatgcgtgc      240
ttaaaccagt gatgtgctcc aggtgttcct gcagtctgca gagatattta ctcttgtagt    300
cttgttgaca gcacagttgt atgtgatttc ttggatgtaa tgtaaaccaa atgaaagata    360
ggaacagttc gtcctcttcc gtatacgaag gtcactgtat catttgtcgt ggcacaagat    420
gatctgcagg caggactgca acatggtttc ttggactgtc ctgaatgccc gttcttgttc    480
tttagttgag ccagagcagc agcctggtgt cggtgcctga gacctgacga agcacacggc    540
aaacaaacaa gtcgcagcag ctagcagggg cgttgccatc gccacaagcc cccaagagac    600
ccgccgagga aagaaaaaa aaactacggc cgccgttgcc aagccgagcg tgcgaaccga    660
tccacggatg ggagatcaga gatcacccac cgcaggcggg cggcagtggc tggcgaggtg    720
cgtccacaga acctgctgca ggtccctgtc cgtcccggcg accccttttc taggcgagca    780
actcccatg gcagagctgc acgcagcagg gcccgtcgtt ggttgcagct ttaacccttt     840
ttgtttaac catacaatgc agagtcgcag aggtgaaaca ggacgaaat tacagaaaag      900
atggtggtgt gccagcagcc ccagcatgaa gaagatcagg acaaaagaaa agcttgtgat    960
tggtgacagc aacaggattg gattggagcc aagctaggca gtgagaggca ggcagcaaga   1020
cgcgtcagcc actgaaatcc agagggcaac ctcggcctca caactcatat ccccttgtgc   1080
tgttgcgcgc cgtggttagc caggtgtgct gcaggcctcc tccttgttta tatatgggag   1140
atgctctcac cctctaaggt                                                1160
```

<210> SEQ ID NO 74
<211> LENGTH: 1532
<212> TYPE: DNA
<213> ORGANISM: Oryza sativa

<400> SEQUENCE: 74

```
tagtcctcta atatatgaaa ttttgatata ggtaaagaag ggtattgcaa ggataagaat      60
gtaaaagaa ataagagtaa tccttaccga taatagtatt ccttctctac cgttaaaagt      120
taaacctgtg cgtgtagcat tttaatccag gatctatcga atccgtccct cgttggcgtg    180
ggcgacgaac acgtgcagaa gaagcttcc ccagaaagca cctcaccgcc tcgccgtctg     240
gcagactggc acgcggggcc ctaccctcgc tgcgcctggg cccgtccgcc ttctgcacac    300
tgtcacgccc ccaccgctc gccgcctcgc gcctctctct ccgcctccgc cgcggccgcc    360
cgacgtgata gcgacacgta ggactcgcca aacacaaaaa atccatcgcg atttttggaa    420
ttttgttaca aaccaaatcc cgcattagag atttaatttg atttaattta attacgtagg    480
agtaccagat aaggagatcg agttaaaaaa gctaacggcg cggcgtggtt atctccgaat    540
cggctgtggc tccccgcgtc ggcgtcggcg cggcggcggc gcgccggccg aaccctggcc    600
gtcggatcgg gcgtcgtcct gggccccacg cgccacgggc ggctgtcgtt tgctcctcgg    660
agcggggtgg gccaccatg gccaccacca caggtcgcgg tcgcggctga cctggcggtg    720
gtcccgtgct cgcggtgttt ttttttttc actctctttc tctcggtgga cagtagcggg   780
ggccgcggcc cgcgggggca gagattgcaa aaacagcgga aacggaagat tgcaaaattg   840
```

| | |
|---|---|
| caactgcttt cctgttttta attcgggatc aaaaagattc tttcgtcggg gtccccgtgc | 900 |
| cattgttgta ttgcgcgtag gtccttgctt gtaaaagata atctccttaa tttttctttt | 960 |
| gtactactag tgtatatgca gtaagaatat accatgagta aaatgaacca caaaactaat | 1020 |
| tacgatatac cattctcatg tagacgttct ctttctttt gctagtcata cgtgcatata | 1080 |
| taaccaaaca aaaaatgtt tgaagtactc ctatccaatt tattactcca gtagacaaca | 1140 |
| aaagaaaatg tttgaagtaa taactgatcc atggtacagt agggttgtcg tcaatcttgt | 1200 |
| gtttctttca ttccattgta cttacaatcg tactccagct agcacagcac aatgggctta | 1260 |
| agctttggac cccaaattct gatcttgtcg gggacccgta cgaaaatact cccgtagaga | 1320 |
| tgcagatacc gtcacaacct acaaccaacg aatgttaaga aaacaaggg aaaaaaaag | 1380 |
| aggcgaattc ggaggagaaa aaacggtggc taaaatatag tgcgggtgtg gggacgcgac | 1440 |
| gcgagcgacg aaagaggaga gaggatgggt tggcctgccc ccccctcccc tgtctataaa | 1500 |
| tgcagaggcg ccgagtgccc tagtcgccgc tc | 1532 |

<210> SEQ ID NO 75
<211> LENGTH: 841
<212> TYPE: DNA
<213> ORGANISM: Oryza sativa

<400> SEQUENCE: 75

| | |
|---|---|
| tcgaggtcat tcatatgctt gagaagagag tcgggatagt ccaaaataaa acaaaggtaa | 60 |
| gattacctgg tcaaaagtga aaacatcagt taaaggtgg tataaagtaa aatatcggta | 120 |
| ataaaaggtg gcccaaagtg aaatttactc ttttctacta ttataaaaat tgaggatgtt | 180 |
| tttgtcggta ctttgatacg tcattttgt atgaattggt ttttaagttt attcgctttt | 240 |
| ggaaatgcat atctgtattt gagtcgggtt ttaagttcgt ttgcttttgt aaatacagag | 300 |
| ggatttgtat aagaaatatc tttagaaaaa cccatatgct aatttgacat aattttgag | 360 |
| aaaaatatat attcaggcga attctcacaa tgaacaataa taagattaaa atagctttcc | 420 |
| cccgttgcag cgcatgggta ttttttctag taaaaataaa agataaactt agactcaaaa | 480 |
| catttacaaa aacaacccct aaagttccta agcccaaag tgctatccac gatccatagc | 540 |
| aagcccagcc caacccaacc caacccaacc caccccagtc cagccaactg gacaatagtc | 600 |
| tccacacccc cccactatca ccgtgagttg tccgcacgca ccgcacgtct cgcagccaaa | 660 |
| aaaaaaaga aagaaaaaaa agaaaaagaa aaacagcag gtgggtccgg gtcgtggggg | 720 |
| ccggaaacgc gaggaggatc gcgagccagc gacgaggccg gccctccctc cgcttccaaa | 780 |
| gaaacgcccc ccatcgccac tatatacata cccccccctc tcctcccatc cccccaaccc | 840 |
| t | 841 |

<210> SEQ ID NO 76
<211> LENGTH: 1392
<212> TYPE: DNA
<213> ORGANISM: Oryza sativa

<400> SEQUENCE: 76

| | |
|---|---|
| ctcgaggtca ttcatatgct tgagaagaga gtcgggatag tccaaaataa aacaaaggta | 60 |
| agattacctg gtcaaaagtg aaaacatcag ttaaaggtg gtataagtaa aatatcggta | 120 |
| ataaaaggtg gcccaaagtg aaatttactc ttttctacta ttataaaaat tgaggatgtt | 180 |
| ttgtcggtac tttgatacgt cattttgta tgaattggtt tttaagttta ttcgcgattt | 240 |

| tggaaatgca tatctgtatt tgagtcgggt tttaagttcg tttgcttttg taaatacaga | 300 |
| ggggatttgta taagaaatat ctttaaaaaa acccatatgc taatttgaca taattttttga | 360 |
| gaaaaatata tattcaggcg aattctcaca atgaacaata ataagattaa aatagcttgc | 420 |
| ccccgttgca gcgatgggta ttttttctag taaaataaaa gataaactta gactcaaaac | 480 |
| atttacaaaa acaacccta aagtcctaaa gcccaaagtg ctatgcacga tccatagcaa | 540 |
| gcccagccca acccaaccca acccaaccca ccccagtgca gccaactggc aaatagtctc | 600 |
| cacaccccgg cactatcacc gtgagttgtc cgcaccaccg cacgtctcgc agccaaaaaa | 660 |
| aaaaaagaa agaaaaaaaa gaaaagaaa aacagcagg tgggtccggg tcgtgggggc | 720 |
| cggaaaagcg aggaggatcg cgagcagcga cgaggccggc cctccctccg cttccaaaga | 780 |
| aacgcccccc atcgccacta tatacatacc ccccctctc ctcccatccc ccaaccccta | 840 |
| ccaccaccac caccaccacc tcctccccc tcgctgccgg acgacgagct cctcccccct | 900 |
| cccctccgc cgccgccggt aaccacccg cgtccctct ctctttcttt ctccgttttt | 960 |
| ttttccgtc tcgtctcgat ctttggcctt ggtagtttgg gggcgagagg cggcttcgtc | 1020 |
| gcccagatcg gtgcgcggga ggggcgggat ctcgcggctg gtctcggcg tgcggccgga | 1080 |
| tcctcgcggg gaatggggct ctcggatgta gatctgatcc gccgttgttg ggggagatga | 1140 |
| tggggcgttt aaaatttcgc catgctaaac aagatcagga agaggggaaa agggcactat | 1200 |
| ggtttatatt tttatatatt tctgctgctg ctcgtcaggc ttagatgtgc tagatctttc | 1260 |
| ttcttcttt tgtgggtag aatttgaatc cctcagcatt gttcatcggt agttttttctt | 1320 |
| ttcatgattt gtgacaaatg cagcctcgtg cggagcttt ttgtaggtag aagatggctg | 1380 |
| acgccgagga ta | 1392 |

<210> SEQ ID NO 77
<211> LENGTH: 743
<212> TYPE: DNA
<213> ORGANISM: Oryza sativa

<400> SEQUENCE: 77

| gaattcccgg acctccatgc ctacatcaac taatttgatt ccttgagttt acgtttagtg | 60 |
| atatgtctat ttttagagct tgttggggct tcggcctcag ctctagccag ccaaacatgt | 120 |
| tctaccaagt accctatgtt ggcatgatat agtgatgcat tataacaata aatgagcgag | 180 |
| ggattgctgg ctgaaaaagc tatactagct gcatttggtt atagttaacc gaactattaa | 240 |
| ttgcgtgtac aacaaaataa aaaaaatgca tgttgcacat tctttcatta acattatgtt | 300 |
| ttggtagtgt gaattagaaa tttgattgac agtagatcga caaacatagt ttcaatatgc | 360 |
| ttaagttagt tatgacttta acatatcagt tccttgata ttttcgtttt agattcgtct | 420 |
| ctctactagt gtgtatgtcc accttccata gcagtgaagg gttccattcc atccctggta | 480 |
| aaaaaaatc aaccactact atttatttcc taaaaagcaa aatgataaaa tatcattttt | 540 |
| ttaataaaaa taaaaaatt tgggggtaca taattgatgt tgccccttgg gattaacctt | 600 |
| aaaaaagggc gaattttcta gggtttggcc aagttttgca atgcaccaaa ttattcccct | 660 |
| tgggccggcc gccaccccaa aaaaaacccc aaccccaac tttccattga aggccgggcc | 720 |
| cccttaaatc ctcatccccc caa | 743 |

<210> SEQ ID NO 78
<211> LENGTH: 144
<212> TYPE: DNA
<213> ORGANISM: Oryza sativa

<400> SEQUENCE: 78

```
taaaaaaggg cgaattttct agggtttggc caagttttgc aatgcaccaa attattcccc      60
ttgggccggc cgccacccca aaaaaaaccc caaccccaa ctttccattg aaggccgggc      120
cccctttaaat cctcatcccc ccaa                                           144
```

<210> SEQ ID NO 79
<211> LENGTH: 612
<212> TYPE: DNA
<213> ORGANISM: Cauliflower mosaic virus

<400> SEQUENCE: 79

```
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg aaaaagaag acgttccaac cacgtcttca     240
aagcaagtgg attgatgtga tggtccgatt gagacttttc aacaaagggt aatatccgga     300
aacctcctcg gattccattg cccagctatc tgtcactttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaaagaa     480
gacgttccaa ccacgtcttc aaagcaagtg gattgatgtg atatctccac tgacgtaagg     540
gatgacgcac aatcccacta tccttcgcaa gacccttcct ctatataagg aagttcattt     600
catttggaga gg                                                         612
```

<210> SEQ ID NO 80
<211> LENGTH: 837
<212> TYPE: DNA
<213> ORGANISM: Coix lacryma-jobi

<400> SEQUENCE: 80

```
agcagactcg cattatcgat ggagctctac caaactggcc ctaggcatta acctaccatg      60
gatcacatcg taaaaaaaaa accctaccat ggatcctatc tgttttctttt ttgccctgaa     120
agagtgaagt catcatcata tttaccatgg cgcgcgtagg agcgcttcgt cgaagaccca     180
taggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactctttc ttcttaataa caatcatacg caaatttttt gcgtattcga     360
gaaaaaaga agattctatc tgtttttttt ttgaaatggc tccaatttat aggaggagcc     420
cgtttaacgg cgtcgacaaa tctaacggac accaaccagc gaatgagcga acccaccagc     480
gccaagctag ccaagcgaag cagacggccg agacgctgac acccttgcct tggcgcggca     540
tctccgtcgc tggctcgctg gctctggccc cttcgcgaga gttccggtcc acctccacct     600
gtgtcggttt ccaactccgt tccgccttcg cgtgggactt gttccgttca tccgttggcg     660
gcatccggaa attgcgtggc gtagagcacg gggccctcct ctcacacggc acggaaccgt     720
cacgagctca cggcaccggc agcacggcgg ggattccttc cccaccaccg ctccttccct     780
ttcccttcct cgcccgccat cataaatagc caccccctccc agcttccttc gccacat      837
```

<210> SEQ ID NO 81
<211> LENGTH: 947
<212> TYPE: DNA

<213> ORGANISM: Oryza sativa

<400> SEQUENCE: 81

```
aatccgaaaa gtttctgcac cgttttcacg tcctaactaa caatataggg aacgtgtgct      60
aaatataaaa tgagacctta tatatgtagc gctgataact agaactatgt aagaaaaact     120
catccaccta ctttagtggc aatcgggcta ataaaaaag agtcgctaca ctagtttcgt      180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagat attttttttt aaaaaaaaat     360
agaatgaaga tattctgaac gtatcggcaa agatttaaac atataattat ataatttat      420
agtttgtgca ttcgttatat cgcacgtcat taaggacatg tcttactcca tctcaatttt     480
tatttagtaa ttaaagacaa ttgacttatt tttattattt atcttttttc gattagatgc     540
aaggtactta cgcacacact ttgtgctcat gtgcatgtgt gagtgcacct cctcaataca     600
cgttcaacta gcgacacatc tccaatatca ctcgcctatt taatacattt aggtagcaat     660
atctgaattc aagcactcca ccatcaccag accacttta ataatatcta aaatacaaaa      720
aataatttta cagaatagca tgaaagtat gaaacgaact atttaggttt ttcacataca      780
aaaaaaaaa gaattttgct cgtgcgcgag cgccaatctc ccatattggg cacacaggca      840
acaacagagt ggctgcccac agaacaaccc acaaaaaacg atgatctaac ggaggacagc     900
aagtccgcaa caaccttta acagcaggct ttgcggccag gagagag                    947
```

<210> SEQ ID NO 82
<211> LENGTH: 721
<212> TYPE: DNA
<213> ORGANISM: Mirabilis mosaic caulimovirus

<400> SEQUENCE: 82

```
tggagattca gaaaatctc catcaacaaa taatccaagt aaggattaat ggattgatca      60
acatccttac cgctatgggt aagattgatg aaaagtcaaa aacaaaaatc aattatgcac     120
accagcatgt gttgatcacc agctattgtg gacaccaat ttcgtccaca gacatcaaca      180
tcttatcgtc ctttgaagat aagataataa tgttgaagat aagagtggga gccaccacta     240
aaacattgct ttgtcaaaag ctaaaaaaga tgatgcccga cagccacttg tgtgaagcat     300
gtgaagccgg tccctccact aagaaaatta gtgaagcatc ttccagtggt ccctccactc     360
acagctcaat cagtgagcaa caggacgaag gaaatgacgt aagccatgac gtctaatccc     420
acaagaattt ccttatataa ggaacacaaa tcagaaggaa gagatcaatc gaaatcaaaa     480
tcggaatcga atcaaaatc ggaatcgaaa tctctcatct ctctctacct tctctctaaa      540
aaacacttag atgtgtgagt aatcacccac ttggggttgt aatatgtagt agtaaataag     600
ggaaccttag ggtataccat tgttgtaata ttattttcag tatcaataaa ataatctttc     660
agtttatctt atattcattt gtgtgacacc gtattcccat aaaaccgatc ctaatctctc     720
c                                                                     721
```

<210> SEQ ID NO 83
<211> LENGTH: 352
<212> TYPE: DNA
<213> ORGANISM: Peanut chlorotic streak caulimovirus

<400> SEQUENCE: 83

```
acagagggat ttctctgaag atcatgtttg ccagctatgc gaacaatcat cgggagatct      60
```

```
tgagccaatc aaagaggagt gatgtagacc taaagcaata atggagccat gacgtaaggg      120
cttacgccat tacgaaataa ttaaaggctg atgtgacctg tcggtctctc agaaccttta      180 cttttatat ttggcgtgta tttttaaatt tccacggcaa tgacgatgtg acctgtgcat      240
ccgctttgcc tataaataag ttttagtttg tattgatcga cacgatcgag aagacacggc      300
catttggacg atcatttgag agtctaaaag aacgagtctt gtaatatgtt tt             352
```

<210> SEQ ID NO 84
<211> LENGTH: 1648
<212> TYPE: DNA
<213> ORGANISM: Sorghum bicolor

<400> SEQUENCE: 84

```
cactcgcaca tctcatggtg tcccaagaac ggcaagagcc agcactgcct ctgcctagca      60
acagcagcag cgccaagcga gcagccgcgt ccatggacgc cagcagcccg gccccgccgc     120
tcctcctccg cgcccccact cccagtccca gcattgacct ccccgctgcc gctggcaagg     180
ccgcggccgt gttcgacctg cggcgggagc ccaagatccc ggcgccattc ctgtggccgc     240
acgaggaggc gcgcccgacc tcggccgcgg agctggaggt tccggtggtg gacgtgggcg     300
tgctgcgcaa tggcgaccgc gcggggctgc ggcgcgccgc ggcgcaggtg gcctcggcgt     360
gcgcgacgca cgggttcttc caggtgtgcg ggcacgcgt ggacgcggcc ctggggcgcg     420
ccgcgctgga cggcgccagc gacttcttcc ggctgccgct ggccgacaag cagcgcgccc     480
ggcgcgtccc cggcaccgtg tccgggtaca cgagcgcgca cgccgaccgg ttcgcgtcca     540
agctcccctg gaaggagacc ctgtccttcg gcttccacga cggcgccgcg tcgcccgtcg     600
tcgtggacta cttcaccggc accctcggcc aagatttcga gccaatgggg cgggtgtacc     660
agaggtactg cgagaagatg aaggagctgt cgctgacgat catggagctg ctggagctga     720
gcctgggcgt ggagcgcggc tactaccggg agttcttcga ggacagccgc tccatcatgc     780
ggtgcaacta ctacccgccg tgcccggagc cggagcgcac gctgggcacg ggcccgcact     840
gcgaccctac ggcgctgacc atcctcctgc aggacgacgt cggcgggctg gaggtgctgg     900
tggacggcga gtggcgcccc gtccggcccg tcccaggcgc catggtcatc aacatcggcg     960
acaccttcat ggcgctgtcg aacgggcggt acaagagctg cctgcaccgc gcggtggtga    1020
accagcggca ggacggcggt cgctggcct tcttcctgtg cccgcgcgag accgggtgg    1080 tgcggccgcc ggccagcagc gccacgccgc ggcagtaccc ggacttcacc tgggccgacc    1140
tcatgcgctt cacgcagcgc cactaccgcg ccgacacccg cacgctggac gccttcaccc    1200
gctggctctc ccacggccca gtccagcccc aggaggcggc ggctccctgc acctagcgag    1260
cgagcgagcg gggccaaaca aacaaggggc aaaggccatc tctttcgccg gggccccgcg    1320
gcggggttcg cccacgtgcg cgcccaggtg ggcgctggcc gcgggcaggt ggcggacatg    1380
tggcctgcgg ccccgcgcc gccttcccat ttttggacgc tgccgcgcat gccgcatgcg    1440
tgcgtcgacg gccctactac ttctactact gctactgcga ctactagtgt acatacgcaa    1500
aaatacatat atacgtattt tctatatata tatatataag caaggcggcc ccccggtgac    1560
cttttctttg tttttgtcga caactgtgtt ttgatcccat tctagctgtt ctatggacca    1620
tggatggttc gttcaatgtt tgtacgta                                        1648
```

<210> SEQ ID NO 85
<211> LENGTH: 1242
<212> TYPE: DNA

<213> ORGANISM: Sorghum bicolor

<400> SEQUENCE: 85

```
atggtgtccc aagaacggca agagccagca ctgcctctgc ctagcaacag cagcagcgcc      60
aagcgagcag ccgcgtccat ggacgccagc agcccggccc cgccgctcct cctccgcgcc     120
cccactccca gtcccagcat tgacctcccc gctgccgctg gcaaggccgc ggccgtgttc     180
gacctgcggc gggagcccaa gatcccggcg ccattcctgt ggccgcacga ggaggcgcgc     240
ccgacctcgg ccgcggagct ggaggttccg gtggtggacg tgggcgtgct gcgcaatggc     300
gaccgcgcgg ggctgcggcg cgccgcggcg caggtggcct cggcgtgcgc gacgcacggg     360
ttcttccagg tgtgcgggca cggcgtggac gcggccctgg ggcgcgccgc gctggacggc     420
gccagcgact tcttccggct gccgctggcc gacaagcagc gcgcccggcg cgtccccggc     480
accgtgtccg ggtacacgag cgcgcacgcc gaccggttcg cgtccaagct ccccctggaag    540
gagaccctgt ccttcggctt ccacgacggc gccgcgtcgc ccgtcgtcgt ggactacttc     600
accggcaccc tcggccaaga tttcgagcca atggggcggg tgtaccagag gtactgcgag     660
aagatgaagg agctgtcgct gacgatcatg gagctgctgg agctgagcct gggcgtggag     720
cgcggctact accgggagtt cttcgaggac agccgctcca tcatgcggtg caactactac     780
ccgccgtgcc ggagccggga gcgcacgctg ggcacgggcc gcactgcga ccctacggcg      840
ctgaccatcc tcctgcagga cgacgtcggc gggctgagg tgctggtgga cggcgagtgg      900
cgccccgtcc ggcccgtccc aggcgccatg gtcatcaaca tcggcgacac cttcatggcg    960
ctgtcgaacg gcggtacaa gagctgcctg caccgcgcgg tggtgaacca gcggcaggag    1020
cggcggtcgc tggccttctt cctgtgcccg cgcgaggacc gggtggtgcg gccgccggcc    1080
agcagcgcca cgccgcggca gtacccggac ttcacctggg ccgacctcat gcgcttcacg    1140
cagcgccact accgcgccga cacccgcacg ctggacgcct tcaccgctg gctctcccac     1200
ggcccagtcc cagcccagga ggcggcggct ccctgcacct ag                        1242
```

<210> SEQ ID NO 86
<211> LENGTH: 413
<212> TYPE: PRT
<213> ORGANISM: Sorghum bicolor

<400> SEQUENCE: 86

```
Met Val Ser Gln Glu Arg Gln Glu Pro Ala Leu Pro Leu Pro Ser Asn
1               5                   10                  15

Ser Ser Ser Ala Lys Arg Ala Ala Ser Met Asp Ala Ser Ser Pro
            20                  25                  30

Ala Pro Pro Leu Leu Leu Arg Ala Pro Thr Pro Ser Pro Ser Ile Asp
        35                  40                  45

Leu Pro Ala Ala Ala Gly Lys Ala Ala Val Phe Asp Leu Arg Arg
    50                  55                  60

Glu Pro Lys Ile Pro Ala Pro Phe Leu Trp Pro His Glu Glu Ala Arg
65                  70                  75                  80

Pro Thr Ser Ala Ala Glu Leu Glu Val Pro Val Val Asp Val Gly Val
                85                  90                  95

Leu Arg Asn Gly Asp Arg Ala Gly Leu Arg Arg Ala Ala Gln Val
            100                 105                 110

Ala Ser Ala Cys Ala Thr His Gly Phe Phe Gln Val Cys Gly His Gly
        115                 120                 125

Val Asp Ala Ala Leu Gly Arg Ala Ala Leu Asp Gly Ala Ser Asp Phe
```

```
                130                 135                 140
Phe Arg Leu Pro Leu Ala Asp Lys Gln Arg Ala Arg Val Pro Gly
145                 150                 155                 160

Thr Val Ser Gly Tyr Thr Ser Ala His Ala Asp Arg Phe Ala Ser Lys
                165                 170                 175

Leu Pro Trp Lys Glu Thr Leu Ser Phe Gly Phe His Asp Gly Ala Ala
                180                 185                 190

Ser Pro Val Val Val Asp Tyr Phe Thr Gly Thr Leu Gly Gln Asp Phe
                195                 200                 205

Glu Pro Met Gly Arg Val Tyr Gln Arg Tyr Cys Glu Lys Met Lys Glu
                210                 215                 220

Leu Ser Leu Thr Ile Met Glu Leu Leu Glu Leu Ser Leu Gly Val Glu
225                 230                 235                 240

Arg Gly Tyr Tyr Arg Glu Phe Phe Glu Asp Ser Arg Ser Ile Met Arg
                245                 250                 255

Cys Asn Tyr Tyr Pro Pro Cys Pro Glu Pro Glu Arg Thr Leu Gly Thr
                260                 265                 270

Gly Pro His Cys Asp Pro Thr Ala Leu Thr Ile Leu Leu Gln Asp Asp
                275                 280                 285

Val Gly Gly Leu Glu Val Leu Val Asp Gly Glu Trp Arg Pro Val Arg
                290                 295                 300

Pro Val Pro Gly Ala Met Val Ile Asn Ile Gly Asp Thr Phe Met Ala
305                 310                 315                 320

Leu Ser Asn Gly Arg Tyr Lys Ser Cys Leu His Arg Ala Val Val Asn
                325                 330                 335

Gln Arg Gln Glu Arg Ser Leu Ala Phe Phe Leu Cys Pro Arg Glu
                340                 345                 350

Asp Arg Val Val Arg Pro Ala Ser Ser Ala Thr Pro Arg Gln Tyr
                355                 360                 365

Pro Asp Phe Thr Trp Ala Asp Leu Met Arg Phe Thr Gln Arg His Tyr
                370                 375                 380

Arg Ala Asp Thr Arg Thr Leu Asp Ala Phe Thr Arg Trp Leu Ser His
385                 390                 395                 400

Gly Pro Val Pro Ala Gln Glu Ala Ala Ala Pro Cys Thr
                405                 410

<210> SEQ ID NO 87
<211> LENGTH: 12906
<212> TYPE: DNA
<213> ORGANISM: Sorghum bicolor

<400> SEQUENCE: 87
cactcgcaca tctcatggtg tcccaagaac ggcaagagcc agcactgcct ctgcctagca      60
acagcagcag cgccaagcga gcagccgcgt ccatggacgc cagcagcccg gccccgccgc     120
tcctcctccg cgccccccact cccagtccca gcattgacct ccccgctgcc gctggcaagg     180
ccgcggccgt gttcgacctg cggcgggagc ccaagatccc ggcgccattc ctgtggccgc     240
acgaggaggc gcgcccgacc tcggccgcgg agctggaggt tccggtggtg gacgtgggcg     300
tgctgcgcaa tggcgaccgc gcgggggctgc ggcgcgccgc ggcgcaggtg gcctcggcgt     360
gcgcgacgca cgggttcttc caggtgtgcg ggcacggcgt ggacgcggcc ctggggcgcg     420
ccgcgctgga cggcgccagc gacttcttcc ggctgccgct ggccgacaag cagcgcgccc     480
ggcgcgtccc cggcaccgtg tccgggtaca cgagcgcgca cgccgaccgg ttcgcgtcca     540
```

```
agctcccctg gaaggagacc ctgtccttcg gcttccacga cggcgccgcg tcgcccgtcg   600
tcgtggacta cttcaccggc accctcggcc aagatttcga gccaatgggg taagcgaagc   660
accgatttac atttaccgcg cgtcggcccc tgaggcctgg gtcttagtct tagcactgca   720
tatacggtcg gtagctctgg atatgatacg tatatatgaa accccgttcc aatcccatgc   780
acggtgtaca caggcgggtg taccagaggt actgcgagaa gatgaaggag ctgtcgctga   840
cgatcatgga gctgctggag ctgagcctgg gcgtggagcg cggctactac cgggagttct   900
tcgaggacag ccgctccatc atgcggtgca actactaccc gccgtgcccg gagccggagc   960
gcacgctggg cacgggcccg cactgcgacc ctacggcgct gaccatcctc ctgcaggacg  1020
acgtcggcgg gctggaggtg ctggtggacg gcgagtggcg ccccgtccgg cccgtcccag  1080
gcgccatggt catcaacatc ggcgacacct tcatggtaac ccctgctctg tttttcttg   1140
tcctcctctt gtcctgtgtg tgtgtatatt cacttctctc tgttttttg ccccgaatcc   1200
tagtggacct aactgacgg attacagcac gcacacgtag gcatgtcatg tagcagcagt   1260
ctgcagcact gtagtactta gcgatgcaat agagacatgc gttccagtcg gttccatctc   1320
ggtgggctac agctacagtc ctacacggac gcggctcgta gtcgtaggga cgggcgcgtt   1380
ctctgtatcc acacacggct gcgcccaggc cgaggcttcc gccgcgggaa agttgcgaca  1440
acagaacggg gtttgtgccg ttggagcgtt gcggagaggc agaggcttgg ggggacgggg   1500
gcgcgatacg ctgcgatggg tgggtgaccg aggcgacgct ttcggcgggg gcccgggcct  1560
gcccaggtgc gcgcggcctc gtcgccttcc cctgtttttt tgatgccgcc gctcggtcct  1620
cggtgttctg gctccgcccg cccgctcgct gggtgcccat cccatctgat ccgatccgct  1680
ccgctccgcg gtggcggtcc tatgcgatgc cgccgcacga gcgcgggggg ccgcccgtgg  1740
aggagtagaa agtggtacaa ggttggttgg aacttggaat tgtgggggt tactgctgct   1800
ggtggctgct gctttgcaac ttgccaggct gctgcctgtt gcccccgcg ttttctagcc    1860
gtttccgctc gcgatccggc acgcggcgcc cacaccgggg ctccagctcg gcccttggc    1920
cgtgtaggta gcaggcactt gcatctgtcc gttcgacacg atgattcttg tgcactgtgt   1980
acgtatgtac taacccttc tggtatgatg tacgcatggc atgcaggcgc tgtcgaacgg    2040
gcggtacaag agctgcctgc accgcgcggt ggtgaaccag cggcaggagc ggcggtcgct   2100
ggccttcttc ctgtgcccgc gcgaggaccg ggtggtgcgg ccgccggcca gcagcgccac   2160
gccgcggcag tacccggact tcacctgggc cgacctcatg cgcttcacgc agcgccacta   2220
ccgcgccgac acccgcacgc tggacgccct cacccgctgg ctctcccacg gcccagtccc   2280
agcccaggag gcggcggctc cctgcaccta gcgagcgagc gagccgggcc aaacaaacaa   2340
ggggcaaagg ccatctcttt cgccggggcc cgcgcgcggg gttcgcccac gtgcgcgccc   2400
aggtgggcgc tggccgcggg caggtggcgg acatgtggcc tgcgggcccc gcgccgcctt   2460
cccattttg gacgctgccg cgcatgccgc atgcgtgcgt cgacggccct actacttcta    2520
ctactgctac tgcgactact agtgtacata cgcaaaaata catatatacg tattttctat   2580
atatatatat ataagcaagg cggccccccg gtgacctttt ctttgttttt gtcgacaact   2640
gtgttttgat cccattctag ctgttctatg gaccatggat ggttcgttca atgtttgtac   2700
gtactccacg taaccaaact actctagtgg actagtagat cgggctcatg tgatgaaact   2760
ggaccgacgg ggacgtcacg tgcgtcaccc gcgtctggta gcggtagcgc acgagcgccg   2820
aatgtttcct gggcccgcaa gagaatcgct tctcatctcc tctcaccatg aatgggaaa    2880
aatgctgcgt cgaaagttcc agacgtttcc aaattccaaa cggttttgtg gcgtccgatc   2940
```

```
catggggcgc cccaaacttc aagacgttt tcaggttcca aatcttcgtg ctccacatca   3000
ccttcttccc agattcattt gcctcgtcgc ttgctctcct gtgttattca cgggtcccac   3060
tgttgccccg tctgcgagaa agaaatttat tagagttgaa gcattcgaca tttcgactga   3120
ctgattgtta gtatcactaa attttgtgca catgtttctt tggtcattca tctctggata   3180 tttttttag ataatggata taaatatcgg gcctctacat ctgaggaagt acacagccaa   3240
ttattttcat ctctggacat gggacgatgg aagaggcaga tagatttagg agacccttca   3300
attcagaatt tcaggtgcac aaggcctgcc tggcttgccc ggattcttgt ttcggacatg   3360
accaactagg ccgcactact tgcactgata gctggagaaa aaacaaaact ttgcaaacag   3420
caggattatc tacaagggaa actccatcca cgtgaaccag catttcaggg agagatgcga   3480
caaaaaaaaa gaggcggcaa caaaaaaatc ttactgcaat tttatctctg cattgaacct   3540
cttccaacca tgccgcatcc tgtactgttt tgtatctttc ccggtggtcc gttgcgttct   3600
cacgcagttg ataacatgca gtcacgcacc accgaatcca gtgtactagg ggtagtgact   3660
tgtcacgcgg aacaacaggt cggtagcacc aagcaagtcg ctgtagactt gggcgtttaa   3720
caacgacttg cacaacagtt caaatatagc atatgcaatt atgcacaaga ttgttcgact   3780
gctatccgac aaactgaaga agctgcccaa ttgaacagaa tgtaccagtg atttccagca   3840
cactatctta cagcagcgtt gagaatgaaa caacaaatgg gggaaaacag atgtgtatta   3900
ttctacagtt acaccaaaga gtttgtcctt tcagcatcaa caagaatcat atgcatatct   3960
agtgacaaaa attcctctaa ttttacccta cttggtaaca gttctcttca acacatatat   4020
ttcacgtgct tgcatcgagt tccttgggcc gccacatcga cttctcgacg caaagcaagc   4080
cctcgttgcc cttggtgtag gtcattcgca cctcccactg cagggacttg gccatgcttt   4140
ccagttcgtt tattgtgtcc gcagtgtccc tcacaatcag tttgccttgg ggcctcagta   4200
cacgatcaac ctcggcaaaa actgccatca atttgcatct gtaaacaagc aacacagatt   4260
tagcatctgt aaacaccaca ggtttcattg caagaagcat aaagcatgca acatgctac    4320 ttgtacatgt caagaaaaca tgtcaaactc aaacacatga aaatcattat tattgttttc   4380
ttgctgaact gatcacatta gttggtttca atttctgagt tccactagta atctatacca   4440
gaaggataga ataatgtcaa gaacaagaga tacaaacctc tttgtgagct ttgagaatag   4500
atggtccgcg tgcagaaggt cataagttct tgggtaagtg ctcaaagact cgcaccagtc   4560
atggtacata ccaaacaaac cacgctcgta aatgatgggc agtgtgtctg gtgaatcaat   4620
cggcacaata ttcatgaccc agaccttttg gtccctcaga gctgcagcaa aactgccatg   4680
caacgatgta aagcattagt aaaaatattg ggttttttaa accaaaacca agaaagataa   4740
ttcctccagc ttaactgaaa gaaagaaaga aaaaactgc ttaatgactt atggtggaca    4800
agttgcctgt tatgttttat gatagctatg tgccagcttg gctaactggt agttatgtag   4860
tgtgatctga attaccaaaa aagagaagaa aaaaaatca tgcccaagaa actgagaaag   4920
acacccattt acttaccctc catacacagc tctcatgtcc attacatttc tcactttgga   4980
ccagtcaatt cccatgccat tcacatacga tttacttaca acccttttcc agtgagcatt   5040
atctgcctcg aaatcttcat ttgcaggctt tccatagacc caaccttgg aaccatcaat    5100 ccagaaagga gtcttctcaa gcctttgtgg ccaaaactct ggccattttg accctcgaac   5160
tttcgagcca acaggcagtt tgtgcatgca tgcttccaaa ggtacattcc tgcaaatcaa   5220
aagattgtgt aagcaaagca gaggaagcac ttcgccgcat tgaaaatacg ttcttctcaa   5280
```

```
agaaacaaaa ccataccaag ctgcatctgc atcatcagat tccttgcaca atggtgggtt    5340
gttttcggat cttttctcat agcaaatgtt gtccattggt ttctgaaata tgaccatacc    5400
aacttgattt aacttatcct tagtcttgtt gaccatcttc cagcacatgg actttgtcaa    5460
agtggacatc gctgaaaaga ttaaggggtc atatgttatg atagaaataa aattcaattt    5520
tgcactgttg gtacatagca tctgttttga acaaatgcaa tccttcctta tccatgaaag    5580
aagttaaccc ctgatactta ggattattca gtactttcac tcatgaactg ctgaatttgt    5640
tctgccagta gttgctatac tagaaatgtt cagtgtacca aacataaatt tggtacgggt    5700
tccttattaa agatgggagg ctgtatggta tttcgacgta acaaatcaag ttagcagcta    5760
ccctacttat ggatatacac ttctcaaaat gaatatacat agttttgata ggtgacatta    5820
attaatataa gaacttcatg cagttagggt gaaactaaac taagcagtta cggaaatacc    5880
attccaaatc tcaacatcct ctgggagctt ttggtaaaca ggagtggcag accagacaaa    5940
gtaaccacca gggcgtaaca agcggttcaa ttccagcaaa agcatgccac ctaaaaggag    6000
tcagtaataa gattcagttc tatagcaaat caataaatga aggaagaca tgtcaccaac    6060 aagacaaacc ttcaatgtgc caagggaccc tgcagcgagc gcaatgaatg acatcaaaga    6120
ctctgctggg gtatggaagt ctcttggtgc ccatcacagc tgatattgct ggaattcccc    6180
tttctaatgc aaattgtact tgagcttcat gctcatcttt cggagcaaaa gacatggtaa    6240
gcacatctct atcaaacatg tagcctccaa agctggcaac tccacaaccg acatctagaa    6300
tgacgcggct tcgtttgccc catgcaatat caggcagtgc ctgtgaatga cagtttaatc    6360
agcatatgat gaaagcaagt gtgataatat caagttcaaa gatgcaacat gaaactttca    6420
taatcatgga cagtactaag cttgcttgat agattaatgt atggatgaga ctaaaaaaaa    6480
ggaaagttgt atccatcaga acgagaggct gaaaacacat ggctggctgt gaaagcctga    6540
tgtcgtttag tctagcataa acaaactgtc ctcagcatgt agatttccat agggtggcat    6600
ttgacaaatt atgattgtgg actagcgaat caatcactga ttctcaaaag tgtgagacag    6660
atgagttcaa gtctaagggg tgactaatat gggatgctgg gatgatgatg atgatatata    6720
cctgctgaat agtatcaata tagtggaggg caccattctt gaactgagtc ccacccccag    6780
ggaacaggag gtagtcacct gatactttaa cccaattttg atgtcccttg tactctgcga    6840
gcctagtgtg aggaacattg ctgtaccata cctgcaaaaa gcagcacaag atggtaataa    6900
gtaaacagag atcttggtca gctaaagatg attcagtgtc gtacaattta gaatagacag    6960
aatcaccttg tccctgctcc ttggccactc aattgggcgt ttatatcctt ctgggagtgg    7020
aacaaggcag gtaggaggct cctcagggca atgcctctca cgatgttcat aatgtttagt    7080
agttcgaagc ttcttgatag ccttctcgtt gtcaaggcaa ggtatgtaat ctgtcgaggc    7140
actgctatta catagtttcc aggaatagct agtcgcatca cctgaagact ttgatgacgc    7200
ttggacttcc ttttcattct tggactctgc agcctgtgtg gggaatgaac cattctgggt    7260
atttgactcc ttcagaagct ctgattgggc cccatcagga aatacctcgt tggagtttga    7320
gctctgatcc ttctctccat tttcttccac cttctcttct atctgaggtt gctcctcctg    7380
agtggcatca ccttcaggct tctcttcttg atcatccttg ctctctccat caggtttttc    7440
atcaccactc tcatttgtga tttcatcatc tttcttctcc ccactcttct ccccgtcacc    7500
atcgttcttc atgtcatctg accgcccttc tgattttcca tttgcatcat caaacatatc    7560
cttggtctca gctttctctg tcggcacttc cggctccttc tcttcaggct tctcctctgg    7620
cttctcagtg aacttctctt ccatcgtggc atccttgtta ttcggctcct ccggcatcgt    7680
```

```
ggcatcattg ttgtcggtgt cctcaaattt ctcagaacct tcaccagcat tgtcctgtga    7740
ggccccaaaa ttgacaggcg caggctgctg cttcaccacc ggcttcttat tcgaggagat    7800
ctccagcggg aagacagtgg acgaggtcat catccacgcg ccgaccaggc agagcgccac    7860
aaagacgacg accgtggtgg tcgtgcagaa cgacgacgac gtcgaggacg gccggcggcc    7920
gtccatcttc ccacctcggc caaatgccat tagtgcctgg cgaacatgta ccagagcacc    7980
gaccttcacg cgatttatct ccaccaacta ctgctggacc aagaaccccc aaaaaaatcg    8040
cacctttgtc tgctttgtgc tgctacagcc gcgcggcacc tgaagcaaac cacaaaaaaa    8100
acttaaatcg ccgcggacat aaatcaaggt gctggatcta aagaacaaac gctggatcta    8160
ctcaagcaac aacggaagga agatccgcta ttggtgctag tattagcttc ttgtttccta    8220
gtactacagc ggctctttcc cagtataaga acacgggaaa acgcggagaa atccccttc    8280 gtggccaaac atggaaagaa aattagtaaa gcgtgtgctt taaaaccccc tcgttctgtt    8340
ccttccgcgg agagctaccg catcttccaa ttgagctggt tctcagctgg gcgcaaaacg    8400
cgcactaatc aatgtccgat tccatccaca aagaaaaaaa agacgggaac agctaatcca    8460
gcagctcgct cgctagctag ctagctcatc ggcggaagga cggaaccagc tttgctggat    8520
ccaggacagc aagagtgtgc aaggagaaag aacggagcag caatgcggat tgcggaggcg    8580
gtggattggt acctcgccgg aaccgaccgg agtggtcgcg gtggccctcc gcgcggatct    8640
cgaagaggag cgaggaaggg gaaggcggat gcgcgtcctt gggttctctg ccaccgcact    8700
gggcctcgcc gcgttataaa ggcgggcggg cgggcgggca gcgcagtgtg agtggagtgc    8760
aatctgttgt gtagtgtgtg aagaggcgga agcggaagcg gaggagatgg gttcgcatta    8820
gacgaccgta cgtaattata cgctatacta gtacttgggt tagattactc gggagatctt    8880
ggccaaaatg tccggtctga gtgtttggta gtttttatgga tttgcccttt taagatgttg    8940
gtatttctcc gggagcttag aaagaagaaa tggcgatgct ttaggccttg tttagatgcg    9000
aaaaaaattt ggatttcgct actgtggcat ttttatttgt ttgtagcaaa tattgtccaa    9060
acacggacta actaagattc atctcgcgat ttacagttaa actgtacaat tagtttttat    9120
tttcatttat atttaatgtt tcatggatgt gtcgaaagat acgatatgat agaaaatttt    9180 gaaaacttt tagttattga ggttaactaa acaatgcctt aattgagaat ttactcgagc    9240
aaaaagagtt aggtcagtct cagtggagag tttcatggtg ttgtttccaa gactgccata    9300
tcatgtgaaa tgaaatgaaa cttggttgaa acactcactc tcaatggaga gtttcatttt    9360
atagtttcat gggcatttaa tttcaatact catagagagt tgatatcgtg ccaactcatt    9420
tcttctctct cttcttaaat acacagtcat atcatcaaaa aaaatcctat gtagcaacat    9480
atttaatgca aataaaactc atatggtgga ctgtaggagt agcattaggc caagggcaca    9540
cacacggtca cggtgtgagt gcgacggtgc gagtgggccc gcggcggtag taagtgcgtg    9600 cgcgccggc gccccctcc gcggcgacga cgcagcggca gcgcgtcgtc cagtgcaccg    9660
tctgctgttc ggcgctgcgg gtcctccgcg ccacggcgca gtgaaccggg cgcgtgcatc    9720
ccgggagcgg cggcttggca ctcccctgct tgtcggtggc ggccgtcggc atcgctcggc    9780
cccggagcgt cacgaggctg ctgattggga gcgagagcga gtagtgggc tggttgggga    9840 caatcccatt cccacccggc ccaccaggct gggactggcc cactagtcac tagtgggtgg    9900
ctcatgggtg tgggtgggct ggctaatgcc gcctgcccaa caaccaaccc aaccctgtgt    9960
gacgctggta ccggtagttg ccgcgccatg gtggactgct gccgcctgat gcctttgcct   10020
```

```
gccacgctcc acgagttgag gcgcaccaaa ctgtgctgtg ctcctgattt gtgctaatcg    10080
gccgacgcgt accattcttt cttcttttcg tctacgcgca gagaggccgg ttgactgttt    10140
cttcgttgga gggccatgtt gactcgtact aataataaaa ataataatac taggttgact    10200
ttttcaattc caacgcagca gtgcaaagct gcccacctat gagcacaggt ccttttttaa    10260
ctccgttttt gtacgtacac acgtactgtc cagcctgtgt ctaataatct taccaaaaac    10320
ctgtcatctc actatcaacc aatcaggctc tccgcctgtt cgtcgaggaa cagcagttgt    10380
tttccctact ccaacataga gtacactatg gacgcacatt accatgccag cttgagctta    10440
gcattgccca ccgttggata actgccatgc cattctcagg ccctgtttag ttcccatcta    10500
aaaatttttc atccattcca tcgaatcttt ggacacatgc atggaacatt aaatgtagat    10560
aaaaaaataa actaattaca cagtttagtt gagaatcgcg agacgaatct tttaagtcta    10620
gttactccat aattagcctt aagtgctaca gtaatccaca tatactaatg acagattaat    10680
tatgcttaat aaatttgtct tacagtttcc tgacgagcta tgtaatttgt tttttatta    10740
gtttctaaaa acccctcccg acatccttcc gacatatccg atgtgacaac caaaaatttt    10800
tcatcttcaa tctaaacagg ccctcactct catcatctca tgccggggca gcaggtccgt    10860
cgtcaggtct gtcgtcccgt cccgtgccgt ctgaagcaac aggcgagaga aacgccgttc    10920
catcggtttg ccgagcgtgc agaggataga gctatactcg atccggagag gattgtgaaa    10980
cgaagcacgg ttaagcagtg ccgcgcacgt gctgctctgc tcctggatcc gatccagatc    11040
gactcggggc gtctcggcct cagcggcgat ggcaatcatc gcgcgcgctg ctggagctgg    11100
acgttttcgt cttgcattgc aggaggcgga acagaacgga gaaagccacg gcgcgctttg    11160
ccgacgccac gcgctgacac gagggacccg ttcagcggcc agcacgcagc ctaatcatgc    11220
ctgtcggggg gagctcatcc gttcctgaat ttgggtcatg ctccagtatc aggtattcag    11280
gtactagtac tcctgagcca tgtgctgcga caaaaagcg aggctcctgt agtagagcct    11340
tgtttactta caaattttt tacattctca gttatattaa atcttgtgac acatgcataa    11400
agcattaaat atacataaaa gaaataatta tttacacagt tacttataat ttgcgaaacg    11460
aatcttttaa gactggttag tttatgatta gataatattt attaaataca aatgaaagta    11520
atattattta tattttgcaa aaagtaaata agacctaggt agctaggcca acgtgagcat    11580
gtcggacccg gaccggttcg ttctacggcg cgtcccgcaa acctgcagcc aggtagtagt    11640
agtacaccgt gcacgggaga ggtgcgccat gcatgctcgg gcaaaagatc atagagaaag    11700
gtgcagcgtt tcagttgcac acctgaccga gtgacgcctc gccttgtttg gctttgttcc    11760
caaaattttt taaaattcct catcacatta aatctttgaa cgaatatatg gagcattaaa    11820
tataaataaa agaaataatt aatcatacaa tttgtctgta atttgcgaga cgaatctttt    11880
gagcctagtt agtttataat taaataatat ttgttaaata caaacgaaaa tgctacgtta    11940
gccaaaacta aaattttct ccaaacgtga cccagcacct tccgatcaat catcactcag    12000
cgggtcacgt cagaagatca gatggacctt gccgtccggg cctgtctctc ggcctcctcc    12060
ccatctggaa cgaacagagg tccagtcctg tttcgagtcg agctgagtcg atcagatggg    12120
cctaaatagg ccgaagacgt aggcaaaggg cccgctgatt tatctgattc ttctaggacc    12180
gtgcatgcgc ggatgggcct aggtggaaac ccaacagatg tgaggcttca agaggaaga    12240
agtccgttac acatggagag ttagtctata tgggataat atttaccaca aacaaataaa    12300
aatactacag tagcgaaatc caaaattttt cacatctaaa caaggcccta gatgttttgt    12360
cagtgccaga ccagagaaaa tctcgtcttc tgctgtcaat agctttgatg attcctggcg    12420
```

-continued

```
gcagaggtaa agcttgcctg ggccttgttt agttccgaaa agtgaaaagt tttcggtact   12480
gtagcacttt tgtttgttcg tgacaaatat catccaatta tggactaact agaattaaaa   12540
gattcgtctc gtgatctaca gctaaactgt gtaattagtt tttgttttcg tctatattta   12600
atgtttcatg catgtgccac aagattcgat gtgacggaga atttttgaaaa tttttttggtt   12660 ttcagagtga actaaacaag gcccagatgt aattgaccat gccatcgagc gcgagttgac   12720
tagagtgagt cggccctgat ggttaagtag tgcagactgc caagtggaca accgtctatc   12780
aactttgcag agtggggcga atgcactgag gatgttggag aggggcaagc caaggtaaac   12840
ttgaggaaag atgcttgttg acactgtagt atgtgaacaa tcctgtttaa ttttgtgtcc   12900
tcgacg                                                              12906
```

<210> SEQ ID NO 88
<211> LENGTH: 1790
<212> TYPE: DNA
<213> ORGANISM: Setaria italica

<400> SEQUENCE: 88

```
tctcatggtg tcccaagcac agcaagagcc agctctgcct cacagcagca gcaccgccaa     60
gcgcgcagcc gcgtcactca tggacgcccg cccggcccag cctctcctcc tccgcgcccc    120
gactcccagc attgacctcc ccgcgtccaa gccggacagg gccgccgcgg cggccggcaa    180
ggccgccgcc gcctccgtgt cgacctgcg gcgggagccc aagatcccgg cgccattcgt    240
gtggccgcac gacgacgcgc ggccggcgtc ggcggcggag ctggacgtgc cgttggtgga    300
cgtgggcgtg ctgcgcaatg gcgaccgcgc ggggctgcgg cgcgctgcgg cgcaggtggc    360
cgcggcgtgc gcgacgcacg ggttcttcca ggtgtgcggg cacggcgtgg gcgcggacct    420
ggcgcgcgcg gcgctggacg gcgccagtga cttcttccgg ctgccgctgg cggagaagca    480
gcgcgcccgg cgcgtcccgg ggaccgtgtc cgggtacacg agcgcgcacg ccgaccggtt    540
cgcgtccaag ctcccctgga aggagaccct ctccttcggg ttccacgacg gcgccgcgtc    600
gcccgtcgtc gtcgactact cgccggcac cctcgggcag gacttcgagg cagtggggcg    660
ggtgtaccag aggtactgcg aggagatgaa ggctctgtcg ctgacgatca tggagctcct    720
ggagctgagc ctgggcgtgg agcgcggcta ctaccgcgac ttcttcgagg acagccgctc    780
catcatgcgg tgcaactact acccgccgtg cccggagccg gagcgcacgc tgggcacggg    840
cccgcactgc gaccccaccg cgctgaccat cctcctccag gacgacgtcg gcgggctcga    900
ggtcctcgtc gacggcgact ggcgcccgt ccgcccgtc ccggcgcca tggtcatcaa    960 catcggcgac accttcatgg ctctgtccaa cgggcggtac aagagctgcc tgcaccgggc   1020
ggtggtgaac cagcggcagg agcggcggtc gctggccttc ttcctgtgcc cgcgcgagga   1080
ccgggtggtg cgcccgccgg ccagcggcgc cgtcggcgag gcgccccgcc gctacccgga   1140
cttcacctgg gccgacctca tgcgcttcac gcagcgccac taccgcgccg acacccgcac   1200
gctggacgcc ttcacacgct ggctctccca cggcccggcc caggacgcgc cagtggcggc   1260
ggcggcttcc acctagctag cggcgcggat ccgaccgagc ccattgacga cgccgtccct   1320
ttccgccgcc gccggggccc gcgcggggt tcacccacg tgcgcgccca ggtgggcgag   1380
gtggcggcct cgtggcccgc gggcccgcg ccgccttccc attttttggc gctgccgccc   1440
cgcgcgcatg ccggatgcgt gcgtccacgg cctactgctg ctactagtgt acatatacaa   1500
acatacatat atacgtagta taaatatata agcaagcggc ccggtgcccc ttttcgtttt   1560
```

```
cttgttttgt cgatcacaat ctctggattc gatggatgga taaatgtttg tacgcatgca   1620
tgtagatggg ctcatgaaat ttcagaatct ggaacggacg aggagctcac gtgcctcttc   1680
cgtgtctggt agcggtagct gcgtgccaaa tgtctggtgg gcccaaagaa attctagtgc   1740
cacccgtccg gatccggcat ccgaaagttc ccgacggttc gacacccgaa              1790

<210> SEQ ID NO 89
<211> LENGTH: 1272
<212> TYPE: DNA
<213> ORGANISM: Setaria italica

<400> SEQUENCE: 89
atggtgtccc aagcacagca agagccagct ctgcctcaca gcagcagcac cgccaagcgc     60
gcagccgcgt cactcatgga cgcccgcccg gcccagcctc tcctcctccg cgccccgact    120
cccagcattg acctccccgc gtccaagccg gacagggccg ccgcggcggc cggcaaggcc    180
gccgccgcct ccgtgttcga cctgcggcg gagcccaaga tcccggcgcc attcgtgtgg    240
ccgcacgacg acgcgcggcc ggcgtcggcg gcggagctgg acgtgccgtt ggtggacgtg    300
ggcgtgctgc gcaatggcga cgcgcgggg ctgcggcgcg ctgcggcgca ggtggccgcg    360
gcgtgcgcga cgcacgggtt cttccaggtg tgcgggcacg gcgtgggcgc ggacctggcg    420
cgcgcggcgc tggacggcgc cagtgacttc ttccggctgc cgctggcgga aagcagcgc    480 gcccggcgct cccgggggac cgtgtccggg tacgagcg cgcacgccga ccggttcgcg    540
tccaagctcc cctggaagga ccctctcc ttcgggttcc acgacggcgc cgcgtcgccc    600
gtcgtcgtcg actacttcgc cggcaccctc gggcaggact cgaggcagt ggggcgggtg    660 taccagaggt actgcgagga gatgaaggct ctgtcgctga cgatcatgga gctcctggag    720
ctgagcctgg gcgtggagcg cggctactac cgcgacttct tcgaggacag ccgctccatc    780
atgcggtgca actactaccc gccgtgcccg gagccggagc gcacgctggg cacgggcccg    840
cactgcgacc ccaccgcgct gaccatcctc tccaggacg acgtcggcgg gctcgaggtc    900
ctcgtcgacg gcgactggcg ccccgtccgc ccgtccccg cgccatggt catcaacatc    960 ggcgacacct tcatggctct gtccaacggg cggtacaaga gctgcctgca ccgggcggtg  1020
gtgaaccagc ggcaggagcg gcggtcgctg gccttcttcc tgtgcccgcg cgaggaccgg  1080
gtggtgcgcc gccggccag cggcgccgtc ggcgaggcgc cccgccgcta cccgacttc  1140 acctgggccg acctcatgcg cttcacgcag cgccactacc gcgccgacac ccgcacgctg  1200
gacgccttca cacgctggct ctcccacggc ccggcccagg acgcgccagt ggcggcggcg  1260
gcttccacct ag                                                        1272

<210> SEQ ID NO 90
<211> LENGTH: 423
<212> TYPE: PRT
<213> ORGANISM: Setaria italica

<400> SEQUENCE: 90

Met Val Ser Gln Ala Gln Gln Glu Pro Ala Leu Pro His Ser Ser
1               5                   10                  15

Thr Ala Lys Arg Ala Ala Ala Ser Leu Met Asp Ala Arg Pro Ala Gln
            20                  25                  30

Pro Leu Leu Leu Arg Ala Pro Thr Pro Ser Ile Asp Leu Pro Ala Ser
        35                  40                  45

Lys Pro Asp Arg Ala Ala Ala Ala Ala Gly Lys Ala Ala Ala Ala Ser
    50                  55                  60
```

```
Val Phe Asp Leu Arg Arg Glu Pro Lys Ile Pro Ala Pro Phe Val Trp
 65                  70                  75                  80

Pro His Asp Asp Ala Arg Pro Ala Ser Ala Ala Glu Leu Asp Val Pro
                 85                  90                  95

Leu Val Asp Val Gly Val Leu Arg Asn Gly Asp Arg Ala Gly Leu Arg
                100                 105                 110

Arg Ala Ala Ala Gln Val Ala Ala Ala Cys Ala Thr His Gly Phe Phe
                115                 120                 125

Gln Val Cys Gly His Gly Val Gly Ala Asp Leu Ala Arg Ala Ala Leu
                130                 135                 140

Asp Gly Ala Ser Asp Phe Phe Arg Leu Pro Leu Ala Glu Lys Gln Arg
145                 150                 155                 160

Ala Arg Arg Val Pro Gly Thr Val Ser Gly Tyr Thr Ser Ala His Ala
                165                 170                 175

Asp Arg Phe Ala Ser Lys Leu Pro Trp Lys Glu Thr Leu Ser Phe Gly
                180                 185                 190

Phe His Asp Gly Ala Ala Ser Pro Val Val Asp Tyr Phe Ala Gly
                195                 200                 205

Thr Leu Gly Gln Asp Phe Glu Ala Val Gly Arg Val Tyr Gln Arg Tyr
210                 215                 220

Cys Glu Glu Met Lys Ala Leu Ser Leu Thr Ile Met Glu Leu Leu Glu
225                 230                 235                 240

Leu Ser Leu Gly Val Glu Arg Gly Tyr Tyr Arg Asp Phe Phe Glu Asp
                245                 250                 255

Ser Arg Ser Ile Met Arg Cys Asn Tyr Tyr Pro Pro Cys Pro Glu Pro
                260                 265                 270

Glu Arg Thr Leu Gly Thr Gly Pro His Cys Asp Pro Thr Ala Leu Thr
                275                 280                 285

Ile Leu Leu Gln Asp Asp Val Gly Gly Leu Glu Val Leu Val Asp Gly
                290                 295                 300

Asp Trp Arg Pro Val Arg Pro Val Pro Gly Ala Met Val Ile Asn Ile
305                 310                 315                 320

Gly Asp Thr Phe Met Ala Leu Ser Asn Gly Arg Tyr Lys Ser Cys Leu
                325                 330                 335

His Arg Ala Val Val Asn Gln Arg Gln Glu Arg Ser Leu Ala Phe
                340                 345                 350

Phe Leu Cys Pro Arg Glu Asp Arg Val Val Arg Pro Pro Ala Ser Gly
                355                 360                 365

Ala Val Gly Glu Ala Pro Arg Arg Tyr Pro Asp Phe Thr Trp Ala Asp
                370                 375                 380

Leu Met Arg Phe Thr Gln Arg His Tyr Arg Ala Asp Thr Arg Thr Leu
385                 390                 395                 400

Asp Ala Phe Thr Arg Trp Leu Ser His Gly Pro Ala Gln Asp Ala Pro
                405                 410                 415

Val Ala Ala Ala Ala Ser Thr
                420

<210> SEQ ID NO 91
<211> LENGTH: 2888
<212> TYPE: DNA
<213> ORGANISM: Setaria italica

<400> SEQUENCE: 91
tctcatggtg tcccaagcac agcaagagcc agctctgcct cacagcagca gcaccgccaa    60
```

-continued

```
gcgcgcagcc gcgtcactca tggacgcccg cccggcccag cctctcctcc tccgcgcccc      120
gactcccagc attgacctcc ccgcgtccaa gccggacagg gccgccgcgg cggccggcaa      180
ggccgccgcc gcctccgtgt tcgacctgcg gcgggagccc aagatcccgg cgccattcgt      240
gtggccgcac gacgacgcgc ggccggcgtc ggcggcggga ctggacgtgc cgttggtgga      300
cgtgggcgtg ctgcgcaatg cgaccgcgc ggggctgcgg cgcgctgcgg cgcaggtggc      360
cgcggcgtgc gcgacgcacg ggttcttcca ggtgtgcggg cacggcgtgg gcgcggacct      420
ggcgcgcgcg gcgctggacg gcgccagtga cttcttccgg ctgccgctgg cggagaagca      480
gcgcgcccgc cgcgtcccgg gaccgtgtc cgggtacacg agcgcgcacg ccgaccggtt      540
cgcgtccaag ctcccctgga aggagaccct ctccttcggg ttccacgacg gcgccgcgtc      600
gcccgtcgtc gtcgactact tcgccggcac cctcgggcag gacttcgagg cagtggggta      660
agtatgtagg aatgaacttg gcacgcattg catccacatg gcgtgctgat cgaacgagct      720
gagccaaccg gcatgcacac atggcgtggc aggcgggtgt accagaggta ctgcgaggag      780
atgaaggctc tgtcgctgac gatcatggag ctcctggagc tgagcctggg cgtggagcgc      840
ggctactacc gcgacttctt cgaggacagc cgctccatca tgcggtgcaa ctactacccg      900
ccgtgcccgg agccggagcg cacgctgggc acgggcccgc actgcgaccc caccgcgctg      960
accatcctcc tccaggacga cgtcggcggg ctcgaggtcc tcgtcgacgg cgactggcgc      1020
cccgtccgcc ccgtccccgg cgccatggtc atcaacatcg gcgacacctt catggtacgg      1080
ccgccgctaa tccatccttt tgttgctctt atctcctctg gcgagtgcga gtaacgaaag      1140
cgctagctcc cctgctcctt gtcctgctct gtttcccaag tcctaatgga gctaaccggg      1200
cagactgcaa cacgcacgcg taggcatgtc acgtagccac cacttgcact gtgctgcgca      1260
gcgacgacgc aacgcggacg tgcgttcgag tcggttccat ctcggcgccg ctacacgcgg      1320
ccgcggctcc tagcctccta gggctcccctg atccctatcc ccgagccctt ccgcgggaaa      1380
agttcgttgg cgacggcaga ggagagccga cgggtccgtg ccgttggagc gtggcggcag      1440
gagaggccgg gagggtgttt tgttgcgttg cgcggcggcg cggaggatgc gatgcgcgg       1500 gcgggcggcg cttcggcgg tggccccgc gacccacgtg cgcgcgcggt tcgtcgcct       1560 tccctgttt ggtgccacct ctctgtgtcc gggaatgggt tggcttagcg gcgaccgaga       1620
ccgggcggtg gtctggcctg ctcccggcgc ccatcccgcc tggtctctca tcctgctcct      1680
cctatgcgcg aggggcctg tagcggctgg agtacaagca gattggttgg gttgggttgc       1740
tgctgcttgg ctgttgcccg cccgctttct agccgtttcc gctcgccatc cggcacgcgg      1800
cgcccacgcc ggggctccag ctcggccct ttggccgtgt gggtggcagg caccctgca       1860 tcgtctcgtg cgtccggttt ccgcgcctgg ccccccgcct tgaggtttcc ctgtgctttt      1920
gacaagactt tcgtagatat atgtgtgtgt atgtgtgtgt gtgcgtgcgc gcgtgtgtgt      1980
atatatatat ataaataaat aacatctgtg aatgatggat tacacgtgta gctgaccggc      2040
tgattgtgtt cgcgtgtgtg tcttcgatgc attgcaggct ctgtccaacg gcggtacaa      2100 gagctgcctg caccgggcgg tggtgaacca gcggcaggag cggcggtcgc tggccttctt      2160
cctgtgcccg cgcgaggacc gggtggtgcg cccgccggcc agcggcgccg tcggcgaggc      2220
gccccgccgc tacccggact tcacctgggc cgacctcatg cgcttcacgc agcgccacta      2280
ccgcgccgac acccgcacgc tggacgcctt cacacgctgg ctctcccacg gcccggccca      2340
ggacgcgcca gtggcggcgg cggcttccac ctagctagcg gcgcggatcc gaccgagccc      2400
```

```
attgacgacg ccgtcccttt ccgccgccgc cggggcccgc gcggggttc accccacgtg    2460
cgcgcccagg tgggcgaggt ggcggcctcg tgcccgcgg gccccgcgcc gccttcccat    2520
ttttgggcgc tgccgccccg cgcgcatgcc ggatgcgtgc gtccacggcc tactgctgct    2580
actagtgtac atatacaaac atacatatat acgtagtata aatatataag caagcggccc    2640
ggtgccccct ttcgttttct tgttttgtcg atcacaatct ctggattcga tggatggata    2700
aatgtttgta cgcatgcatg tagatgggct catgaaattt cagaatctgg aacgacgag    2760
gagctcacgt gcctcttccg tgtctggtag cggtagctgc gtgccaaatg tctggtgggc    2820
ccaaagaaat tctagtgcca cccgtccgga tccggcatcc gaaagttccc gacggttcga    2880
cacccgaa                                                             2888

<210> SEQ ID NO 92
<211> LENGTH: 1567
<212> TYPE: DNA
<213> ORGANISM: Oryza sativa

<400> SEQUENCE: 92
tgcccagaca gctcgccctg cacacacaca cacactcaca ctcacacacg ctctcaactc     60
actcccgctc aacacagcgc tcacttctca tctccaatct catggtggcc gagcacccca    120
cgccaccaca ccgcaccaa ccaccgccca tggactccac cgccggctct ggcattgccg    180
ccccggcggc ggcggcggtg tgcgacctga ggatggagcc caagatcccg gagccattcg    240
tgtggccgaa cggcgacgcg aggccggcgt cggcggcgga gctggacatg cccgtggtcg    300
acgtgggcgt gctccgcgac ggcgacgccg aggggctgcg ccgcgccgcg cgcaggtgg    360
ccgccgcgtg cgccacgcac gggttcttcc aggtgtccga gcacggcgtc gacgccgctc    420
tggcgcgcgc cgcgctcgac ggcgccagcg acttcttccg cctcccgctc gccgagaagc    480
gccgcgcgcg ccgcgtcccg ggcaccgtgt ccggctacac cagcgcccac gccgaccgct    540
tcgcctccaa gctcccatgg aaggagaccc tctccttcgg cttccacgac gcgccgccg    600
cccccgtcgt cgccgactac ttctccagca ccctcggccc cgacttcgcg ccaatgggga    660
gggtgtacca gaagtactgc gaggagatga aggagctgtc gctgacgatc atggaactcc    720
tggagctgag cctgggcgtg gagcgaggct actacaggga gttcttcgcg gacagcagct    780
caatcatgcg gtgcaactac tacccgccat gccggagcc ggagcggacg ctcggcacgg    840
gcccgcactg cgaccccacc gccctcacca tcctcctcca ggacgacgtc ggcggcctcg    900
aggtcctcgt cgacggcgaa tggcgccccg tcagccccgt ccccggcgcc atggtcatca    960
acatcggcga caccttcatg gcgctgtcga acgggaggta taagagctgc ctgcacaggg   1020
cggtggtgaa ccagcggcgg gagcggcggt cgctggcgtt cttcctgtgc cgcggggagg   1080
acagggtggt gcggccgccg ccgagcgccg ccacgccgca gcactacccg gacttcacct   1140
gggccgacct catgcgcttc acgcagcgcc actaccgcgc cgacacccgc acgctcgacg   1200
ccttcacgcg ctggctcgcg ccgccggccg ccgacgccgc cgcgacggcg caggtcgagg   1260
cggccagctg atcgccgaac ggaacgaaac ggaacgaaca gaagccgatt tttggcgggg   1320
cccacgccca cgtgaggccc cacgtggaca gtgggcccgg gcgagagtgg cacccacgtg   1380
gaccgcgggc cccgcgccgc cttccaattt tggaccctac cgctgtacat attcatatat   1440
tgcaagaaga agcaaaacgt acgtgtgggt tgggttgggc ttctctctat tactaaaaaa   1500
aatataatgg aacgacggat gaatggatgc ttatttattt atctaaattg aattcgaatt   1560
cggctca                                                             1567
```

<210> SEQ ID NO 93
<211> LENGTH: 1170
<212> TYPE: DNA
<213> ORGANISM: Oryza sativa

<400> SEQUENCE: 93

```
atggtggccg agcaccccac gccaccacag ccgcaccaac caccgcccat ggactccacc      60
gccggctctg gcattgccgc cccggcggcg cggcggtgt gcgacctgag gatggagccc     120
aagatcccgg agccattcgt gtggccgaac ggcgacgcga ggccggcgtc ggcggcggag    180
ctggacatgc ccgtggtcga cgtgggcgtg ctccgcgacg gcgacgccga ggggctgcgc    240
cgcgccgcgg cgcaggtggc cgccgcgtgc gccacgcacg ggttcttcca ggtgtccgag    300
cacggcgtcg acgccgctct ggcgcgcgcc gcgctcgacg gcgccagcga cttcttccgc    360
ctcccgctcg ccgagaagcg ccgcgcgcgc cgcgtcccgg caccgtgtc cggctacacc     420
agcgcccacg ccgaccgctt cgcctccaag ctcccatgga aggagaccct ctccttcggc    480
ttccacgacc gcgccgccgc ccccgtcgtc gccgactact ctccagcac cctcggcccc     540
gacttcgcgc caatggggag ggtgtaccag aagtactgcg aggagatgaa ggagctgtcg    600
ctgacgatca tggaactcct ggagctgagc ctgggcgtgg agcgaggcta ctacagggag    660
ttcttcgcgg acagcagctc aatcatgcgg tgcaactact accgccatg cccggagccg     720
gagcggacgc tcggcacggg cccgcactgc gaccccaccg ccctcaccat cctcctccag    780
gacgacgtcg gcggcctcga ggtcctcgtc gacggcgaat ggcgccccgt cagccccgtc    840
cccggcgcca tggtcatcaa catcggcgac accttcatgg cgctgtcgaa cgggaggtat    900
aagagctgcc tgcacagggc ggtggtgaac cagcggcggg agcggcggtc gctggcgttc    960
ttcctgtgcc cgcgggagga cagggtggtg cggccgccgc cgagcgccgc cacgccgcag   1020
cactacccgg acttcacctg gccgacctc atgcgcttca cgcagcgcca ctaccgcgcc   1080
gacacccgca cgctcgacgc cttcacgcgc tggctcgcgc cgccgccgc cgacgccgcc   1140
gcgacggcgc aggtcgaggc ggccagctga                                     1170
```

<210> SEQ ID NO 94
<211> LENGTH: 389
<212> TYPE: PRT
<213> ORGANISM: Oryza sativa

<400> SEQUENCE: 94

Met Val Ala Glu His Pro Thr Pro Pro Gln Pro His Gln Pro Pro Pro
1               5                   10                  15

Met Asp Ser Thr Ala Gly Ser Gly Ile Ala Ala Pro Ala Ala Ala
            20                  25                  30

Val Cys Asp Leu Arg Met Glu Pro Lys Ile Pro Glu Pro Phe Val Trp
        35                  40                  45

Pro Asn Gly Asp Ala Arg Pro Ala Ser Ala Ala Glu Leu Asp Met Pro
    50                  55                  60

Val Val Asp Val Gly Val Leu Arg Asp Gly Asp Ala Glu Gly Leu Arg
65                  70                  75                  80

Arg Ala Ala Ala Gln Val Ala Ala Ala Cys Ala Thr His Gly Phe Phe
                85                  90                  95

Gln Val Ser Glu His Gly Val Asp Ala Ala Leu Ala Arg Ala Ala Leu
            100                 105                 110

Asp Gly Ala Ser Asp Phe Phe Arg Leu Pro Leu Ala Glu Lys Arg Arg

|  | | | 115 | | | | | 120 | | | | | 125 | | |
|--|--|--|--|--|--|--|--|--|--|--|--|--|--|--|--|

Ala Arg Arg Val Pro Gly Thr Val Ser Gly Tyr Thr Ser Ala His Ala
    130                  135                  140

Asp Arg Phe Ala Ser Lys Leu Pro Trp Lys Glu Thr Leu Ser Phe Gly
145                  150                  155                  160

Phe His Asp Arg Ala Ala Ala Pro Val Val Ala Asp Tyr Phe Ser Ser
                165                  170                  175

Thr Leu Gly Pro Asp Phe Ala Pro Met Gly Arg Val Tyr Gln Lys Tyr
            180                  185                  190

Cys Glu Glu Met Lys Glu Leu Ser Leu Thr Ile Met Glu Leu Leu Glu
                195                  200                  205

Leu Ser Leu Gly Val Glu Arg Gly Tyr Tyr Arg Glu Phe Phe Ala Asp
    210                  215                  220

Ser Ser Ser Ile Met Arg Cys Asn Tyr Tyr Pro Pro Cys Pro Glu Pro
225                  230                  235                  240

Glu Arg Thr Leu Gly Thr Gly Pro His Cys Asp Pro Thr Ala Leu Thr
                245                  250                  255

Ile Leu Leu Gln Asp Asp Val Gly Gly Leu Glu Val Leu Val Asp Gly
            260                  265                  270

Glu Trp Arg Pro Val Ser Pro Val Pro Gly Ala Met Val Ile Asn Ile
        275                  280                  285

Gly Asp Thr Phe Met Ala Leu Ser Asn Gly Arg Tyr Lys Ser Cys Leu
290                  295                  300

His Arg Ala Val Val Asn Gln Arg Arg Glu Arg Ser Leu Ala Phe
305                  310                  315                  320

Phe Leu Cys Pro Arg Glu Asp Arg Val Val Arg Pro Pro Ser Ala
                325                  330                  335

Ala Thr Pro Gln His Tyr Pro Asp Phe Thr Trp Ala Asp Leu Met Arg
            340                  345                  350

Phe Thr Gln Arg His Tyr Arg Ala Asp Thr Arg Thr Leu Asp Ala Phe
                355                  360                  365

Thr Arg Trp Leu Ala Pro Pro Ala Ala Asp Ala Ala Thr Ala Gln
        370                  375                  380

Val Glu Ala Ala Ser
385

```
<210> SEQ ID NO 95
<211> LENGTH: 3140
<212> TYPE: DNA
<213> ORGANISM: Oryza sativa

<400> SEQUENCE: 95
tgcccagaca gctcgccctg cacacacaca cacactcaca ctcacacacg ctctcaactc    60
actcccgctc aacacagcgc tcacttctca tctccaatct catggtggcc gagcacccca   120
cgccaccaca gccgcaccaa ccaccgccca tggactccac cgccggctct ggcattgccg   180
ccccggcggc ggcggcggtg tgcgacctga ggatggagcc caagatcccg gagccattcg   240
tgtggccgaa cggcgacgcg aggccggcgt cggcggcgga gctggacatg cccgtggtcg   300
acgtgggcgt gctccgcgac ggcgacgccg aggggctgcg ccgcgccgcg cgcaggtgg    360 ccgccgcgtg cgccacgcac gggttcttcc aggtgtccga gcacggcgtc gacgccgctc   420
tggcgcgcgc cgcgctcgac ggcgccagcg acttcttccg cctcccgctc gccgagaagc   480
gccgcgcgcg ccgcgtcccg ggcaccgtgt ccggctacac cagcgcccac gccgaccgct   540
```

```
tcgcctccaa gctcccatgg aaggagaccc tctccttcgg cttccacgac cgcgccgccg   600
cccccgtcgt cgccgactac ttctccagca ccctcggccc cgacttcgcg ccaatggggt   660
aattaaaacg atggtggacg acattgcatt tcaaattcaa acaaattcca aaacacaccg   720
accgagatta tgctgaattc aaacgcgttt gtgcgcgcag gagggtgtac cagaagtact   780
gcgaggagat gaaggagctg tcgctgacga tcatggaact cctggagctg agcctgggcg   840
tggagcgagg ctactacagg gagttcttcg cggacagcag ctcaatcatg cggtgcaact   900
actacccgcc atgcccggag ccggagcgga cgctcggcac gggcccgcac tgcgaccccca   960 ccgccctcac catcctcctc caggacgacg tcggcggcct cgaggtcctc gtcgacggcg  1020
aatggcgccc cgtcagcccc gtccccggcg ccatggtcat caacatcggc gacaccttca  1080
tggtaaacca tctcctattc tcctctcctc tgttctcctc tgcttcgaag caacagaaca  1140
agtaattcaa gctttttttt ctctctcgcg cgaaattgac gagaaaaata agatcgtggt  1200
aggggcgggg ctttcagctg aaagcgggaa gaaaccgacc tgacgtgatt tctctgttcc  1260
aatcacaaac aatggaatgc cccactcctc catgtgttat gatttatctc acatcttata  1320
gttaatagga gtaagtaaca agctacttttt tcatattat agttcgtttg atttttttt   1380 tttaaagttt tttagttttt atccaaattt attgaaaaac ttagcaacgt ttataatacc  1440
aaattagtct catttagttt aatattgtat atttttgat aatatattta tgttatatta   1500
aaaatattac tatattttc tataaacatt attaaaagcc atttataata taaaatggaa   1560
ggagtaatta atatggatct cccccgacat gagaatattt tccgatggtg tgacgacgcc  1620
atgtaagctt cggtgggcct ggacggccag aggtgccaac agccacgtcc aacaacccct  1680
gggtcccccc ctaacactcc aaacagtagt gagtagtgtc tcgtcgcgtt ttagtatttg  1740
atgacaaaca aagtgtgagt tgagttagcc accaccaact tgcacacgag cacatacatt  1800
tgtgtccatt ctcgccagtc acttccatct ctagtcctaa ctcctatcta gcgatgtaag  1860
cggataattt catcatccgt atataaacct gtttgttata gttaatttcc tatataatac  1920
tataacagta tacattttaa aagaaaacaa aattaggata aacaggccct gctcctatcc  1980
atccatggca cttggaagga ccagactcgg tcatgccatg ccaagccaag atatgggtta  2040
tggaagagta gagaagagga gagatgagag ataagcatgc gttctcctcc tcgttggatg  2100
tgtattttgg agggatttgt gtagtagtag cagcggcgcc gcggggacgg atgcggatgg  2160
tggcgctttc ggtggcgttt tcccgggggg gttttggttt ggcgcttggg ggggatggca  2220
tggcgcggcg tgcggctgca cgccacacac acgcgcgcgc acgcacgtac gtcgtcgtcg  2280
ccgcgggcgg acggtagctt agggtggtgt gttccgcgcg cgggcgcgga ttgttccatg  2340
ccgatcgatt tggcgccacc ctcgccgcgg ctcttgtcgc gtcgtgcgcc tctctcgcgc  2400
ggtttgtcct tgtcgcgttg ctcagccggc gacggggca cggacattgg cgatgtagcc   2460
ctgcacgtgt cggcctctcc gttgatgaat gatgatgtat gtatgtattt ttttttgtct  2520
gaaggaattt gtgggggaatt gttgtgtgtg caggcgctgt cgaacgggag gtataagagc  2580
tgcctgcaca gggcggtggt gaaccagcgg cgggagcggc ggtcgctggc gttcttcctg  2640
tgcccgcggg aggacagggt ggtgcggccg ccgccgagcg ccgccacgcc gcagcactac  2700
ccggacttca cctgggccga cctcatgcgc ttcacgcagc gccactaccg cgccgacacc  2760
cgcacgctcg acgccttcac gcgctggctc gcgccgccgg ccgccgacgc cgccgcgacg  2820
gcgcaggtca aggcggccag ctgatcgccg aacggaacga aacggaacga acagaagccg  2880 attttttggcg gggcccacgc ccacgtgagg ccccacgtgg acagtgggcc cgggcggagg  2940
```

<210> SEQ ID NO 96
<211> LENGTH: 1170
<212> TYPE: DNA
<213> ORGANISM: Triticum aestivum

<400> SEQUENCE: 96

```
atggacacca gccctgcaac tcccctgctc ctccagcctc ctgctcccag cattgacccg      60
ttcgccgcca aggcggccgt caacaagggc ggcggcgcgg caaccgcggt gtacgacctc     120
cggagggagc cgaagatccc cgccccgttc gtgtggccgc acgccgaggt gcgccccacc     180
acggcccagg agctggccgt gccggtggtg gacgtgggcg tgctgcgcaa tggcgacgcc     240
gcggggctcc gccgcgccgt ggcgcaggtg gccgcggcgt gcgccacgca cggggttcttc     300
caggtgtccg gcacggcgt ggacgaggcc ctggcgcgcg cggcgctgga cggcgcgagc     360
ggcttcttcc ggctgccgct ggccgagaag cagcgcgcgc ggcgcgtccc ggggaccgtg     420
tccgggtaca cgagcgcgca cgccgaccgg ttcgcctcca agctccctg aaggagacc      480
ctctccttcg gcttccacga ccgcgccggc gccgcgcccg tcgtggtgga ctacttcacc     540
agcaccctcg gccggactca cgagccaatg gggagggtgt accaggagta ctgcgggaag     600
atgaaggagc tgtcgctgag gatcatggag ctgctggagc tgagccaggg cgtggagaag     660
cgcgggtact accgggagtt cttcgcggac agcagctcca tcatgcggtg caactactac     720
ccgccgtgcc cggagccgga cgcacgctg ggcacgggcc cgcactgcga ccccacggcg     780
ctcaccatcc tactgcagga cgacgtgggc gggctgagg tcctcgtcga cggcgactgg     840
cgccccgtcc gccccgtccc cggcgccatg gtcatcaaca tcggcgacac cttcatggcg     900
ctgtcgaacg gcggtacaa gagctgcctg caccgcgcgg tggtgaaccg gcggcaggag     960
cggcggtcgc tggccttctt cctgtgcccg cgcgaggacc gcgtggtgcg gccgccgccg    1020
ggcctgagga gcccgcggcg gtaccggac ttcacctggg ctgacctcat gcgcttcacg    1080
cagcgccact accgcgccga cacgcgcacc ctcgacgcct tcacccagtg gttctcctcc    1140
tcctcctcct cggcccagga ggcggcctga                                    1170
```

<210> SEQ ID NO 97
<211> LENGTH: 389
<212> TYPE: PRT
<213> ORGANISM: Triticum aestivum

<400> SEQUENCE: 97

```
Met Asp Thr Ser Pro Ala Thr Pro Leu Leu Gln Pro Ala Pro
 1               5                   10                  15

Ser Ile Asp Pro Phe Ala Ala Lys Ala Ala Val Asn Lys Gly Gly Gly
            20                  25                  30

Ala Ala Thr Ala Val Tyr Asp Leu Arg Arg Glu Pro Lys Ile Pro Ala
        35                  40                  45

Pro Phe Val Trp Pro His Ala Glu Val Arg Pro Thr Thr Ala Gln Glu
    50                  55                  60

Leu Ala Val Pro Val Val Asp Val Gly Val Leu Arg Asn Gly Asp Ala
65                  70                  75                  80
```

Ala Gly Leu Arg Arg Ala Val Ala Gln Val Ala Ala Cys Ala Thr
                85                  90                  95

His Gly Phe Phe Gln Val Ser Gly His Gly Val Asp Glu Ala Leu Ala
            100                 105                 110

Arg Ala Ala Leu Asp Gly Ala Ser Gly Phe Phe Arg Leu Pro Leu Ala
        115                 120                 125

Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Arg Ala Gly Ala Ala Pro Val Val Val
                165                 170                 175

Asp Tyr Phe Thr Ser Thr Leu Gly Pro Asp Tyr Glu Pro Met Gly Arg
            180                 185                 190

Val Tyr Gln Glu Tyr Cys Gly Lys Met Lys Glu Leu Ser Leu Arg Ile
        195                 200                 205

Met Glu Leu Leu Glu Leu Ser Gln Gly Val Glu Lys Arg Gly Tyr Tyr
    210                 215                 220

Arg Glu Phe Phe Ala Asp Ser Ser Ser Ile Met Arg Cys Asn Tyr Tyr
225                 230                 235                 240

Pro Pro Cys Pro Glu Pro Glu Arg Thr Leu Gly Thr Gly Pro His Cys
                245                 250                 255

Asp Pro Thr Ala Leu Thr Ile Leu Leu Gln Asp Asp Val Gly Gly Leu
            260                 265                 270

Glu Val Leu Val Asp Gly Asp Trp Arg Pro Val Arg Pro Val Pro Gly
        275                 280                 285

Ala Met Val Ile Asn Ile Gly Asp Thr Phe Met Ala Leu Ser Asn Gly
    290                 295                 300

Arg Tyr Lys Ser Cys Leu His Arg Ala Val Val Asn Arg Arg Gln Glu
305                 310                 315                 320

Arg Arg Ser Leu Ala Phe Phe Leu Cys Pro Arg Glu Asp Arg Val Val
                325                 330                 335

Arg Pro Pro Pro Gly Leu Arg Ser Pro Arg Arg Tyr Pro Asp Phe Thr
            340                 345                 350

Trp Ala Asp Leu Met Arg Phe Thr Gln Arg His Tyr Arg Ala Asp Thr
        355                 360                 365

Arg Thr Leu Asp Ala Phe Thr Gln Trp Phe Ser Ser Ser Ser Ser Ser
    370                 375                 380

Ala Gln Glu Ala Ala
385

<210> SEQ ID NO 98
<211> LENGTH: 3050
<212> TYPE: DNA
<213> ORGANISM: Triticum aestivum

<400> SEQUENCE: 98
ctcatggtgc tccagaccgc tcagcaagaa ccatccctga cgcgtccgcc tcactgcagc     60
gtcgccagcg cgcgctcgcc ggcggccatg gacaccagcc ctgcaactcc cctgctcctc    120
cagcctcctg ctcccagcat tgacccgttc gccgccaagg cggccgtcaa caagggcggc    180
ggcgcggcaa ccgcggtgta cgacctccgg agggagccga agatccccgc ccgttcgtg    240 tggccgcacg ccgaggtgcg ccccaccacg gcccaggagc tggccgtgcc ggtggtggac    300

```
gtgggcgtgc tgcgcaatgg cgacgccgcg gggctccgcc gcgccgtggc gcaggtggcc    360
gcggcgtgcg ccacgcacgg gttcttccag gtgtccgggc acggcgtgga cgaggccctg    420
gcgcgcgcgg cgctggacgg cgcgagcggc ttcttccggc tgccgctggc cgagaagcag    480
cgcgcgcggc gcgtcccggg gaccgtgtcc gggtacacga gcgcgcacgc cgaccggttc    540
gcctccaagc tccctggaa ggagaccctc tccttcggct ccacgaccg cgccggcgcc    600 gcgcccgtcg tggtggacta cttcaccagc accctcgggc cggactacga gccaatgggg    660
taatatatcc acccgcccac accctatcc ggccagcacg aatccatccc cgccactgca    720
tttttttcct tttgtttccg cgcgaccgta cgttcgatcg gcgcccacgt acgtacgtgc    780
gtacgcagta gcagtacttg aagccgccgt actacgtgct gagtagtgac aactgaacac    840
gtgcaggagg gtgtaccagg agtactgcgg gaagatgaag gagctgtcgc tgaggatcat    900
ggagctgctg gagctgagcc agggcgtgga gaagcgcggg tactaccggg agttcttcgc    960
ggacagcagc tccatcatgc ggtgcaacta ctacccgccg tgcccggagc cggagcgcac    1020
gctgggcacg ggcccgcact gcgaccccac ggcgctcacc atcctactgc aggacgacgt    1080
gggcgggctg gaggtcctcg tcgacggcga ctggcgcccc gtccgccccg tccccggcgc    1140
catggtcatc aacatcggcg acaccttcat ggtaattact cctctctcag cgttgctttc    1200
gctgattaat tgcagaaaca gtagtcaact acccatgctc tgttccgctg tgctctgctt    1260
cccaacgagc gaaccggccc ataaaaactg ccttgctgtc ttggaaccaa gaggaaaggg    1320
accgtgggag cctaccgaca cgacgtgatt gcactctgct tcctaacaag cgagccgccg    1380
gtagggctat caccgtaagg gctccttga ttcaaaggaa tttcttagga tttctgaagg    1440
attgaaatcc ttaggatttt ttcctatgtt ggtacttcga ttcataggat tgaatcccat    1500
aggatttttt tcctatgaaa tcttctgtac tacatttcat aggaaatcta acatccactc    1560 caacctttt ttatatttcc tttgttttc atgtgccatc aaacactcct tgttaatcct    1620
ataggattca agtgggcatg ccactccaat cctatacttt tcccattcct acgttttcaa    1680
aatcctacga atcaaagagg ccctaaagct gctgacatga cgtgatttt tttttcttt    1740 cttctttcct ttctcagctc caatcaacgc tggttattag atcattagag tggacaggtt    1800
gaattaacat gcagtagtta gtagttagca gccacaaacg ggtcccgttc tctgaagtct    1860
gaactgacat aagtcctgat catcgaccat tcttttgcttc ctaggacgat gcctgttgga    1920
acttgcgtcc aatgcccgtt agggagtggt aattgtcatc acttttagac tcgtcgattc    1980
cactgatgaa gacgtagcac atggatgagc caacgtatcc gtttctagtg gtctcgaaaa    2040
gtagggtttc attcattcta tctatctatc cgtccgtcca aaagggctgc gatgcgagca    2100
cttgagtcgg agccaatcag agcgcgagaa aagatagggg gggtagcaag ccatgtcgga    2160
ggggcgtttg cttccggcag gtttggattc ttgtggtagg cgggcggctc tgtacagtag    2220
cggcggtgac ggtgaggtgg cggcgctttc ggtggcgggc caaccaggt gcatgcacgc    2280 gcgctcgtcg ttttcccgcc tgaatctgcc gctgcgccca tggcaagggg gtgggtgctg    2340
ccgccgggcg atggagtaga tcacggtcgc cgtcgggctc ggccagttga tcacggttcg    2400
ttcgtgcggt actaggttcc cccacggcac tgtgactgca tcgttccggc cctcgccatt    2460
ggcgatcggg caatctcctg ttcatccgtc gctgttgatt cctcggccac gatagaccat    2520
gcgcgtgccg gtcgtcgccc cgtcgcgctc gcttcacgtg ctcgtcgcgt ggctcccgtc    2580
ccacacgagg ccgccgcttt ctgacccagt ggagcgcgtg atttacagtt tatatatgtc    2640
gctgcatttt tcttttttgtg tgctgctcat tttgcttgga cggagaccgg gaacgattag    2700
```

```
ccacggatct aacgcgttgt tgcttgtttt caatgcatgc atgcaggcgc tgtcgaacgg    2760
gcggtacaag agctgcctgc accgcgcggt ggtgaaccgg cggcaggagc ggcggtcgct    2820
ggccttcttc ctgtgcccgc gcgaggaccg cgtggtgcgg ccgccgccgg gcctgaggag    2880
cccgcggcgg tacccggact tcacctgggc tgacctcatg cgcttcacgc agcgccacta    2940
ccgcgccgac acgcgcaccc tcgacgcctt cacccagtgg ttctcctcct cctcctcctc    3000
ggcccaggag gcggcctgat tctgctctgc cacgaaacga tcggtccaca              3050
```

<210> SEQ ID NO 99
<211> LENGTH: 1486
<212> TYPE: DNA
<213> ORGANISM: Hordeum vulgare

<400> SEQUENCE: 99

```
gaccagtagc atatagttttt tcttgtgttt gccatggtgg acgtgtcgaa ctttgtagaa      60
gccaatggca atgcagcagt atcgattcct gccatggaag ttgctgggag tcctcacgtc     120
ccgttcgttc ctcgggacgc gaacgcgaca gacagcaaga atgccaagga cgtcctcgac     180
ctctggcggc agcagaaaca aatcccggct cccttcatct ggccccacgc cgacgcgcgg     240
ccgtcgtcga tcttggagct ggacgtgccc gtggtcgaca tcggcgcggc cctgcacagc     300
gccgccggga tggcccgcgc cgcggcgcag gtggccgagg catgcgcgag ccacggcttc     360
ttccaggtga ccgggcacgg cgtcgacccc cgcctggccc aagcagcgct cgacggcgca     420
gcggacttct tccgcctgcc gctcgccacc aagcagcgcg cccgccgatc cccggggacc     480
gtcaaagggt acgcctccgc ccacgccgac cgcttcgccg ccaagcttcc ctggaaggag     540
actctctcct tcatccacaa ccacgtccac gaggacgtcg cgcccgcgc aagcagtcac      600 gtcgtcgact acttcacctc cgcccttggc gacgacttca tgcacctagg ggaggtgtac     660
caggagtact gtgaggcgat ggaggacgcg tcgctggcga taatggaggt gctggggtg     720 agcctggggc tggggagagg gtactacagg gacttcttcg ccgacggcag ctccatcatg     780
aggtgcaact actacccgcg gtgccccgag ccggaccgga cgctgggac ggggccgcac      840 tgcgacccgt cggcgctgac catcctgctg caggacggca aggtggacgg gctccaggtg     900
ctcgtcgacg gcgcatggcg ctccgtgcgg cccaagcccg gcgagctcgt cgtaaacatc     960
ggcgacacct tcatggcgct gtcgaacggc cggtacaaga gctgcctcca ccgcgcggtg    1020
gtgcaccggg agaaggagcg ccggtcgctg gcctacttcc tcgcccccgcg ggaggaccgg   1080 gtggttcgcc cgccgccttc gccggcgccg gcgccgcggc tctacccgga cttcacctgg   1140
gcggagctca tgcgattcac gcagcgccac taccgcgccg acgcccgcac gctcgacgcc   1200
ttcgcgtgct ggctcgacct gcccagctgc cccaccacgc cccaggccca agggactgtc   1260
tagtgtctgt gatgtatcat ctgtctcagc tgttgtatac gaccacttgt gtctgctagc   1320
tctgcgcttg tgtttcttat gtgagctaac taactaaata gtgtgtatat ttcttgccgc   1380
gccttatgca agccctagtc tagaacatgt aataattaac ttaagcatat acgttgatct   1440
ttggtgtatt tttcatattt ccttcataat gaataatcta ttatgc                   1486
```

<210> SEQ ID NO 100
<211> LENGTH: 1230
<212> TYPE: DNA
<213> ORGANISM: Hordeum vulgare

<400> SEQUENCE: 100

```
atggtggacg tgtcgaactt tgtagaagcc aatggcaatg cagcagtatc gattcctgcc      60
atggaagttg ctgggagtcc tcacgtcccg ttcgttcctc gggacgcgaa cgcgacagac     120
agcaagaatg ccaaggacgt cctcgacctc tggcggcagc agaaacaaat cccggctccc     180
ttcatctggc cccacgccga cgcgcggccg tcgtcgatct ggagctgga cgtgcccgtg      240
gtcgacatcg gcgcggccct gcacagcgcc gccgggatgg cccgcgccgc ggcgcaggtg     300
gccgaggcat gcgcgagcca cggcttcttc aggtgaccg gcacggcgt cgaccccgcg       360
ctggcccaag cagcgctcga cggcgcagcg gacttcttcc gcctgccgct cgccaccaag     420
cagcgcgccc gccgatcccc ggggaccgtc aaagggtacg cctccgccca cgccgaccgc    480
ttcgccgcca agcttccctg aaggagact ctctccttca tccacaacca cgtccacgag     540
gacgtcggcg cccgcgcaag cagtcacgtc gtcgactact tcacctccgc ccttggcgac    600
gacttcatgc acctagggga ggtgtaccag gagtactgtg aggcgatgga ggacgcgtcg    660
ctggcgataa tggaggtgct gggggtgagc ctggggctgg ggagagggta ctacagggac    720
ttcttcgccg acggcagctc catcatgagg tgcaactact acccgcggtg cccggagccg    780
gaccggacgc tggggacggg gccgcactgc gacccgtcgg cgctgaccat cctgctgcag    840
gacggcgagg tggacgggct ccaggtgctc gtcgacggcg catggcgctc cgtgcggccc    900
aagcccggcg agctcgtcgt aaacatcggc gacaccttca tggcgctgtc gaacggccgg    960
tacaagagct gcctccaccg cgcggtggtg caccgggaga aggagcgccg gtcgctggcc   1020
tacttcctcg ccccgcggga ggaccgggtg gttcgcccgc cgccttcgcc ggcgccggcg   1080
ccgcggctct acccggactt cacctgggcg gagctcatgc gattcacgca gcgccactac   1140
cgcgccgacg cccgcacgct cgacgccttc gcgtgctggc tcgacctgcc cagctgcccc   1200
accacgcccc aggcccaagg gactgtctag                                    1230
```

<210> SEQ ID NO 101
<211> LENGTH: 409
<212> TYPE: PRT
<213> ORGANISM: Hordeum vulgare

<400> SEQUENCE: 101

```
Met Val Asp Val Ser Asn Phe Val Glu Ala Asn Gly Asn Ala Ala Val
1               5                   10                  15

Ser Ile Pro Ala Met Glu Val Ala Gly Ser Pro His Val Pro Phe Val
            20                  25                  30

Pro Arg Asp Ala Asn Ala Thr Asp Ser Lys Asn Ala Lys Asp Val Leu
        35                  40                  45

Asp Leu Trp Arg Gln Gln Lys Gln Ile Pro Ala Pro Phe Ile Trp Pro
    50                  55                  60

His Ala Asp Ala Arg Pro Ser Ser Ile Leu Glu Leu Asp Val Pro Val
65                  70                  75                  80

Val Asp Ile Gly Ala Ala Leu His Ser Ala Ala Gly Met Ala Arg Ala
                85                  90                  95

Ala Ala Gln Val Ala Glu Ala Cys Ala Ser His Gly Phe Phe Gln Val
            100                 105                 110

Thr Gly His Gly Val Asp Pro Ala Leu Ala Gln Ala Ala Leu Asp Gly
        115                 120                 125

Ala Ala Asp Phe Phe Arg Leu Pro Leu Ala Thr Lys Gln Arg Ala Arg
    130                 135                 140

Arg Ser Pro Gly Thr Val Lys Gly Tyr Ala Ser Ala His Ala Asp Arg
145                 150                 155                 160
```

Phe Ala Ala Lys Leu Pro Trp Lys Glu Thr Leu Ser Phe Ile His Asn
        165                 170                 175

His Val His Glu Asp Val Gly Ala Arg Ala Ser Ser His Val Val Asp
        180                 185                 190

Tyr Phe Thr Ser Ala Leu Gly Asp Asp Phe Met His Leu Gly Glu Val
        195                 200                 205

Tyr Gln Glu Tyr Cys Glu Ala Met Glu Asp Ala Ser Leu Ala Ile Met
        210                 215                 220

Glu Val Leu Gly Val Ser Leu Gly Leu Gly Arg Gly Tyr Tyr Arg Asp
225                 230                 235                 240

Phe Phe Ala Asp Gly Ser Ser Ile Met Arg Cys Asn Tyr Tyr Pro Arg
                245                 250                 255

Cys Pro Glu Pro Asp Arg Thr Leu Gly Thr Gly Pro His Cys Asp Pro
        260                 265                 270

Ser Ala Leu Thr Ile Leu Leu Gln Asp Gly Glu Val Asp Gly Leu Gln
        275                 280                 285

Val Leu Val Asp Gly Ala Trp Arg Ser Val Arg Pro Lys Pro Gly Glu
290                 295                 300

Leu Val Val Asn Ile Gly Asp Thr Phe Met Ala Leu Ser Asn Gly Arg
305                 310                 315                 320

Tyr Lys Ser Cys Leu His Arg Ala Val His Arg Glu Lys Glu Arg
                325                 330                 335

Arg Ser Leu Ala Tyr Phe Leu Ala Pro Arg Glu Asp Arg Val Val Arg
                340                 345                 350

Pro Pro Pro Ser Pro Ala Pro Ala Pro Arg Leu Tyr Pro Asp Phe Thr
                355                 360                 365

Trp Ala Glu Leu Met Arg Phe Thr Gln Arg His Tyr Arg Ala Asp Ala
370                 375                 380

Arg Thr Leu Asp Ala Phe Ala Cys Trp Leu Asp Leu Pro Ser Cys Pro
385                 390                 395                 400

Thr Thr Pro Gln Ala Gln Gly Thr Val
                405

<210> SEQ ID NO 102
<211> LENGTH: 1423
<212> TYPE: DNA
<213> ORGANISM: Sorghum bicolor

<400> SEQUENCE: 102

```
cctctcatca caggccccag cctcactctt ctcacagcaa gacatcgcag cctcacaacc    60
acacagcaac gtgatcgcca tgggcgggct caccatggag caggccttcg tgcaggcccc   120
cgagcaccgc cccaagccca ccgtcaccga ggccaccggc atcctggtca tcgacctctc   180
gcctctcacc gccagcgaca ccgacgcggc cgcggtggac gcgctggccg ccgaggtggg   240
cgcggcgagc cgggactggg gcttcttcgt ggtggttggc cacggcgtgc ccgcggagac   300
cgtggcgcgc gcgacggcgg cgcagcgcgc gttcttcgcg ctgccggcgg agcggaaggc   360
cgccgtgcgg aggagcgagg cggagccgct cgggtactac gagtcggagc acaccaagaa   420
cgtcagggac tggaaggagg tgttcgacct cgtcccgcgc gatccgccgc cgccagcagc   480
cgtggccgac ggcgagctcg tcttcaagaa caagtgcccc aggatctgcc gggcttcag   540
agaggcgctg gaggagtacg cggcagcgat ggaggagctg tcgttcaagc tgctggagct   600
gatcgcccgg agcttgaagc tgaggcccga ccggctgcac ggcttcttca aggaccagac   660
```

```
gacgttcatc cggctgaacc actaccctcc atgcccgagc cggacctgg cgctgggagt      720
ggggcggcac aaggacgcgg gggcgctgac catcctgtac caggacgaag tgggcgggct      780
ggacgtccgg cggcgctcct ccgacggcgg cggcggcgag tgggtgcggg tgaggcccgt      840
gccggagtcg ttcgtcatca acgtcggcga cctcgtccag gtgtggagca acgacaggta      900
cgagagcgcg gagcaccggg tgtcggtgaa ctcggcgagg gagaggttct ccatgcccta      960
cttcttcaac ccggcgagct acaccatggt ggagccggtg gaggagctgg tgagcgacga     1020
cgacccgccc aggtacgacg cctacagctg gggcgagttc ttcagcacca ggaagaacag     1080
caacttcaag aagctcagcg tggagaacat tcagatcgcg catttcaaga gaccctcgt      1140
cctcgcctag ataagcagca ggatactaca ggtctacagg actaggacaa gccgatcgag     1200
gtgaccggcc gtcgtcttca gattcagtat atgcgtgtcg ccgttcgtgt tagaacaaat     1260
taataatgtg cgcgctgtgt gctgtgtgtg tggagtaaaa aaaaactaaa catggatgtg     1320
catgttcaaa aaaaaaaaca tggatgcgag tatgtttggg aataataaca ggcttgtgac     1380
ggtctggttt atttgcaaat tcaaaccgaa ttggttgatc ttc                       1423
```

<210> SEQ ID NO 103
<211> LENGTH: 1071
<212> TYPE: DNA
<213> ORGANISM: Sorghum bicolor

<400> SEQUENCE: 103

```
atgggcgggc tcaccatgga gcaggccttc gtgcaggccc ccgagcaccg ccccaagccc       60
accgtcaccg aggccaccgg catcctggtc atcgacctct cgcctctcac cgccagcgac      120
accgacgcgg ccgcggtgga cgcgctggcc gccgaggtgg gcgcggcgag ccgggactgg      180
ggcttcttcg tggtggttgg ccacggcgtg cccgcggaga ccgtgccgcg cgcgacggcg      240
gcgcagcgcg cgttcttcgc gctgccggcg gagcggaagg ccgccgtgcg gaggagcgag      300
gcggagccgc tcgggtacta cgagtcggag cacaccaaga acgtcaggga ctggaaggag      360
gtgttcgacc tcgtcccgcg cgatccgccg ccgccagcag ccgtggccga cggcgagctc      420
gtcttcaaga caagtggcc ccaggatctg ccgggcttca gagaggcgct ggaggagtac      480
gcggcagcga tggaggagct gtcgttcaag ctgctggagc tgatcgcccg gagcttgaag      540
ctgaggcccg accggctgca cggcttcttc aaggaccaga cgacgttcat ccggctgaac      600
cactaccctc catgcccgag cccggacctg cgctgggagt ggggcggca aaggacgcg       660
ggggcgctga ccatcctgta ccaggacgaa gtgggcgggc tggacgtccg gcggcgctcc      720
tccgacggcg gcggcggcga gtgggtgcgg gtgaggcccg tgccggagtc gttcgtcatc      780
aacgtcggcg acctcgtcca ggtgtggagc aacgacaggt acgagagcgc ggagcaccgg      840
gtgtcggtga actcggcgag ggagaggttc tccatgccct acttcttcaa cccggcgagc      900
tacaccatgg tggagccggt ggaggagctg gtgagcgacg acgacccgcc caggtacgac      960
gcctacagct ggggcgagtt cttcagcacc aggaagaaca gcaacttcaa gaagctcagc     1020
gtggagaaca ttcagatcgc gcatttcaag agaccctcg tcctcgccta g               1071
```

<210> SEQ ID NO 104
<211> LENGTH: 356
<212> TYPE: PRT
<213> ORGANISM: Sorghum bicolor

<400> SEQUENCE: 104

Met Gly Gly Leu Thr Met Glu Gln Ala Phe Val Gln Ala Pro Glu His

```
  1               5                   10                  15
Arg Pro Lys Pro Thr Val Thr Glu Ala Thr Gly Ile Leu Val Ile Asp
             20                  25                  30

Leu Ser Pro Leu Thr Ala Ser Asp Thr Asp Ala Ala Val Asp Ala
             35                  40                  45

Leu Ala Glu Val Gly Ala Ser Arg Asp Trp Gly Phe Val
 50                  55                  60

Val Val Gly His Gly Val Pro Ala Glu Thr Val Ala Arg Ala Thr Ala
 65                  70                  75                  80

Ala Gln Arg Ala Phe Phe Ala Leu Pro Ala Glu Arg Lys Ala Val
                 85                  90                  95

Arg Arg Ser Glu Ala Glu Pro Leu Gly Tyr Tyr Glu Ser Glu His Thr
                100                 105                 110

Lys Asn Val Arg Asp Trp Lys Glu Val Phe Asp Leu Val Pro Arg Asp
                115                 120                 125

Pro Pro Pro Pro Ala Ala Val Ala Asp Gly Glu Leu Val Phe Lys Asn
130                 135                 140

Lys Trp Pro Gln Asp Leu Pro Gly Phe Arg Glu Ala Leu Glu Tyr
145                 150                 155                 160

Ala Ala Ala Met Glu Glu Leu Ser Phe Lys Leu Leu Glu Leu Ile Ala
                165                 170                 175

Arg Ser Leu Lys Leu Arg Pro Asp Arg Leu His Gly Phe Phe Lys Asp
                180                 185                 190

Gln Thr Thr Phe Ile Arg Leu Asn His Tyr Pro Pro Cys Pro Ser Pro
                195                 200                 205

Asp Leu Ala Leu Gly Val Gly Arg His Lys Asp Ala Gly Ala Leu Thr
    210                 215                 220

Ile Leu Tyr Gln Asp Glu Val Gly Gly Leu Asp Val Arg Arg Ser
225                 230                 235                 240

Ser Asp Gly Gly Gly Glu Trp Val Arg Val Arg Pro Val Pro Glu
                245                 250                 255

Ser Phe Val Ile Asn Val Gly Asp Leu Val Gln Val Trp Ser Asn Asp
                260                 265                 270

Arg Tyr Glu Ser Ala Glu His Arg Val Ser Val Asn Ser Ala Arg Glu
    275                 280                 285

Arg Phe Ser Met Pro Tyr Phe Asn Pro Ala Ser Tyr Thr Met Val
    290                 295                 300

Glu Pro Val Glu Glu Leu Val Ser Asp Asp Pro Pro Arg Tyr Asp
305                 310                 315                 320

Ala Tyr Ser Trp Gly Glu Phe Phe Ser Thr Arg Lys Asn Ser Asn Phe
                325                 330                 335

Lys Lys Leu Ser Val Glu Asn Ile Gln Ile Ala His Phe Lys Lys Thr
                340                 345                 350

Leu Val Leu Ala
        355

<210> SEQ ID NO 105
<211> LENGTH: 1499
<212> TYPE: DNA
<213> ORGANISM: Sorghum bicolor

<400> SEQUENCE: 105
cctctcatca caggccccag cctcactctt ctcacagcaa gacatcgcag cctcacaacc    60
acacagcaac gtgatcgcca tgggcgggct caccatggag caggccttcg tgcaggcccc   120
```

```
cgagcaccgc cccaagccca ccgtcaccga ggccaccggc atcctggtca tcgacctctc    180
gcctctcacc gccagcgaca ccgacgcggc cgcggtggac gcgctggccg ccgaggtggg    240
cgcggcgagc cgggactggg gcttcttcgt ggtggttggc cacggcgtgc ccgcggagac    300
cgtggcgcgc gcgacggcgg cgcagcgcgc gttcttcgcg ctgccggcgg agcggaaggc    360
cgccgtgcgg aggagcgagg cggagccgct cgggtactac gagtcggagc acaccaagaa    420
cgtcagggac tggaaggagg tgttcgacct cgtcccgcgc gatccgccgc cgccagcagc    480
cgtggccgac ggcgagctcg tcttcaagaa caagtggccc caggatctgc cgggcttcag    540
gtgacgaaat caactatct tttcgatcat atttaccat taatagttt aacaataatt       600 gaactttttt ttgcagagag gcgctggagg agtacgcggc agcgatggag gagctgtcgt    660
tcaagctgct ggagctgatc gcccggagct gaagctgag gcccgaccgg ctgcacggct    720
tcttcaagga ccagacgacg ttcatccggc tgaaccacta ccctccatgc ccgagcccgg    780
acctggcgct gggagtgggg cggcacaagg acgcggggc gctgaccatc ctgtaccagg    840
acgaagtggg cgggctggac gtccggcggc gctcctccga cggcggcggc ggcgagtggg    900
tgcgggtgag gcccgtgccg gagtcgttcg tcatcaacgt cggcgacctc gtccaggtgt    960
ggagcaacga caggtacgag agcgcggagc accgggtgtc ggtgaactcg gcgagggaga    1020
ggttctccat gccctacttc ttcaacccgg cgagctacac catggtggag ccggtggagg    1080
agctggtgag cgacgacgac ccgcccaggt acgacgccta cagctggggc gagttcttca    1140
gcaccaggaa gaacagcaac ttcaagaagc tcagcgtgga gaacattcag atcgcgcatt    1200
tcaagaagac cctcgtcctc gcctagataa gcagcaggat actacaggtc tacaggacta    1260
ggacaagccg atcgaggtga ccggccgtcg tcttcagatt cagtatatgc gtgtcgccgt    1320
tcgtgttaga acaaattaat aatgtgcgcg ctgtgtgctg tgtgtgtgga gtaaaaaaaa    1380
actaaacatg gatgtgcatg ttcaaaaaaa aaaacatgga tgcgagtatg tttgggaata    1440
ataacaggct tgtgacggtc tggttttatt gcaaattcaa accgaattgg ttgatcttc     1499
```

<210> SEQ ID NO 106
<211> LENGTH: 1490
<212> TYPE: DNA
<213> ORGANISM: Setaria italica

<400> SEQUENCE: 106

```
accccacaca cacacccgca ctgcatgcgg cgtcctagct aatcagtcgc tgctggcagc     60
ctcacaagtc acacaactcc gacgcaggaa agctcgatcc atcgccatgg gcggcttctc    120
catggatcag tccttcgtgc aggccccgga gcaccgcccc aagcccaccg tcaccgaggc    180
cacgggcatc ccgctcatcg acctctcgcc actcaccggc ggtggcggcg cgacgcggc     240 cgccgtggac gcgctggccg ccgaggtggg cgcggcgagc cgggactggg gcttcttcgt    300
ggtggtgggc cacggtgtgc cggcggagac cgtggcgcgc gccacggagg cgcagcgcgc    360
gttcttcgcc ctgccggcgg agcggaaagc cgccgtgcgg aggagcgagg cggagccgct    420
cgggtactac gagtcggagc acaccaagaa cgtcagggac tggaaggagg tgtacgacct    480
cgtcccgggc gggcttcagc cgccgatagc cgtggccgac ggcgaggtcg tgttcgaaaa    540
caagtggccc gaagacctgc cgggattcag agaggcgttg gaggagtaca tgcaagcgat    600
ggaagagctg gcattcaaga tactggagct gatcgcccgg agcctgaacc tgaggcctga    660
cagactgcac ggcttcttca aggaccagac caccttcatc cggctcaacc actaccctcc    720
```

```
ctgcccgagc ccgacctcg ccctcggcgt cggccggcac aaggacgccg agcactgac     780 catcctctac caggacgacg tcggcgggct cgacgtccgg cgccgttccg acggcgattg    840
ggtccgcgtc aagcctgtcc ccgactcctt catcatcaac gtcggcgacc tcatccaggt   900
ttggagcaac gacaggtacg agagcgcgga gcaccgggtt acggtgaact cggccaagga   960
gaggttctcc aggccctact tcttcaaccc ggcgggctac accatggtgg agccggtgga  1020
ggagctggtg agcgaggagg acccgccccg tacgacgcc tacaactggg caacttctt   1080 cagcaccagg aagaacagca acttcaagaa gctgagcgtg gagaacatcc agatcgcgca  1140
tttcaagagg agcgtcgccg cctaggatac gcacagaaag atcccatatg ctgacttgct  1200
gatgaggcga caggcggccg tgtcgtcttc agattcagag actgggagta acatttgtg   1260 cggtgttctg taatcgtgat gtgacgaaaa ctttagatat atgtttggaa ataacagcct  1320
tgtgttggtc tggcttatcc gcaaagtcaa gattttcttc tacattttgg gattattgtt  1380
ggtaagcatt aagcaacgtc cagttcttac ttcttagctc gatcagtgga cgtaggaccg  1440
gcctctgatg acaagggtga tttatgagaa atgtcatgta tatatgttcc              1490

<210> SEQ ID NO 107
<211> LENGTH: 1059
<212> TYPE: DNA
<213> ORGANISM: Setaria italica

<400> SEQUENCE: 107
atgggcggct ctccatgga tcagtccttc gtgcaggccc ccgagcaccg ccccaagccc     60
accgtcaccg aggccacggg catcccgctc atcgacctct cgccactcac cggcggtggc   120
ggcggcgacg cggccgccgt ggacgcgctg ccgccgagg tgggcgcggc gagccgggac    180
tggggcttct tcgtggtggt ggggcacggt gtgccggcgg agaccgtggc gcgcgccacg   240
gaggcgcagc gcgcgttctt cgccctgccg gcggagcgga agccgccgt gcggaggagc    300 gaggcggagc cgctcgggta ctacgagtcg gagcacacca gaacgtcag ggactggaag    360 gaggtgtacg acctcgtccc gggcgggctt cagccgccga tagccgtggc cgacggcgag   420
gtcgtgttcg aaaacaagtg gcccgaagac ctgccgggat tcagagaggc gttggaggag   480
tacatgcaag cgatggaaga gctggcattc aagatactgg agctgatcgc ccggagcctg   540
aacctgaggc ctgacagact gcacggcttc ttcaaggacc agaccaccttt catccggctc   600 aaccactacc ctccctgccc gagccccgac ctcgccctcg gcgtcggccg cacaaggac   660 gccgagcac tgaccatcct ctaccaggac gacgtcggcg gctcgacgt ccggcgccgt   720 tccgacggcg attgggtccg cgtcaagcct gtccccgact ccttcatcat caacgtcggc   780
gacctcatcc aggtttggag caacgacagg tacgagagcg cggagcaccg ggttacggtg   840
aactcggcca aggagaggtt ctccaggccc tacttcttca cccggcggg ctacaccatg    900 gtggagccgg tggaggagct ggtgagcgag gaggacccgc ccggtacga cgcctacaac   960 tggggcaact tcttcagcac caggaagaac agcaacttca agaagctgag cgtggagaac  1020
atccagatcg cgcatttcaa gaggagcgtc gccgcctag                         1059

<210> SEQ ID NO 108
<211> LENGTH: 352
<212> TYPE: PRT
<213> ORGANISM: Setaria italica

<400> SEQUENCE: 108

Met Gly Gly Phe Ser Met Asp Gln Ser Phe Val Gln Ala Pro Glu His
```

```
           1               5                  10                 15
         Arg Pro Lys Pro Thr Val Thr Glu Ala Thr Gly Ile Pro Leu Ile Asp
                         20                 25                 30

Leu Ser Pro Leu Thr Gly Gly Gly Gly Asp Ala Ala Val Asp
                         35             40                 45

Ala Leu Ala Ala Glu Val Gly Ala Ala Ser Arg Asp Trp Gly Phe Phe
                 50                  55                 60

Val Val Val Gly His Gly Val Pro Ala Glu Thr Val Ala Arg Ala Thr
         65                  70                     75                 80

Glu Ala Gln Arg Ala Phe Phe Ala Leu Pro Ala Glu Arg Lys Ala Ala
                         85                 90                 95

Val Arg Arg Ser Glu Ala Glu Pro Leu Gly Tyr Tyr Glu Ser Glu His
                         100                105                110

Thr Lys Asn Val Arg Asp Trp Lys Glu Val Tyr Asp Leu Val Pro Gly
                         115                120                125

Gly Leu Gln Pro Pro Ile Ala Val Ala Asp Gly Glu Val Val Phe Glu
                 130                 135                140

Asn Lys Trp Pro Glu Asp Leu Pro Gly Phe Arg Glu Ala Leu Glu Glu
         145                 150                 155                160

Tyr Met Gln Ala Met Glu Glu Leu Ala Phe Lys Ile Leu Glu Leu Ile
                         165                170                175

Ala Arg Ser Leu Asn Leu Arg Pro Asp Arg Leu His Gly Phe Phe Lys
                         180                185                190

Asp Gln Thr Thr Phe Ile Arg Leu Asn His Tyr Pro Pro Cys Pro Ser
                         195                200                205

Pro Asp Leu Ala Leu Gly Val Gly Arg His Lys Asp Ala Gly Ala Leu
                 210                 215                220

Thr Ile Leu Tyr Gln Asp Val Gly Gly Leu Asp Val Arg Arg Arg
         225                 230                 235                240

Ser Asp Gly Asp Trp Val Arg Val Lys Pro Val Pro Asp Ser Phe Ile
                         245                250                255

Ile Asn Val Gly Asp Leu Ile Gln Val Trp Ser Asn Asp Arg Tyr Glu
                         260                265                270

Ser Ala Glu His Arg Val Thr Val Asn Ser Ala Lys Glu Arg Phe Ser
                         275                280                285

Arg Pro Tyr Phe Phe Asn Pro Ala Gly Tyr Thr Met Val Glu Pro Val
                         290                295                300

Glu Glu Leu Val Ser Glu Asp Pro Pro Arg Tyr Asp Ala Tyr Asn
         305                 310                 315                320

Trp Gly Asn Phe Phe Ser Thr Arg Lys Asn Ser Asn Phe Lys Lys Leu
                         325                330                335

Ser Val Glu Asn Ile Gln Ile Ala His Phe Lys Arg Ser Val Ala Ala
                         340                345                350

<210> SEQ ID NO 109
<211> LENGTH: 1886
<212> TYPE: DNA
<213> ORGANISM: Setaria italica

<400> SEQUENCE: 109
accccacaca cacacccgca ctgcatgcgg cgtcctagct aatcagtcgc tgctggcagc      60
ctcacaagtc acacaactcc gacgcaggaa agctcgatcc atcgccatgg gcggcttctc     120
catggatcag tccttcgtgc aggccccga gcaccgcccc aagcccaccg tcaccgaggc     180
```

| | |
|---|---|
| cacgggcatc cgctcatcg acctctcgcc actcaccggc ggtggcggcg gcgacgcggc | 240 |
| cgccgtggac gcgctggccg ccgaggtggg cgcggcgagc cgggactggg gcttcttcgt | 300 |
| ggtggtgggg cacggtgtgc cggcggagac cgtgcgcgc gccacggagg cgcagcgcgc | 360 |
| gttcttcgcc ctgccggcgg agcggaaagc cgccgtgcgg aggagcgagg cggagccgct | 420 |
| cgggtactac gagtcggagc acaccaagaa cgtcagggac tggaaggagg tgtacgacct | 480 |
| cgtcccgggc gggcttcagc cgccgatagc cgtggccgac ggcgaggtcg tgttcgaaaa | 540 |
| caagtggccc gaagacctgc cgggattcag gtgaatcaac ttgcgcatat tgttgtttct | 600 |
| ggcattgcat atgatcgtcg tgccagtatg ttttgacaat attttgttt tcatattttt | 660 |
| ggtgaagatg gaaaatcttt tgttgaaata atcagggaat tttcacatct tttttaatc | 720 |
| aaagatagaa taggttcggt tactgaattt tgatgatgga cagaaaaagc tgtgttttca | 780 |
| ctttccatct cagcgatgtt tttttgtgga tgaattctcc taaattttg tcttttcatg | 840 |
| ttaaaacttg aacgggaatt ctcgcagaga ggcgttggag gagtacatgc aagcgatgga | 900 |
| agagctggca ttcaagatac tggagctgat cgcccgagc ctgaacctga ggcctgacag | 960 |
| actgcacggc ttcttcaagg accagaccac cttcatccgg ctcaaccact accctccctg | 1020 |
| cccgagcccc gacctcgccc tcggcgtcgg ccggcacaag gacgccggag cactgaccat | 1080 |
| cctctaccag gacgacgtcg gcgggctcga cgttccggcgc cgttccgacg gcgattgggt | 1140 |
| ccgcgtcaag cctgtccccg actccttcat catcaacgtc ggcgacctca tccaggtaca | 1200 |
| acaaacaaaa acacacgtca ttctcaaatc ttttcgtgct gttaatgctc attcacgaat | 1260 |
| tgatatctta catgaacgac tgagactttt tcaggtttgg agcaacgaca ggtacgagag | 1320 |
| cgcggagcac cgggttacgg tgaactcggc caaggagagg ttctccaggc cctacttctt | 1380 |
| caacccggcg ggctacacca tggtggagcc ggtggaggag ctggtgagcg aggaggaccc | 1440 |
| gccccggtac gacgcctaca actggggcaa cttcttcagc accaggaaga acagcaactt | 1500 |
| caagaagctg agcgtggaga acatccagat cgccgcatttc aagaggagcg tcgccgccta | 1560 |
| ggatacgcac agaaagatcc catatgctga cttgctgatg aggcgacagg cggccgtgtc | 1620 |
| gtcttcagat tcagagactg ggagtaaaca tttgtgcggt gttctgtaat cgtgatgtga | 1680 |
| cgagaacttt agatatatgt ttggaaataa cagccttgtg ttggtctggc ttatccgcaa | 1740 |
| agtcaagatt tcttctaca ttttgggatt attgttggta agcattaagc aacgtccagt | 1800 |
| tcttacttct tagctcgatc agtggacgta ggaccggcct ctgatgacaa gggtgattta | 1860 |
| tgagaaatgt catgtatata tgttcc | 1886 |

<210> SEQ ID NO 110
<211> LENGTH: 1379
<212> TYPE: DNA
<213> ORGANISM: Oryza sativa

<400> SEQUENCE: 110

| | |
|---|---|
| aagccacacg cacacacaca cacacgctga cacacgagac gaaacacttgt gctacagctt | 60 |
| ctcgccacca gctactgatc gaccatgggc ggcctctcca tggaccaggc gttcgtgcag | 120 |
| gcccccgagc accgccccaa ggcgtccgtc gccgaggccg acggcatccc ggtcatcgac | 180 |
| ctctcccctc tcctcgccgc cggcgatggc gacgccgacg gggtggacgc gctcgcggcg | 240 |
| gaggtcggga gggcgagccg ggactgggc ttcttcgtgg tggtgcgcca cggtgtgccc | 300 |
| gcggaggcgt ggcgcgcgc ggcggaggcg cagaggacgt tcttcgcgct gccgccggag | 360 |
| cggagggcgg ccgtggcgcg gagcgaggcg gcgccgatgg ggtactacgc gtccgagcac | 420 |

```
accaagaacg tcagggactg gaaggaggtg ttcgacctcg tcccgcgcca gacgccgccg    480
ccgccgacga ccgccgtggc cgacggcgac ctggtgttcg acaacaagtg gcccgacgac    540
ctgccgggat tcaggaggc aatggaggag tacggcgaag cggtggagga gctggcgttc     600
aagctgctgg agctgatcgc caggagcctc ggcctgagac ccgaccgcct ccatggcttc    660
ttcaaggacg accagaccac cttcatccgg ctcaaccact accctccctg cccgagcccc    720
gacctcgccc tcggcgtcgg ccgccacaag gacgccggcg cgctcaccgt gctctaccag    780
gacgatgtcg gcggcctcga cgtccgccgc cgatccgacg gcgagtgggt gcgcgtcagg    840
cccgtccctc actccttcat catcaacgtc ggcgacatca tccaggtgtg gagcaatgac    900
aggtacgaga gcgcggagca ccgggtggcg gtgaacgtgg agaaggagag gttctccatc    960
cctttcttct tcaacccggc gggccacacc atggtggagc cactggagga ggtcgtgagc   1020
gacgagagcc cggccaggta caacccctac aactggggcg aattcttcag caccaggaag   1080
aacagcaact tcaagaagct ggacgtggag aacgtccaga tcacgcatttt caggaagaat   1140 taacgcgccg gctagatcat gttcagtaaa ttttcagatg atgatgcgtg gacaaccata   1200
tagcctttgc gtcataagtt aataatgtct gtgacagtat atcatgtaaa caatcgtatg   1260
atgtggcttc tctatctgcc ggtgatggta atgtgacatt gtagaagagg gtttgtgaga   1320
tacttccttc acttaacttt tacgaatgaa tatagacaac cacaacatcc ttgtcgtga    1379

<210> SEQ ID NO 111
<211> LENGTH: 1059
<212> TYPE: DNA
<213> ORGANISM: Oryza sativa

<400> SEQUENCE: 111
atgggcggcc tctccatgga ccaggcgttc gtgcaggccc ccgagcaccg ccccaaggcg     60
tccgtcgccg aggccgacgg catcccggtc atcgacctct cccctctcct cgccgccggc    120 gatgcgacg ccgacggggt ggacgcgctc gcggcggagg tcgggagggc gagccgggac     180 tgggcttct tcgtggtggt gcgccacggt gtgcccgcgg aggcggtggc gcgcgcggcg     240
gaggcgcaga ggacgttctt cgcgctgccg ccggagcgga gggcggccgt ggcgcggagc    300
gaggcggcgc cgatggggta ctacgcgtcc gagcacacca agaacgtcag ggactggaag    360
gaggtgttcg acctcgtccc gcgccagacg ccgccgccgc cgacgaccgc cgtggccgac    420
ggcgacctgg tgttcgacaa caagtggccc gacgacctgc cgggattcag ggaggcaatg    480
gaggagtacg gcgaagcggt ggaggagctg gcgttcaagc tgctggagct gatcgccagg    540
agcctcggcc tgagacccga ccgcctccat ggcttcttca aggacgacca gaccaccttc    600
atccggctca accactaccc tccctgcccg agccccgacc tcgccctcgg cgtcggccgc    660
cacaaggacg ccggcgcgct caccgtgctc taccaggacg atgtcggcgg cctcgacgtc    720
cgccgccgat ccgacggcga gtgggtgcgc gtcaggcccg tccctcactc cttcatcatc    780
aacgtcggcg acatcatcca ggtgtggagc aatgacaggt acgagagcgc ggagcaccgg    840
gtggcggtga acgtggagaa ggagaggttc tccatcccctt tcttcttcaa cccggcgggc    900
cacaccatgg tggagccact ggaggaggtc gtgagcgacg agagcccggc caggtacaac    960
ccctacaact ggggcgaatt cttcagcacc aggaagaaca gcaacttcaa gaagctggac   1020
gtggagaacg tccagatcac gcatttcagg aagaattaa                           1059

<210> SEQ ID NO 112
```

```
<211> LENGTH: 352
<212> TYPE: PRT
<213> ORGANISM: Oryza sativa

<400> SEQUENCE: 112

Met Gly Gly Leu Ser Met Asp Gln Ala Phe Val Gln Ala Pro Glu His
1               5                   10                  15

Arg Pro Lys Ala Ser Val Ala Glu Ala Asp Gly Ile Pro Val Ile Asp
            20                  25                  30

Leu Ser Pro Leu Leu Ala Ala Gly Asp Gly Asp Ala Asp Gly Val Asp
        35                  40                  45

Ala Leu Ala Ala Glu Val Gly Arg Ala Ser Arg Asp Trp Gly Phe Phe
    50                  55                  60

Val Val Val Arg His Gly Val Pro Ala Glu Ala Val Arg Ala Ala
65                  70                  75                  80

Glu Ala Gln Arg Thr Phe Phe Ala Leu Pro Pro Glu Arg Arg Ala Ala
                85                  90                  95

Val Ala Arg Ser Glu Ala Ala Pro Met Gly Tyr Tyr Ala Ser Glu His
            100                 105                 110

Thr Lys Asn Val Arg Asp Trp Lys Glu Val Phe Asp Leu Val Pro Arg
        115                 120                 125

Gln Thr Pro Pro Pro Thr Thr Ala Val Ala Asp Gly Asp Leu Val
    130                 135                 140

Phe Asp Asn Lys Trp Pro Asp Asp Leu Pro Gly Phe Arg Glu Ala Met
145                 150                 155                 160

Glu Glu Tyr Gly Glu Ala Val Glu Leu Ala Phe Lys Leu Leu Glu
                165                 170                 175

Leu Ile Ala Arg Ser Leu Gly Leu Arg Pro Asp Arg Leu His Gly Phe
            180                 185                 190

Phe Lys Asp Asp Gln Thr Thr Phe Ile Arg Leu Asn His Tyr Pro Pro
        195                 200                 205

Cys Pro Ser Pro Asp Leu Ala Leu Gly Val Gly Arg His Lys Asp Ala
    210                 215                 220

Gly Ala Leu Thr Val Leu Tyr Gln Asp Asp Val Gly Gly Leu Asp Val
225                 230                 235                 240

Arg Arg Arg Ser Asp Gly Glu Trp Val Arg Val Arg Pro Val Pro His
                245                 250                 255

Ser Phe Ile Ile Asn Val Gly Asp Ile Ile Gln Val Trp Ser Asn Asp
            260                 265                 270

Arg Tyr Glu Ser Ala Glu His Arg Val Ala Val Asn Val Glu Lys Glu
        275                 280                 285

Arg Phe Ser Ile Pro Phe Phe Asn Pro Ala Gly His Thr Met Val
    290                 295                 300

Glu Pro Leu Glu Glu Val Val Ser Asp Glu Ser Pro Ala Arg Tyr Asn
305                 310                 315                 320

Pro Tyr Asn Trp Gly Phe Phe Ser Thr Arg Lys Asn Ser Asn Phe
                325                 330                 335

Lys Lys Leu Asp Val Glu Asn Val Gln Ile Thr His Phe Arg Lys Asn
            340                 345                 350

<210> SEQ ID NO 113
<211> LENGTH: 2027
<212> TYPE: DNA
<213> ORGANISM: Oryza sativa

<400> SEQUENCE: 113
```

| | | | | | |
|---|---|---|---|---|---|
| aagccacacg | cacacacaca | cacacgctga | cacacgagac | gaacacttgt | gctacagctt | 60
| ctcgccacca | gctactgatc | gaccatgggc | ggcctctcca | tggaccaggc | gttcgtgcag | 120
| gcccccgagc | accgcccaa | ggcgtccgtc | gccgaggccg | acggcatccc | ggtcatcgac | 180
| ctctcccctc | tcctcgccgc | cggcgatggc | gacgccgacg | gggtgacgc | gctcgcggcg | 240
| gaggtcggga | gggcgagccg | ggactgtggc | ttcttcgtgg | tggtgcgcca | cggtgtgccc | 300
| gcggaggcg | tggcgcgcgc | ggcggaggcg | cagaggacgt | tcttcgcgct | gccgccggag | 360
| cggagggcgg | ccgtggcgcg | gagcgaggcg | gcgccgatgg | ggtactacgc | gtccgagcac | 420
| accaagaacg | tcagggactg | gaaggaggtg | ttcgacctcg | tcccgcgcca | gacgccgccg | 480
| ccgccgacga | ccgccgtggc | cgacggcgac | ctggtgttcg | acaacaagtg | gcccgacgac | 540
| ctgccgggat | tcaggtcagg | tcaccacatc | gatcgatcgt | cttcttcatc | ctcgcatcaa | 600
| ttcagttcaa | cctcatcgaa | ttcttgagca | gggaggcaat | ggaggagtac | ggcgaagcgg | 660
| tggaggagct | ggcgttcaag | ctgctggagc | tgatcgccag | gagcctcggc | ctgagacccg | 720
| accgcctcca | tggcttcttc | aaggacgacc | agaccaccct | catccggctc | aaccactacc | 780
| ctccctgccc | gagccccgac | ctcgccctcg | gcgtcggccg | ccacaaggac | gccggcgcgc | 840
| tcaccgtgct | ctaccaggac | gatgtcggcg | gcctcgacgt | ccgccgccga | tccgacggcg | 900
| agtgggtgcg | cgtcaggccc | gtccctcact | ccttcatcat | caacgtcggc | gacatcatcc | 960
| aggtactttt | tttttgagc | agctacatat | ttatcaacaa | attttcttct | aacaatttat | 1020
| cggacataaa | tatattacaa | tgaaagaata | attgtatcat | aacttgtgtg | tccttatatg | 1080
| taagttttag | aaatcctata | gtaacatggt | attttcgcga | aagcggagat | tgtgagaccg | 1140
| tatcttttca | cccatgcgcg | tcatatgatt | tttttttctt | gccaacttaa | ataaatttca | 1200
| aagtaaatct | aatagattaa | aattatgtga | aacttacata | taagttttct | acggtaacac | 1260
| gctattttca | cgaaacggag | gtcgttccaa | gttgaatgaa | tcttgaagta | aatctaacga | 1320
| tttaaaatta | tgtgcataca | cgttatatta | cagttatata | caagttataa | tataattaca | 1380
| ctacaattat | aacggtattc | atagttgaca | aacttttaaa | agagaattag | ttaataaata | 1440
| tataacaaca | ttgtagttta | attgttacta | tttgacatca | tttttatttg | cattttgaat | 1500
| ttgactgaaa | aaattgagag | tgcgcttgtc | caggtgtgga | gcaatgacag | gtacgagagc | 1560
| gcggagcacc | gggtggcggt | gaacgtggag | aaggagaggt | tctccatccc | tttcttcttc | 1620
| aacccggcgg | gccacaccat | ggtggagcca | ctggaggagg | tcgtgagcga | cgagagcccg | 1680
| gccaggtaca | accctacaa | ctggggcgaa | ttcttcagca | ccaggaagaa | cagcaacttc | 1740
| aagaagctgg | acgtggagaa | cgtccagatc | acgcatttca | ggaagaatta | acgcgccggc | 1800
| tagatcatgt | tcagtaaatt | ttcagatgat | gatgcgtgga | caaccatata | gcctttgcgt | 1860
| cataagttaa | taatgtctgt | gacagtatat | catgtaaaca | atcgtatgat | gtggcttctc | 1920
| tatctgccgg | tgatggtaat | gtgacattgt | agaagagggt | ttgtgagata | cttccttcac | 1980
| ttaactttta | cgaatgaata | tagacaacca | caacatcctt | gtcgtga | | 2027

<210> SEQ ID NO 114
<211> LENGTH: 1747
<212> TYPE: DNA
<213> ORGANISM: Triticum aestivum

<400> SEQUENCE: 114

| | | | | | |
|---|---|---|---|---|---|
| tcactcaagg | ccacaacaca | ctcgccagtc | catcgccacc | atacgtgaca | acttgagtta | 60

```
cttgatctgt tgctcatcga tctcgacatc gccatgggcg gcctctccat ggaccaggcc      120
ttcgtgcagg cccccgagca tcgcaccaag gcgaacctcg ccgacgcggc cggcatcccg      180
gtcatcgacc tctcccctct cgccgccggc gacaaggccg gcctggacgc cctcgcggcc      240
gaggtgggca gggcgagccg tgactgggg ttcttcgtgg tggtgcgcca cggcgtgccg       300
gcggagacgg tggcgcgggc gctggaggcg cagagggcct tcttcgcgct gcccgcggac      360
cggaaggcgg ccgtgcggag ggacgaggcg gcgccgctgg ggtactacga gtcggagcac      420
accaagaacg tcagggactg gaaggaggtg ttcgacctcg tccccgcga ccgccgccg        480 cctgccgcgg ttgccgacgg cgagctcatg ttcgagaaca gtggcccga ggacctgccg       540 gggttcagag aggctctcga agagtacgag aaagcgatgg aggagctggc gttcaagctg      600
ctggagctga tcgcccggag cctgggactg agaccggacc ggctgcacgg cttcttcaag      660
gaccagacca ccttcatccg gctgaaccac taccgcct gccccagccc cgacctcgcc        720
ctcggcgtcg tcgccacaa ggacgccggc gcgctcacca tcctctacca ggacgacgtc       780
ggcgggctcg acgtccggcg ccgctccgac ggcgagtggg tgcgcgtcag gcctgtcccg      840
gactcctacg tcatcaacgt cggcgacatc atccaggtgt ggagcaacga caggtacgag      900
agcgcggagc acagggtgtc ggtgaactcg cacaaggaga ggttctccat gccctacttc      960
ttcgaccccg ggagcgacgc catgatcgag ccgttggagg agatggtgag cgacgaaagg     1020
ccggccaggt acgacgccta caactgggc aacttcttca gcaccaggaa gaacagcaac      1080
ttcaggaagc tcgccgtcga aaacgtccag atcgcacact tcagaaagga ccgaccttaa     1140
atgaaggatc cctcatgaat tcatgatcct tccgctctcc tcagtgatcc tagtgctaca    1200
actacaagca tctccccgtt tgtagtaatc atatataaat aagtattccc tccgtaaact    1260
aatataagag catttaaaac actactctag tgatctaaat gctcttatat tagtttacag    1320
agagagtatt gtgtattaat aatgactttc tctgtttcaa ataagtgat gacgtggttt     1380 tagttcaatt ttttttagag aggaggcatc tgacgggcct taaactgagg accttagagt    1440
acaaacaagg ttcgacgaaa gtaagtttaa gggatacaag gccgtagcca acaaaacgcg    1500
acgcagcgcg caatctaaaa tcagcgtgct gtcaaggtag ctggagacgt ccatgccgtt    1560
aatctctctc aagaagctcg ccgaagctca gtgcaccttg cgtgcactct tgtgaagagc    1620
accttcacgt gtccttgtc ctgagatttt gtcaacagtt tccatgactg caagaaaaac    1680
actagtttgt ataatagctc agcgggatgt cgaatgaatt gcccctcaat caaagcttta   1740
tttctag                                                              1747
```

<210> SEQ ID NO 115
<211> LENGTH: 1047
<212> TYPE: DNA
<213> ORGANISM: Triticum aestivum

<400> SEQUENCE: 115

```
atgggcggcc tctccatgga ccaggccttc gtgcaggccc cgagcatcg caccaaggcg        60 aacctcgccg acgcggccgg catcccggtc atcgacctct cccctctcgc cgccggcgac      120
aaggccggcc tggacgccct cgcggccgag gtgggcaggg cgagccgtga ctgggggttc      180
ttcgtggtgg tgcgccacgg cgtgccggcg gagacggtgg cgcgggcgct ggaggcgcag      240
agggccttct tcgcgctgcc cgcggaccgg aaggcggcc tgcggaggga cgaggcggcg      300
ccgctggggt actacgagtc ggagcacacc aagaacgtca gggactggaa ggaggtgttc      360
gacctcgtcc ccgcgagcc gccgccgcct gccgcggttg ccgacggcga gctcatgttc      420
```

```
gagaacaagt ggcccgagga cctgccgggg ttcagagagg ctctcgaaga gtacgagaaa      480
gcgatggagg agctggcgtt caagctgctg gagctgatcg cccggagcct gggactgaga      540
ccggaccggc tgcacggctt cttcaaggac cagaccacct tcatccggct gaaccactac      600
ccgccctgcc ccagccccga cctcgccctc ggcgtcggtc gccacaagga cgccggcgcg      660
ctcaccatcc tctaccagga cgacgtcggc gggctcgacg tccggcgccg ctccgacggc      720
gagtgggtgc gcgtcaggcc tgtcccggac tcctacgtca tcaacgtcgg cgacatcatc      780
caggtgtgga gcaacgacag gtacgagagc gcggagcaca gggtgtcggt gaactcgcac      840
aaggagaggt tctccatgcc ctacttcttc gaccccggga gcgacgccat gatcgagccg      900
ttggaggaga tggtgagcga cgaaaggccg gccaggtacg acgcctacaa ctggggcaac      960
ttcttcagca ccaggaagaa cagcaacttc aggaagctcg ccgtcgaaaa cgtccagatc     1020
gcacacttca gaaaggaccg accttaa                                         1047
```

<210> SEQ ID NO 116
<211> LENGTH: 348
<212> TYPE: PRT
<213> ORGANISM: Triticum aestivum
<400> SEQUENCE: 116

```
Met Gly Gly Leu Ser Met Asp Gln Ala Phe Val Gln Ala Pro Glu His
1               5                   10                  15

Arg Thr Lys Ala Asn Leu Ala Asp Ala Ala Gly Ile Pro Val Ile Asp
            20                  25                  30

Leu Ser Pro Leu Ala Ala Gly Asp Lys Ala Gly Leu Asp Ala Leu Ala
        35                  40                  45

Ala Glu Val Gly Arg Ala Ser Arg Asp Trp Gly Phe Phe Val Val Val
    50                  55                  60

Arg His Gly Val Pro Ala Glu Thr Val Ala Arg Ala Leu Glu Ala Gln
65                  70                  75                  80

Arg Ala Phe Phe Ala Leu Pro Ala Asp Arg Lys Ala Ala Val Arg Arg
                85                  90                  95

Asp Glu Ala Ala Pro Leu Gly Tyr Tyr Glu Ser Glu His Thr Lys Asn
            100                 105                 110

Val Arg Asp Trp Lys Glu Val Phe Asp Leu Val Pro Arg Glu Pro Pro
        115                 120                 125

Pro Pro Ala Ala Val Ala Asp Gly Glu Leu Met Phe Glu Asn Lys Trp
    130                 135                 140

Pro Glu Asp Leu Pro Gly Phe Arg Glu Ala Leu Glu Glu Tyr Glu Lys
145                 150                 155                 160

Ala Met Glu Glu Leu Ala Phe Lys Leu Leu Glu Leu Ile Ala Arg Ser
                165                 170                 175

Leu Gly Leu Arg Pro Asp Arg Leu His Gly Phe Phe Lys Asp Gln Thr
            180                 185                 190

Thr Phe Ile Arg Leu Asn His Tyr Pro Pro Cys Pro Ser Pro Asp Leu
        195                 200                 205

Ala Leu Gly Val Gly Arg His Lys Asp Ala Gly Ala Leu Thr Ile Leu
    210                 215                 220

Tyr Gln Asp Asp Val Gly Gly Leu Asp Val Arg Arg Ser Asp Gly
225                 230                 235                 240

Glu Trp Val Arg Val Arg Pro Val Pro Asp Ser Tyr Val Ile Asn Val
                245                 250                 255
```

```
Gly Asp Ile Ile Gln Val Trp Ser Asn Asp Arg Tyr Glu Ser Ala Glu
            260                 265                 270

His Arg Val Ser Val Asn Ser His Lys Glu Arg Phe Ser Met Pro Tyr
        275                 280                 285

Phe Phe Asp Pro Gly Ser Asp Ala Met Ile Glu Pro Leu Glu Glu Met
        290                 295                 300

Val Ser Asp Glu Arg Pro Ala Arg Tyr Asp Ala Tyr Asn Trp Gly Asn
305                 310                 315                 320

Phe Phe Ser Thr Arg Lys Asn Ser Asn Phe Arg Lys Leu Ala Val Glu
                325                 330                 335

Asn Val Gln Ile Ala His Phe Arg Lys Asp Arg Pro
            340                 345
```

<210> SEQ ID NO 117
<211> LENGTH: 1863
<212> TYPE: DNA
<213> ORGANISM: Triticum aestivum

<400> SEQUENCE: 117

```
tcactcaagg ccacaacaca ctcgccagtc catcgccacc atacgtgaca acttgagtta    60
cttgatctgt tgctcatcga tctcgacatc gccatgggcg gcctctccat ggaccaggcc   120
ttcgtgcagg cccccgagca tcgcaccaag gcgaacctcg ccgacgcggc cggcatcccg   180
gtcatcgacc tctcccctct cgccgccggc gacaaggccg gcctggacgc cctcgcggcc   240
gaggtgggca gggcgagccg tgactggggg ttcttcgtgg tggtgcgcca cggcgtgccg   300
gcggagacgt ggcgcgggc gctggaggcg cagagggcct tcttcgcgct gcccgcggac   360
cggaaggcgg ccgtgcggag ggacgaggcg gcgccgctgg ggtactacga gtcggagcac   420
accaagaacg tcagggactg gaaggaggtg ttcgacctcg tcccccgcga gccgccgccg   480
cctgccgcgg ttgccgacgg cgagctcatg ttcgagaaca gtggcccga ggacctgccg    540
gggttcaggt acgtcatca actcaatcaa ttctgcgacc ccgagagaaa tggttcacta   600
ttattcgtgg ttcatacgta tgattcagac gttaatctcg atgcaaattg atttgtgcat   660
gcagagaggc tctcgaagag tacgagaaag cgatggagga gctggcgttc aagctgctgg   720
agctgatcgc ccggagcctg ggactgagac cggaccggct gcacggcttc ttcaaggacc   780
agaccacctt catccggctg aaccactacc cgccctgccc cagccccgac ctcgccctcg   840
gcgtcggtcg ccacaaggac gccggcgcgc tcaccatcct ctaccaggac gacgtcggcg   900
ggctcgacgt ccggcgccgc tccgacgcg agtgggtgcg cgtcaggcct gtcccggact   960
cctacgtcat caacgtcggc gacatcatcc aggtgtggag caacgacagg tacgagagcg  1020
cggagcacag ggtgtcggtg aactcgcaca aggagaggtt ctccatgccc tacttcttcg  1080
accccgggag cgacgccatg atcgagccgt tggaggagat ggtgagcgac gaaaggccgg  1140
ccaggtacga cgcctacaac tggggcaact tcttcagcac caggaagaac agcaacttca  1200
ggaagctcgc cgtcgaaaac gtccagatcg cacacttcag aaaggaccga ccttaaatga  1260
aggatccctc atgaattcat gatccttccg ctctcctcag tgatcctagt gctacaacta  1320
caagcatctc cccgtttgta gtaatcatat ataataagt attccctccg taaactaata   1380
taagagcatt taaaacacta ctctagtgat ctaaatgctc ttatattagt ttacagagag  1440
agtattgtgt attaataatg actttctctg tttcaaaata agtgatgacg tggttttagt  1500
tcaattttt ttagagagga ggcatctgac gggccttaaa ctgaggacct tagagtacaa   1560
acaaggttcg acgaaagtaa gtttaaggga tacaaggccg tagccaacaa aacgcgacgc  1620
```

```
agcgcgcaat ctaaaatcag cgtgctgtca aggtagctgg agacgtccat gccgttaatc   1680
tctctcaaga agctcgccga agctcagtgc accttgcgtg cactcttgtg aagagcacct   1740
tcacgtgtcc tttgtcctga gattttgtca acagtttcca tgactgcaag aaaaacacta   1800
gtttgtataa tagctcagcg ggatgtcgaa tgaattgccc ctcaatcaaa gctttatttc   1860
tag                                                                 1863
```

<210> SEQ ID NO 118
<211> LENGTH: 349
<212> TYPE: PRT
<213> ORGANISM: Hordeum vulgare

<400> SEQUENCE: 118

```
Met Gly Gly Leu Ser Met Gly Gln Ala Phe Val Gln Ala Pro Glu His
1               5                   10                  15

Arg Thr Lys Pro Thr Leu Ala Asp Ala Asp Gly Ile Pro Val Ile Asp
            20                  25                  30

Leu Ser Pro Leu Ala Ala Gly Asp Glu Ala Gly Val Asp Ala Leu Ala
        35                  40                  45

Ala Glu Val Gly Arg Ala Ser Arg Asp Trp Gly Phe Phe Val Val Val
    50                  55                  60

Arg His Gly Val Pro Ala Glu Thr Val Ala Arg Ala Leu Glu Ala Gln
65                  70                  75                  80

Arg Ala Phe Phe Ala Leu Pro Ala Glu Arg Lys Ala Ala Val Arg Arg
                85                  90                  95

Asp Glu Ala Ala Pro Leu Gly Tyr Tyr Glu Ser Glu His Thr Lys Asn
            100                 105                 110

Val Arg Asp Trp Lys Glu Val Phe Asp Phe Val Pro Arg Glu Pro Pro
        115                 120                 125

Pro Pro Ala Ala Val Ala Asp Gly Glu Leu Val Phe Glu Asn Lys Trp
    130                 135                 140

Pro Glu Asp Leu Pro Gly Phe Arg Val Ala Phe Glu Glu Tyr Ala Lys
145                 150                 155                 160

Ala Met Glu Glu Leu Ala Phe Lys Leu Leu Glu Leu Ile Ala Arg Ser
                165                 170                 175

Leu Gly Leu Thr Pro Asp Arg Leu Asn Gly Phe Phe Lys Asp His Gln
            180                 185                 190

Thr Thr Phe Ile Arg Leu Asn His Tyr Pro Pro Cys Pro Ser Pro Asp
        195                 200                 205

Leu Ala Leu Gly Val Gly Arg His Lys Asp Ala Gly Ala Leu Thr Val
    210                 215                 220

Leu Tyr Gln Asp Asp Val Gly Gly Leu Asp Val Arg His Arg Ser Asp
225                 230                 235                 240

Gly Glu Trp Val Arg Val Arg Pro Val Pro Asp Ser Tyr Val Ile Asn
                245                 250                 255

Val Gly Asp Ile Ile Gln Val Trp Ser Asn Asp Arg Tyr Glu Ser Ala
            260                 265                 270

Glu His Arg Val Ser Val Asn Ser Asp Lys Glu Arg Phe Ser Met Pro
        275                 280                 285

Tyr Phe Phe Asn Pro Gly Ser Asp Ala Met Val Glu Pro Leu Glu Glu
    290                 295                 300

Met Val Ser Asp Glu Arg Pro Ala Arg Tyr Asp Ala Tyr Asn Trp Gly
305                 310                 315                 320
```

His Phe Phe Ser Thr Arg Lys Asn Ser Asn Phe Lys Lys Leu Asp Val
                325                 330                 335

Glu Asn Val Gln Ile Ala His Phe Arg Lys Leu His Leu
            340                 345

<210> SEQ ID NO 119
<211> LENGTH: 1963
<212> TYPE: DNA
<213> ORGANISM: Sorghum bicolor

<400> SEQUENCE: 119

| | | | | | |
|---|---|---|---|---|---|
| tataaatacc | acgccatgta | cttctctgct | tctacacttc | tccagcttct | ctcatgccat | 60 |
| accactagtg | caaggtccta | gatttacact | tggtgctaca | gcttcttcct | ccctccctcc | 120 |
| cctctctagg | cagctagcac | gcagcgcagc | acacgaaaca | tctattgacc | ggccgcctcc | 180 |
| gccgggatc | cataattact | atactaccaa | tcggccagcg | tcatgccgac | gccgtcgcac | 240 |
| ctcgcgaacc | cgcgctactt | cgacttccgt | gcggcgcggc | gggtgccgga | gacgcacgcc | 300 |
| tggccggggc | tgcacgacca | ccccgtcgtg | gacggcggcg | cgccggggcc | agacgccgtc | 360 |
| cccgtggtgg | acctcgcggg | ggcggcggac | gagccgagag | ccgcggtggt | ggcccaagtg | 420 |
| gcgcgcgccg | ccgagcaatg | gggcgcgttc | ctgctcacgg | gcacggcgt | ccccgcggag | 480 |
| ctgctggcgc | gcgtcgagga | ccggatcgcc | accatgttcg | cgctgccagc | ggacgacaag | 540 |
| atgcgcgccg | tgcgcgggcc | tggcgacgcc | tgcggctacg | gctccccgcc | catctcctcc | 600 |
| ttcttctcca | agtgcatgtg | gtcggaggga | tacaccttct | cgccggccaa | cctccgcgcc | 660 |
| gacctccgca | agctctggcc | taaggccggc | gacgactaca | ccagcttctg | tgatgtgatg | 720 |
| gaggagttcc | acaagcacat | gcgtgccctc | gcggacaagc | tgctggagct | gttcctcatg | 780 |
| gcgctggggc | tcaccgacga | gcaggtcggc | ggcgtggagg | cggagcggag | gatcgccgag | 840 |
| acgatgaccg | ccaccatgca | cctcaactgg | taccctcggt | gcccggaccc | gcgccgcgcg | 900 |
| ctggggctga | tcgcgcacac | cgactcgggc | ttcttcacct | tcgtgctgca | gagcctcgtc | 960 |
| ccggggctgc | agctcttccg | ccacgccccg | gaccggtggg | tggcggtgcc | ggcggtaccg | 1020 |
| ggcgccttcg | tcgtcaacgt | gggcgacctc | ttccacatcc | tcaccaacgg | ccggttccac | 1080 |
| agcgtgtacc | accgcgccgt | cgtgaaccgg | gacctcgaca | ggatatctct | cggctacttc | 1140 |
| ctcggcccgc | cgccgcacgc | caaggtggcg | ccgctaaggg | aggccgtgcc | gcccggccgc | 1200 |
| accccgcgt | accgcgccgt | cacgtggccc | gagtacatgg | gcgtccgcaa | gaaggccttc | 1260 |
| accaccggcg | catccgcgct | caagatggtc | gccctcgccg | ccgccgccgc | cgccgccgac | 1320 |
| ctcgacgatg | acgccggtgc | tggcgccgcc | gccgaacctg | tcgtccatca | gcagctactc | 1380 |
| gtctcgtcgt | agccgatcga | tcgccggatc | ggtcgagact | gatgatgatg | atgcatatat | 1440 |
| actcgtcgat | ggagtagaca | gactaatcaa | gcaaccctga | actatgaat | gcatgcgtgc | 1500 |
| gcttcgtgct | tgcttgcgca | tgcagctagc | aggcttcatt | ccgttccgca | gctgctctgc | 1560 |
| tccaacctgc | tctgctggat | tgatgtatat | ggtagaagaa | ttaagagatc | gatggatgac | 1620 |
| ggaggaagaa | gaagacgaag | acgacgatga | ggaaaaggac | acgctgtacg | tagctggttc | 1680 |
| ttctagtcta | gtttacagca | ggccgggcgg | ccggctgctg | cttccaatcg | agtttgtcgt | 1740 |
| tactgacgat | tgttagtgga | tcgattaact | aatctggaat | tctggattat | taatataatg | 1800 |
| catgtggttt | ggcatctggc | gtaaagcagg | taatggtacc | tagccagtag | ccagtagcca | 1860 |
| ggctggtcaa | tgataggtct | ataccctgat | cctgtactgt | tgtttctttc | ggtctttctg | 1920 |
| agagagaaaa | aaaacgaata | tatggcgtac | tcaattcatc | aaa | | 1963 |

<210> SEQ ID NO 120
<211> LENGTH: 1170
<212> TYPE: DNA
<213> ORGANISM: Sorghum bicolor

<400> SEQUENCE: 120

```
atgccgacgc cgtcgcacct cgcgaacccg cgctacttcg acttccgtgc ggcgcggcgg      60
gtgccggaga cgcacgcctg gccggggctg cacgaccacc ccgtcgtgga cggcggcgcg     120
ccggggccag acgccgtccc cgtggtggac ctcgcggggg cggcggacga gccgagagcc     180
gcggtggtgg cccaagtggc gcgcgccgcc gagcaatggg gcgcgttcct gctcacgggg     240
cacggcgtcc ccgcggagct gctggcgcgc gtcgaggacc ggatcgccac catgttcgcg     300
ctgccagcgg acgacaagat gcgcgccgtg cgcgggcctg gcgacgcctg cggctacggc     360
tccccgccca tctcctcctt cttctccaag tgcatgtggt cggagggata caccttctcg     420
ccggccaacc tccgcgccga cctccgcaag ctctggccta aggccggcga cgactacacc     480
agcttctgtg atgtgatgga ggagttccac aagcacatgc gtgccctcgc ggacaagctg     540
ctggagctgt tcctcatggc gctggggctc accgacgagc aggtcggcgg cgtggaggcg     600
gagcggagga tcgccgagac gatgaccgcc accatgcacc tcaactggta ccctcggtgc     660
ccggacccgc gccgcgcgct ggggctgatc gcgcacaccg actcgggctt cttcaccttc     720
gtgctgcaga gcctcgtccc ggggctgcag ctcttccgcc acgccccgga ccggtgggtg     780
gcggtgccgg cggtaccggg cgccttcgtc gtcaacgtgg cgacctcttc cacatcctc     840
accaacggcc ggttccacag cgtgtaccac cgcgccgtcg tgaaccggga cctcgacagg     900
atatctctcg gctacttcct cggcccgccg ccgcacgcca aggtggcgcc gctaagggag     960
gccgtgccgc ccggccgcac ccccgcgtac cgcgccgtca cgtggcccga gtacatgggc    1020
gtccgcaaga aggccttcac caccggcgca tccgcgctca agatggtcgc cctgccgcc    1080
gccgccgccg ccgccgacct cgacgatgac gccggtgctg gcgccgccgc cgaacctgtc    1140
gtccatcagc agctactcgt ctcgtcgtag                                    1170
```

<210> SEQ ID NO 121
<211> LENGTH: 389
<212> TYPE: PRT
<213> ORGANISM: Sorghum bicolor

<400> SEQUENCE: 121

Met Pro Thr Pro Ser His Leu Ala Asn Pro Arg Tyr Phe Asp Phe Arg
1               5                   10                  15

Ala Ala Arg Arg Val Pro Glu Thr His Ala Trp Pro Gly Leu His Asp
            20                  25                  30

His Pro Val Val Asp Gly Gly Ala Pro Gly Pro Asp Ala Val Pro Val
        35                  40                  45

Val Asp Leu Ala Gly Ala Ala Asp Glu Pro Arg Ala Ala Val Val Ala
    50                  55                  60

Gln Val Ala Arg Ala Ala Glu Gln Trp Gly Ala Phe Leu Leu Thr Gly
65                  70                  75                  80

His Gly Val Pro Ala Glu Leu Leu Ala Arg Val Glu Asp Arg Ile Ala
                85                  90                  95

Thr Met Phe Ala Leu Pro Ala Asp Asp Lys Met Arg Ala Val Arg Gly
            100                 105                 110

Pro Gly Asp Ala Cys Gly Tyr Gly Ser Pro Pro Ile Ser Ser Phe Phe

|     |     |     |     | 115 |     |     |     |     | 120 |     |     |     |     | 125 |     |
| --- | --- | --- | --- | --- | --- | --- | --- | --- | --- | --- | --- | --- | --- | --- | --- |
| Ser | Lys | Cys | Met | Trp | Ser | Glu | Gly | Tyr | Thr | Phe | Ser | Pro | Ala | Asn | Leu |
|     | 130 |     |     |     |     | 135 |     |     |     |     | 140 |     |     |     |     |
| Arg | Ala | Asp | Leu | Arg | Lys | Leu | Trp | Pro | Lys | Ala | Gly | Asp | Asp | Tyr | Thr |
| 145 |     |     |     |     | 150 |     |     |     |     | 155 |     |     |     |     | 160 |
| Ser | Phe | Cys | Asp | Val | Met | Glu | Glu | Phe | His | Lys | His | Met | Arg | Ala | Leu |
|     |     |     |     | 165 |     |     |     |     | 170 |     |     |     |     | 175 |     |
| Ala | Asp | Lys | Leu | Leu | Glu | Leu | Phe | Leu | Met | Ala | Leu | Gly | Leu | Thr | Asp |
|     |     |     | 180 |     |     |     |     | 185 |     |     |     |     | 190 |     |     |
| Glu | Gln | Val | Gly | Gly | Val | Glu | Ala | Glu | Arg | Arg | Ile | Ala | Glu | Thr | Met |
|     |     | 195 |     |     |     |     | 200 |     |     |     |     | 205 |     |     |     |
| Thr | Ala | Thr | Met | His | Leu | Asn | Trp | Tyr | Pro | Arg | Cys | Pro | Asp | Pro | Arg |
|     | 210 |     |     |     |     | 215 |     |     |     |     | 220 |     |     |     |     |
| Arg | Ala | Leu | Gly | Leu | Ile | Ala | His | Thr | Asp | Ser | Gly | Phe | Phe | Thr | Phe |
| 225 |     |     |     |     | 230 |     |     |     |     | 235 |     |     |     |     | 240 |
| Val | Leu | Gln | Ser | Leu | Val | Pro | Gly | Leu | Gln | Leu | Phe | Arg | His | Ala | Pro |
|     |     |     |     | 245 |     |     |     |     | 250 |     |     |     |     | 255 |     |
| Asp | Arg | Trp | Val | Ala | Val | Pro | Ala | Val | Pro | Gly | Ala | Phe | Val | Val | Asn |
|     |     |     | 260 |     |     |     |     | 265 |     |     |     |     | 270 |     |     |
| Val | Gly | Asp | Leu | Phe | His | Ile | Leu | Thr | Asn | Gly | Arg | Phe | His | Ser | Val |
|     |     | 275 |     |     |     |     | 280 |     |     |     |     | 285 |     |     |     |
| Tyr | His | Arg | Ala | Val | Val | Asn | Arg | Asp | Leu | Asp | Arg | Ile | Ser | Leu | Gly |
|     | 290 |     |     |     |     | 295 |     |     |     |     | 300 |     |     |     |     |
| Tyr | Phe | Leu | Gly | Pro | Pro | His | Ala | Lys | Val | Ala | Pro | Leu | Arg | Glu |     |
| 305 |     |     |     |     | 310 |     |     |     |     | 315 |     |     |     |     | 320 |
| Ala | Val | Pro | Pro | Gly | Arg | Thr | Pro | Ala | Tyr | Arg | Ala | Val | Thr | Trp | Pro |
|     |     |     |     | 325 |     |     |     |     | 330 |     |     |     |     | 335 |     |
| Glu | Tyr | Met | Gly | Val | Arg | Lys | Lys | Ala | Phe | Thr | Thr | Gly | Ala | Ser | Ala |
|     |     |     | 340 |     |     |     |     | 345 |     |     |     |     | 350 |     |     |
| Leu | Lys | Met | Val | Ala | Leu | Ala | Ala | Ala | Ala | Ala | Ala | Asp | Leu | Asp |     |
|     |     | 355 |     |     |     |     | 360 |     |     |     |     | 365 |     |     |     |
| Asp | Asp | Ala | Gly | Ala | Gly | Ala | Ala | Ala | Glu | Pro | Val | Val | His | Gln | Gln |
|     | 370 |     |     |     |     | 375 |     |     |     |     | 380 |     |     |     |     |
| Leu | Leu | Val | Ser | Ser |     |     |     |     |     |     |     |     |     |     |     |
| 385 |     |     |     |     |     |     |     |     |     |     |     |     |     |     |     |

```
<210> SEQ ID NO 122
<211> LENGTH: 2321
<212> TYPE: DNA
<213> ORGANISM: Sorghum bicolor

<400> SEQUENCE: 122
```

| | | | | | |
|---|---|---|---|---|---|
| tataaatacc | acgccatgta | cttctctgct | tctacacttc | tccagcttct | ctcatgccat | 60 |
| accactagtg | caaggtccta | gatttacact | tggtgctaca | gcttcttcct | ccctccctcc | 120 |
| cctctctagg | cagctagcac | gcagcgcagc | acacgaaaca | tctattgacc | ggccgcctcc | 180 |
| gccggggatc | cataattact | atactaccaa | tcggccagcg | tcatgccgac | gccgtcgcac | 240 |
| ctcgcgaacc | cgcgctactt | cgacttccgt | gcggcgcggc | gggtgccgga | gacgcacgcc | 300 |
| tggccggggc | tgcacgacca | ccccgtcgtg | gacggcggcg | cgccggggcc | agacgccgtc | 360 |
| ccgtggtgg | acctcgcggg | ggcggcggac | gagccgagag | ccgcggtggt | ggcccaagtg | 420 |
| gcgcgcgccg | ccgagcaatg | gggcgcgttc | ctgctcacgg | gcacggcgt | ccccgcggag | 480 |
| ctgctggcgc | gcgtcgagga | ccggatcgcc | accatgttcg | cgctgccagc | ggacgacaag | 540 |

| | |
|---|---|
| atgcgcgccg tgcgcgggcc tggcgacgcc tgcggctacg gctccccgcc catctcctcc | 600 |
| ttcttctcca agtgcatgtg gtcggaggga tacaccttct cgccggccaa cctccgcgcc | 660 |
| gacctccgca agctctggcc taaggccggc gacgactaca ccagcttctg gtacgtgcac | 720 |
| ccgccggccg cgcgccgcca cacaccgtac ccacacacgt gcgcgctcgc gcctagctac | 780 |
| tagtagctgc tttgctttgc ttacctttga ttctcgcctt tgccatgcat atgcatgatg | 840 |
| cacgtacagg tactgcaggt acaacatgtc acacgcacgc acgcacgcac aacccatagt | 900 |
| ccgatacgat acatcatcga tcgacgtgtc gtcaccgtct aaggccatgc atgcatgcaa | 960 |
| gcacacgcct agacctttt agcatgctgg ctgacgagga gtatactagc taataagcta | 1020 |
| cttgtcactg cgcgtcttgc ttaattacac tagtgcatat ttctacagtg atgtgatgga | 1080 |
| ggagttccac aagcacatgc gtgccctcgc ggacaagctg ctggagctgt tcctcatggc | 1140 |
| gctggggctc accgacgagc aggtcggcgg cgtggaggcg gagcggagga tcgccgagac | 1200 |
| gatgaccgcc accatgcacc tcaactggta ccctcggtgc ccggaccgc gccgcgcgct | 1260 |
| ggggctgatc gcgcacaccg actcgggctt cttcaccttc gtgctgcaga gcctcgtccc | 1320 |
| ggggctgcag ctcttccgcc acgccccgga ccggtgggtg gcggtgccgg cggtaccggg | 1380 |
| cgccttcgtc gtcaacgtgg gcgacctctt ccacatcctc accaacggcc ggttccacag | 1440 |
| cgtgtaccac cgcgccgtcg tgaaccggga cctcgacagg atatctctcg gctacttcct | 1500 |
| cggcccgccg ccgcacgcca aggtggcgcc gctaagggag gccgtgccgc ccggccgcac | 1560 |
| ccccgcgtac cgcgccgtca cgtggcccga gtacatgggc gtccgcaaga aggccttcac | 1620 |
| caccggcgca tccgcgctca agatggtcgc cctcgccgcc gccgccgcg ccgccgacct | 1680 |
| cgacgatgac gccggtgctg gcgccgccgc cgaacctgtc gtccatcagc agctactcgt | 1740 |
| ctcgtcgtag ccgatcgatc gccggatcgg tcgagactga tgatgatgat gcatatatac | 1800 |
| tcgtcgatgg agtagacaga ctaatcaagc aaccctgaaa ctatgaatgc atgcgtgcgc | 1860 |
| ttcgtgcttg cttgcgcatg cagctagcag gcttcattcc gttccgcagc tgctctgctc | 1920 |
| caacctgctc tgctggattg atgtatatgg tagaagaatt aagagatcga tggatgacgg | 1980 |
| aggaagaaga agacgaagac gacgatgagg aaaaggacac gctgtacgta gctggttctt | 2040 |
| ctagtctagt ttacagcagg ccgggcggcc ggctgctgct tccaatcgag tttgtcgtta | 2100 |
| ctgacgattg ttagtggatc gattaactaa tctggaattc tggattatta atataatgca | 2160 |
| tgtggtttgg catctggcgt aaagcaggta atggtaccta gccagtagcc agtagccagg | 2220 |
| ctggtcaatg ataggtctat accctgatcc tgtactgttg tttctttcgg tctttctgag | 2280 |
| agagaaaaaa aacgaatata tggcgtactc aattcatcaa a | 2321 |

<210> SEQ ID NO 123
<211> LENGTH: 1796
<212> TYPE: DNA
<213> ORGANISM: Setaria italica

<400> SEQUENCE: 123

| | |
|---|---|
| actagtgcaa ggtcctagat ttacacttgg tgcttgcttg tttcttccta gttgctactg | 60 |
| gtagcacgca gtggctggct ggccgtaatc tattgtctgg gctcgatcgg tgattaggaa | 120 |
| gtagccaaag caagctaagg ccgccgccgc cgccgccatg ccgacgccgt cgcacctcaa | 180 |
| gaacccgctc tacttcgact tccgcgccgc gcggcgggtg ccggagtccc acgcctggcc | 240 |
| ggggctcgac gaccacccg tgtggacgg cggcggcgcg ccggggtccc cggacgccgt | 300 |
| gccggtggtg gacctgcgcg agccgggcgc cgcggcggtg gcccgcgtgg cgcgcgccgc | 360 |

```
cgagcagtgg ggcgcgttcc tgctcaccgg ccacggcgtc cccgcggagc tcctggcgcg      420
cgtcgaggac cgcgtcgcgt gcatgttcgc gctgccggcc gccgacaaga tgcgcgccgt      480
gcgcgggccg ggggacgcct gcggctacgg ctcgccgccc atctcctcct tcttctccaa      540
gtgcatgtgt tccagggct acaccttctc gccggcctcc ctccgccgcg acctccgcaa       600
gctctggccc aaggccggcg acgactacga cagcttctgt gacgtgatgg aggagttcca      660
caaggagatg cgcgccctcg ccgacaggct cctggagctg ttcctcaggg cgctcgggct      720
caccggcgag caggtcggcg ccgtcgaggc ggagcggagg atcggcgaga cgatgaccgc      780
caccatgcac ctcaactggt atccgaggtg cccggacccg cggcgcgcgc tggggctgat      840
cgcgcacacg gactcgggct tcttcacctt cgtgctgcag agcctcgtgc cggggctgca      900
gctgttccgg cacggcccca accggtgggg ggcggtgccg gccgtgccgg cgccttcgt      960
cgtcaacgtc ggcgacctct tccacatcct cacgaacggc cgcttccaca cgtgtacca      1020
ccgccgcgtc gtcaaccggg acctcgaccg gatatcgctc ggctacttcc tcggcccgcc      1080
gccccacgcc aaggtggcgc cgctccggga ggtcgtgccg ccgggccggg ccccgccta      1140
ccgcgccgtc acgtggcccg agtacatggg cgtccgcaag aaggccttca ccaccggcgc      1200
ctccgcgctc aagatggtcg ccgccgccgc cgccgccacc gaatccgacg acaccgacgc      1260
agccgccgcc gccgttcacc agccgccggt cgtcgtctca tcgtagccga tcgatcgccg      1320
gaaacacaga cgatgcatac cgtaccccga gcaatctaat caaaacaagg catccattct      1380
cgcgcgcatg cagcggccag ccgggcttcc gcagctgctc ggcctcctct gctggctgtg      1440
gaaatggaaa attttaatct gagatgaaga cgaagacgaa gacgaaacgg agaggaaaag      1500
gacatgctgt agctgtttct tctagttgcg caggccgctc ccagtcgagt ttgtcgttac      1560
tgacgattat tactctgatg aaaactaatc tgaattaatg catgtagttt ggcaatttgg      1620
tactaaaggt aggcacctag ccaggctggt caatgatagg tctataacct gatcctgttc      1680
tctgttgttt tcctttgtct gagaaaaaat ggaaataatt gatccggccg gacgggtgta      1740
ctgataggtg atgctgaatt gctgatgcaa gaggttgcga gctgcagtga gcagca         1796
```

<210> SEQ ID NO 124
<211> LENGTH: 1149
<212> TYPE: DNA
<213> ORGANISM: Setaria italica

<400> SEQUENCE: 124

```
atgccgacgc cgtcgcacct caagaacccg ctctacttcg acttccgcgc cgcgcggcgg       60
gtgccggagt cccacgcctg ccggggctc gacgaccacc ccgtggtgga cggcggcggc       120
gcgcggggt cccggacgc cgtgccggtg gtggacctgc gcgagccggg cgccgcggcg        180
gtggcccgcg tggcgcgcgc cgccgagcag tggggcgcgt tcctgctcac cggccacggc      240
gtccccgcg agctcctggc gcgcgtcgag gaccgcgtcg cgtgcatgtt cgcgctgccg       300
gccgccgaca agatgcgcgc cgtgcgcggg ccggggggacg cctgcggcta cggctcgccg     360
cccatctcct ccttcttctc caagtgcatg tggtccgagg gctacacctt ctcgccggcc      420
tccctccgcc gcgacctccg caagctctgg cccaaggccg gcgacgacta cgacagcttc      480
tgtgacgtga tggaggagtt ccacaaggag atgcgcgccc tcgccgacag gctcctggag      540
ctgttcctca gggcgctcgg gctcaccggc gagcaggtcg gcgccgtcga ggcggagcgg      600
aggatcggcg agacgatgac cgccaccatg cacctcaact ggtatccgag gtgcccggac      660
```

-continued

```
ccgcggcgcg cgctggggct gatcgcgcac acggactcgg gcttcttcac cttcgtgctg    720
cagagcctcg tgccggggct gcagctgttc cggcacggcc ccaaccggtg ggtggcggtg    780
ccggccgtgc cgggcgcctt cgtcgtcaac gtcggcgacc tcttccacat cctcacgaac    840
ggccgcttcc acagcgtgta ccaccgcgcc gtcgtcaacc gggacctcga ccggatatcg    900
ctcggctact tcctcggccc gccgcccac gccaaggtgg cgccgctccg ggaggtcgtg     960
ccgccgggcc gggcccccgc ctaccgcgcc gtcacgtggc ccgagtacat gggcgtccgc   1020
aagaaggcct tcaccaccgg cgcctccgcg ctcaagatgg tcgccgccgc cgccgccgcc   1080
accgaatccg acgacaccga cgcagccgcc gccgccgttc accagccgcc ggtcgtcgtc   1140
tcatcgtag                                                          1149
```

<210> SEQ ID NO 125
<211> LENGTH: 382
<212> TYPE: PRT
<213> ORGANISM: Setaria italica

<400> SEQUENCE: 125

```
Met Pro Thr Pro Ser His Leu Lys Asn Pro Leu Tyr Phe Asp Phe Arg
1               5                   10                  15

Ala Ala Arg Arg Val Pro Glu Ser His Ala Trp Pro Gly Leu Asp Asp
            20                  25                  30

His Pro Val Val Asp Gly Gly Ala Pro Gly Ser Pro Asp Ala Val
        35                  40                  45

Pro Val Val Asp Leu Arg Glu Pro Gly Ala Ala Val Ala Arg Val
    50                  55                  60

Ala Arg Ala Ala Glu Gln Trp Gly Ala Phe Leu Leu Thr Gly His Gly
65                  70                  75                  80

Val Pro Ala Glu Leu Leu Ala Arg Val Glu Asp Arg Val Ala Cys Met
                85                  90                  95

Phe Ala Leu Pro Ala Ala Asp Lys Met Arg Ala Val Arg Gly Pro Gly
            100                 105                 110

Asp Ala Cys Gly Tyr Gly Ser Pro Pro Ile Ser Ser Phe Phe Ser Lys
        115                 120                 125

Cys Met Trp Ser Glu Gly Tyr Thr Phe Ser Pro Ala Ser Leu Arg Arg
    130                 135                 140

Asp Leu Arg Lys Leu Trp Pro Lys Ala Gly Asp Asp Tyr Asp Ser Phe
145                 150                 155                 160

Cys Asp Val Met Glu Glu Phe His Lys Glu Met Arg Ala Leu Ala Asp
                165                 170                 175

Arg Leu Leu Glu Leu Phe Leu Arg Ala Leu Gly Leu Thr Gly Glu Gln
            180                 185                 190

Val Gly Ala Val Glu Ala Glu Arg Arg Ile Gly Glu Thr Met Thr Ala
        195                 200                 205

Thr Met His Leu Asn Trp Tyr Pro Arg Cys Pro Asp Pro Arg Arg Ala
    210                 215                 220

Leu Gly Leu Ile Ala His Thr Asp Ser Gly Phe Phe Thr Phe Val Leu
225                 230                 235                 240

Gln Ser Leu Val Pro Gly Leu Gln Leu Phe Arg His Gly Pro Asn Arg
                245                 250                 255

Trp Val Ala Val Pro Ala Val Pro Gly Ala Phe Val Val Asn Val Gly
            260                 265                 270

Asp Leu Phe His Ile Leu Thr Asn Gly Arg Phe His Ser Val Tyr His
        275                 280                 285
```

| | | | | | | | | | | | |
|---|---|---|---|---|---|---|---|---|---|---|---|
| Arg | Ala | Val | Val | Asn | Arg | Asp | Leu | Asp | Arg | Ile | Ser | Leu | Gly | Tyr | Phe |
| | 290 | | | | 295 | | | | | 300 | |

Arg Ala Val Val Asn Arg Asp Leu Asp Arg Ile Ser Leu Gly Tyr Phe
    290                 295                 300

Leu Gly Pro Pro His Ala Lys Val Ala Pro Leu Arg Glu Val Val
305         310             315             320

Pro Pro Gly Arg Ala Pro Ala Tyr Arg Ala Val Thr Trp Pro Glu Tyr
            325             330                 335

Met Gly Val Arg Lys Lys Ala Phe Thr Thr Gly Ala Ser Ala Leu Lys
            340             345             350

Met Val Ala Ala Ala Ala Ala Thr Glu Ser Asp Asp Thr Asp Ala
        355             360             365

Ala Ala Ala Ala Val His Gln Pro Pro Val Val Val Ser Ser
        370             375             380

<210> SEQ ID NO 126
<211> LENGTH: 2146
<212> TYPE: DNA
<213> ORGANISM: Setaria italica

<400> SEQUENCE: 126

```
actagtgcaa ggtcctagat ttacacttgg tgcttgcttg tttcttccta gttgctactg    60
gtagcacgca gtggctggct ggccgtaatc tattgtctgg gctcgatcgg tgattaggaa   120
gtagccaaag caagctaagg ccgccgccgc cgccgccatg ccgacgccgt cgcacctcaa   180
gaacccgctc tacttcgact ccgcgccgc gcggcgggtg ccggagtccc acgcctggcc   240
ggggctcgac gaccaccccg tggtggacgc cggcggcgcg ccggggtccc cggacgccgt   300
gccggtggtg gacctgcgcg agccgggcgc cgcggcggtg gcccgcgtgg cgcgcgccgc   360
cgagcagtgg ggcgcgttcc tgctcaccgg ccacggcgtc cccgcggagc tcctggcgcg   420
cgtcgaggac cgcgtcgcgt gcatgttcgc gctgccggcc gccgacaaga tgcgcgccgt   480
gcgcgggccg ggggacgcct gcggctacgg ctcgccgccc atctcctcct tcttctccaa   540
gtgcatgtgg tccgagggct acaccttctc gccggcctcc ctccgccgcg acctccgcaa   600
gctctggccc aaggccggcg acgactacga cagcttctgg tacgtcgtcg tctatagcta   660
gtagctagcc gccggcacac gtgcgcctga cctgctccgc catgcatggt gcacgtatgc   720
agatcgatca cacgcaccga tcgatcgacg tgtcccggtc aaggccatgc atgcatgcaa   780
gcaaccaaca gcacgcctcc tgatactgct tgttgcttac accgttggta tgtgcctgtt   840
gcctacagtg acgtgatgga ggagttccac aaggagatgc gcgccctcgc cgacaggctc   900
ctggagctgt tcctcagggc gctcgggctc accggcgagc aggtcggcgc cgtcgaggcg   960
gagcggagga tcggcgagac gatgaccgcc accatgcacc tcaactggta tgtgccatgc  1020
catgaccacc tgcgtctatg aactaacgga agcttccatc gcgtgtccat gacgatttag  1080
aagctgtagt ccagagcttg agacaaacga acgaagctt acatggtggc gtgacgtgtc   1140
gcgtgcaggt atccgaggtg cccggacccg cggcgcgcgc tggggctgat cgcgcacacg  1200
gactcgggct tcttcaccctt cgtgctgcag agcctcgtgc cggggctgca gctgttccgg  1260
cacggcccca accggtgggt ggcggtgccg gccgtgccgg cgccttcgt cgtcaacgtc   1320
ggcgacctct tccacatcct cacgaacggc cgcttccaca gcgtgtacca ccgcgccgtc  1380
gtcaaccggg acctcgaccg gatatcgctc ggctacttcc tcggcccgcc gccccacgcc  1440
aaggtggcgc cgctccggga ggtcgtgccg ccgggccggg ccccgcccta ccgcgccgtc  1500
acgtggcccg agtacatggg cgtccgcaag aaggccttca ccaccggcgc ctccgcgctc  1560
```

| | |
|---|---|
| aagatggtcg ccgccgccgc cgccgccacc gaatccgacg acaccgacgc agccgccgcc | 1620 |
| gccgttcacc agccgccggt cgtcgtctca tcgtagccga tcgatcgccg gaaacacaga | 1680 |
| cgatgcatac cgtaccccga gcaatctaat caaaacaagg catccattct cgcgcgcatg | 1740 |
| cagcggccag ccgggcttcc gcagctgctc ggcctcctct gctggctgtg gaaatggaaa | 1800 |
| attttaatct gagatgaaga cgaagacgaa gacgaaacgg agaggaaaag gacatgctgt | 1860 |
| agctgtttct tctagttgcg caggccgctc ccagtcgagt ttgtcgttac tgacgattat | 1920 |
| tactctgatg aaaactaatc tgaattaatg catgtagttt ggcaatttgg tactaaaggt | 1980 |
| aggcacctag ccaggctggt caatgatagg tctataacct gatcctgttc tctgttgttt | 2040 |
| tcctttgtct gagaaaaaat ggaataatt gatccggccg gacgggtgta ctgataggtg | 2100 |
| atgctgaatt gctgatgcaa gaggttgcga gctgcagtga gcagca | 2146 |

<210> SEQ ID NO 127
<211> LENGTH: 1933
<212> TYPE: DNA
<213> ORGANISM: Oryza sativa

<400> SEQUENCE: 127

| | |
|---|---|
| actactcatt ccactattgt aaagtcatag aaaaaattta tatagagaga aaaaattagt | 60 |
| gttgttattg ttactggctt tctgccagac gagacgagcg agcgcgcgag tgtgttgctc | 120 |
| tctggtcatc gtcgtcgtcg tcgcgatgcc gacgccgtcg cacttgaaga acccgctctg | 180 |
| cttcgacttc cgggcggcga ggcgggtgcc ggagacgcac gcgtggccgg ggctggacga | 240 |
| ccacccggtg gtgacggcg gcggcggcgg cggcgaggac gcggtgccgg tggtggacgt | 300 |
| cggggcgggc gacgcggcgg cgcgggtggc gcgggcggcg gagcagtggg gcgcgttcct | 360 |
| tctggtcggg cacggcgtgc cggcggcgct gctgtcgcgc gtcgaggagc gcgtcgcccg | 420 |
| cgtgttctcc ctgccggcgt cggagaagat gcgcgccgtc cgcggccccg gcgagccctg | 480 |
| cggctacggc tcgccgccca tctcctcctt cttctccaag ctcatgtggt ccgagggcta | 540 |
| caccttctcc ccttcctccc tccgctccga gctccgccgc ctctggccca agtccggcga | 600 |
| cgactacctc ctcttctgtg acgtgatgga ggagtttcac aaggagatgc ggcggctagc | 660 |
| cgacgagttg ctgaggttgt tcttgagggc gctggggctc accggcgagg aggtcgccgg | 720 |
| agtcgaggcg gagaggagga tcggcgagag gatgacggcg acggtgcacc tcaactggta | 780 |
| cccgaggtgc ccggagccgc ggcgagcgct ggggctcatc gcgcacacgg actcgggctt | 840 |
| cttcaccttc gtgctccaga gcctcgtccc ggggctgcag ctgttccgtc gagggcccga | 900 |
| ccggtgggtg gcggtgccgg cggtggcggg ggccttcgtc gtcaacgtcg gcgacctctt | 960 |
| ccacatcctc accaacggcc gcttccacag cgtctaccac cgcgccgtcg tgaaccgcga | 1020 |
| ccgcgaccgg gtctcgctcg gctacttcct cggcccgccg ccggacgccg aggtggcgcc | 1080 |
| gctgccggag gccgtgccgg ccggccgag ccccgcctac cgcgctgtca cgtggccgga | 1140 |
| gtacatggcc gtccgcaaga aggccttcgc caccggcggc tccgccctca agatggtctc | 1200 |
| caccgacgcc gccgccgccg ccgacgaaca cgacgacgtc gccgccgccg ccgacgtcca | 1260 |
| cgcataagct atagctacta gctacctcga tctcacgcaa aaaaaaaag aaacaattaa | 1320 |
| tagagcaaaa aaaaaagaa gagaaatgg tggtacttgt gtttaaggtt tcctccatgc | 1380 |
| aaaatggttt gcatgcatgc atgcaaagct agcatctgca gctgcaagaa ttacaagagc | 1440 |
| agagaagcag acagctagat ggagataatt aattaattaa ttaatctaat taagcatgca | 1500 |
| ataattaaga ttattattct gatttcagaa ctgaaaaaaa aagtgtggtt aattaattat | 1560 |

| | | | |
|---|---|---|---|
| tggttaggct | taattttatc | tagatgtaga | aaaagaatca agatcttcaa gcaagagaga | 1620 |
| agaggatcga | agaagaagga | aaagaaaacg | aaaaggacat gctgtgttgt ctcttctagt | 1680 |
| tgtaccctgg | ctgctgatta | agtgctttgt | tttgttgctg caagcttgtc gttactgatt | 1740 |
| attagttagt | tatgcatcta | attgattaaa | ctaatctgtt tggcattttg gctcgagcta | 1800 |
| agctatagcc | aggctggtca | atgataggaa | cttgtacaat ttaagcaatt gaacctgatc | 1860 |
| ctgtactggc | atgtatgtat | atatgcaagt | gatgagaacc actagctagt atagctagac | 1920 |
| atgtatttgt | ata | | | 1933 |

<210> SEQ ID NO 128
<211> LENGTH: 1122
<212> TYPE: DNA
<213> ORGANISM: Oryza sativa

<400> SEQUENCE: 128

| | | | | |
|---|---|---|---|---|
| atgccgacgc | cgtcgcactt | gaagaacccg | ctctgcttcg acttccgggc ggcgaggcgg | 60 |
| gtgccggaga | cgcacgcgtg | gccggggctg | acgaccacc cggtggtgga cggcggcggc | 120 |
| ggcggcggcg | aggacgcggt | gccggtggtg | gacgtcgggg cgggcgacgc ggcggcgcgg | 180 |
| gtggcgcggg | cggcggagca | gtggggcgcg | ttccttctgg tcgggcacgg cgtgccggcg | 240 |
| gcgctgctgt | cgcgcgtcga | ggagcgcgtc | gcccgcgtgt tctccctgcc ggcgtcggag | 300 |
| aagatgcgcg | ccgtccgcgg | ccccggcgag | ccctgcggct acggctcgcc gcccatctcc | 360 |
| tccttcttct | ccaagctcat | gtggtccgag | ggctacacct tctccccttc ctccctccgc | 420 |
| tccgagctcc | gccgcctctg | gcccaagtcc | ggcgacgact acctcctctt ctgtgacgtg | 480 |
| atggaggagt | tcacaaagga | gatgcggcgg | ctagccgacg agttgctgag gttgttcttg | 540 |
| agggcgctgg | ggctcaccgg | cgaggaggtc | gccggagtcg aggcggagag gaggatcggc | 600 |
| gagaggatga | cggcgacggt | gcacctcaac | tggtacccga ggtgcccgga gccgcggcga | 660 |
| gcgctggggc | tcatcgcgca | cacggactcg | gcttcttca ccttcgtgct ccagagcctc | 720 |
| gtcccggggc | tgcagctgtt | ccgtcgaggg | cccgaccggt gggtggcggt gccggcggtg | 780 |
| gcgggggcct | tcgtcgtcaa | cgtcggcgac | ctcttccaca tcctcaccaa cggccgcttc | 840 |
| cacagcgtct | accaccgcgc | cgtcgtgaac | cgcgaccgcg accgggtctc gctcggctac | 900 |
| ttcctcggcc | cgccgccgga | cgccgaggtg | gcgccgctgc cggaggccgt gccggccggc | 960 |
| cggagccccg | cctaccgcgc | tgtcacgtgg | ccggagtaca tggccgtccg caagaaggcc | 1020 |
| ttcgccaccg | cgcggctccgc | cctcaagatg | gtctccaccg acgccgccgc cgccgccgac | 1080 |
| gaacacgacg | acgtcgccgc | cgccgccgac | gtccacgcat aa | 1122 |

<210> SEQ ID NO 129
<211> LENGTH: 373
<212> TYPE: PRT
<213> ORGANISM: Oryza sativa

<400> SEQUENCE: 129

Met Pro Thr Pro Ser His Leu Lys Asn Pro Leu Cys Phe Asp Phe Arg
1               5                   10                  15

Ala Ala Arg Arg Val Pro Glu Thr His Ala Trp Pro Gly Leu Asp Asp
            20                  25                  30

His Pro Val Val Asp Gly Gly Gly Gly Gly Glu Asp Ala Val Pro
        35                  40                  45

Val Val Asp Val Gly Ala Gly Asp Ala Ala Ala Arg Val Ala Arg Ala

```
                   50                  55                  60
Ala Glu Gln Trp Gly Ala Phe Leu Leu Val Gly His Gly Val Pro Ala
 65                  70                  75                  80

Ala Leu Leu Ser Arg Val Glu Arg Val Ala Arg Val Phe Ser Leu
                 85                  90                  95

Pro Ala Ser Glu Lys Met Arg Ala Val Arg Gly Pro Gly Glu Pro Cys
                100                 105                 110

Gly Tyr Gly Ser Pro Pro Ile Ser Ser Phe Phe Ser Lys Leu Met Trp
                115                 120                 125

Ser Glu Gly Tyr Thr Phe Ser Pro Ser Ser Leu Arg Ser Glu Leu Arg
                130                 135                 140

Arg Leu Trp Pro Lys Ser Gly Asp Asp Tyr Leu Leu Phe Cys Asp Val
145                 150                 155                 160

Met Glu Glu Phe His Lys Glu Met Arg Arg Leu Ala Asp Glu Leu Leu
                165                 170                 175

Arg Leu Phe Leu Arg Ala Leu Gly Leu Thr Gly Glu Glu Val Ala Gly
                180                 185                 190

Val Glu Ala Glu Arg Arg Ile Gly Glu Arg Met Thr Ala Thr Val His
                195                 200                 205

Leu Asn Trp Tyr Pro Arg Cys Pro Glu Pro Arg Arg Ala Leu Gly Leu
210                 215                 220

Ile Ala His Thr Asp Ser Gly Phe Phe Thr Phe Val Leu Gln Ser Leu
225                 230                 235                 240

Val Pro Gly Leu Gln Leu Phe Arg Arg Gly Pro Asp Arg Trp Val Ala
                245                 250                 255

Val Pro Ala Val Ala Gly Ala Phe Val Val Asn Val Gly Asp Leu Phe
                260                 265                 270

His Ile Leu Thr Asn Gly Arg Phe His Ser Val Tyr His Arg Ala Val
                275                 280                 285

Val Asn Arg Asp Arg Asp Arg Val Ser Leu Gly Tyr Phe Leu Gly Pro
                290                 295                 300

Pro Pro Asp Ala Glu Val Ala Pro Leu Pro Glu Ala Val Pro Ala Gly
305                 310                 315                 320

Arg Ser Pro Ala Tyr Arg Ala Val Thr Trp Pro Glu Tyr Met Ala Val
                325                 330                 335

Arg Lys Lys Ala Phe Ala Thr Gly Gly Ser Ala Leu Lys Met Val Ser
                340                 345                 350

Thr Asp Ala Ala Ala Ala Asp Glu His Asp Asp Val Ala Ala Ala
                355                 360                 365

Ala Asp Val His Ala
                370

<210> SEQ ID NO 130
<211> LENGTH: 2040
<212> TYPE: DNA
<213> ORGANISM: Oryza sativa

<400> SEQUENCE: 130
actactcatt ccactattgt aaagtcatag aaaaaattta tatagagaga aaaaattagt      60
gttgttattg ttactggctt tctgccagac gagacgagcg agcgcgcgag tgtgttgctc     120
tctggtcatc gtcgtcgtcg tcgcgatgcc gacgccgtcg cacttgaaga acccgctctg     180
cttcgacttc cgggcggcga ggcgggtgcc ggagacgcac gcgtggccgg gctggacga     240 ccacccggtg gtggacggcg gcggcggcgg cggcgaggac gcggtgccgg tggtggacgt     300
```

```
cggggcgggc gacgcggcgg cgcgggtggc gcgggcggcg gagcagtggg gcgcgttcct    360
tctggtcggg cacggcgtgc cggcggcgct gctgtcgcgc gtcgaggagc gcgtcgcccg    420
cgtgttctcc ctgccggcgt cggagaagat gcgcgccgtc cgcggccccg gcgagccctg    480
cggctacggc tcgccgccca tctcctcctt cttctccaag ctcatgtggt ccgagggcta    540
caccttctcc ccttcctccc tccgctccga gctccgccgc tctggccca agtccggcga    600 cgactaccte ctcttctggt atatatacat atatactctc ccatgcattc catgcacata    660
cactctacgt atatatctac ctctacgtat atatctacgt attgatctac gtataatata    720
cgcagtgacg tgatggagga gtttcacaag gagatgcggc ggctagccga cgagttgctg    780
aggttgttct tgagggcgct ggggctcacc ggcgaggagg tcgccggagt cgaggcggag    840
aggaggatcg gcgagaggat gacggcgacg gtgcacctca actggtaccc gaggtgcccg    900
gagccgcggc gagcgctggg gctcatcgcg cacacggact cgggcttctt caccttcgtg    960
ctccagagcc tcgtcccggg gctgcagctg ttccgtcgag ggcccgaccg gtgggtggcg   1020
gtgccggcgg tggcgggggc cttcgtcgtc aacgtcggcg acctcttcca catcctcacc   1080
aacggccgct tccacagcgt ctaccaccgc gccgtcgtga accgcgaccg cgaccgggtc   1140
tcgctcggct acttcctcgg cccgccgccg gacgccgagg tggcgccgct gccggaggcc   1200
gtgccggccg gccggagccc cgcctaccgc gctgtcacgt ggccggagta catggccgtc   1260
cgcaagaagg ccttcgccac cggcggctcc gccctcaaga tggtctccac cgacgccgcc   1320
gccgccgccg acgaacacga cgacgtcgcc gccgccgccg acgtccacgc ataagctata   1380
gctactagct acctcgatct cacgcaaaaa aaaaagaaa caattaatag agcaaaaaaa    1440 aaagaagag aaaatggtgg tacttgtgtt taaggtttcc tccatgcaaa atggtttgca    1500
tgcatgcatg caaagctagc atctgcagct gcaagaatta caagagcaga gaagcagaca    1560
gctagatgga gataattaat taattaatta atctaattaa gcatgcaata attaagatta    1620
ttattctgat ttcagaactg aaaaaaaaag tgtggttaat taattattgg ttaggcttaa    1680
ttttatctag atgtagaaaa agaatcaaga tcttcaagca agagagaaga ggatcgaaga    1740
agaaggaaaa gaaaacgaaa aggacatgct gtgttgtctc ttctagttgt accctggctg    1800
ctgattaagt gctttgtttt gttgctgcaa gcttgtcgtt actgattatt agttagttat    1860
gcatctaatt gattaaacta atctgttttgg cattttggct cgagctaagc tatagccagg    1920
ctggtcaatg ataggaactt gtacaatta agcaattgaa cctgatcctg tactggcatg    1980
tatgtatata tgcaagtgat gagaaccact agctagtata gctagacatg tatttgtata    2040
```

<210> SEQ ID NO 131
<211> LENGTH: 1332
<212> TYPE: DNA
<213> ORGANISM: Hordeum vulgare

<400> SEQUENCE: 131

```
acactcactc ctcaatccat ccgtctccac cattgctcgc tagctcgagc tctactagct     60
agcactgcaa agtcagccgg gccggagttg atttggtcct tgttagcttg accgatcgta    120
tacgtatcgc caggatgccg acgccgtcgc acctgagcaa ggacccgcac tacttcgact    180
tccgggcggc gcggcgggtg ccggagacac acgcgtggcc gggctgcac gaccacccgg    240 tggtggacgg cggcggcgcg ggcggagggc cggacgcggt gccggtggtg acatgcgcg    300 acccgtgcgc cgcggaggcg gtggcgctgg ccgcgcagga ctggggcgcc ttcctcttgc    360
```

| | |
|---|---|
| agggccacgg cgtcccgttg gagctgctgg cccgcgtgga ggccgcgata gcgggcatgt | 420 |
| tcgcgctgcc ggcgtcggag aagatgcgcg ccgtgcggcg gcccggcgac tcgtgcggct | 480 |
| acgggtcgcc gcccatctcc tccttcttct ccaagtgcat gtggtccgag ggctacacct | 540 |
| tctccccggc caacctccgc tccgacctcc gcaagctctg gcccaaggcc ggccacgact | 600 |
| accgccactt ctgtgccgtg atggaggagt tccacaggga gatgcgcgtt ctggccgaca | 660 |
| agctgctgga gctgttcctg gtggcccctcg ggctcaccgg cgagcaggtc gccgccgtcg | 720 |
| agtcggagca caagatcgcc gagaccatga ccgccacaat gcacctcaac tggtacccca | 780 |
| agtgcccgga cccgaagcga gcgctgggcc tgatcgcgca cacggactcg ggcttcttca | 840 |
| ccttcgtgct ccagagcctg gtgcccgggc tgcagctgtt ccggcacggc cccgaccgtt | 900 |
| gggtgacggt gcccgccgtg ccgggcgcca tggtcgtcaa cgtcggcgac ctcttccaca | 960 |
| tcctcaccaa tggccgcttc cacagcgtct accaccgcgc cgtcgtcaac cgcgacagcg | 1020 |
| accggatatc gctggggtac ttcctcggcc cgcccgccca cgttaaggtg gcgccgctca | 1080 |
| gggaggccct cgccggcacg cccgctgcct accgcgccgt cacgtggccc gagtacatgg | 1140 |
| gcgtgcgcaa gaaggccttc accaccggcc cctccgcgct caagatggtc gccatctcca | 1200 |
| ccgacgacgc cgccgacgtc ctccccgacg tcctctcgtc gtagatcggc gccggccatc | 1260 |
| acccggccgg ccaagagacc gatctataca acaattagt gaacaaaaaa aaaaaaaaa | 1320 |
| aaaaaaaaaa aa | 1332 |

<210> SEQ ID NO 132
<211> LENGTH: 1110
<212> TYPE: DNA
<213> ORGANISM: Hordeum vulgare

<400> SEQUENCE: 132

| | |
|---|---|
| atgccgacgc cgtcgcacct gagcaaggac ccgcactact tcgacttccg ggcggcgcgg | 60 |
| cgggtgccgg agacacacgc gtggccgggg ctgcacgacc accccggtggt ggacggcggc | 120 |
| ggcgcgggcg gagggccgga cgcggtgccg gtggtggaca tgcgcgaccc gtgcgccgcg | 180 |
| gaggcggtgg cgctggccgc gcaggactgg ggcgccttcc tcttgcaggg ccacggcgtc | 240 |
| ccgttggagc tgctggcccg cgtggaggcc gcgatagcgg gcatgttcgc gctgccggcg | 300 |
| tcggagaaga tgcgcgccgt gcggcggccc ggcgactcgt gcggctacgg gtcgccgccc | 360 |
| atctcctcct tcttctccaa gtgcatgtgg tccgagggct acaccttctc cccggccaac | 420 |
| ctccgctccg acctccgcaa gctctggccc aaggccggcc acgactaccg ccacttctgt | 480 |
| gccgtgatgg aggagttcca cagggagatg cgcgttctgg ccgacaagct gctggagctg | 540 |
| ttcctggtgg ccctcgggct caccggcgag caggtcgccg ccgtcgagtc ggagcacaag | 600 |
| atcgccgaga ccatgaccgc cacaatgcac ctcaactggt accccaagtg cccggacccg | 660 |
| aagcgagcgc tgggcctgat cgcgcacacg gactcgggct tcttcacctt cgtgctccag | 720 |
| agcctggtgc ccgggctgca gctgttccgg cacggccccg accgttgggt gacggtgccc | 780 |
| gccgtgccgg gcgccatggt cgtcaacgtc ggcgacctct ccacatcct caccaatggc | 840 |
| cgcttccaca gcgtctacca ccgcgccgtc gtcaaccgcg acagcgaccg gatatcgctg | 900 |
| gggtacttcc tcggcccgcc cgcccacgtt aaggtggcgc cgctcaggga ggccctcgcc | 960 |
| ggcacgcccg ctgcctaccg cgccgtcacg tggcccgagt acatgggcgt gcgcaagaag | 1020 |
| gccttcacca ccggcgcctc cgcgctcaag atggtcgcca tctccaccga cgacgccgcc | 1080 |
| gacgtcctcc ccgacgtcct ctcgtcgtag | 1110 |

<210> SEQ ID NO 133
<211> LENGTH: 369
<212> TYPE: PRT
<213> ORGANISM: Hordeum vulgare

<400> SEQUENCE: 133

Met Pro Thr Pro Ser His Leu Ser Lys Asp Pro His Tyr Phe Asp Phe
1               5                   10                  15

Arg Ala Ala Arg Val Pro Glu Thr His Ala Trp Pro Gly Leu His
            20                  25                  30

Asp His Pro Val Val Asp Gly Gly Ala Gly Gly Pro Asp Ala
        35                  40                  45

Val Pro Val Val Asp Met Arg Asp Pro Cys Ala Ala Glu Ala Val Ala
    50                  55                  60

Leu Ala Ala Gln Asp Trp Gly Ala Phe Leu Leu Gln Gly His Gly Val
65                  70                  75                  80

Pro Leu Glu Leu Leu Ala Arg Val Glu Ala Ala Ile Ala Gly Met Phe
            85                  90                  95

Ala Leu Pro Ala Ser Glu Lys Met Arg Ala Val Arg Arg Pro Gly Asp
        100                 105                 110

Ser Cys Gly Tyr Gly Ser Pro Pro Ile Ser Ser Phe Phe Ser Lys Cys
    115                 120                 125

Met Trp Ser Glu Gly Tyr Thr Phe Ser Pro Ala Asn Leu Arg Ser Asp
130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Val Leu Ala Asp Lys
            165                 170                 175

Leu Leu Glu Leu Phe Leu Val Ala Leu Gly Leu Thr Gly Glu Gln Val
        180                 185                 190

Ala Ala Val Glu Ser Glu His Lys Ile Ala Glu Thr Met Thr Ala Thr
    195                 200                 205

Met His Leu Asn Trp Tyr Pro Lys Cys Pro Asp Pro Lys Arg Ala Leu
210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
            245                 250                 255

Val Thr Val Pro Ala Val Pro Gly Ala Met Val Val Asn Val Gly Asp
        260                 265                 270

Leu Phe His Ile Leu Thr Asn Gly Arg Phe His Ser Val Tyr His Arg
    275                 280                 285

Ala Val Val Asn Arg Asp Ser Asp Arg Ile Ser Leu Gly Tyr Phe Leu
    290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
            325                 330                 335

Val Arg Lys Lys Ala Phe Thr Thr Gly Ala Ser Ala Leu Lys Met Val
        340                 345                 350

Ala Ile Ser Thr Asp Asp Ala Ala Asp Val Leu Pro Asp Val Leu Ser
    355                 360                 365

Ser

<210> SEQ ID NO 134
<211> LENGTH: 1653
<212> TYPE: DNA
<213> ORGANISM: Triticum aestivum
<220> FEATURE:
<221> NAME/KEY: misc_feature
<222> LOCATION: (1594)..(1600)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t

<400> SEQUENCE: 134

```
cacgagatcc atccgtctcc accattgctc gctagctcga gctcctagct agtactgcaa      60
agtcagccgg ggagttgatt tggtccttct tggcttgacc gatcgtacgt gccgccagga     120
tgccgacgcc ggcgcacctg agcaaggacc cgcgctactt cgacttccgg gcggcgcggc     180
gggtgccgga gacgcacgcg tggcccgggc tgcacgacca ccccgtggtg gacggcagcg     240
gcgcgggcgg agggccggac gcggtgccgg tggtggacat gcgcgacccg tgcgcggcgg     300
aggcggtggc gctggcggcg caggactggg gcgccttcct cctggagggc cacggcgtcc     360
cgttggagct gctggcgcgc gtggaggccg cgatcgcggg catgttcgcg ctgccggcgt     420
cggagaagat gcgcgccgtg cggcggcccg gcgactcgtg cggctacggg tcgccgccca     480
tctcctcctt cttctccaag tgcatgtggt ccgagggcta caccttctcc ccggccaacc     540
tccgctccga cctccgcaag ctctggccca aggccggcca cgactaccgc cacttctgcg     600
ccgtgatgga ggagttccac agggagatgc gcgcgctggc cgacaagctg ctggagctgt     660
tcctggtggc cctcgggctc accggcgagc aggtcgccgc cgtcgagtcc gagcagaaga     720
tcgccgagac catgaccgcc acaatgcacc tcaactggta ccccaagtgc ccggacccga     780
agcgggcgct gggcctgatc gcgcacacgg actcgggctt cttcaccttc gtgctgcaga     840
gccttgtgcc cgggctgcag ctgttccggc acggccccga ccggtgggtg acggtgcccg     900
ccgtgccggg ggccatggtc gtcaacgtcg gcgacctctt ccagatcctc accaacggcc     960
gcttccacag cgtctaccac cgcgccgtcg tcaaccgcga cagcgaccgg atatcgctcg    1020
gctacttcct cggcccgccc gcccacgtca aggtggcgcc gctcaggag gccctggccg    1080
gcacgcccgc cgcctaccgc gccgtcacgt ggcccgagta catgggcgtg cgcaagaagg    1140
ccttcaccac cggcgcctcc gcgctcaaga tggtcgccat ctccactgac aacgacgccg    1200
ccaaccacac ggacgacctg atctcgtcgt agatcggcgc cggccatcac cggccggcca    1260
agggatcgat ctacacacac aattagtgaa caaaaaatg ccagagatgg tgcatggtgg     1320
gctggtagct tagctgaggt agctaggagg aagagcgcgc gtgcggctgt cgttcgtgcg    1380
gctgttcccg caaaaaaaaa aaaggttccc tccatatatg tctccatgca gaactgcaga    1440
tgctggtggt ggatgcgtcc atgcagcagg gaacgaacta attgtaagaa aatcaagcaa    1500
acttagttct acatctgtaa ttaagtatgc atgccacttg gtttaattca attcaagtgc    1560
agaaaaaatt atgatgggaa aaaaaaagac atgnnnnnnn aaaaaaaaaa aaaaaaaaa    1620
aaaaaaaaaa aaaaaaaaaa naaaaaaaa aaa                                  1653
```

<210> SEQ ID NO 135
<211> LENGTH: 1113
<212> TYPE: DNA
<213> ORGANISM: Triticum aestivum

```
<400> SEQUENCE: 135
atgccgacgc cggcgcacct gagcaaggac ccgcgctact tcgacttccg ggcggcgcgg      60
cgggtgccgg agacgcacgc gtggcccggg ctgcacgacc accccgtggt ggacggcagc     120
ggcgcgggcg gagggccgga cgcggtgccg gtggtggaca tgcgcgaccc gtgcgcggcg     180
gaggcggtgg cgctggcggc gcaggactgg ggcgccttcc tcctggaggg ccacggcgtc     240
ccgttggagc tgctggcgcg cgtggaggcc gcgatcgcgg gcatgttcgc gctgccggcg     300
tcggagaaga tgcgcgccgt gcggcggccc ggcgactcgt gcggctacgg gtcgccgccc     360
atctcctcct tcttctccaa gtgcatgtgg tccgagggct acaccttctc cccgccaac      420 ctccgctccg acctccgcaa gctctggccc aaggccggcc acgactaccg ccacttctgc     480
gccgtgatgg aggagttcca cagggagatg cgcgcgctgg ccgacaagct gctggagctg     540
ttcctggtgg ccctcgggct caccggcgag caggtcgccg ccgtcgagtc cgagcagaag     600
atcgccgaga ccatgaccgc cacaatgcac ctcaactggt accccaagtg cccggacccg     660
aagcgggcgc tgggcctgat cgcgcacacg gactcgggct tcttcacctt cgtgctgcag     720
agccttgtgc ccgggctgca gctgttccgg cacggccccg accggtgggt gacggtgccc     780
gccgtgccgg gggccatggt cgtcaacgtc ggcgacctct tccagatcct caccaacggc     840
cgcttccaca gcgtctacca ccgcgccgtc gtcaaccgcg acagcgaccg gatatcgctc     900
ggctacttcc tcggcccgcc cgcccacgtc aaggtggcgc cgctcaggga ggccctggcc     960
ggcacgcccg ccgcctaccg cgccgtcacg tggcccgagt acatgggcgt gcgcaagaag    1020
gccttcacca ccgcgccctc cgcgctcaag atggtcgcca tctccactga caacgacgcc    1080
gccaaccaca cggacgacct gatctcgtcg tag                                 1113

<210> SEQ ID NO 136
<211> LENGTH: 370
<212> TYPE: PRT
<213> ORGANISM: Triticum aestivum

<400> SEQUENCE: 136

Met Pro Thr Pro Ala His Leu Ser Lys Asp Pro Arg Tyr Phe Asp Phe
1               5                   10                  15

Arg Ala Ala Arg Arg Val Pro Glu Thr His Ala Trp Pro Gly Leu His
                20                  25                  30

Asp His Pro Val Val Asp Gly Ser Gly Ala Gly Gly Pro Asp Ala
            35                  40                  45

Val Pro Val Asp Met Arg Asp Pro Cys Ala Ala Glu Ala Val Ala
        50                  55                  60

Leu Ala Ala Gln Asp Trp Gly Ala Phe Leu Leu Glu Gly His Gly Val
65                  70                  75                  80

Pro Leu Glu Leu Leu Ala Arg Val Glu Ala Ala Ile Ala Gly Met Phe
                85                  90                  95

Ala Leu Pro Ala Ser Glu Lys Met Arg Ala Val Arg Arg Pro Gly Asp
                100                 105                 110

Ser Cys Gly Tyr Gly Ser Pro Pro Ile Ser Ser Phe Ser Lys Cys
            115                 120                 125

Met Trp Ser Glu Gly Tyr Thr Phe Ser Pro Ala Asn Leu Arg Ser Asp
                130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Ala Leu Ala Asp Lys
```

|  |  | 165 |  |  |  | 170 |  |  |  | 175 |  |
|---|---|---|---|---|---|---|---|---|---|---|---|

Leu Leu Glu Leu Phe Leu Val Ala Leu Gly Leu Thr Gly Glu Gln Val
            180                185              190

Ala Ala Val Glu Ser Glu Gln Lys Ile Ala Glu Thr Met Thr Ala Thr
     195              200               205

Met His Leu Asn Trp Tyr Pro Lys Cys Pro Asp Pro Lys Arg Ala Leu
210                215                220

Gly Leu Ile Ala His Thr Asp Ser Gly Phe Phe Thr Phe Val Leu Gln
225              230              235           240

Ser Leu Val Pro Gly Leu Gln Leu Phe Arg His Gly Pro Asp Arg Trp
            245              250           255

Val Thr Val Pro Ala Val Pro Gly Ala Met Val Val Asn Val Gly Asp
     260              265               270

Leu Phe Gln Ile Leu Thr Asn Gly Arg Phe His Ser Val Tyr His Arg
            275              280           285

Ala Val Val Asn Arg Asp Ser Asp Arg Ile Ser Leu Gly Tyr Phe Leu
     290              295               300

Gly Pro Pro Ala His Val Lys Val Ala Pro Leu Arg Glu Ala Leu Ala
305              310              315           320

Gly Thr Pro Ala Ala Tyr Arg Ala Val Thr Trp Pro Glu Tyr Met Gly
            325              330           335

Val Arg Lys Lys Ala Phe Thr Thr Gly Ala Ser Ala Leu Lys Met Val
     340              345               350

Ala Ile Ser Thr Asp Asn Asp Ala Ala Asn His Thr Asp Asp Leu Ile
            355              360           365

Ser Ser
370

<210> SEQ ID NO 137
<211> LENGTH: 1884
<212> TYPE: DNA
<213> ORGANISM: Triticum aestivum
<400> SEQUENCE: 137

| tatatataca | gctccttgta | cttctctcgt | tcttacactc | actcctcaat | ccatccgtct | 60 |
| ccaccattgc | tgctagctc | gagctcctag | ctagtactgc | aaagtcagcc | ggggagttga | 120 |
| tttggtcctt | cttggcttga | ccgatcgtac | gtgccgccag | gatgccgacg | ccggcgcacc | 180 |
| tgagcaagga | cccgcgctac | ttcgacttcc | gggcggcgcg | gcgggtgccg | gagacgcacg | 240 |
| cgtggcccgg | gctgcacgac | caccccgtgg | tggacgcag | cggcgcgggc | ggagggccgg | 300 |
| acgcggtgcc | ggtggtggac | atgcgcgacc | cgtgcgcggc | ggaggcggtg | gcgctggcgg | 360 |
| cgcaggactg | gggcgccttc | ctcctggagg | gccacgcgt | cccgttggag | ctgctggcgc | 420 |
| gcgtggaggc | cgcgatcgcg | ggcatgttcg | cgctgccggc | gtcggagaag | atgcgcgccg | 480 |
| tgcggcggcc | cggcgactcg | tgcggctacg | ggtcgccgcc | catctcctcc | ttcttctcca | 540 |
| agtgcatgtg | gtccgagggc | tacaccttct | ccccggccaa | cctccgctcc | gacctccgca | 600 |
| agctctggcc | caaggccggc | cacgactacc | gccacttctg | gtacgtacgc | ggccgccga | 660 |
| tgcgcatata | cacgtcatag | tacggcacct | acctaactgg | ctctggccaa | ccgtccgtac | 720 |
| acacgtgaag | gggcgacgtg | tccgactccg | accatgcatg | catgcacgcg | cgcgaaactt | 780 |
| gttactcctg | ttctgctatg | gcagcagcta | gccgcgtgtg | tccgttcgta | ggagtagtta | 840 |
| cttacacagt | tacacttacg | ccgtccgtcg | tgttcctcga | cgtgcagcgc | cgtgatggag | 900 |

```
gagttccaca gggagatgcg cgcgctggcc gacaagctgc tggagctgtt cctggtggcc    960
ctcgggctca ccggcgagca ggtcgccgcc gtcgagtccg agcagaagat cgccgagacc   1020
atgaccgcca caatgcacct caactggtac gttccactac tactccagta gtacaagtac   1080
aatatataga atacaaatgg cagcagccac gacgacacgt actccaccat gcagcaaagc   1140
atatattgtc ggtgcggcgg ttgacacgga gttgtgtcgt gtcgttgatt cacaggtacc   1200
ccaagtgccc ggacccgaag cgggcgctgg gcctgatcgc gcacacggac tcgggcttct   1260
tcaccttcgt gctgcagagc cttgtgcccg ggctgcagct gttccggcac ggccccgacc   1320
ggtgggtgac ggtgcccgcc gtgccggggg ccatggtcgt caacgtcggc gacctcttcc   1380
agatcctcac caacggccgc ttccacagcg tctaccaccg cgccgtcgtc aaccgcgaca   1440
gcgaccggat atcgctcggc tacttcctcg gcccgcccgc ccacgtcaag gtggcgccgc   1500
tcagggaggc cctggccggc acgccgccgc cctaccgcgc cgtcacgtgg cccgagtaca   1560
tgggcgtgcg caagaaggcc ttcaccaccg gcgcctccgc gctcaagatg gtcgccatct   1620
ccactgacaa cgacgccgcc aaccacacgg acgacctgat ctcgtcgtag atcggcgccg   1680
gccatcaccg gccggccaag ggatcgatct acacacacaa ttagtgaaca aaaaaatgcc   1740
agagatggtg catggtgggc tggtagctta gctgaggtag ctaggaggaa gagcgcgcgt   1800
gcggctgtcg ttcgtgcggc tgttcccgca aaaaaaaaa ggtttcctcc atatakgtcc   1860
ccakscaaaa tsgmaawgct gggg                                          1884
```

```
<210> SEQ ID NO 138
<211> LENGTH: 20
<212> TYPE: RNA
<213> ORGANISM: Artificial Sequence
<220> FEATURE:
<223> OTHER INFORMATION: suppression oligo

<400> SEQUENCE: 138
acggguucuu ccaggugugc                                                 20

<210> SEQ ID NO 139
<211> LENGTH: 20
<212> TYPE: RNA
<213> ORGANISM: Artificial Sequence
<220> FEATURE:
<223> OTHER INFORMATION: suppression oligo

<400> SEQUENCE: 139
cacggguucu uccaggugug                                                 20

<210> SEQ ID NO 140
<211> LENGTH: 20
<212> TYPE: RNA
<213> ORGANISM: Artificial Sequence
<220> FEATURE:
<223> OTHER INFORMATION: suppression oligo

<400> SEQUENCE: 140
cauugaccuc cccgcuggca                                                 20

<210> SEQ ID NO 141
<211> LENGTH: 20
<212> TYPE: RNA
<213> ORGANISM: Artificial Sequence
<220> FEATURE:
<223> OTHER INFORMATION: suppression oligo

<400> SEQUENCE: 141
```

```
ccagcgggga ggucaaugcu                                                 20

<210> SEQ ID NO 142
<211> LENGTH: 20
<212> TYPE: RNA
<213> ORGANISM: Artificial Sequence
<220> FEATURE:
<223> OTHER INFORMATION: suppression oligo

<400> SEQUENCE: 142
cccagcauug accuccccgc                                                 20

<210> SEQ ID NO 143
<211> LENGTH: 20
<212> TYPE: RNA
<213> ORGANISM: Artificial Sequence
<220> FEATURE:
<223> OTHER INFORMATION: suppression oligo

<400> SEQUENCE: 143
cgcgcucgug uacccggaca                                                 20

<210> SEQ ID NO 144
<211> LENGTH: 20
<212> TYPE: RNA
<213> ORGANISM: Artificial Sequence
<220> FEATURE:
<223> OTHER INFORMATION: suppression oligo

<400> SEQUENCE: 144
cucccggcgc aggucgaaca                                                 20

<210> SEQ ID NO 145
<211> LENGTH: 20
<212> TYPE: RNA
<213> ORGANISM: Artificial Sequence
<220> FEATURE:
<223> OTHER INFORMATION: suppression oligo

<400> SEQUENCE: 145
guguacccgg acacggugcc                                                 20

<210> SEQ ID NO 146
<211> LENGTH: 20
<212> TYPE: RNA
<213> ORGANISM: Artificial Sequence
<220> FEATURE:
<223> OTHER INFORMATION: suppression oligo

<400> SEQUENCE: 146
ugcagggaag cuguccgggc                                                 20

<210> SEQ ID NO 147
<211> LENGTH: 20
<212> TYPE: RNA
<213> ORGANISM: Artificial Sequence
<220> FEATURE:
<223> OTHER INFORMATION: suppression oligo

<400> SEQUENCE: 147
uucuuccagg ugugcgggca                                                 20

<210> SEQ ID NO 148
<211> LENGTH: 20
<212> TYPE: RNA
```

```
<213> ORGANISM: Artificial Sequence
<220> FEATURE:
<223> OTHER INFORMATION: suppression oligo

<400> SEQUENCE: 148 agaucccgc gccauuccug                                                    20

<210> SEQ ID NO 149
<211> LENGTH: 20
<212> TYPE: RNA
<213> ORGANISM: Artificial Sequence
<220> FEATURE:
<223> OTHER INFORMATION: suppression oligo

<400> SEQUENCE: 149
augcagggaa gcuguccggg                                                   20

<210> SEQ ID NO 150
<211> LENGTH: 20
<212> TYPE: RNA
<213> ORGANISM: Artificial Sequence
<220> FEATURE:
<223> OTHER INFORMATION: suppression oligo

<400> SEQUENCE: 150
auuccugugg ccgcaggaag                                                   20

<210> SEQ ID NO 151
<211> LENGTH: 20
<212> TYPE: RNA
<213> ORGANISM: Artificial Sequence
<220> FEATURE:
<223> OTHER INFORMATION: suppression oligo

<400> SEQUENCE: 151
cagcggggag gucaaugcug                                                   20

<210> SEQ ID NO 152
<211> LENGTH: 20
<212> TYPE: RNA
<213> ORGANISM: Artificial Sequence
<220> FEATURE:
<223> OTHER INFORMATION: suppression oligo

<400> SEQUENCE: 152
caggaauggc gcggggaucu                                                   20

<210> SEQ ID NO 153
<211> LENGTH: 20
<212> TYPE: RNA
<213> ORGANISM: Artificial Sequence
<220> FEATURE:
<223> OTHER INFORMATION: suppression oligo

<400> SEQUENCE: 153
gacuacuucg ucggcacccu                                                   20

<210> SEQ ID NO 154
<211> LENGTH: 20
<212> TYPE: RNA
<213> ORGANISM: Artificial Sequence
<220> FEATURE:
<223> OTHER INFORMATION: suppression oligo

<400> SEQUENCE: 154
gccaggauuu cgagccaaug                                                   20
```

```
<210> SEQ ID NO 155
<211> LENGTH: 20
<212> TYPE: RNA
<213> ORGANISM: Artificial Sequence
<220> FEATURE:
<223> OTHER INFORMATION: suppression oligo

<400> SEQUENCE: 155
ggaacauuug gagggaggcg                                               20

<210> SEQ ID NO 156
<211> LENGTH: 20
<212> TYPE: RNA
<213> ORGANISM: Artificial Sequence
<220> FEATURE:
<223> OTHER INFORMATION: suppression oligo

<400> SEQUENCE: 156
gggaggucaa ugcuggggcu                                               20

<210> SEQ ID NO 157
<211> LENGTH: 20
<212> TYPE: RNA
<213> ORGANISM: Artificial Sequence
<220> FEATURE:
<223> OTHER INFORMATION: suppression oligo

<400> SEQUENCE: 157
uuggcucgaa auccuggccg                                               20

<210> SEQ ID NO 158
<211> LENGTH: 20
<212> TYPE: RNA
<213> ORGANISM: Artificial Sequence
<220> FEATURE:
<223> OTHER INFORMATION: suppression oligo

<400> SEQUENCE: 158
acggguucuu ccaggugugc                                               20

<210> SEQ ID NO 159
<211> LENGTH: 20
<212> TYPE: RNA
<213> ORGANISM: Artificial Sequence
<220> FEATURE:
<223> OTHER INFORMATION: suppression oligo

<400> SEQUENCE: 159
cacggguucu uccaggugug                                               20

<210> SEQ ID NO 160
<211> LENGTH: 20
<212> TYPE: RNA
<213> ORGANISM: Artificial Sequence
<220> FEATURE:
<223> OTHER INFORMATION: suppression oligo

<400> SEQUENCE: 160
cauugaccuc cccgcuggca                                               20

<210> SEQ ID NO 161
<211> LENGTH: 20
<212> TYPE: RNA
<213> ORGANISM: Artificial Sequence
<220> FEATURE:
```

```
<223> OTHER INFORMATION: suppression oligo

<400> SEQUENCE: 161
ccagcgggga ggucaaugcu                                                    20

<210> SEQ ID NO 162
<211> LENGTH: 20
<212> TYPE: RNA
<213> ORGANISM: Artificial Sequence
<220> FEATURE:
<223> OTHER INFORMATION: suppression oligo

<400> SEQUENCE: 162
cccagcauug accuccccgc                                                    20

<210> SEQ ID NO 163
<211> LENGTH: 20
<212> TYPE: RNA
<213> ORGANISM: Artificial Sequence
<220> FEATURE:
<223> OTHER INFORMATION: suppression oligo

<400> SEQUENCE: 163
cgcgcucgug uacccggaca                                                    20

<210> SEQ ID NO 164
<211> LENGTH: 20
<212> TYPE: RNA
<213> ORGANISM: Artificial Sequence
<220> FEATURE:
<223> OTHER INFORMATION: suppression oligo

<400> SEQUENCE: 164
cucccggcgc aggucgaaca                                                    20

<210> SEQ ID NO 165
<211> LENGTH: 20
<212> TYPE: RNA
<213> ORGANISM: Artificial Sequence
<220> FEATURE:
<223> OTHER INFORMATION: suppression oligo

<400> SEQUENCE: 165
guguacccgg acacggugcc                                                    20

<210> SEQ ID NO 166
<211> LENGTH: 20
<212> TYPE: RNA
<213> ORGANISM: Artificial Sequence
<220> FEATURE:
<223> OTHER INFORMATION: suppression oligo

<400> SEQUENCE: 166
ugcagggaag cguccgggc                                                     20

<210> SEQ ID NO 167
<211> LENGTH: 20
<212> TYPE: RNA
<213> ORGANISM: Artificial Sequence
<220> FEATURE:
<223> OTHER INFORMATION: suppression oligo

<400> SEQUENCE: 167
uucuuccagg ugugcgggca                                                    20
```